US012753346B1

(12) United States Patent
Smith et al.

(10) Patent No.: US 12,753,346 B1
(45) **Date of Patent: *Oct. 6, 2026**

(54) CONTROL OF PYROLYSIS CONDITIONS AND FEEDSTOCK FOR THE PRODUCTION OF DESIRABLE COMPOUNDS

(71) Applicant: Talipot Cool Extract (IP), LLC

(72) Inventors: Matthew William Smith, Camarillo, CA (US); Haijun Wan, Camarillo, CA (US); Kevin Daniel Dolinar, Ventura, CA (US)

(73) Assignee: Talipot Cool Extract (IP), LLC, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/891,091

(22) Filed: Aug. 18, 2022

Related U.S. Application Data

(63) Continuation of application No. 17/231,948, filed on Apr. 15, 2021, now abandoned.

(Continued)

(51) Int. Cl.
*C10B 53/02* (2006.01)
*B01D 11/02* (2006.01)

(Continued)

(52) U.S. Cl.
CPC .............. *C10B 53/02* (2013.01); *B01D 11/02* (2013.01); *B01D 11/0288* (2013.01); *C07D 493/04* (2013.01); *C10B 57/04* (2013.01)

(58) Field of Classification Search
CPC ..................................................... C10B 53/02
See application file for complete search history.

(56) References Cited

U.S. PATENT DOCUMENTS 1,369,428 A 2/1921 Hawley
3,545,129 A 12/1970 Schreiber et al.

(Continued)

FOREIGN PATENT DOCUMENTS

CN 1997590 A 7/2007
CN 103053244 B 12/2014

(Continued)

OTHER PUBLICATIONS

Kochanek J, Long RL, Lisle AT, Flematti GR (2016) "Karrikins Identified in Biochars Indicate Post-Fire Chemical Cues Can Influence Community Diversity and Plant Development". PLoS ONE 11(8): e0161234. doi:10.1371/journal.pone.0161234.*

(Continued)

*Primary Examiner* — Jonathan Luke Pilcher
(74) *Attorney, Agent, or Firm* — Avyno Law P.C.

(57) ABSTRACT

A method for increasing the production of desired inorganic or organic compounds, including soluble signaling compounds, from the pyrolysis of biomass is provided comprising the steps of: (i) obtaining a biomass source; (ii) pyrolyzing the biomass source at various temperatures between 400-600° C. and, at each of the various temperatures, retaining the biomass within the region of higher heating temperature for a period of not longer than one day and not less than 1 minute whereby the pyrolysis of the biomass at various temperature for various hold times produces various biochars; (iii) creating extracts from each of the various biochars produced at varying temperatures and hold times; (iv) determining which of the extracts from each of the various biochars produced at varying temperatures and hold times produces the most desired soluble signaling compound; and (v) collecting biochar extract from biochar produced at the temperature and heat treatment time determined to produce the most desired soluble signaling com- (Continued)

pound. The method also can include other steps of extraction and purification. A biochar having high levels of desirable organic compounds or soluble signaling compounds is also provided, where the biochar is derived from a biomass source that together with predefined pyrolysis parameters produces resulting biochar having increased levels of the desirable organic compounds. The desirable soluble signaling compounds may be those known to increase seed germination rates and early plant growth. Such desirable compounds can be collected in a biochar extract by contacting the biochar with an extraction media.

19 Claims, 94 Drawing Sheets

Related U.S. Application Data

(60) Provisional application No. 63/010,253, filed on Apr. 15, 2020.

(51) Int. Cl.
*C07D 493/04* (2006.01)
*C10B 57/04* (2006.01)

(56) References Cited

U.S. PATENT DOCUMENTS 3,648,409 A 3/1972 Johnson et al.
3,698,133 A 10/1972 Schreiber
3,841,974 A 10/1974 Osborne
3,947,996 A 4/1976 Watts
4,153,514 A 5/1979 Garrett et al.
4,268,275 A 5/1981 Chittick
4,344,979 A 8/1982 Gago et al.
4,383,391 A 5/1983 Thomas et al.
4,421,524 A 12/1983 Chittick
4,438,593 A 3/1984 McNew et al.
4,487,958 A 12/1984 Ream et al.
4,495,165 A 1/1985 Gurza
4,497,637 A 2/1985 Purdy et al.
4,501,644 A 2/1985 Thomas
4,530,702 A 7/1985 Fetters et al.
4,553,351 A 11/1985 Edgar
4,618,735 A 10/1986 Bridle et al.
4,735,017 A 4/1988 Gago et al.
4,861,351 A 8/1989 Nicholas et al.
4,992,480 A 2/1991 Mahajan et al.
5,015,423 A 5/1991 Eguchi et al.
5,032,618 A 7/1991 Marchionna et al.
5,087,786 A 2/1992 Nubel et al.
5,204,102 A 4/1993 Coles et al.
5,221,290 A 6/1993 Dell
5,368,626 A 11/1994 Schnuda
5,462,908 A 10/1995 Liang et al.
5,504,259 A 4/1996 Diebold et al.
5,508,060 A 4/1996 Perman et al.
5,755,058 A 5/1998 Guyot et al.
5,756,194 A 5/1998 Shogren et al.
5,820,640 A 10/1998 Ikura et al.
5,857,807 A 1/1999 Longo, Sr.
5,863,467 A 1/1999 Mariner et al.
5,916,029 A 6/1999 Smith et al.
6,133,328 A 10/2000 Lightner
6,227,473 B1 5/2001 Arnold
6,228,806 B1 5/2001 Mehta
6,329,922 B1 12/2001 Kosugi et al.
6,339,031 B1 1/2002 Tan
6,548,026 B1 4/2003 Cameron et al.
6,747,067 B2 6/2004 Melnichuk et al.
6,811,703 B2 11/2004 Elliott
6,841,065 B2 1/2005 Smith et al.
6,841,085 B2 1/2005 Werpy et al.
6,923,838 B2 8/2005 Maubert et al.
6,994,827 B2 2/2006 Safir et al.
7,033,972 B2 4/2006 Shikada et al.
7,226,566 B2 6/2007 Beierle
7,282,189 B2 10/2007 Zauderer
7,458,999 B2 12/2008 Schenck et al.
7,846,979 B2 12/2010 Rojey et al.
7,888,540 B2 2/2011 Deluga et al.
7,947,155 B1 5/2011 Green et al.
8,173,044 B1 5/2012 Cheiky et al.
8,197,573 B2 6/2012 Scharf
8,236,065 B2 8/2012 Tateishi et al.
8,236,085 B1 8/2012 Cheiky et al.
8,317,891 B1 11/2012 Cheiky et al.
8,317,892 B1 11/2012 Cheiky et al.
8,318,997 B2 11/2012 Mcalister
8,361,186 B1 1/2013 Shearer et al.
8,430,937 B2 4/2013 Cheiky et al.
8,431,757 B2 4/2013 Cheiky et al.
8,568,493 B2 10/2013 Cheiky et al.
8,747,797 B2 6/2014 Shearer et al.
8,986,581 B2 3/2015 Eddy et al.
9,260,666 B2 2/2016 Aelion et al.
9,326,451 B1 5/2016 Madsen et al.
9,478,324 B1 10/2016 Favetta et al.
9,493,379 B2 11/2016 Cheiky et al.
9,527,780 B2 12/2016 Wilson et al.
9,809,502 B2 11/2017 Bontchev et al.
9,873,639 B1 1/2018 Doccola et al.
9,968,911 B2 5/2018 Eddy et al.
9,980,912 B2 5/2018 Belcher et al.
10,065,163 B2 * 9/2018 Malyala .................. B01J 20/20
10,265,670 B2 4/2019 Belcher et al.
11,097,241 B2 * 8/2021 Kim ....................... A23K 50/00
11,124,461 B2 9/2021 Walker et al.
11,866,329 B2 * 1/2024 Kim ....................... C01B 32/05
2002/0012725 A1 1/2002 Carlson
2003/0119552 A1 6/2003 Laumen et al.
2004/0111968 A1 6/2004 Day et al.
2004/0128909 A1 7/2004 Thomas
2006/0225345 A1 10/2006 Westrate
2006/0283221 A1 12/2006 Camisa
2007/0123420 A1 5/2007 Hayashi et al.
2008/0006519 A1 1/2008 Badger
2008/0016769 A1 1/2008 Pearson
2008/0093209 A1 4/2008 Noto
2008/0109922 A1 5/2008 Wang
2008/0216391 A1 9/2008 Cortright et al.
2008/0223269 A1 9/2008 Paoluccio
2008/0300435 A1 12/2008 Cortright et al.
2008/0317657 A1 12/2008 Hall et al.
2008/0317907 A1 12/2008 Thomas et al.
2009/0007484 A1 1/2009 Smith
2009/0081292 A1 3/2009 Otomo et al.
2009/0126433 A1 5/2009 Piskorz et al.
2009/0139139 A1 6/2009 David et al.
2009/0151251 A1 6/2009 Manzer et al.
2009/0183430 A1 7/2009 Schubert et al.
2009/0217575 A1 9/2009 Raman et al.
2009/0217584 A1 9/2009 Raman et al.
2009/0253947 A1 10/2009 Brandvold et al.
2009/0308787 A1 12/2009 O'connor et al.
2010/0040510 A1 2/2010 Randhava et al.
2010/0162780 A1 7/2010 Scharf
2010/0180805 A1 7/2010 Cheiky
2010/0218417 A1 9/2010 Bauldreay et al.
2010/0223839 A1 9/2010 Garcia-Perez et al.
2010/0236309 A1 9/2010 Celia
2010/0236987 A1 9/2010 Kreis
2010/0240900 A1 9/2010 Zhang et al.
2010/0257775 A1 10/2010 Cheiky
2010/0270505 A1 10/2010 Gallaspy et al.
2010/0300866 A1 12/2010 Van et al.
2010/0310447 A1 12/2010 Yaniv et al.
2010/0311157 A1 12/2010 Van et al.
2011/0003693 A1 1/2011 Spittle
2011/0023566 A1 2/2011 Lodwig et al.
2011/0044761 A1 2/2011 Chang
2011/0053771 A1 3/2011 Goodwin

(56) References Cited

U.S. PATENT DOCUMENTS

| | | | |
|---|---|---|---|
| 2011/0072872 | A1 | 3/2011 | Hartle et al. |
| 2011/0081336 | A1 | 4/2011 | Medoff |
| 2011/0092726 | A1 | 4/2011 | Clarke |
| 2011/0100359 | A1 | 5/2011 | North |
| 2011/0172092 | A1 | 7/2011 | Lee et al. |
| 2011/0177466 | A1 | 7/2011 | Cheiky |
| 2011/0209386 | A1 | 9/2011 | Cheiky et al. |
| 2011/0212004 | A1 | 9/2011 | Cheiky et al. |
| 2011/0258912 | A1 | 10/2011 | O'connor et al. |
| 2012/0060574 | A1 | 3/2012 | Rose |
| 2012/0103040 | A1 | 5/2012 | Wolf et al. |
| 2012/0125064 | A1 | 5/2012 | Joseph et al. |
| 2012/0208254 | A1 | 8/2012 | Smith et al. |
| 2012/0220454 | A1 | 8/2012 | Chen et al. |
| 2012/0237994 | A1 | 9/2012 | Das et al. |
| 2012/0283493 | A1 | 11/2012 | Olson et al. |
| 2012/0286209 | A1 | 11/2012 | Cheiky et al. |
| 2012/0291346 | A1 | 11/2012 | Rose |
| 2012/0304718 | A1 | 12/2012 | Cheiky et al. |
| 2012/0304719 | A1 | 12/2012 | Cheiky et al. |
| 2013/0025188 | A1 | 1/2013 | Cheiky et al. |
| 2013/0025190 | A1 | 1/2013 | Cheiky et al. |
| 2013/0123103 | A1 | 5/2013 | Anderson et al. |
| 2013/0213101 | A1 | 8/2013 | Shearer et al. |
| 2014/0016709 | A1 | 1/2014 | Ko et al. |
| 2014/0024528 | A1 | 1/2014 | Smith et al. |
| 2014/0037536 | A1 | 2/2014 | Reimerink-Schats et al. |
| 2014/0161709 | A1 | 6/2014 | Karthikeyan |
| 2014/0177136 | A1 | 6/2014 | Kim et al. |
| 2014/0345341 | A1 | 11/2014 | Fiato et al. |
| 2014/0345343 | A1 | 11/2014 | Wilson et al. |
| 2014/0349847 | A1 | 11/2014 | Schrader |
| 2014/0352378 | A1 | 12/2014 | Shearer et al. |
| 2015/0101372 | A1 | 4/2015 | Cheiky et al. |
| 2015/0128672 | A1 | 5/2015 | Shearer et al. |
| 2015/0157661 | A1 | 6/2015 | Eddy et al. |
| 2015/0251965 | A1 | 9/2015 | Stacy |
| 2015/0361369 | A1 | 12/2015 | Tait et al. |
| 2016/0023959 | A1 | 1/2016 | Bontchev et al. |
| 2016/0102024 | A1 | 4/2016 | Schrader et al. |
| 2016/0326067 | A1 | 11/2016 | Bontchev et al. |
| 2016/0362607 | A1 | 12/2016 | Weaver et al. |
| 2016/0368831 | A1 | 12/2016 | Bontchev et al. |
| 2017/0174578 | A1 | 6/2017 | Belcher et al. |
| 2017/0175394 | A1 | 6/2017 | Simmons |
| 2017/0304791 | A1* | 10/2017 | Malyala .................. A61L 9/012 |
| 2018/0126349 | A1 | 5/2018 | Belcher et al. |
| 2021/0284536 | A9* | 9/2021 | Kim ................... B01D 11/0288 |
| 2022/0174985 | A1* | 6/2022 | Kim ....................... A23K 40/10 |

FOREIGN PATENT DOCUMENTS

| | | | |
|---|---|---|---|
| CN | 104628792 | A | 5/2015 |
| EP | 0140811 | A2 | 5/1985 |
| GB | 2479469 | A | 10/2011 |
| IN | 201811029622 | A | 2/2020 |
| KR | 100819505 | B | 4/2008 |
| WO | 8204223 | A1 | 12/1982 |
| WO | 2004037747 | A2 | 5/2004 |
| WO | 2009004652 | A1 | 1/2009 |
| WO | 2010084230 | A1 | 7/2010 |
| WO | 2010129988 | A1 | 11/2010 |
| WO | 2011006717 | A2 | 1/2011 |
| WO | 2011014916 | A1 | 2/2011 |
| WO | 2011097183 | A2 | 8/2011 |
| WO | 2011143380 | A2 | 11/2011 |
| WO | 2011143718 | A1 | 11/2011 |
| WO | 2011159154 | A1 | 12/2011 |
| WO | 2012094736 | A1 | 7/2012 |
| WO | 2014091279 | A1 | 6/2014 |
| WO | 2014146205 | A1 | 9/2014 |
| WO | 2016054431 | A1 | 4/2016 |
| WO | 2016187161 | A1 | 11/2016 |

OTHER PUBLICATIONS

Gavin R. Flematti, Mark T. Waters, Adrian Scaffidi, David J. Merritt, Emilio L. Ghisalberti, Kingsley W. Dixon, Steven M. Smith, Karrikin and Cyanohydrin Smoke Signals Provide Clues to New Endogenous Plant Signaling Compounds, Molecular Plant, vol. 6, Issue 1,2013, pp. 29-37, https://doi.org/10.1093/mp/sss132.*

Lou, Y., Joseph, S., Li, L., Graber, E. R., Liu, X., and Pan, G. (2016). "Water extract from straw biochar used for plant growth promotion: An initial test," BioRes. 11(1), 249-266.*

Ahmad, et al., "Biochar as a Sorbent for Contaminant Management in Soil and Water: A Review," Chernosphere, vol. 99, pp. 19-33 (Nov. 27, 2013).

Beesley, et al.; A review of biochars' potential role in the remediation, revegetation and restoration of contaminated soils; Environmental Pollution 159 (2011) 3269-3232.

Berek, et al.; Improving Soil Productivity with Biochars; ICGAI, Yogyakarta, Indonesia; Nov. 11-14, 2013; 23 pp; Abstract.

Biliaderis, et al., "Functional Food Carbohydrates," CRC Press 2006, Ch. 16, pp. 517-518.

Bucheli, et al., "Polycyclic Aromatic Hydrocarbons and Polychlorinated Aromatic Compounds in Biochar," Biochar for Environmental Management, Ch. 21, pp. 595-622 (Jan. 2015).

Buerschaper, R., "Thermal & Electrical Conductivity of Graphite & Carbon at Low Temperatures," Jour. of App. Physics, pp. 452-454 (1944).

Cheng, et al., "Stability of Black Carbon in Soils Across a Climatic Gradient," Jour. of Geophysical Research Biogeosciences, vol. 113, G02027, pp. 1-10 (2008).

Chew, T.L. and Bhatia, S., "Catalytic Processes Towards the Production of Biofuels in a Palm Oil and Oil Palm Biomass-based Biorefinery," Bioresource Tech., vol. 99, pp. 7911-8922 (2008).

Chia, Chee H. et al: "Characterization of an enriched biochar", Journal of Analytical and Applied Pyrolysis, vol. 108, Jul. 1, 2014 (Jul. 1, 2014), pp. 26-34, XP055827400, NL ISSN:0165-2370, DOI: 101016/j.jaap.2014.05.021.

Demirbas, A., "Effects of Temperature & Particle Size on Bio-Char Yield from Pyrolysis of Agricultural Residues," J. Anal. Pyrolysis, vol. 72, pp. 243-248 (2004).

Downie: Biochar Production and Use: Environmental Risks and Rewards: PhD Thesis: The University of New South Wales; Sydney, Australia, p. 1-16, p. 155-168 (2011).

Elliott, D.C. and Neuenschwander, G.G., "Liquid Fuels by Low-Severity Hydrotreating of Biocrude," Dev. in Thermochernicai Biomass Conversion, vol. 1, pp. 611-621 (1996).

European Search Report (Supplemental Report) dated Aug. 17, 2017 for EP 14875314.8.

Extended European Search Report issued by the European Patent Office for European Patent Application No. 12797129.9 dated Mar. 6, 2015 (7 pgs.).

Extended European Search Report issued by the European Patent Office for European Patent Application No. 12817137.8 dated Jul. 13, 2015 (8 pgs.).

Faludi, J., "World Changing Change Your Thinking a Carbon-Negative Fuel," Oct. 16, 2007; www.worldchanging.com (9 pgs.).

Flematti et al., "Karrikin and Cyanohydrin Smoke Signals Provide Clues to New Endogenous Plant Signaling Compounds" Molecular Plant, vol. 6, No. 1, pp. 29-37, Jan. 2013.

Gehrer, r. and Hayek, K., "A Fully Programmable Systemm for the Study of Catalytic Gas Reactions," J. Physc. E: Sci. Instrum., vol. 18, pp. 836-838 (1985).

Graber, E.R., et al., "A humic substances product extracted from biochar reduces Arabidopsis root hair density and length under P-sufficient and P-starvation conditions", Plant Soil, 395, pp. 21-30, May 29, 2015 (May 29, 2015).

Gray, et al., "Water Update in Biochars: The Roles of Porosity and Hydrophobicity; Biomass and Bioenergy," vol. 6, No. 1, pp. 196-205 (Jan. 23, 2014).

Greenfacts; Facts on Health and the Environment; Dioxins; Apr. 13, 2017; 3pp.; retrieved from https://www.greenfacts.org/en/d on Aug. 15, 2004.

(56) References Cited

OTHER PUBLICATIONS

Hadjittofi, et al.; Activated biochar derived from cactus fibres—Preparation, characterization and application on Cu (II) removal from aqueous solutions; Bioresource Techology; vol. 159; May 2014; pp. 460-464.
Hua, et al., "Impacts Upon Soil Quality and Plant Growth of Bamboo Charcoal Addition to Composted Sludge," Environmental Technology, vol. 33, No. 1, pp. 61-68 (Jan. 18, 2012).
Innovation Fluides Supercritiques, Explore, Use, Make the Most of Supercritical Fluids, Nov. 27, 2015. Online, retrieved from the Internet on Mar. 6, 2017; html; 2 pp.
Intani et al., Phytotoxicity of Corncob Biochar before and after Heat Treatment and Washing; MDPI; Dec. 2018; 18 pages.
Jindo, et al., "Biochar Influences the Microbial Community Structure During Manure Composting with Agricultural Wastes," Science of the Total Environment, vol. 416, pp. 476-481 (Feb. 2012).
Karmakar, et al., "Plant Defence Activators Inducing Systematic Resistance in Zingiber Officinale Rosc. Against Pythium Aphanidermatum (Edson) Fitz.," Indian Journal of Biotechnology, vol. 2, pp. 591-595 (2003).
Kim, et al., "Characteristics of Crosslinked Potato Starch & Starch-Filled Linear Low-Density Polyethylene Films," Carbohydrate Polymers, vol. 50, pp. 331-337 (2002).
Kochanek et al. "Karrikins Identified in Biochars Indicate Post-Fire Chemical Cues Can Influence Community Diversity and Plant Development" PLOS One, DOI:10.1371/journal.pone.0161234, pp. 1-19, Aug. 18, 2016.
Kolton, et al.; Impact of Biochar Application to Soil on the Root-Associated Bacterial Community Structure of Fully Developed Greenhouse Pepper Plants; Appl. Env. Micro, Jul. 2011, p. 4924-4930.
Laird, D., "The Charcoal Vision: A Win Win Scenario," Agron, J., vol. 100, No. 1, pp. 178-181 (2008).
Lashari, et al., "Effect of Amendment of Biochar-manure Compost in Conjunction with Pyroligneous Solution on Soil Quality and Wheat Yield of a salt-stresed Cropland from Central China Great Plain," Field Crops Research, vol. 144, pp. 113-118 (Mar. 20, 2013).
Lehmann, J., "Nutrient Avail. & Leaching in an Archaeological Anthrosol & Ferraisol of the Central Amazon Basin: Fertilizer, Manure and Charcoal Amendments," Plant Soil, vol. 249, pp. 343-357 (2003).
Lima, et al., "Physiochemical and Adsorption Properties of Fast-Pyrolysis Bio-Chars and their Steam Activated Counterparts," J.Chem. Tech. Biotechnical, vol. 85, pp. 1515-1521 (2010).
Liu, et al., "An Experimental Study of Rheological Properties and Stability Characteristics of Biochar-Glycerol-Water Slurry Fuels," Fuel Processing Technology, vol. 153, Issue 1. pp. 37-42 (Aug. 5, 2016).
Lou et al. "Water extract from straw biochar used for plant growth promotion: An initial test," BioRes. 11(1), 249-266 (2016).
Mathews, J.A., "Carbon-negative Biofuels", Energy Policy, vol. 36, pp. 940-945 (2008).
McHenry, Mark P., "Agricultural Bio-char Production, Renewable Energy Generation and Farm Carbon Sequestration in Western Australia: Certainty, Uncertainty and Risk," Agriculature, Ecosystems and Environments, vol. 129, pp. 1-7 (2009).
Mohan, et al., "Pyrolysis of Wood/Biomass for Bio-Oil: A Critical Review," Energy & Fuels, vol. 20, pp. 848-889 (2006).
Norman, et al.; "Best Management Practices for Reclaiming Surface Mines in Washington and Oregon," Open-File Report 0-92-2, revised ed. Dec. 1997; www.oregongeology.org Feb. 9, 2010 (128 pgs.).
Ogawa et al "Carbon sequestration by carbonization of biomass and forestation: Three case studies" Mitigation and Adaptation Strategies for Global Change vol. 11, pp. 429-444 (2006).
Oh, et al.; Utilization of biochar impregnated with anaerobically digested slurry as slow-release fertilizer; Journal of Plant Nutrition and Soil Science; vol. 177; Issue 1; Feb. 2014; pp. 97-103.
Omata, et al., "Optimization of Cu Oxide Catalyst for Methanol Synthesis under High CO2 Partial Pressure Using Combinatorial Tools," App. Catalyst A: General, vol. 262, pp. 207-214 (2004).
Preston, C.M. and Schmidt, M.W., "Black (Pyrogenic) Carbon; a Synthesis of Current Knowledge & Uncertainties w/ Special Consideration of Boreal Regions," Biogeosciences, vol. 3, pp. 397-420 (2006).
Rosenberg, et al., "More on Commercial Carbon Resistors as Low Pressure Gauges," Intl. Jour of Impat. Eng., vol. 34, pp. 732-742 (2007).
Schmidt, et al.; Biochar and biochar-compost as soil amendments to a vineyard soil: Influences on plant growth, nutrient update, plant health and grape quality; Agriculture, Ecosystems and Environment; vol. 191, Issue 15; Jun. 2014; pp. 117-123.
Sharma, R.K. and Bakhshl, N.N., "Catalytic Upgrading of Pyrolysis Oil," Energy & Fuels, vol. 7, pp. 306-314 (1993).
Shivaram. et al., "Flow and Yield Behavior of Ultrafine Mallee Biochar Slurry Fuels: The Effect of Particle Size Distributon and Additives." 10th Japan/China Symposium on Coal and C1 Chemistry, vol. 104, pp. 326-332 (Feb. 2013).
Sorrenti; (Doctoral Thesis): Biochar in prerrennial crops: Nutritional, Agronomical and Environmental implications; University of Bologna; Mar. 1, 2015; Abstract; 121 pp.
Supplemental European Search Report dated Aug. 17, 2017 for EP 14875314.8.
Takeishi, K., "Dirnethy Ether & Catalyst Development for Production of Syngas," Biofuels, vol. 1(1), pp. 217-226 (2010).
Tryon, E.H.; "Effect of Charcoal on Certain Physical, Chemical, & Biological Properties of Forest Soils," Ecological Monographs, vol. 18, No. 1, pp. 81-115 (Jan. 1948).
Wikipedia; Bacillus Thuringiensis; Dec. 27, 2015; online, retrieved from the Internet on Mar. 6, 2017; ; 6 pp.
Xusheng, et al., "Implications of Production and Agricultural Utilization of Biochar and its International Dynamic," Transactions of the CSAE, vol. 27, No. 2, 7 pgs. (2011) with English Abstract.

* cited by examiner

- Actinovate blended with Peat at 1:12 v/v
- Inoculated media and incubate at 25°C
- White colonies after 3 days

- Actinovate blended with Treated Biochar at 1:12 v/v
- Inoculated media and incubate at 25°C
- White colonies after 3 days Biochar Pellets Biochar Extrudates Biochar + Sulfur Prills FIG. 40a
Direct Sieve
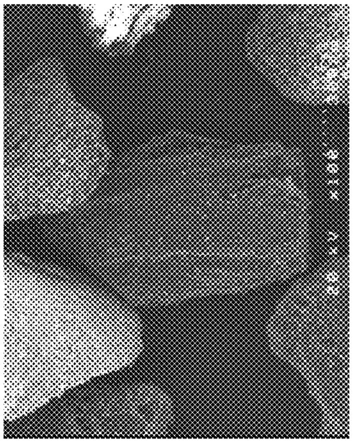
FIG. 40b
Medium grind
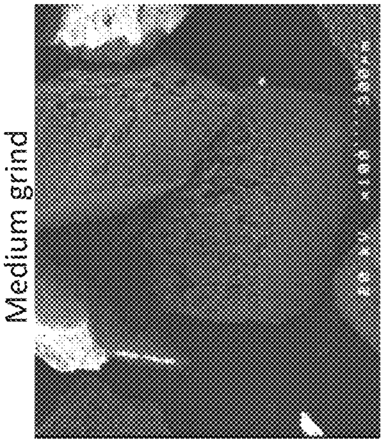
FIG. 40c
Fine Grind
FIG. 40d
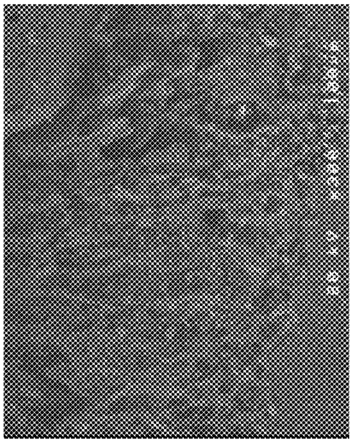
FIG. 40e
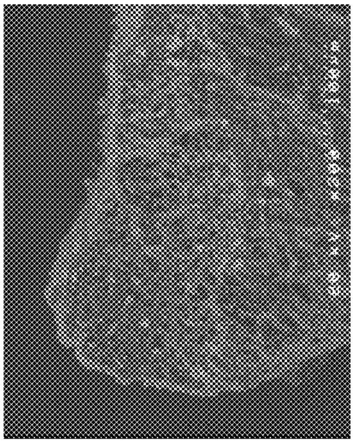
FIG. 40f

Figure X

TGA Results

Acetone Raw Biochar Extractions

Coconut Biochar #1 | Coconut Biochar #2 | Pine Biochar #1 | Pine Biochar #2 | Pine Biochar #3

Treatment extracts inorganics from biochar

Materials, procedures and experimental matrix

Biochars (BCs) used, extraction and impregnation procedures:

- VBC and BCN as "non-phytotoxic raw biochars," and PBC as "phytotoxic raw biochar"
- 100 mL of the raw BCs extracted 4-8 times with 100mL portions of DCN (until the extracts turn colorless)
- Dichloromethane (DCM) extracts distilled under vacuum, the extracted ROCs + a small residual DCM amounts vacuum impregnated in the corresponding clean BCs, the latter dried under vacuum and heating to remove all solvent experimental matrix "non-phytotoxic raw biochars" "phytotoxic raw biochars"

| VBC series | | | BCN series | | | BCN series | |
|---|---|---|---|---|---|---|---|
| Solid BC | Inoculant | | Solid BC | Inoculant | | Solid BC | Inoculant |
| VBC raw | none | | BCN raw | none | | PBC raw | none |
| VBC clean | none | | BCN clean | none | | PBC clean | none |
| VBC clean | pure DCM | | BCN clean | PBC extract | | PBC clean | VBC extract |
| VBC clean | PBC extract | | | | | PBC clean | BCN extract |

- Each sample seeded with 20 Cress and 20 Radish seeds (our "standard" toxicology tests)
- Germination counted 2.5 days after seeding

FIG. 68A

VBC series-results

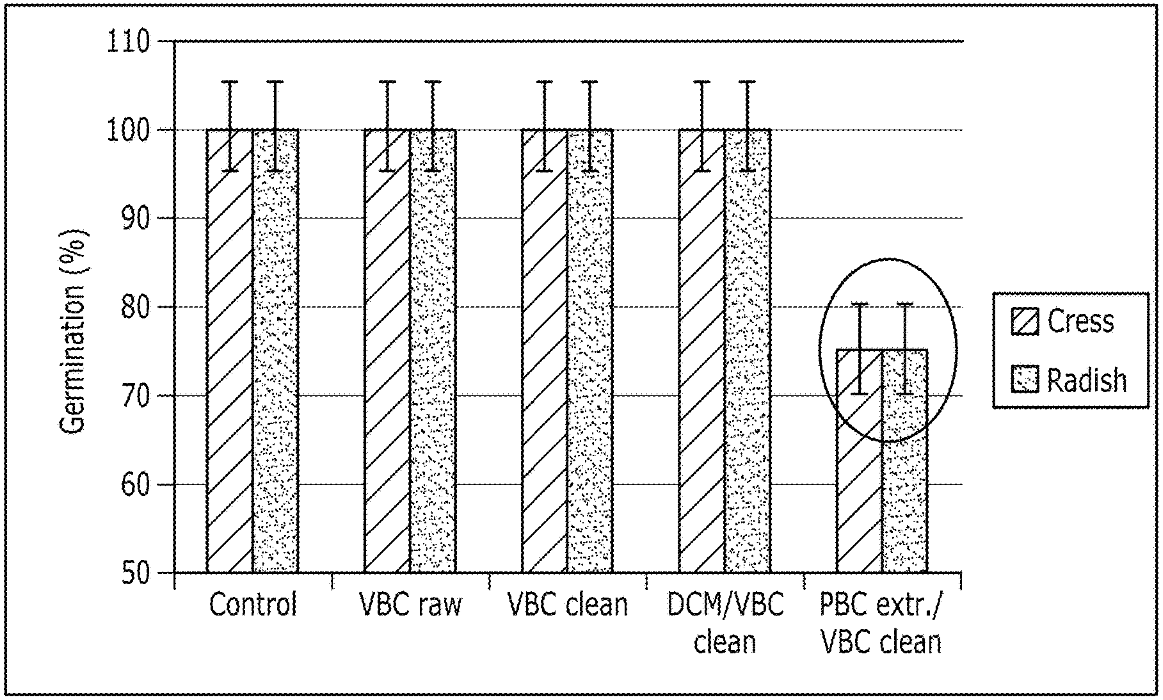

Summary: impregnation of a "non-phytotoxic biochar" with ROCs extracted from a "phytotoxic biochar" leads to phytotoxic results (reduced germination)

Legend:
Control=tested VBC (Cress) and perlite (Radish)
VBC raw=raw biochar
VBC clean=VBC after DCM organics extraction and drying
DCM/VBC clean=clean VBC re-impregnated with pure DCM (0.2 mL DCM/10 ml BC)
PBC extr. /VBC clean=clean VBC impregnated with PBC extract and dried (0.2 ml extr. / 10 ml BC)

FIG. 68C

BCN series-results

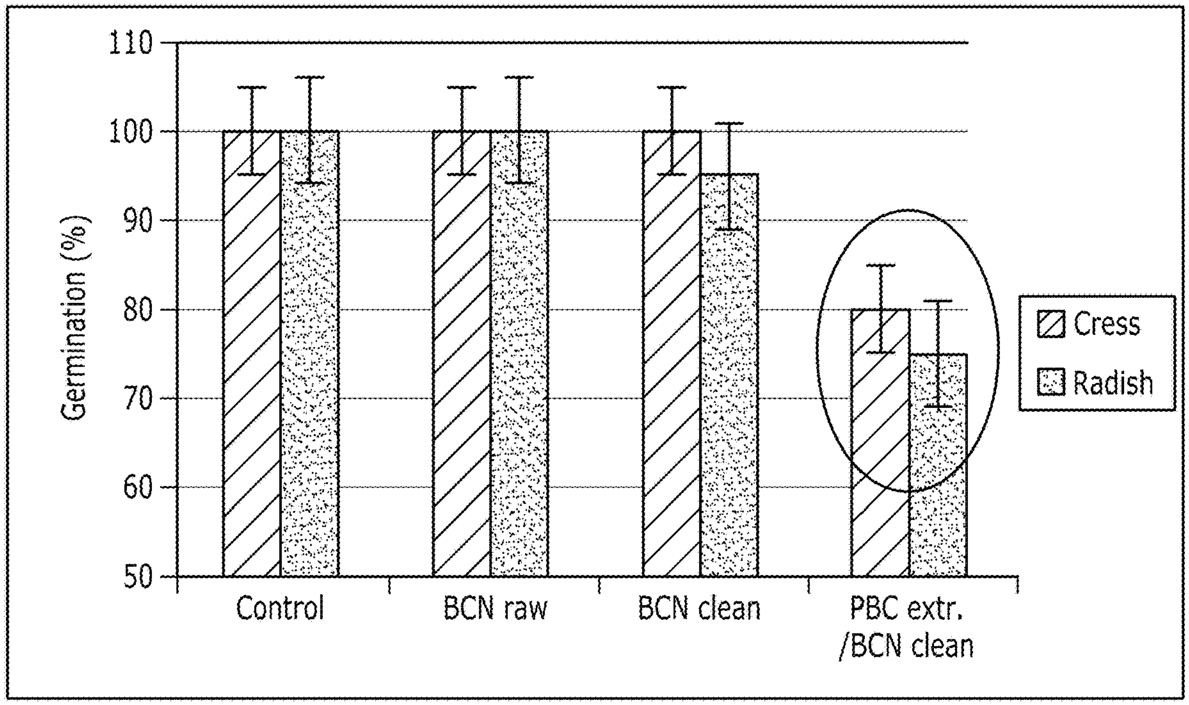

<u>Summary:</u> impregnation of a "non-phytotoxic biochar" with ROCs extracted from a "phytotoxic biochar" leads to phytotoxic results (reduced germination)

<u>Legend:</u>
Control=tested VBC (Cress) and perlite (Radish)
BCN raw=raw biochar
BCN clean=BCN after DCM organics extraction and drying
PBC extr./BCN clean=clean BCN impregnated with PBC extract and dried (0.2 mL extr./10 ml BC)

FIG. 68D

PBC series-results

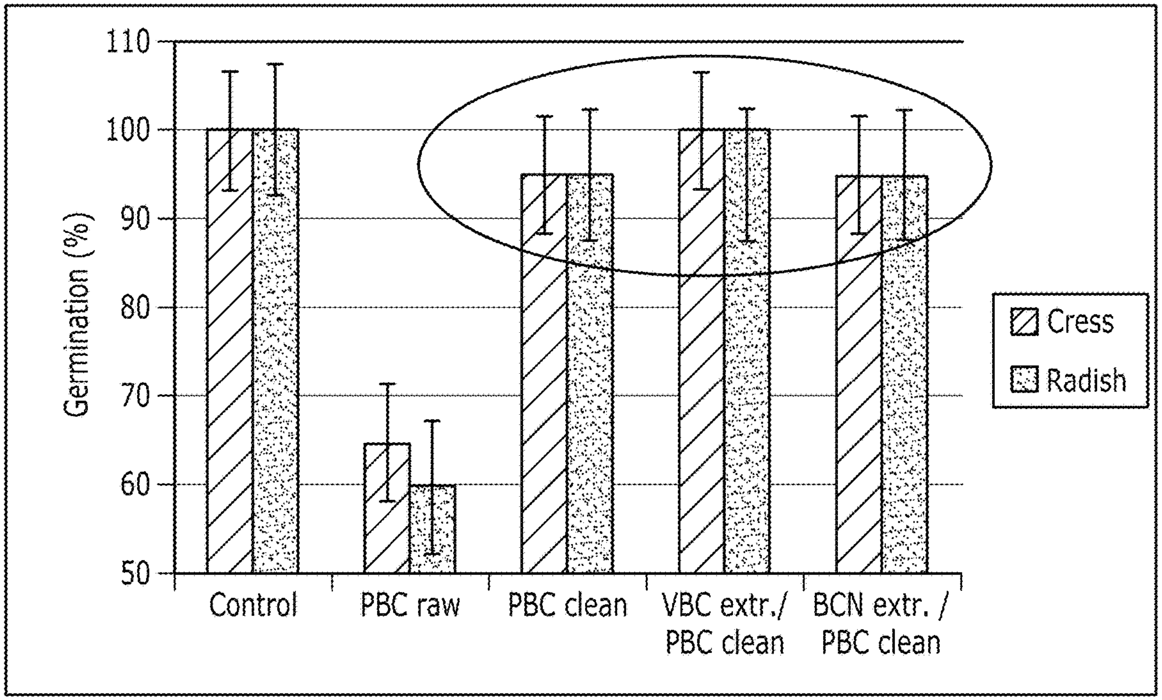

Summary: DCM extraction of a "phytotoxic biochar" leads to a biochar with better germination (less phototoxicity)

Legend:
Control=tested VBC (Cress) and perlite (Radish)
PBC raw=raw biochar
PBC clean=PBC after DCM organics extraction and drying
VBC extr./PPC clean=clean PBC impregnated with VBC extract and dried (0.2 mL DCM/10 ml BC)
BCN extr./PBC clean=clean PBC impregnated with VBC extract and dried (0.2 mL DCM/10 ml BC)

FIG. 68E

Most likely

| | Water | TBC-1 | TBC-4 | TBC-5 | TBC-6 | 10 ppb | 1 ppb | 0.5 ppb | 0.05 ppb | 0.005 ppb |
|---|---|---|---|---|---|---|---|---|---|---|
| M-206 | 16.67 | 40.00 | 16.67 | 13.33 | 26.67 | 33.33 | 36.67 | 43.33 | 40.00 | 50.00 |
| M-401 | 53.33 | 60.00 | 50.00 | 50.00 | 70.00 | 56.67 | 76.67 | 80.00 | 66.67 | 76.67 |

| | Water | TBC-1 | TBC-4 | TBC-5 | TBC-6 | 10 ppb | 1 ppb | 0.5 ppb | 0.05 ppb | 0.005 ppb |
|---|---|---|---|---|---|---|---|---|---|---|
| M-206 | 16.67 | 30.00 | 23.33 | 13.33 | 50.00 | 43.33 | 53.33 | 50.00 | 26.67 | 50.00 |
| M-401 | 66.67 | 56.67 | 56.67 | 63.33 | 66.67 | 63.33 | 80.00 | 80.00 | 76.67 | 80.00 |

The diluted centrifuge and filter press waste waters significantly increase percent coverage (p<0.05) and shoot biomass of tall fescue (p<0.0001). Flood irrigated The diluted centrifuge and filter press waste waters significantly increase percent coverage but did shoot biomass of tall fescue (p<.012). Top down irrigated The Filter Press waste water significantly increase turf biomass.

CONTROL OF PYROLYSIS CONDITIONS AND FEEDSTOCK FOR THE PRODUCTION OF DESIRABLE COMPOUNDS

CROSS-REFERENCE TO RELATED APPLICATIONS

This application is a continuation of U.S. patent application Ser. No. 17/231,948, filed on Apr. 15, 2021, titled Control of Pyrolysis Conditions and Feedstock for the Production of Desirable Compounds, which claims priority to U.S. Provisional Application Ser. No. 63/010,253, filed on Apr. 15, 2020, titled Control of Pyrolysis Conditions and Feedstock for the Production of Desirable Compounds, both applications of which are incorporated into this application by reference in their entirety.

FIELD OF INVENTION

The invention relates to the production of desired inorganic or organic compounds through controlled pyrolysis of selected biomass to create a biochar having high levels of desirable residual organic and inorganic compounds, particularly soluble signaling compounds and then extracting these residual organic and inorganic compounds from the biochar to produce a biochar extract with the desired compounds.

BACKGROUND

Biochar has been known for many years as a soil enhancer. It contains highly porous, high carbon content material similar to the type of very dark, fertile anthropogenic soil found in the Amazon Basin known as Terra Preta. Terra Preta has very high charcoal content and is made from a mixture of charcoal, bone, manure, among other substances. Biochar is created by the pyrolysis of biomass, which generally involves heating and/or burning of organic matter, in a reduced oxygen environment, at a predetermined rate. Such heating and/or burning is stopped when the matter reaches a charcoal like stage. The highly porous material of biochar is perfectly suited to host beneficial microbes, retain nutrients, hold water, and act as a delivery system for a range of beneficial compounds suited to specific applications.

Due to various factors, including but not limited to compounds added before, during or after pyrolysis, feedstock, pyrolysis method, pyrolysis conditions, post-pyrolysis storage, and post-pyrolysis treatment, biochars may contain significant or important residual compounds, many of which are organic. The amount and type of residual organic compounds will vary between biochars, but often include a mixture of fatty acids, aromatics, phenolics, and ketones. Similarly, inorganic compounds potentially containing plant macro- and micronutrients as well as other substances which may be beneficial to plants or microbial life may be present on or in the carbon matrix of the biochar. Being able to extract residual compounds can improve the biochar properties for various applications such as use in agriculture or animals, especially when the compounds are deleterious. In addition, extraction of residual compounds allows for the production of a mixture of residual compounds, to include a mixture of these compounds in solution, and preferably a method to collect specific residual compounds of interest or of use.

SUMMARY

The present invention relates to methods for extracting residual organic and inorganic compounds from biochar.

This method can be used for the purpose of reducing the remaining residual compounds in the biochar or for the purpose of collecting the extracted residual compounds in various forms.

The method includes ways to selectively extract certain compounds or certain groups of compounds. The method also includes ways to purify or concentrate the extracted organic and inorganic compounds into more useful products or mixtures. The invention also includes the resulting biochar extract itself and methods for its use and application.

For example, according to one example, the method for capturing material extracted from biochar may include (i) providing a biochar that includes soluble signaling compounds; (ii) contacting the biochar with an extraction media, wherein the extraction media removes at least some of the soluble signaling compounds from the biochar, thereby creating a biochar extract containing soluble signaling compounds and (ii) collecting the biochar extract.

The biochar extract, once collected, may be further processed to remove the majority of biochar particles or to concentrate the soluble signaling compounds. The biochar extract may be applied to seeds, soil, or plants or into a biochar. The soluble signaling compounds may include, for example, cyanohydrins, butenolides and/or karrikins, where the karrikin levels may exceed 10 ng/g. The extraction media used may be water or ethanol.

One extraction method may optimize the remaining level of soluble signaling compounds in the biochar and produce a biochar extract, where the biochar extract may, for example, extract karrikins. The biochar extraction may be further processed to concentrate the amount of extracted compounds in the extract and/or to remove deleterious substances. In some examples, the biochar extract may even be further treated with surfactant to improve the availability and effectiveness of the soluble signaling compounds.

The biochar used in the extraction method may be derived from a source of biomass that together with predefined pyrolysis parameters that produces a resulting biochar, for example, having karrikin levels that exceeds 10 ng/g, or in some cases, that exceeds 40 ng/g.

In some example, the biochar extract may include properties that improve seed germination and early plant development, may have karrikin levels that exceed 0.005 ppb, and/or have high levels of soluble signaling compounds that are known to increase seed germination rates and early plant growth. The biochar extract may include soluble signaling compounds that are, for example, cyanohydrins, butenolides, and/or karrikins. In some case, the level of karrikin in the biochar extract may exceed 1 ppt and/or exceed 0.005 ppb.

A further method is provided for applying biochar extract to seeds where the biochar extract is applied at rates of less than 10 oz/100 lb seeds. Yet another method is provided for applying biochar extract in-furrow to soil where the biochar extract is applied at rates of less than 25 oz/Acre.

Other devices, apparatus, systems, methods, features and advantages of the invention are or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention.

FIGS. 40*a-f* illustrates the effects of size and grinding on particle structure of a biochar derived from a second biomass.

FIG. 68*a-e* illustrate how phytotoxic biochar can become harmless and a harmless biochar can become phytotoxic when the residual organic compounds are extracted from each of the biochars and then reinfused into the other biochar.

DESCRIPTION OF THE INVENTION

Figure 1:
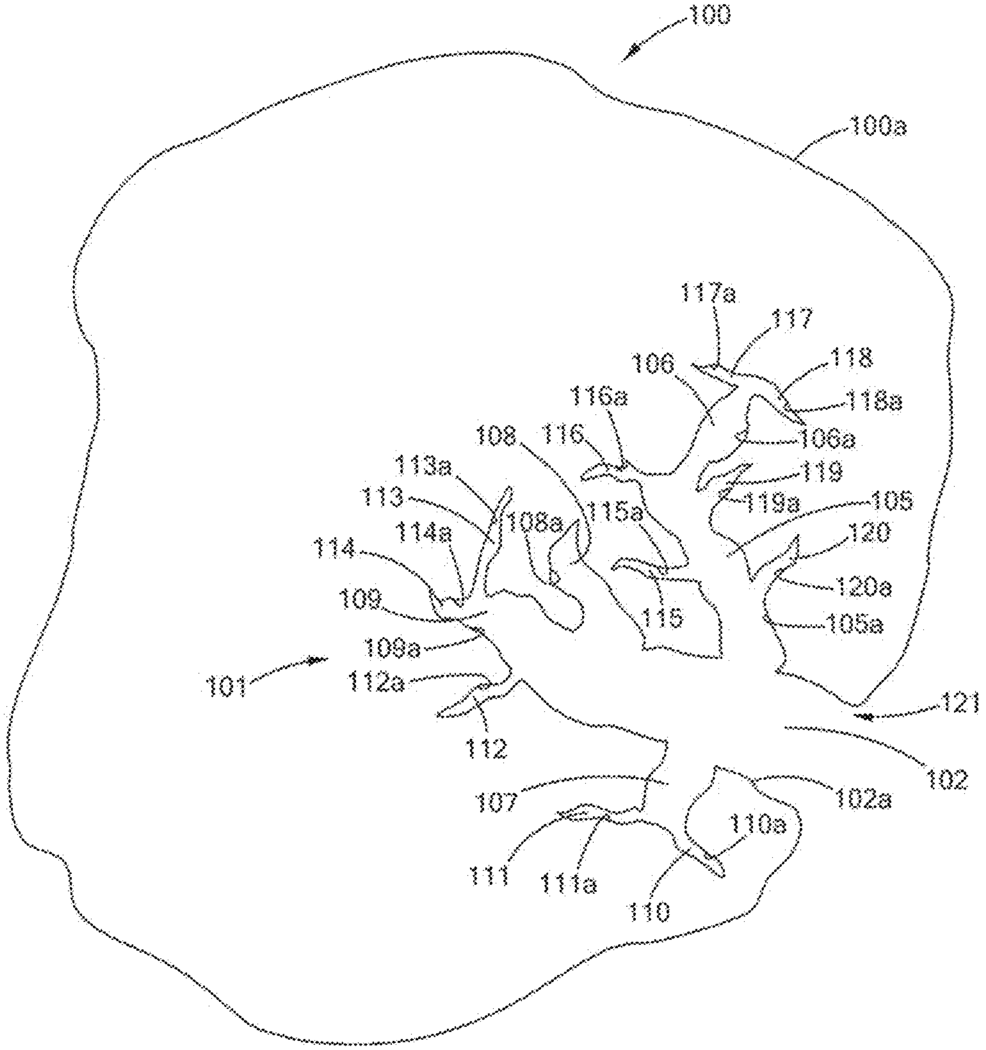
FIG. 1 illustrates a cross-section of one example of a raw biochar particle.

As illustrated in the attached figures, the present invention relates to a method for extracting compounds from biochar and capturing said extracted compounds. The resulting biochar and extracts can be used in industries, including but not limited to agriculture, animal health, human health, composting, and specialty chemicals.

For the purposes of this application, prior treatment of the raw biochar, as described below, is not required as part of an extraction process. However, treatment may be done prior to an extraction step, as part of an extraction method, or following an extraction step. This is because the properties of the raw biochar can be modified to significantly increase the biochar's ability to retain water and/or nutrients while also, in many cases, creating an environment beneficial to microorganisms. The processing of the biochar can also ensure that the pH of biochar used in the present application is suitable for its application, which has been a challenge for raw biochars. The properties of biochar may also be modified to allow for a more efficient release of certain compounds during the extraction process, or conversely the treatment may allow for the retention of certain compounds which are unwanted in the extracted product. In certain applications, the fines of treated biochars treatment prior to extraction can be used to adjust the extraction method's effectiveness or selectivity or improve the qualities of the resulting biochar. In other applications, treatment following extraction can be used to improve the properties of the biochar. It should also be noted that multiple extractions can be performed on the biochar, at different times, with zero to many different treatments applied to the biochar within the interval between extractions.

Biochars derived from different biomass or produced with differing parameters, such as higher or lower pyrolysis temperature or variations in residence time, will have different physical and chemical properties and can behave quite differently in different applications. For example, some chars will have a high amount of total residual organic compounds, while others will have relatively low levels. In addition, some biochars will have different types of residual organic compounds or different ratios of similar residual organic compounds. Additionally, in some biochars, these compounds, even if present in the same amounts, may be better suited for extraction than in other biochars. Depending on the application for the biochar product or the application for the biochar extract, the differences in the starting biochar properties will make certain biochars a better fit for using certain extraction methods over others.

Currently biochar has mostly been a scientific curiosity, not found in wide spread use or large scale commercial applications, and instead has been relegated to small niche applications. It is, however, known, that biochar, having certain characteristics can host beneficial microbes, retain nutrients and supplements, hold liquids for agricultural applications. Accordingly, these same characteristics of biochar can be harnessed for other application such as composting, remediation, or animal maintenance, care and feeding.

For purposes of this application, the term "biochar" shall be given its broadest possible meaning and shall include any solid carbonaceous materials obtained from the pyrolysis, torrefaction, gasification or any other thermal and/or chemical conversion of a biomass. For purposes of this application, the solid carbonaceous material may include, but not be limited to, BMF char disclosed and taught by U.S. Pat. No. 8,317,891, which is incorporated into this application by reference. Pyrolysis is generally defined as a thermochemical decomposition of organic material at elevated temperatures in the absence of, or with reduced levels of oxygen. When the biochar is referred to as "treated" or undergoes "treatment," it shall mean raw, pyrolyzed biochar that has undergone additional physical, biological, and/or chemical processing.

As used herein, unless specified otherwise, the terms "carbonaceous", "carbon based", "carbon containing", and similar such terms are to be given their broadest possible meaning, and would include materials containing carbon in various states, crystallinities, forms and compounds.

As used herein, unless stated otherwise, room temperature is 25° C. And, standard temperature and pressure is 25° C. and 1 atmosphere. Unless stated otherwise, generally, the term "about" is meant to encompass a variance or range of ±10%, the experimental or instrument error associated with obtaining the stated value, and preferably the larger of these.

A. Biochars

Typically, biochars include porous carbonaceous materials, such as charcoal, that are used as soil amendments or other suitable applications. Biochar most commonly is created by pyrolysis of a biomass. In addition to the benefits to plant growth, yield and quality, etc.; biochar provides the benefit of reducing carbon dioxide ($CO_2$) in the atmosphere by serving as a method of carbon sequestration. Thus, biochar has the potential to help mitigate climate change, via carbon sequestration. However, to accomplish this important, yet ancillary benefit, to any meaningful extent, the use of biochar in agricultural applications must become widely accepted, e.g., ubiquitous. Unfortunately, because of the prior failings in the biochar arts, this has not occurred. It is believed that with the solutions of the present invention may this level of use of biochar be achieved; and more importantly, yet heretofore unobtainable, realize the benefit of significant carbon dioxide sequestration.

In general, one advantage of putting biochar in soil includes long term carbon sequestration. It is theorized that as worldwide carbon dioxide emissions continue to mount, benefits may be obtained by, controlling, mitigating and reducing the amount of carbon dioxide in the atmosphere and the oceans. It is further theorized that increased carbon dioxide emissions are associated with the increasing industrial development of developing nations, and are also associated with the increase in the world's population. In addition to requiring more energy, the increasing world population will require more food. Thus, rising carbon dioxide emissions can be viewed as linked to the increasing use of natural resources by an ever increasing global population. As some suggest, this larger population brings with it further demands on food production requirements. Biochar uniquely addresses both of these issues by providing an effective carbon sink, e.g., carbon sequestration agent, as well as, an agent for improving and increasing agricultural output. In particular, biochar is unique in its ability to increase agricultural production, without increasing carbon dioxide emission, and preferably reducing the amount of carbon dioxide in the atmosphere. However, as discussed above, this unique ability of biochar has not been realized, or seen, because of the inherent problems and failings of prior biochars including, for example, high pH, phytotoxicity due to high metals content and/or residual organics, and dramatic product inconsistencies.

Biochar can be made from basically any source of carbon, for example, from hydrocarbons (e.g., petroleum based materials, coal, lignite, peat) and from a biomass (e.g., woods, hardwoods, softwoods, waste paper, coconut shell, manure, chaff, food waste, etc.). Combinations and variations of these starting materials, and various and different members of each group of starting materials can be, and are, used. Thus, the large number of vastly different starting materials leads to biochars having different properties.

Many different pyrolysis or carbonization processes can be, and are used, to create biochars. In general, these processes involve heating the starting material under positive pressure, reduced pressure, vacuum, inert atmosphere, or flowing inert atmosphere, through one or more heating cycles where the temperature of the material is generally brought above about 400° C., and can range from about 300° C. to about 900° C. The percentage of residual carbon formed and several other initial properties are strong functions of the temperature and time history of the heating cycles. In general, the faster the heating rate and the higher the final temperature the lower the char yield. Conversely, in general, the slower the heating rate or the lower the final temperature the greater the char yield. The higher final temperatures also lead to modifying the char properties by changing the inorganic mineral matter compositions, which in turn, modify the char properties. Ramp, or heating rates, hold times, cooling profiles, pressures, flow rates, and type of atmosphere can all be controlled, and typically are different from one biochar supplier to the next. These differences potentially lead to a biochar having different properties, further framing the substantial nature of one of the problems that the present inventions address and solve. Generally, in carbonization most of the non-carbon elements, hydrogen and oxygen are first removed in gaseous form by the pyrolytic decomposition of the starting materials, e.g., the biomass. The free carbon atoms group or arrange into crystallographic formations known as elementary graphite crystallites. Typically, at this point the mutual arrangement of the crystallite is irregular, so that free interstices exist between them. Thus, pyrolysis involves thermal decomposition of carbonaceous material, e.g., the biomass, eliminating non-carbon species, and producing a fixed carbon structure.

As noted above, raw or untreated biochar is generally produced by subjecting biomass to either a uniform or varying pyrolysis temperature (e.g., 300° C. to 550° C. to 750° C. or more) for a prescribed period of time in a reduced oxygen environment. This process may either occur quickly, with high reactor temperature and short residence times, slowly with lower reactor temperatures and longer residence times, or anywhere in between. To achieve better results, the biomass from which the char is obtained may be first stripped of debris, such as bark, leaves and small branches, although this is not necessary. The biomass may further include feedstock to help adjust the pH and particle size distribution in the resulting raw biochar. In some applications, it is desirous to have biomass that is fresh, less than six months old, and with an ash content of less than 3%. Further, by using biochar derived from different biomass, e.g., pine, oak, hickory, birch and coconut shells from different regions, and understanding the starting properties of the raw biochar, the treatment methods can be tailored to ultimately yield a treated biochar with predetermined, predictable physical and chemical properties.

In general, biochar particles can have a very wide variety of particle sizes and distributions, usually reflecting the sizes occurring in the input biomass. Additionally, biochar can be ground or crushed after pyrolysis to further modify the particle sizes. Typically, for agricultural uses, biochars with consistent, predictable particle sizes are more desirable. By way of example, the biochar particles can have particle sizes as shown or measured in Table 1 below. When referring to a batch having ¼ inch particles, the batch would have particles that will pass through a 3 mesh sieve, but will not pass through (i.e., are caught by or sit atop) a 4 mesh sieve.

TABLE 1

| U.S. Mesh (i.e., mesh) | Inches | Microns (μm) | Millimeters (mm) |
|---|---|---|---|
| 3 | 0.2650 | 6730 | 6.370 |
| 4 | 0.1870 | 4760 | 4.760 |
| 5 | 0.1570 | 4000 | 4.000 |
| 6 | 0.1320 | 3360 | 3.360 |
| 7 | 0.1110 | 2830 | 2.830 |
| 8 | 0.0937 | 2380 | 2.380 |
| 10 | 0.0787 | 2000 | 2.000 |
| 12 | 0.0661 | 1680 | 1.680 |
| 14 | 0.0555 | 1410 | 1.410 |
| 16 | 0.0469 | 1190 | 1.190 |
| 18 | 0.0394 | 1000 | 1.000 |
| 20 | 0.0331 | 841 | 0.841 |
| 25 | 0.0280 | 707 | 0.707 |
| 30 | 0.0232 | 595 | 0.595 |
| 35 | 0.0197 | 500 | 0.500 |
| 40 | 0.0165 | 400 | 0.400 |
| 45 | 0.0138 | 354 | 0.354 |
| 50 | 0.0117 | 297 | 0.297 |
| 60 | 0.0098 | 250 | 0.250 |
| 70 | 0.0083 | 210 | 0.210 |
| 80 | 0.0070 | 177 | 0.177 |
| 100 | 0.0059 | 149 | 0.149 |
| 120 | 0.0049 | 125 | 0.125 |
| 140 | 0.0041 | 105 | 0.105 |
| 170 | 0.0035 | 88 | 0.088 |
| 200 | 0.0029 | 74 | 0.074 |
| 230 | 0.0024 | 63 | 0.063 |
| 270 | 0.0021 | 53 | 0.053 |
| 325 | 0.0017 | 44 | 0.044 |
| 400 | 0.0015 | 37 | 0.037 |

For most applications, it is desirable to use biochar particles having particle sizes from about 3/4 mesh to about 60/70 mesh, about 4/5 mesh to about 20/25 mesh, or about 4/5 mesh to about 30/35 mesh. It being understood that the desired mesh size, and mesh size distribution can vary depending upon a particular application for which the biochar is intended.

FIG. 1 illustrates a cross-section of one example of a raw biochar particle. As illustrated in FIG. 1, a biochar particle 100 is a porous structure that has an outer surface **100*a* and a pore structure 101 formed within the biochar particle 100**. As used herein, unless specified otherwise, the terms "porosity", "porous", "porous structure", and "porous morphology" and similar such terms are to be given their broadest possible meaning, and would include materials having open pores, closed pores, and combinations of open and closed pores, and would also include macropores, mesopores, and micropores and combinations, variations and continuums of these morphologies. Unless specified otherwise, the term "pore volume" is the total volume occupied by the pores in a particle or collection of particles; the term "inter-particle void volume" is the volume that exists between a collection of particle; the term "solid volume or volume of solid means" is the volume occupied by the solid material and does not include any free volume that may be associated with the pore or inter-particle void volumes; and the term "bulk volume" is the apparent volume of the material including the particle volume, the inter-particle void volume, and the internal pore volume.

The pore structure 101 forms an opening 121 in the outer surface 100*a* of the biochar particle 100. The pore structure 101 has a macropore 102, which has a macropore surface 102*a*, and which surface 102*a* has an area, i.e., the macropore surface area. (In this diagram only a single micropore is shown. If multiple micropores are present than the sum of their surface areas would equal the total macropore surface area for the biochar particle.) From the macropore 102, several mesopores 105, 106, 107, 108 and 109 are present, each having its respective surfaces 105*a*, 106*a*, 107*a*, 108*a* and 109*a*. Thus, each mesopore has its respective surface area; and the sum of all mesopore surface areas would be the total mesopore surface area for the particle. From the mesopores, e.g., 107, there are several micropores 110, 111, 112, 113, 114, 115, 116, 117, 118, 119 and 120, each having its respective surfaces 110*a*, 111*a*, 112*a*, 113*a*, 114*a*, 115*a*, 116*a*, 117*a*, 118*a*, 119*a* and 120*a*. Thus, each micropore has its respective surface area and the sum of all micropore surface areas would be the total micropore surface area for the particle. The sum of the macropore surface area, the mesopore surface area and the micropore surface area would be the total pore surface area for the particle.

Macropores are typically defined as pores having a diameter greater than 300 nm, mesopores are typically defined as diameter from about 1-300 nm, and micropores are typically defined as diameter of less than about 1 nm, and combinations, variations and continuums of these morphologies. The macropores each have a macropore volume, and the sum of these volumes would be the total macropore volume. The mesopores each have a mesopore volume, and the sum of these volumes would be the total mesopore volume. The micropores each have a micropore volume, and the sum of these volumes would be the total micropore volume. The sum of the macropore volume, the mesopore volume and the micropore volume would be the total pore volume for the particle.

Additionally, the total pore surface area, volume, mesopore volume, etc., for a batch of biochar would be the actual, estimated, and preferably calculated sum of all of the individual properties for each biochar particle in the batch.

It should be understood that the pore morphology in a biochar particle may have several of the pore structures shown, it may have mesopores opening to the particle surface, it may have micropores opening to particle surface, it may have micropores opening to macropore surfaces, or other combinations or variations of interrelationship and structure between the pores. It should further be understood that the pore morphology may be a continuum, where moving inwardly along the pore from the surface of the particle, the pore transitions, e.g., its diameter becomes smaller, from a macropore, to a mesopore, to a micropore, e.g., macropore 102 to mesopore 109 to micropore 114.

In general, the biochars have porosities that can range from 0.2 $cm^3/cm^3$ to about 0.8 $cm^3/cm^3$ and more preferably about 0.2 $cm^3/cm^3$ to about 0.5 $cm^3/cm^3$. (Unless stated otherwise, porosity is provided as the ratio of the total pore volumes (the sum of the micro+meso+macro pore volumes) to the solid volume of the biochar. Porosity of the biochar particles can be determined, or measured, by measuring the micro-, meso-, and macro pore volumes, the bulk volume, and the inter particle volumes to determine the solid volume by difference. The porosity is then calculated from the total pore volume and the solid volume.

Figure 2C:
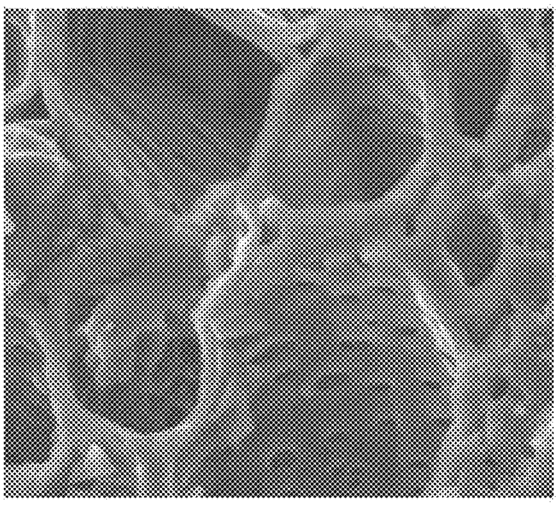
FIG. 2*c* is a SEM (10 KV×3.00K 10.0 μm) of pore morphology of treated biochar made from coconut shells.
Figure 2B:
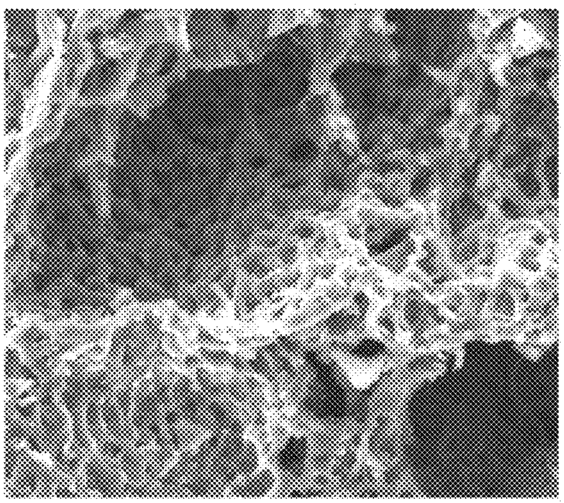
FIG. 2*b* is a SEM (10 KV×3.00K 10.0 μm) of pore morphology of treated biochar made from birch.
Figure 2A:
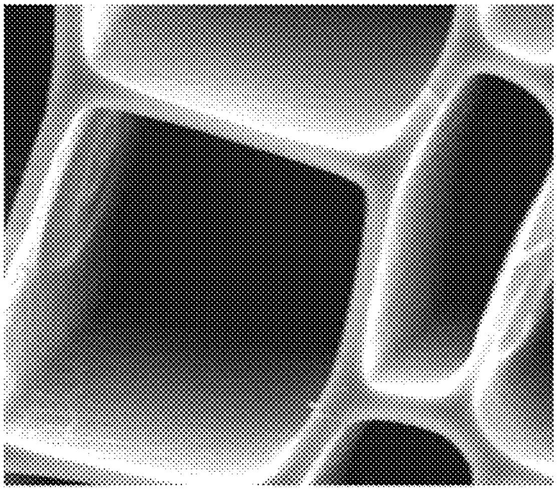
FIG. 2*a* is a SEM (10 KV×3.00K 10.0 μm) of pore morphology of treated biochar made from pine.

As noted above, the use of different biomass potentially leads to biochars having different properties, including, but not limited to different pore structures. By way of example, FIGS. 2A, 2B and 2C illustrate Scanning Electron Microscope ("SEM") images of various types of treated biochars showing the different nature of their pore morphology. FIG. 2A is biochar derived from pine. FIG. 2B is biochar derived from birch. FIG. 2C is biochar derived from coconut shells.

The surface area and pore volume for each type of pore, e.g., macro-, meso- and micro- can be determined by direct measurement using $CO_2$ adsorption for micro-, $N_2$ adsorption for meso- and macro pores and standard analytical surface area analyzers and methods, for example, particle analyzers such as Micrometrics instruments for meso- and micro pores and impregnation capacity for macro pore volume. Mercury porosimetry, which measures the macroporosity by applying pressure to a sample immersed in mercury at a pressure calibrated for the minimum pore diameter to be measured, may also be used to measure pore volume.

Figure 3:
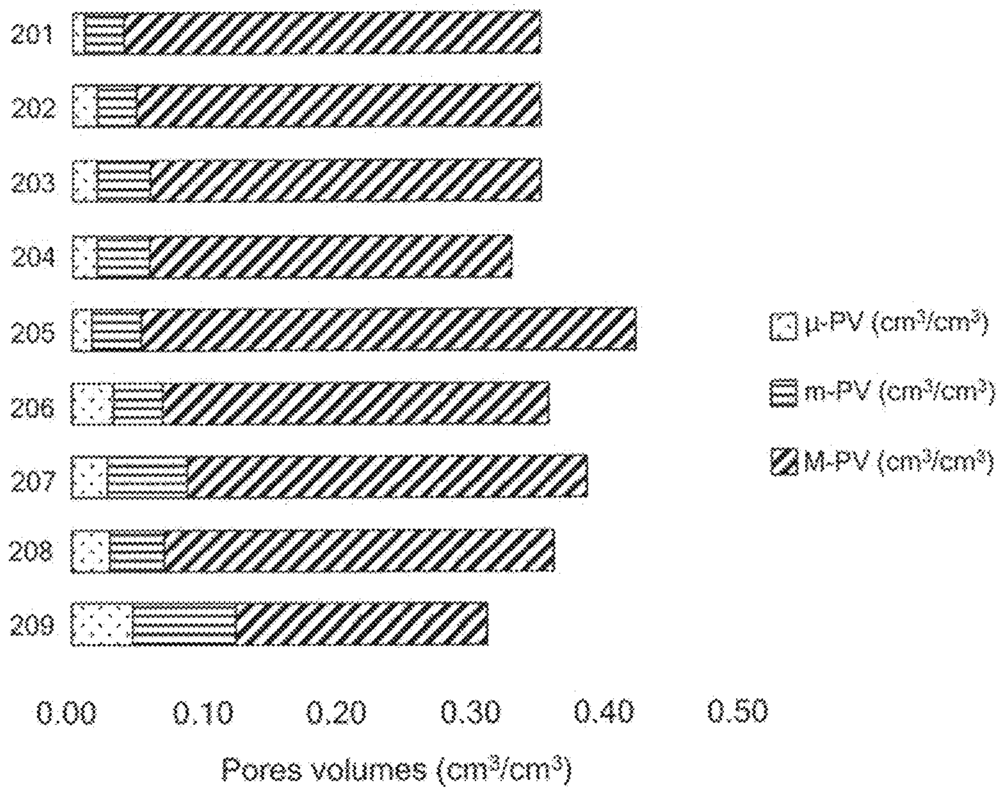
FIG. 3 is a chart showing porosity distribution of various biochars.

The total micropore volume can be from about 2% to about 25% of the total pore volume. The total mesopore volume can be from about 4% to about 35% of the total pore volume. The total macropore volume can be from about 40% to about 95% of the total pore volume. By way of example, FIG. 3 shows a bar chart setting out examples of the pore volumes for sample biochars made from peach pits 201, juniper wood 202, a first hard wood 203, a second hard wood 204, fir and pine waste wood 205, a first pine 206, a second pine 207, birch 208 and coconut shells 209.

As explained further below, treatment can increase usable pore volumes and, among other things, remove obstructions in the pores, which leads to increased retention properties and promotes further performance characteristics of the biochar. Knowing the properties of the starting raw biochar, one can treat the biochar to produce controlled, predictable and optimal resulting physical and chemical properties.

B. Treatment

The rationale for treating the biochar after pyrolysis is that given the large pore volume and large surface are of the biochars, it is most efficient to make significant changes in the physical and chemical properties of the biochar by treating both the internal and external surfaces and internal pore volume of the char. Testing has demonstrated that if the biochar is treated, at least partially, in a manner that causes the forced infusion and/or diffusion of liquids into and/or out of the biochar pores (through mechanical, physical, or chemical means), certain properties of the biochar can be altered or improved over and above simply contacting these liquids with the biochar. By knowing the properties of the raw biochar and the optimal desired properties of the treated biochar, the raw biochar can then be treated in a manner that results in the treated biochar having controlled optimized properties.

For purposes of this application, treating and/or washing the biochar in accordance with the present invention involves more than a simple wash or soak, which generally only impacts the exterior surfaces and a small percentage of the interior surface area. "Washing" or "treating" in accordance with the present invention, and as used below, involves treatment of the biochar in a manner that causes the forced, accelerated or assisted infusion and/or diffusion of liquids and/or additivities into and/or out of the biochar pores (through mechanical, physical, or chemical means) such that certain properties of the biochar can be altered or improved over and above simply contacting these liquids with the biochar or so that treatment becomes more efficient or rapid from a time standpoint over simple contact or immersion.

In particular, effective treatment processes can mitigate deleterious pore surface properties, remove undesirable substances from pore surfaces or volume, and impact anywhere from between 10% to 99% or more of pore surface area of a biochar particle. By modifying the usable pore surfaces through treatment and removing deleterious substances from the pore volume, the treated biochars can exhibit a greater capacity to retain water and/or other nutrients as well as being more suitable habitats for some forms of microbial life. Through the use of treated biochars, agricultural applications can realize increased moisture control, increased nutrient retention, reduced water usage, reduced water requirements, reduced runoff or leaching, increased nutrient efficiency, reduced nutrient usage, increased yields, increased yields with lower water requirements and/or nutrient requirements, increases in beneficial microbial life, improved performance and/or shelf life for inoculated bacteria, and any combination and variation of these and other benefits.

Treatment further allows the biochar to be modified to possess certain known properties that enhance the benefits received from the use of biochar. While the selection of feedstock, raw biochar and/or pyrolysis conditions under which the biochar was manufactured can make treatment processes less cumbersome, more efficient and further controlled, treatment processes can be utilized that provide for the biochar to have desired and generally sustainable resulting properties regardless of the biochar source or pyrolysis conditions. As explained further below, treatment can (i) repurpose problematic biochars, (ii) handle changing biochar material sources, e.g., seasonal and regional changes in the source of biomass, (iii) provide for custom features and functions of biochar for particular soils, regions or agricultural purposes; (iv) increase the retention properties of biochar, (v) provide for large volumes of biochar having desired and predictable properties, (vi) provide for biochar having custom properties, (vii) handle differences in biochar caused by variations in pyrolysis conditions or manufacturing of the "raw" biochar; and (viii) address the majority, if not all, of the problems that have, prior to the present invention, stifled the large scale adoption and use of biochars.

Treatment can wash both the interior and exterior pore surfaces, remove harmful chemicals, introduce beneficial substances, and alter certain properties of the biochar and the pore surfaces and volumes. This is in stark contrast to simple washing which generally only impacts the exterior surfaces and a small percentage of the interior surface area. Treatment can further be used to coat substantially all of the biochar pore surfaces with a surface modifying agent or impregnate the pore volume with additives or treatment to provide a predetermined feature to the biochar, e.g., surface charge and charge density, surface species and distribution, targeted nutrient addition, magnetic modifications, root growth facilitator, and water absorptivity and water retention properties. Just as importantly, treatment can also be used to remove undesirable substances from the biochar, such as dioxins or other toxins either through physical removal or through chemical reactions causing neutralization.

Figure 4:
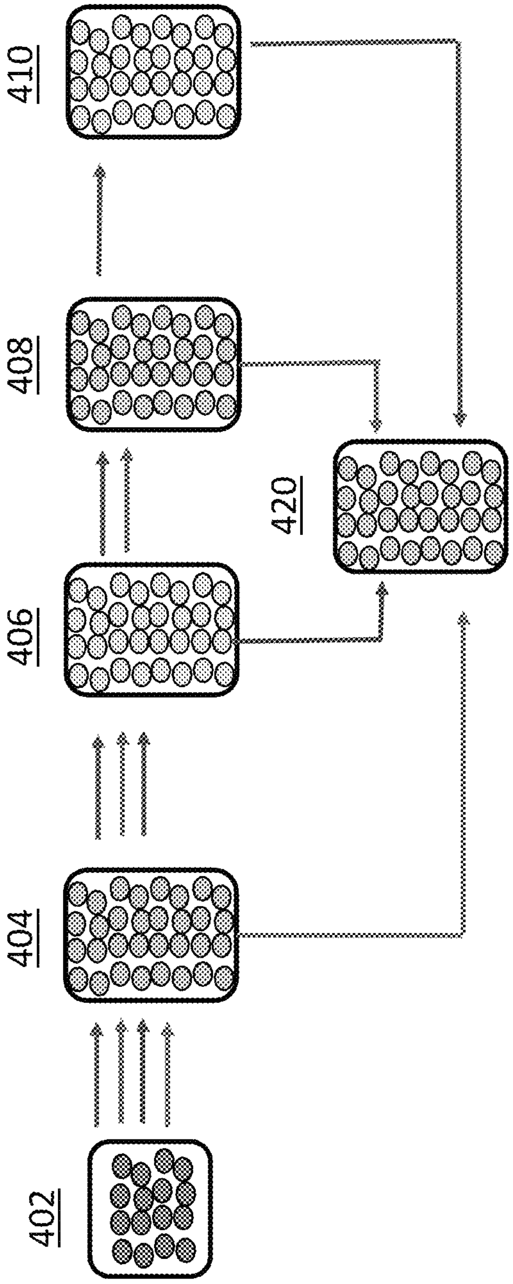
FIG. 4 is a flow chart process diagram of one implementation of a process for treating the raw biochar in accordance with the invention.

FIG. 4 is a schematic flow diagram of one example treatment process 400 for use in accordance with the present invention. As illustrated, the treatment process 400 starts with raw biochar 402 that may be subjected to one or more reactors or treatment processes prior to bagging 420 the treated biochar for resale. For example, 404 represents reactor 1, which may be used to treat the biochar. The treatment may be a simple water wash or may be an acid wash used for the purpose of altering the pH of the raw biochar particles 402. The treatment may also contain a surfactant or detergent to aid the penetration of the treatment solution into the pores of the biochar. The treatment may optionally be heated, cooled, or may be used at ambient temperature or any combination of the three. For some applications, depending upon the properties of the raw biochar, a water and/or acid/alkaline wash 404 (the latter for pH adjustment) may be the only necessary treatment prior to bagging the biochar 420. If, however, the moisture content of the biochar needs to be adjusted, the treated biochar may then be put into a second reactor 406 for purposes of reducing the moisture content in the washed biochar. From there, the treated and moisture adjusted biochar may be bagged 420.

Again, depending upon the starting characteristics of the raw biochar and the intended application for the resale product, further processing may still be needed or desired. In this case, the treated moisture adjusted biochar may then be passed to a third reactor 408 for inoculation, which may include the impregnation of biochar with beneficial additives, such as nutrients, bacteria, microbes, fertilizers or other additives. Thereafter, the inoculated biochar may be bagged 420, or may be yet further processed, for example, in a fourth reactor 410 to have further moisture removed from or added to the biochar. Further moisture adjustment may be accomplished by placing the inoculated biochar in a fourth moisture adjustment reactor 410 or circulating the biochar back to a previous moisture adjustment reactor (e.g. reactor 406). Those skilled in the art will recognize that the ordering in which the raw biochar is processed and certain processes may be left out, depending on the properties of the starting raw biochar and the desired application for the biochar. For example, the treatment and inoculation processes may be performed without the moisture adjustment step, inoculation processes may also be performed with or without any treatment, pH adjustment or any moisture adjustment. All the processes may be completed alone or in the conjunction with one or more of the others.

Figure 4A:
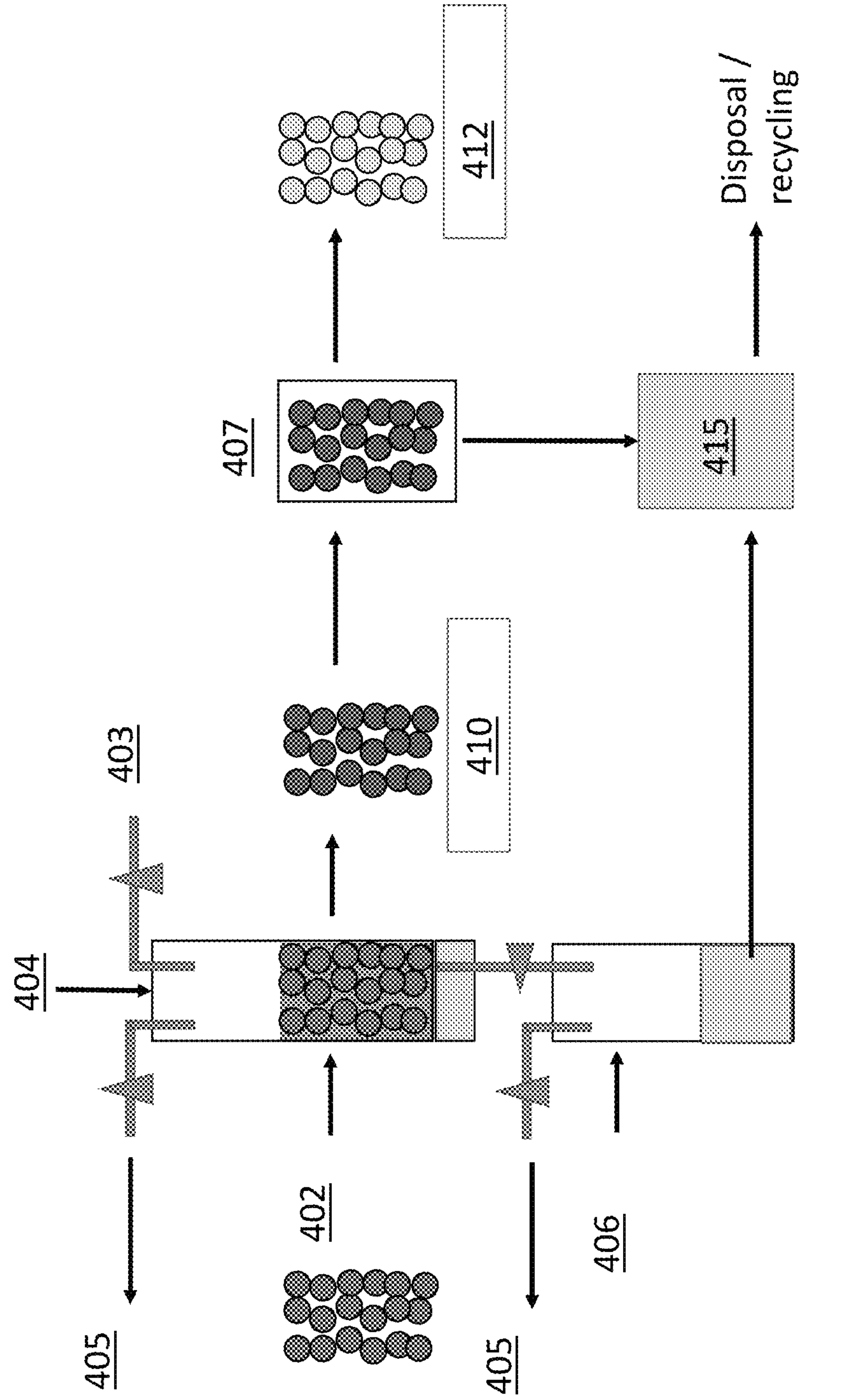
FIG. 4*a* illustrates a schematic of one example of an implementation of a biochar treat processes that that includes washing, pH adjustment and moisture adjustment.
Figure 4B:
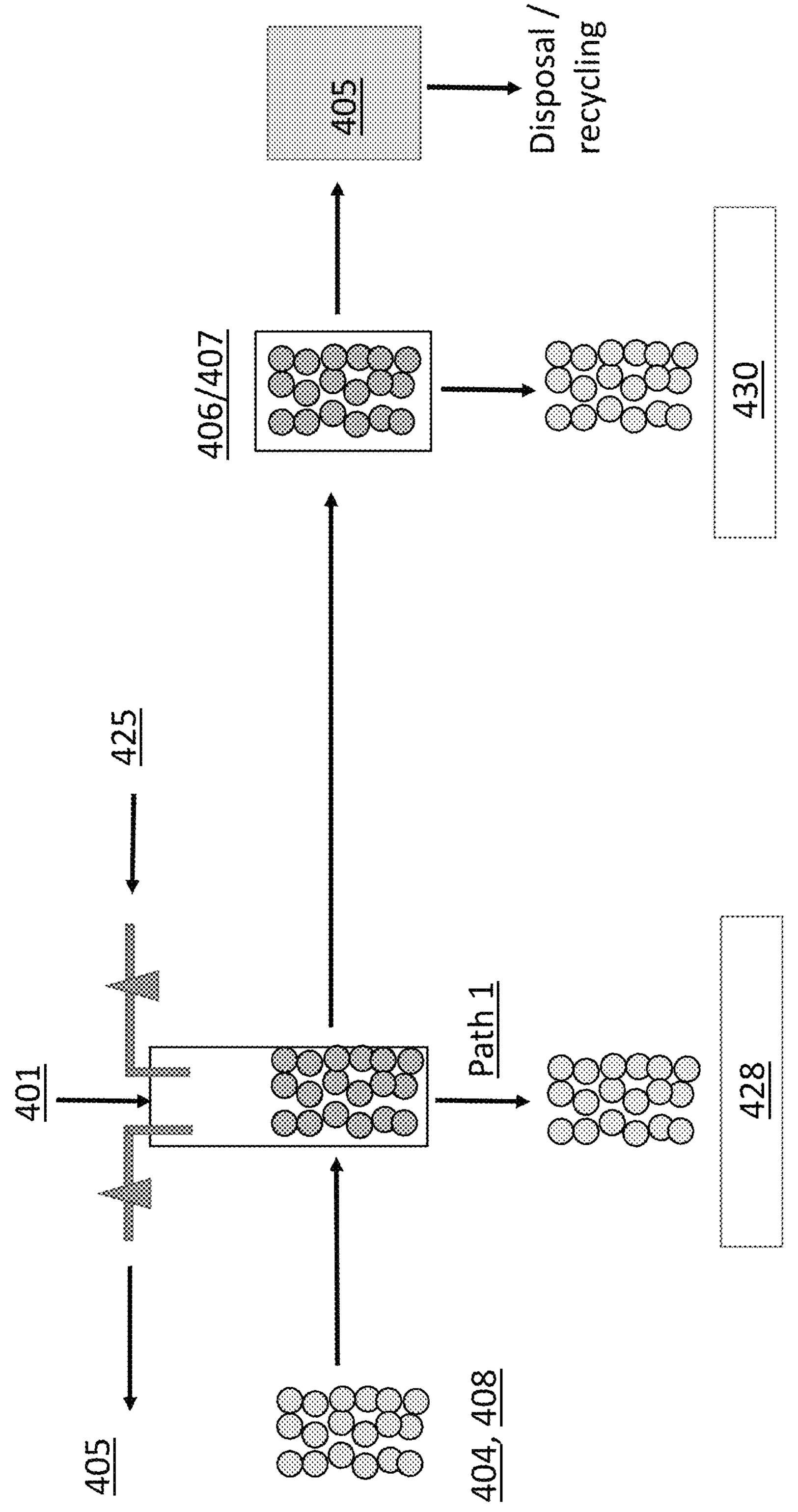
FIG. 4*b* illustrates yet another example of an implementation of a biochar treatment processing that includes inoculation.

For example, FIG. 4*a* illustrates a schematic of one example of an implementation of biochar processing that includes washing the pores and both pH and moisture adjustment. FIG. 4*b* illustrates yet another example of an implementation of biochar processing that includes inoculation.

As illustrated in FIG. 4*a*, raw biochar 402 is placed into a reactor or tank 404. A washing or treatment liquid 403 is then added to a tank and a partial vacuum, using a vacuum pump, 405 is pulled on the tank. The treating or washing liquid 403 may be used to clean or wash the pores of the biochar 402 or adjust the chemical or physical properties of the surface area or pore volume, such as pH level, usable pore volume, or VOC content, among other things. The vacuum can be applied after the treatment liquid 403 is added or while the treatment liquid 403 is added. Thereafter, the washed/adjusted biochar 410 may be moisture adjusted by vacuum exfiltration 406 to pull the extra liquid from the washed/moisture adjusted biochar 410 or may be placed in a centrifuge 407, heated or subjected to pressure gradient changes (e.g., blowing air) for moisture adjustment. The moisture adjusted biochar 412 may then be bagged or subject to further treatment. Any excess liquids 415 collected from the moisture adjustment step may be disposed of or recycled, as desired. Optionally, biochar fines may be collected from the excess liquids 415 for further processing, for example, to create a slurry, cakes, or biochar extrudates.

Optionally, rather than using a vacuum pump 405, a positive pressure pump may be used to apply positive pressure to the tank 404. In some situations, applying positive pressure to the tank may also function to force or accelerate the washing or treating liquid 403 into the pores of the biochar 402. Any change in pressure in the tank 404 or across the surface of the biochar could facilitate the exchange of gas and/or moisture into and out of the pores of the biochar with the washing or treating liquid 403 in the tank. Accordingly, changing the pressure in the tank and across the surface of the biochar, whether positive or negative, is within the scope of this invention.

As illustrated FIG. 4*b*, the washed/adjusted biochar 410 or the washed/adjusted and moisture adjusted biochar 412 may be further treated by inoculating or impregnating the pores of the biochar with an additive 425. The biochar 410, 412 placed back in a reactor 401, an additive solution 425 is placed in the reactor 401 and a vacuum, using a vacuum pump, 405 is applied on the tank. Again, the vacuum can be applied after the additive solution 425 is added to the tank or while the additive solution 425 is being added to the tank. Thereafter, the washed, adjusted and inoculated biochar 428 can be bagged. Alternatively, if further moisture adjustment is required, the biochar can be further moisture adjusted by vacuum filtration 406 to pull the extra liquid from the washed/moisture adjusted biochar 410 or may be placed in a centrifuge 407 for moisture adjustment. The resulting biochar 430 can then be bagged. Any excess liquids 415 collected from the moisture adjustment step may be disposed of or recycled, as desired. Optionally, biochar particulates or "fines" which easily are suspended in liquid may be collected from the excess liquids 415 for further processing, for example, to create a slurry, biochar extrudates, or merely a biochar product of a consistently smaller particle size. As described above, both processes of the FIGS. 4*a* and 4*b* can be performed with a surfactant solution in place of, or in conjunction with, the vacuum 405.

While known processes exist for the above described processes, research associated with the present invention has shown improvement and the ability to better control the properties and characteristics of the biochar if the processes are performed through the infusion and diffusion of liquids into and out of the biochar pores. One such treatment process that can be used is vacuum impregnation and vacuum and/or centrifuge extraction. Another such treatment process that can be used is the addition of a surfactant to infused liquid, which infused liquid may be optionally heated, cooled, or used at ambient temperature or any combination of the three.

Since research associated with the present invention has identified what physical and chemical properties have the highest impact on plant growth and/or soil health, the treatment process can be geared to treat different forms of raw biochar to achieve treated biochar properties known to enhance these characteristics. For example, if the pH of the biochar needs to be adjusted to enhance the raw biochar performance properties, the treatment may be the infusion of an acid solution into the pores of the biochar using vacuum, surfactant, or other treatment means. This treatment of pore infusion through, for example, the rapid, forced infusion of liquid into and out the pores of the biochar, has further been proven to sustain the adjusted pH levels of the treated biochar for much longer periods than biochar that is simply immersed in an acid solution for the same period of time. By way of another example, if the moisture content needs to be adjusted, then excess liquid and other selected substances (e.g. chlorides, dioxins, and other chemicals, to include those previously deposited by treatment to catalyze or otherwise react with substances on the interior or exterior surfaces of the biochar) can be extracted from the pores using vacuum and/or centrifuge extraction or by using various heating techniques. The above describes a few examples of treatment that result in treated biochar having desired performance properties identified to enhance soil health and plant life.

Figure 5:
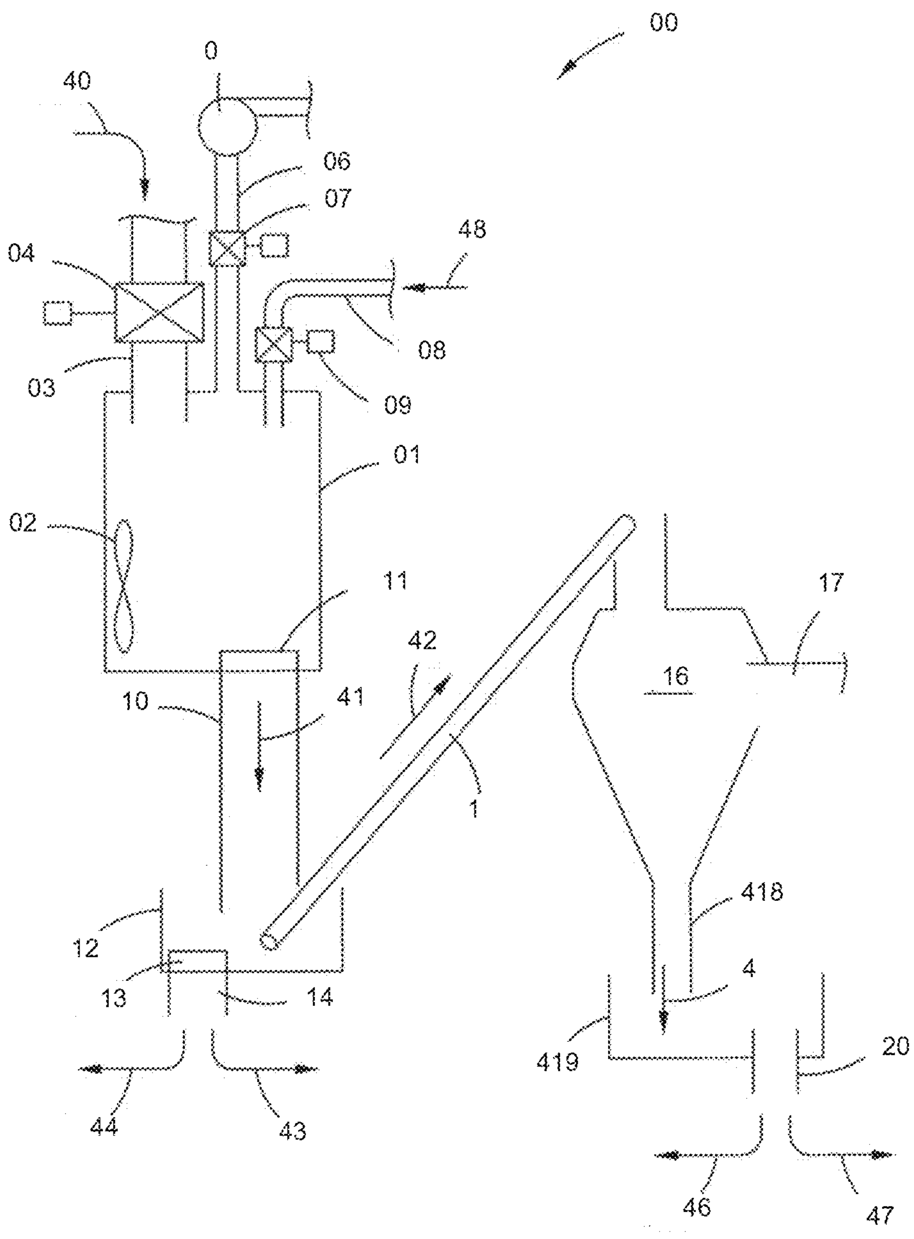
FIG. 5 is a schematic flow diagram of one example of a treatment system for use in accordance with the present invention.

FIG. 5 illustrates one example of a system 500 that utilizes vacuum impregnation to treat raw biochar. Generally, raw biochar particles, and preferably a batch of biochar particles, are placed in a reactor, which is connected to a vacuum pump, and a source of treating liquid (i.e. water or acidic/basis solution). When the valve to the reactor is closed, the pressure in the reactor is reduced to values ranging from 750 Torr to 400 Torr to 10 Torr or less. The biochar is maintained under vacuum ("vacuum hold time") for anywhere from seconds to 1 minute to 10 minutes, to 100 minutes, or possibly longer. By way of example, for about a 500 pound batch of untreated biochar, a vacuum hold time of from about 1 to about 5 minutes can be used if the reactor is of sufficient size and sufficient infiltrate is available to adjust the necessary properties. While under the vacuum the treating liquid may then be introduced into the vacuum chamber containing the biochar. Alternatively, the treating liquid may be introduced into the vacuum chamber before the biochar is placed under a vacuum. Optionally, treatment may also include subjecting the biochar to elevated temperatures from ambient to about 250° C. or reduced temperatures to about −25° C. or below, with the limiting factor being the temperature and time at which the infiltrate can remain flowable as a liquid or semi-liquid.

The infiltrate or treating liquid is drawn into the biochar pore, and preferably drawn into the macropores and mesopores. Depending upon the specific doses applied and pore structure of the biochar, the infiltrate can coat anywhere from 10% to 50% to 100% of the total macropore and mesopore surface area and can fill or coat anywhere from a portion to nearly all (10%-100%) of the total macropore and mesopore volume.

As described above, the treating liquid can be left in the biochar, with the batch being a treated biochar batch ready for packaging, shipment and use in an agricultural or other application. The treating liquid may also be removed through drying, subsequent vacuum processing, centrifugal force (e.g., cyclone drying machines or centrifuges), with the batch being a treated biochar batch ready for packaging, shipment and use in an agricultural application. A second, third or more infiltration, removal, infiltration and removal, and combinations and variations of these may also be performed on the biochar with optional drying steps between infiltrations to remove residual liquid from and reintroduce gasses to the pore structure if needed. In any of these stages the liquid may contain organic or inorganic surfactants to assist with the penetration of the treating liquid.

As illustrated in FIG. 5, a system 500 for providing a biochar, preferably having predetermined and uniform properties. The system 500 has a vacuum infiltration tank 501. The vacuum infiltration tank 501 has an inlet line 503 that has a valve 504 that seals the inlet line 503. In operation, the starting biochar is added to vacuum infiltration tank 501 as shown by arrow 540. Once the tank is filled with the starting biochar, a vacuum is pulled on the tank, by a vacuum pump connected to vacuum line 506, which also has valve 507. The starting biochar is held in the vacuum for a vacuum hold time. Infiltrate, as shown by arrow 548 is added to the tank 501 by line 508 having valve 509. The infiltrate is mixed with the biochar in the tank 501 by agitator 502. The mixing process is done under vacuum for a period of time sufficient to have the infiltrate fill the desired amount of pore volume, e.g., up to 100% of the macropores and mesopores.

Alternatively, the infiltrate may be added to the vacuum infiltration tank 501 before vacuum is pulled on the tank. In this manner, infiltrate is added in the tank in an amount that can be impregnated into the biochar. As the vacuum is pulled, the biochar is circulated in the tank to cause the infiltrate to fill the pore volume. To one skilled in the art, it should be clear that the agitation of the biochar during this process can be performed through various means, such as a rotating tank, rotating agitator, pressure variation in the tank itself, or other means. Additionally, the biochar may be dried using conventional means before even the first treatment. This optional pre-drying can remove liquid from the pores and in some situations may increase the efficiency of impregnation due to pressure changes in the tank.

Pressure is then restored in the tank 501 and the infiltrated biochar is removed, as shown by arrow 541, from the tank 501 to bin 512, by way of a sealing gate 511 and removal line 510. The infiltrated biochar is collected in bin 512, where it can be further processed in several different ways. The infiltrated biochar can be shipped for use as a treated biochar as shown by arrow 543. The infiltrated biochar can be returned to the tank 501 (or a second infiltration tank). If returned to the tank 501 the biochar can be processed with a second infiltration step, a vacuum drying step, a washing step, or combinations and variations of these. The infiltrated biochar can be moved by conveyor 514, as shown by arrow 542, to a drying apparatus 516, e.g., a centrifugal dryer or heater, where water, infiltrate or other liquid is removed by way of line 517, and the dried biochar leaves the dryer through discharge line 518 as shown by arrow 545, and is collected in bin 519. The biochar is removed from the bin by discharge 520. The biochar may be shipped as a treated biochar for use in an agriculture application, as shown by arrow 547. The biochar may also be further processed, as shown by 546. Thus, the biochar could be returned to tank 501 (or a second vacuum infiltration tank) for a further infiltration step. The drying step may be repeated either by returning the dry biochar to the drying apparatus 516, or by running the biochar through a series of drying apparatus, until the predetermined dryness of the biochar is obtained, e.g., between 50% to less than 1% moisture.

The system 500 is illustrative of the system, equipment and processes that can be used for, and to carry out the present inventions. Various other implementations and types of equipment can be used. The vacuum infiltration tank can be a sealable off-axis rotating vessel, chamber or tank. It can have an internal agitator that also when reversed can move material out, empty it, (e.g., a vessel along the lines of a large cement truck, or ready mix truck, that can mix and move material out of the tank, without requiring the tank's orientation to be changed). Washing equipment may be added or utilized at various points in the process, or may be carried out in the vacuum tank, or drier, (e.g., wash fluid added to biochar as it is placed into the drier for removal). Other steps, such as bagging, weighing, the mixing of the biochar with other materials, e.g., fertilized, peat, soil, etc. can be carried out. In all areas of the system referring to vacuum infiltration, optionally positive pressure can be applied, if needed, to enhance the penetration of the infiltrate or to assist with re-infusion of gaseous vapors into the treated char. Additionally, where feasible, especially in positive pressure environments, the infiltrate may have soluble gasses added which then can assist with removal of liquid from the pores, or gaseous treatment of the pores upon equalization of pressure.

As noted above, the biochar may also be treated using a surfactant. The same or similar equipment used in the vacuum infiltration process can be used in the surfactant treatment process. Although it is not necessary to apply a vacuum in the surfactant treatment process, the vacuum infiltration tank or any other rotating vessel, chamber or tank can be used. In the surfactant treatment process, a surfactant, such as yucca extract, is added to the infiltrate, e.g., acid wash or water. The quantity of the surfactant added to the infiltrate may vary depending upon the surfactant used. For example, organic yucca extract can be added at a rate of between 0.1-20%, but more preferably 1-5% by volume of the infiltrate. The infiltrate with surfactant is then mixed with the biochar in a tumbler for several minutes, e.g., 3-5 minutes, without applied vacuum. Optionally, a vacuum or positive pressure may be applied with the surfactant to improve efficiency, but is not necessary. Additionally, infiltrate to which the surfactant or detergent is added may be heated or may be ambient temperature or less. Similarly, the mixture of the surfactant or detergent, as well as the char being treated may be heated, or may be ambient temperature, or less. After tumbling, excess free liquid can be removed in the same manner as described above in connection with the vacuum infiltration process. Drying, also as described above in connection with the vacuum infiltration process, is an optional additional step. Besides *yucca* extract, a number of other surfactants may be used for surfactant treatment, which include, but are not limited to, the following: nonionic types, such as, ethoxylated alcohols, phenols-lauryl alcohol ethoxylates, Fatty acid esters-sorbitan, tween 20, amines, amides-imidazoles; anionic types, such as sulfonates-arylalkyl sulfonates and sulfate-sodium dodecyl sulfate; cationic types, such as alkyl-amines or ammoniums-quaternary ammoniums; and amphoteric types, such as betaines-cocamidopropyl betaine.

Optionally, the biochar may also be treated by applying ultrasonics. In this treatment process, the biochar may be contacted with a treating liquid that is agitated by ultrasonic waves. By agitating the treating liquid, contaminants may be dislodged or removed from the biochar due to bulk motion of the fluid in and around the biocarbon, pressure changes, including cavitation in and around contaminants on the surface, as well as pressure changes in or near pore openings (cavitation bubbles) and internal pore cavitation.

In this manner, agitation will cause contaminants of many forms to be released from the internal and external structure of the biochar. The agitation also encourages the exchange of water, gas, and other liquids with the internal biochar structure. Contaminants are transported from the internal structure to the bulk liquid (treating fluid) resulting in biochar with improved physical and chemical properties. The effectiveness of ultrasonic cleaning is tunable as bubble size and number is a function of frequency and power delivered by the transducer to the treating fluid In one example, applying ultrasonic treatment, raw wood based biochar between 10 microns to 10 mm with moisture content from 0% to 90% may be mixed with a dilute mixture of acetic acid and water (together the treating liquid) in a processing vessel that also translates the slurry (the biochar/treating liquid mixture). During translation, the slurry passes near an ultrasonic transducer to enhance the interaction between the fluid and biochar. The biochar may experience one or multiple washes of dilute acetic acid, water, or other treating fluids. The biochar may also make multiple passes by ultrasonic transducers to enhance physical and chemical properties of the biochar. For example, once a large volume of slurry is made, it can continuously pass an ultrasonic device and be degassed and wetted to its maximum, at a rapid processing rate. The slurry can also undergo a separation process in which the fluid and solid biochar are separated at 60% effectiveness or greater.

Through ultrasonic treatment, the pH of the biochar, or other physical and chemical properties may be adjusted and the mesopore and macropore surfaces of the biochar may be cleaned and enhanced. Further, ultrasonic treatment can be used in combination with bulk mixing with water, solvents, additives (fertilizers, etc.), and other liquid based chemicals to enhance the properties of the biochar. After treatment, the biochar may be subject to moisture adjustment, further treatment and/or inoculation using any of the methods set forth above.

C. Benefits of Treatment

As illustrated above, the treatment process, whether using vacuum, surfactant or ultrasonic treatment, or a combination thereof, may include two steps, which in certain applications, may be combined: (i) washing and (ii) inoculation of the pores with an additive. When the desired additive is the same and that being inoculated into the pores, e.g., water, the step of washing the pores and inoculating the pores with an additive may be combined.

While not exclusive, washing is generally done for one of three purposes: (i) to modify the surface of the pore structure of the biochar (i.e., to allow for increased retention of liquids); (ii) to modify the pH of the biochar; and/or (iii) to remove undesired and potentially harmful compounds or gases.

1. Increases Water Holding Capacity/Water Retention Capacity

As demonstrated below, the treatment processes of the invention modify the surfaces of the pore structure to provide enhanced functionality and to control the properties of the biochar to achieve consistent and predicable performance. Using the above treatment processes, anywhere from at least 10% of the total pore surface area up to 90% or more of the total pore surface area may be modified. In some implementations, it may be possible to achieve modification of up to 99% or more of the total pore surface area of the biochar particle. Using the processes set forth above, such modification may be substantially and uniformly achieved for an entire batch of treated biochar.

For example, it is believed that by treating the biochar as set forth above, the hydrophilicity of the surface of the pores of the biochar is modified, allowing for a greater water retention capacity. Further, by treating the biochars as set forth above, gases and other substances are also removed from the pores of the biochar particles, also contributing to the biochar particles' increased water holding capacity. Thus, the ability of the biochar to retain liquids, whether water or additives in solution, is increased, which also increases the ability to load the biochar particles with large volumes of inoculant, infiltrates and/or additives.

A batch of biochar has a bulk density, which is defined as weight in grams (g) per $cm^3$ of loosely poured material that has or retains some free space between the particles. The biochar particles in this batch will also have a solid density, which is the weight in grams (g) per $cm^3$ of just particles, i.e., with the free space between the particles removed. The solid density includes the air space or free space that is contained within the pores, but not the free space between particles. The actual density of the particles is the density of the material in grams (g) per $cm^3$ of material, which makes up the biochar particles, i.e., the solid material with pore volume removed.

In general, as bulk density increases the pore volume is expected to decrease. When the pore volume is macro or mesoporous, the ability of the material to hold infiltrate, e.g., inoculant is directly proportional to the pore volume, thus it is also expected to decrease as bulk density increases. With the infiltration processes, the treated biochars can have impregnation capacities that are larger than could be obtained without infiltration, e.g., the treated biochars can readily have 30%, 40%, 50%, or most preferably, 60%-100% of their total pore volume filled with an infiltrate, e.g., an inoculant. The impregnation capacity is the amount of a liquid that a biochar particle, or batch of particles, can absorb. The ability to make the pores surface hydrophilic, and to infuse liquid deep into the pore structure through the application of positive or negative pressure and/or a surfactant, alone or in combination, provides the ability to obtain these high impregnation capabilities. The treated biochars can have impregnation capacities, i.e., the amount of infiltrate that a particle can hold on a volume held/total volume of a particle basis, that is greater than 0.2 $cm^3/cm^3$ to 0.8 $cm^3/cm^3$. Resulting bulk densities of treated biochar can range from 0.1-0.6 $g/cm^3$ and sometimes preferably between 0.3-0.6 $g/cm^3$ and can have solid densities ranging from 0.2-1.2 $g/cm^3$.

Figure 6:
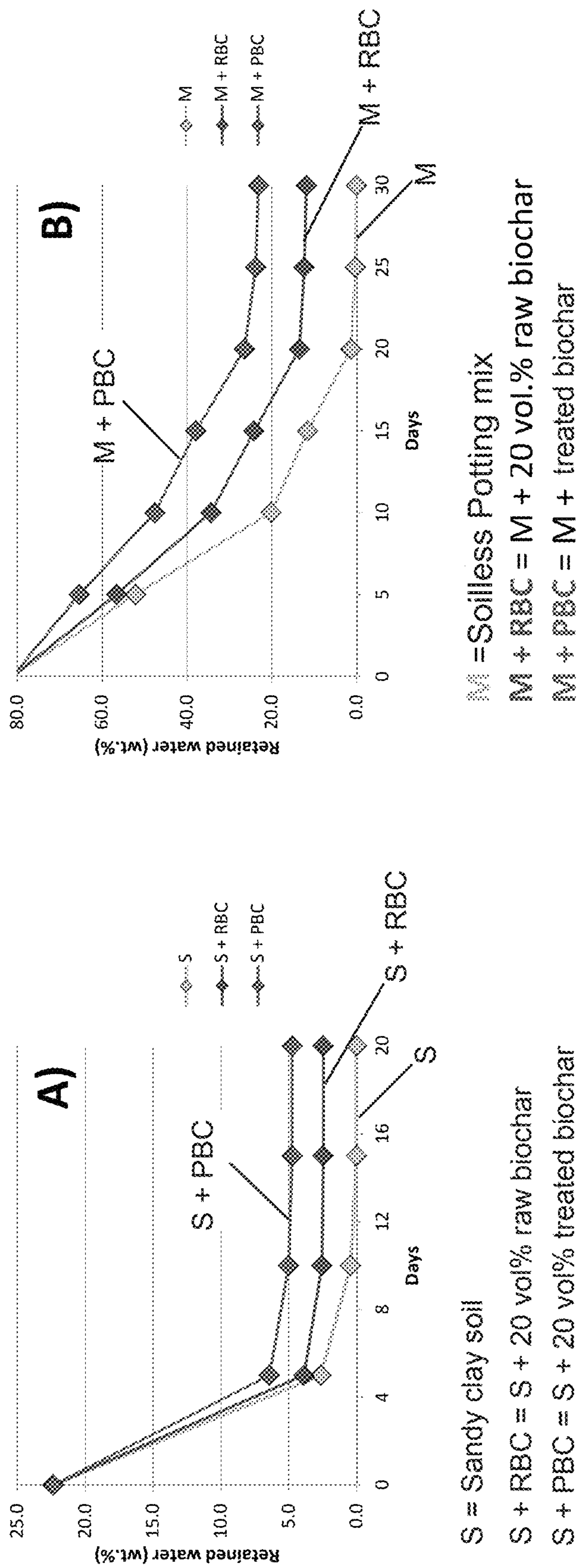
FIG. 6 is a chart showing the water holding capacities of treated biochar as compared to raw biochar and sandy clay loam soil and as compared to raw biochar and sunshine potting soil.

Accordingly, by using the treatment above, the water retention capacity of biochar can be greatly increased over the water retention capacities of various soil types and even raw biochar, thereby holding water and/or nutrients in the plant's root zone longer and ultimately reducing the amount of applied water (through irrigation, rainfall, or other means) needed by up to 50% or more. FIG. 6 is a chart showing the water retention capacities of soils versus raw and treated biochar. The soils sampled are loam and sandy clay soil and a common commercial horticultural mix. The charts show the retained water as a function of time.

In chart A, the bottom line represents the retained water in the sandy claim loam soil over time. The middle line represents the retained water in the sandy clay soil with 20% by volume percent of unprocessed raw biochar. The top line represents the retained water in the sandy clay loam soil with 20% by volume percent of treated biochar (adjusted and inoculated biochar). Chart B represents the same using a soilless potting mix rather than sandy clay loam soil.

Figure 7:
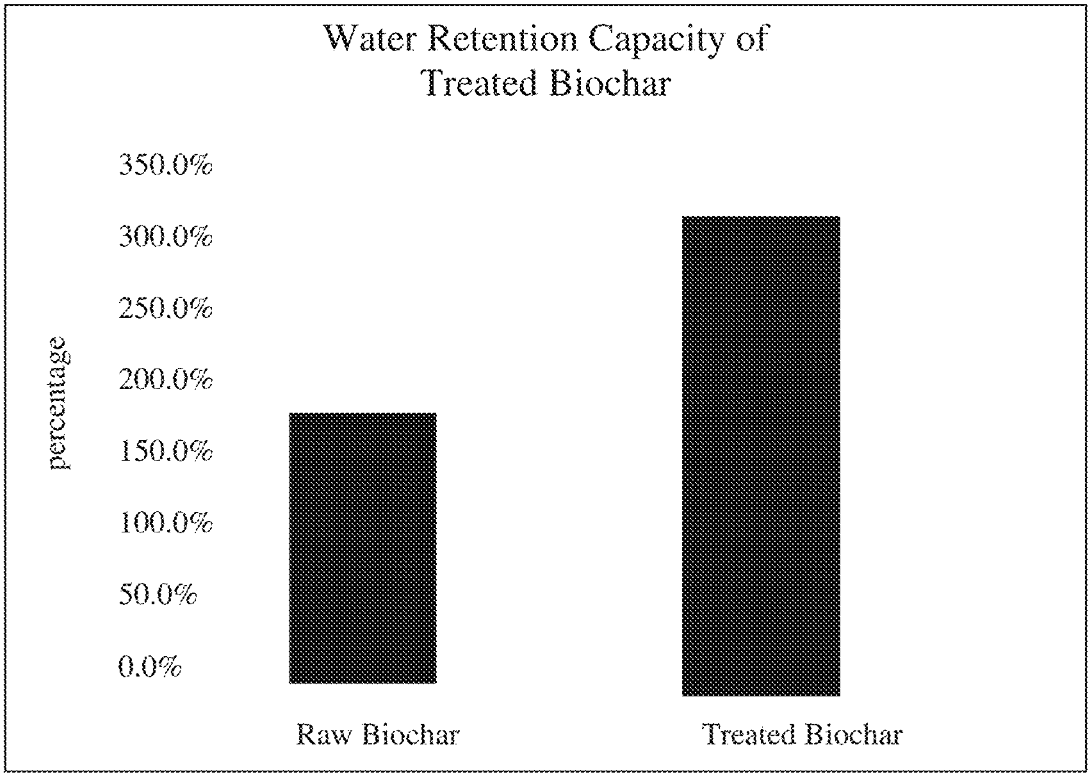
FIG. 7 illustrates the different water retention capacities of raw biochar versus treated biochar measured gravimetrically.

As illustrated in FIG. 7, testing showed a treated biochar had an increased water retention capacity of approximately 1.5 times that of the raw biochar from the same feedstock. Similar results have been seen with biochars derived from various feedstocks. With certain biochar types, the water retention capacity of treated biochar could be as great as three times that of raw biochar.

"Water holding capacity," which may also be referred to as "Water Retention Capacity," is the amount of water that can be held both internally within the porous structure and in the interparticle void spaces in a given batch of particles. While a summary of the method of measure is provided above, a more specific method of measuring water holding capacity/water retention capacity is measured by the following procedure: (i) drying a sample of material under temperatures of 105° C. for a period of 24 hours or using another scientifically acceptable technique to reduce the moisture content of the material to less than 2%, less than 1%; and preferably less than 0.5% (ii) placing a measured amount of dry material in a container; (iii) filling the container having the measured amount of material with water such that the material is completely immersed in the water; (iv) letting the water remain in the container having the measured amount of material for at least ten minutes or treating the material in accordance with the invention by infusing with water when the material is a treated biochar; (v) draining the water from the container until the water ceases to drain; (vi) weighing the material in the container (i.e., wet weight); (vii) again drying the material by heating it under temperatures of 105° C. for a period of 24 hours or using another scientifically acceptable technique to reduce the moisture content of the material to less than 2% and preferably less than 1%; and (viii) weighing the dry material again (i.e., dry weight) and, for purposes of a volumetric measure, determining the volume of the material.

Figure 8:
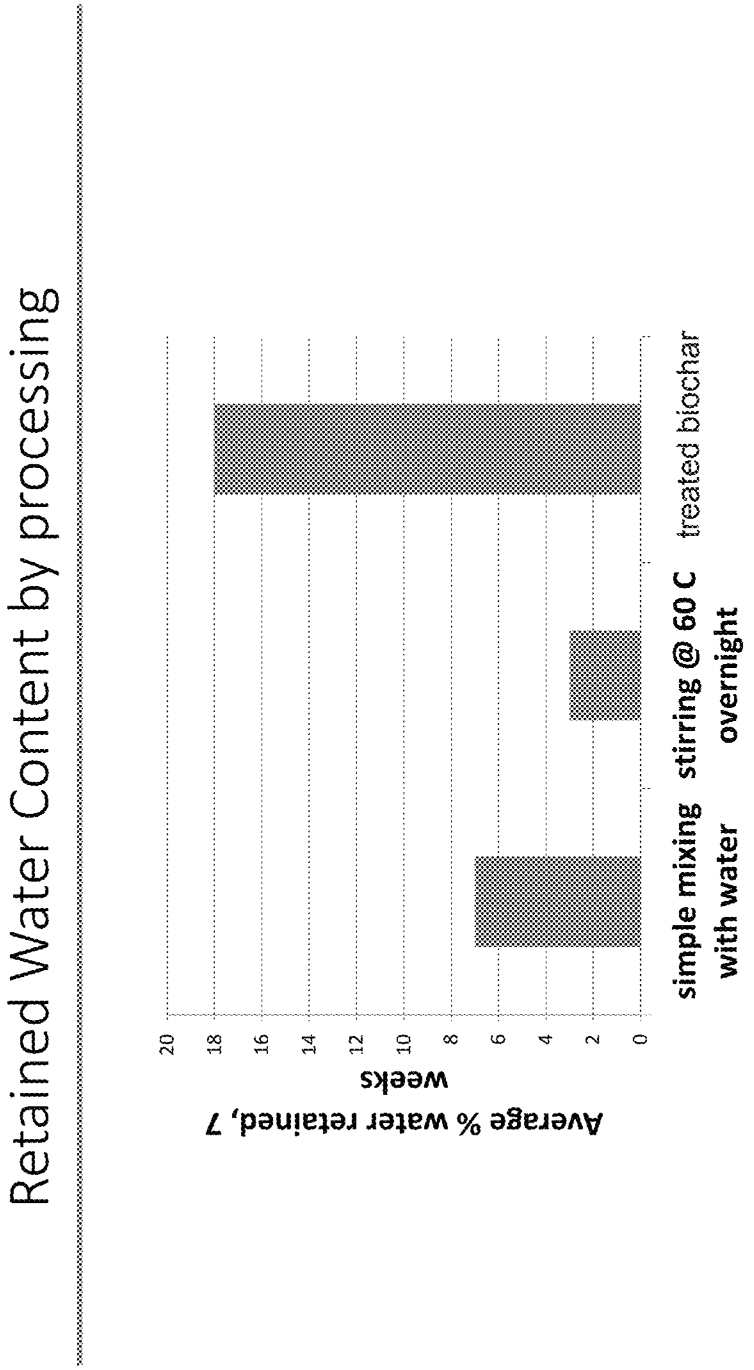
FIG. 8 is a chart showing the retained water in vacuum impregnated biochar over other biochars after a seven week period.

Measured gravimetrically, the water holding/water retention capacity is determined by measuring the difference in weight of the material from step (vi) to step (viii) over the weight of the material from step (viii) (i.e., wet weight-dry weight/dry weight). FIG. 8 illustrates the different water retention capacities of raw biochar versus treated biochar measured gravimetrically. As illustrated, water retention capacity of raw biochar can be between 100-200%, whereas treated biochar can have water retention capacities measured gravimetrically between 200-400%.

Water holding capacity can also be measured volumetrically and represented as a percent of the volume of water retained in the biochar after gravitationally draining the excess water/volume of biochar The volume of water retained in the biochar after draining the water can be determined from the difference between the water added to the container and water drained off the container or from the difference in the weight of the wet biochar from the weight of the dry biochar converted to a volumetric measurement. This percentage water holding capacity for treated biochar may be 50-55 percent and above by volume.

Given biochar's increased water retention capacity, the application of the treated biochar and even the raw biochar can greatly assist with the reduction of water and/or nutrient application. It has been discovered that these same benefits can be imparted to agricultural growth.

Treated biochar of the present invention has also demonstrated the ability to retain more water than raw biochar after exposure to the environment for defined periods of time. For purposes of this application "remaining water content" can be defined as the total amount of water that remains held by the biochar after exposure to the environment for certain amount of time. Exposure to environment is exposure at ambient temperature and pressures. Under this definition, remaining water content can be measured by (i) creating a sample of biochar that has reached its maximum water holding capacity; (ii) determining the total water content by thermogravimetric analysis ($H_2O$ (TGA)), as described above on a sample removed from the output of step (i) above, (iii) exposing the biochar in the remaining sample to the environment for a period of 2 weeks (15 days, 360 hrs.); (iv) determining the remaining water content by thermogravimetric analysis ($H_2O$ (TGA)); and (v) normalizing the remaining (retained) water in mL to 1 kg or 1 L biochar. The percentage of water remaining after exposure for this two-week period can be calculated by the remaining water content of the biochar after the predetermined period over the water content of the biochar at the commencement of the two-week period. Using this test, treated biochar has shown to retain water at rates over 4× that of raw biochar. Testing has further demonstrated that the following amount of water can remain in treated biochar after two weeks of exposure to the environment: 100-650 mL/kg; 45-150 mL/L; 12-30 gal/ton; 3-10 gal/yd$^3$ after 360 hours (15 days) of exposure to the environment. In this manner, and as illustrated in FIG. 8, biochar treated with a process consistent with those described in this disclosure can increase the amount of retained water in biochar about 3 times compared to other methods even after seven weeks. In general, the more porous and the higher the surface area of a given material, the higher the water retention capacity. Further, it is theorized that by modifying the hydrophilicity/hydrophobicity of the pore surfaces, greater water holding capacity and controlled release may be obtained. Thus, viewed as a weight percent, e.g., the weight of retained water to weight of biochar, examples of the present biochars can retain more than 5% of their weight, more than 10% of their weight, and more than 15% of their weight, and even more than 50% of their weight compared to an average soil which may retain 2% or less, or between 100-600 ml/kg by weight of biochar.

Tests have also shown that treated biochars that show weight loss of >1% in the interval between 43-60° C. when analyzed by the Thermal Gravimetric Analysis (TGA) (as described below) demonstrate greater water holding and content capacities over raw biochars. Weight loss of >5%-15% in the interval between 38-68° C. when analyzed by the Thermal Gravimetric Analysis (TGA) using sequences of time and temperature disclosed in the following paragraphs or others may also be realized. Weight percentage ranges may vary from between >1%-15% in temperature ranges between 38-68° C., or subsets thereof, to distinguish between treated biochar and raw biochar.

Figure 9:
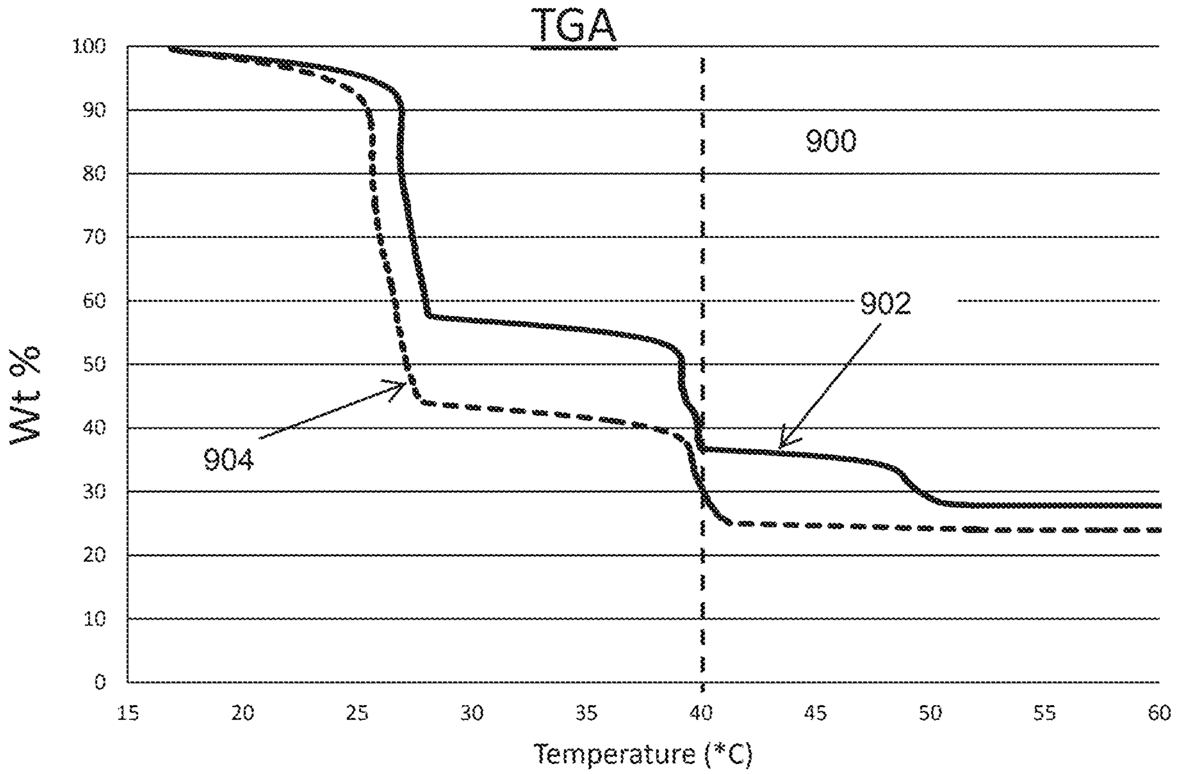
FIG. 9 is a chart showing the weight loss of treated biochars versus raw biochar samples when heated at varying temperatures using a TGA testing method.

FIG. 9 is a chart 900 showing the weight loss of treated biochars 902 versus raw biochar samples 904 when heated at varying temperatures using the TGA testing described below. As illustrated, the treated biochars 902 continue to exhibit weight loss when heated between 40-60° C. when analyzed by the Thermal Gravimetric Analysis (TGA) (described below), whereas the weight loss in raw biochar 804 between the same temperature ranges levels off. Thus, testing demonstrates the presence of additional moisture content in treated biochars 902 versus raw biochars 904.

In particular, the treated biochars 902 exhibit substantial water loss when heated in inert gas such as nitrogen following treatment. More particularly, when heated for 25 minutes at each of the following temperatures 20, 30, 40, 50 and 60° C. the treated samples lose about 5-% to 15% in the interval 43-60° C. and upward of 20-30% in the interval between 38-68° C. The samples to determine the water content of the raw biochar were obtained by mixing a measured amount of biochar and water, stirring the biochar and water for 2 minutes, draining off the water, measuring moisture content and then subjecting the sample to TGA. The samples for the treated biochar were obtained by using the same measured amount of biochar as used in the raw biochar sample and using treatment process consistent with those described in this disclosure. The moisture content is then measured and the sample is subjected to TGA described above.

The sequences of time and temperature conditions for evaluating the effect of biochars heating in inert atmosphere is defined in this application as the "Bontchev-Cheyne Test" ("BCT"). The BCT is run using samples obtained, as described above, and applying Thermal Gravimetric Analysis (TGA) carried out using a Hitachi STA 7200 analyzer under nitrogen flow at the rate of 110 mL/min. The biochar samples are heated for 25 minutes at each of the following temperatures: 20, 30, 40, 50 and 60° C. The sample weights are measured at the end of each dwell step, at the beginning and at the end of the experiment. The analyzer also continually measures and records weight over time. Biochars treated with a process consistent with those described in this disclosure to enhance water holding or retention capacities typically exhibit weight loss of >5% in the interval between 38-68° C., >1% in the interval between 43-60° C. Biochars with greater water holding or retention capacities can exhibit >5% weight loss in the interval between 43-60° C. measured using the above described BCT.

Figure 10:
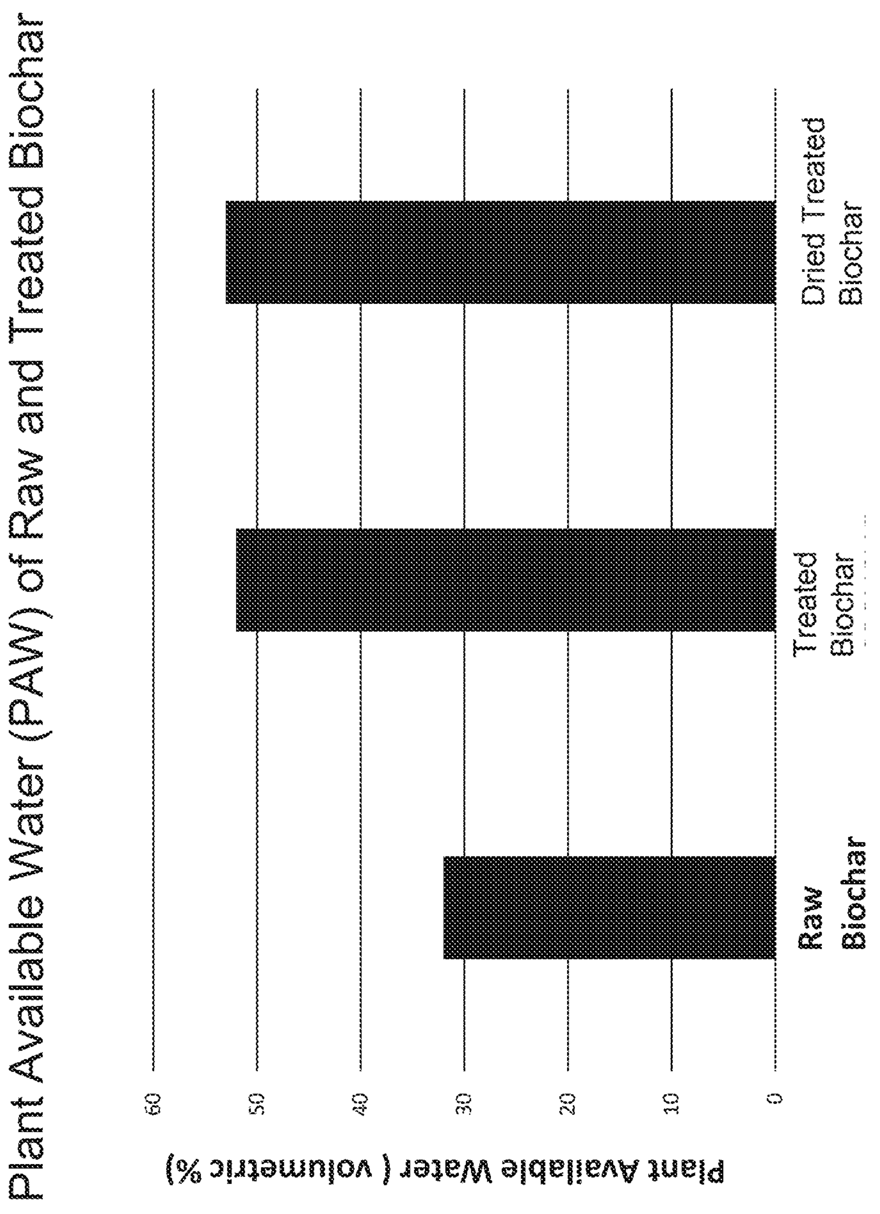
FIG. 10 illustrates the plant available water in raw biochar, versus treated biochar and treated dried biochar.

Lastly, as illustrated in FIG. 10, plant available water is greatly increased in treated biochar over that of raw biochar. FIG. 10 illustrates the plant available water in raw biochar, versus treated biochar and treated dried biochar and illustrates that treated biochar can have a plant available water percent of greater than 35% by volume.

"Plant Available Water" is the amount of unbound water in a material available for plants to uptake. This is calculated by subtracting the volumetric water content at the permanent wilting point from the volumetric water content at field capacity, which is the point when no water is available for the plants. Field capacity is generally expressed as the bulk water content retained in at −33 J/kg (or −0.33 bar) of hydraulic head or suction pressure. Permanent wilting point is generally expressed as the bulk water content retained at −1500 J/kg (or −15 bar) of hydraulic head or suction pressure. Methods for measuring plant available water are well-known in the industry and use pressure plate extractors, which are commercially available or can be built using well-known principles of operation.

2. Adjusts pH

Figure 11:
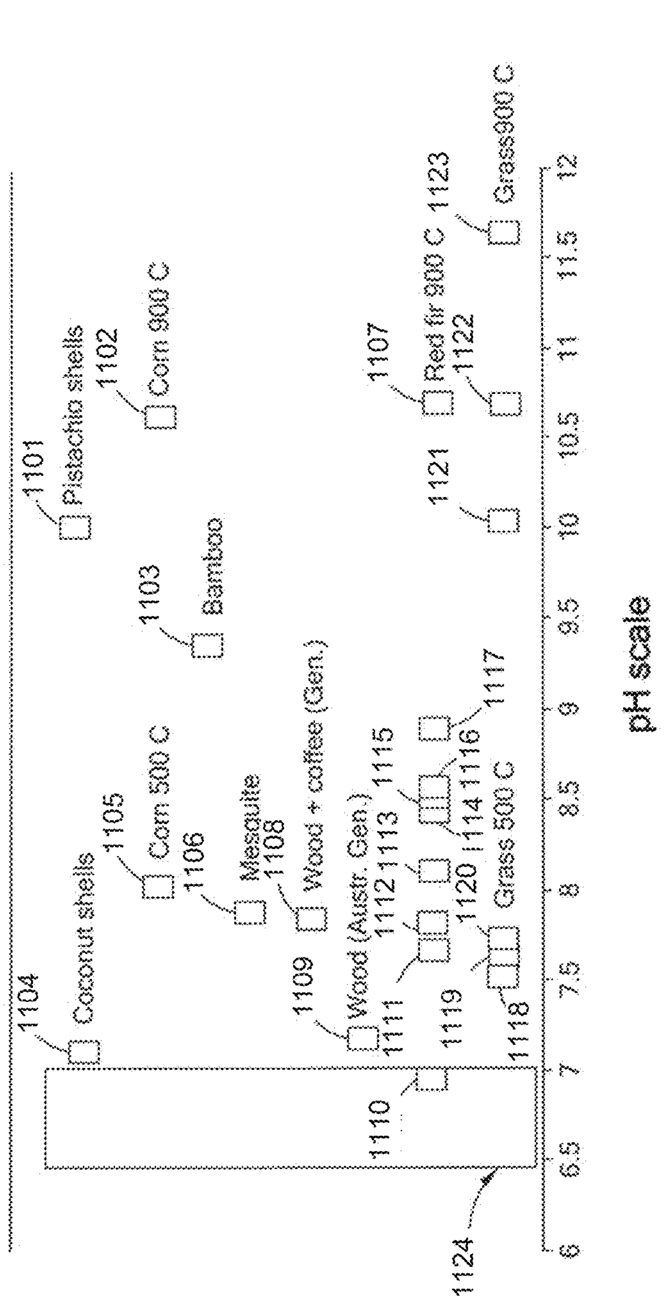
FIG. 11 is a graph showing the pH of various starting biochars that were made from different starting materials and pyrolysis process temperatures.
Figure 12:
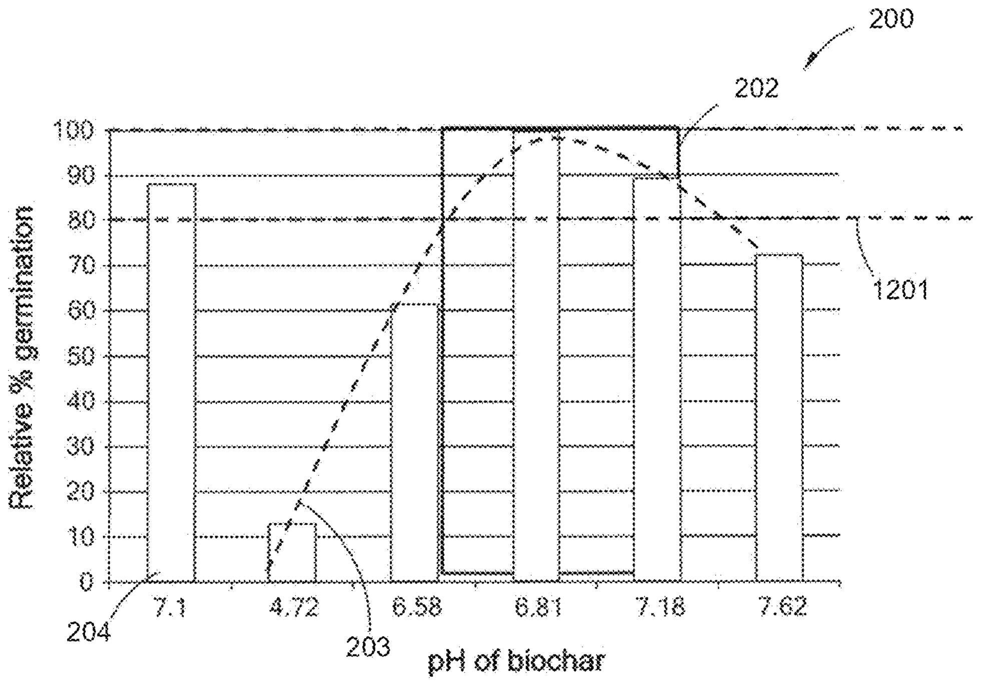
FIG. 12 is a chart showing various pH ranges and germination for treated biochars.

With regard to treatment for pH adjustment, the above described vacuum infiltration processes and/or surfactant treatment processes have the ability to take raw biochars having detrimental or deleterious pHs and transform those biochars into a treated biochar having pH that is in an optimal range for most plant growth, and soil health. Turning to FIG. 11, a graph 1100 is provided that shows the pH of various starting raw biochars that were made from different starting materials and pyrolysis process temperatures, including coconut shells 1104, pistachio shells 1101, corn at 500° C. 1105, corn at 900° C. 1102, bamboo 1103, mesquite 1106, wood and coffee 1108, wood (Australia) 1109, various soft woods 1110, 1111, 1112, 1113, 1114, 1115, 1116, 1117, red fir at 900° C. 1107, various grasses at 500° C. 1118, 1119, 1120, grass 1121, and grass at 900° C. 1123. The treatment processes described in this disclosure, can be used to alter the pH from the various undesirable pH levels and bring the pH into the preferred, optimal range 1124 for most plant growth, soil health and combinations of these. FIG. 12 is a chart 1200 showing percentage of germination for lettuce plants for particular pHs, and a desired germination range 1201. A control 1204 is compared with an optimal pH range 1202, and a distribution 1203 of growth rates across pHs is shown.

If treated for pH adjustment, the treated biochar takes a few days after treatment for the pH to normalize. Once normalized, tests have proven that pH altered biochar remains at a stable pH, typically the treatment is used to lower the stable pH to below that of the raw biochar, for up to 12 months or more after treatment. Although in certain situations, the pH could be altered to be higher than the raw biochar when needed.

For example, the treatment process of the present invention can remove and/or neutralize inorganic compounds, such as the calcium hydroxide ($(CaOH)_2$), potassium oxide ($K_2OK_2OK_20$), magnesium oxide (MgO), magnesium hydroxide ($Mg(OH)_2$), and many others that are formed during pyrolysis, and are fixed to the biochar pore surfaces. These inorganics, in particular calcium hydroxide, adversely affect the biochar's pH, making the pH in some instances as high as 8.5, 9.5, 10.5 and 11.2. These high pH ranges are deleterious, detrimental to crops, and may kill or adversely affect the plants, sometimes rendering an entire field a loss.

The calcium hydroxide, and other inorganics, cannot readily and quickly be removed by simple washing of the biochar, even in an acid bath. It cannot be removed by drying the biochar, such as by heating or centrifugal force. It is theorized that these techniques and methodologies cannot reach or otherwise affect the various pore surfaces, e.g., macro-, meso- and micro- in any viable or efficacious manner; and thus cannot remove or otherwise neutralize the calcium hydroxide.

Upon modification of the pore surface area by removal and/or neutralization of deleterious substances, such as calcium hydroxide, the pH of the biochar can be reduced to the range of about pH 5 to about pH 8, and more preferably from about pH 6.4 to about 7.2, and still more preferably around 6.5 to 6.8, recognizing that other ranges and pHs are contemplated and may prove useful, under specific environmental or agricultural situations or for other applications. Thus, the present treated biochars, particles, batches and both, have most, essentially all, and more preferably all, of their pore surfaces modified by the removal, neutralization and both, of the calcium hydroxide that is present in the starting biochar material. These treated biochars have pHs in the range of about 5 to about 8, about 6.5 to about 7.5, about 6.4 to about 7, and about 6.8. Prior to and before testing, biochar is passed through a 2 mm sieve before pH is measured. All measurements are taken according to Rajkovich et. al, *Corn growth and nitrogen nutrition after additions of biochars with varying properties to a temperate soil*, Biol. Fertil. Soils (2011), from which the International Biochar Initiative (IBI) method is based.

There are a wide variety of tests, apparatus and equipment for making pH measurements. For example, and preferably when addressing the pH of biochar, batches, particles and pore surfaces of those particles, two appropriates for measuring pH are the Test Method for the US Composting Council ("TMCC") 4.11-A and the pH Test Method promulgated by the International Biochar Initiative. The test method for the TMCC comprises mixing biochar with distilled water in 1:5 [mass:volume] ratio, e.g., 50 grams of biochar is added to 250 ml of pH 7.0±0.02 water and is stirred for 10 minutes; the pH is then the measured pH of the slurry. The pH Test Method promulgated by the International Biochar Initiative comprises 5 grams of biochar is added to 100 ml of water pH=7.0±0.02 and the mixture is tumbled for 90 minutes; the pH of the slurry is measured at the end of the 90 minutes of tumbling.

3. Removing/Neutralizing Deleterious Materials

Further, the treatment processes are capable of modifying the pore surfaces to remove or neutralize deleterious materials that are otherwise difficult, if not for all practical purpose, impossible to mitigate. For example, heavy metals, transition metals, sodium and phytotoxic organics, polycyclic aromatic hydrocarbons, volatile organic compounds (VOCs), and perhaps other phytotoxins. Thus, by treating the biochar in accordance with the treatment processes set forth and described above, the resulting treated biochar has essentially all, and more preferably all, of their pore surfaces modified by the removal, neutralization and both, of one or more deleterious, harmful, or potentially harmful material that is present in the starting biochar material.

For example, treatment can reduce the total percentage of residual organic compounds (ROC), including both the percentage of heavy ROCs and percentage of VOCs. Through treatment, the total ROC can be reduced to 0-25% wt. %, percentage heavy ROC content can be reduced to 0-20% wt. % and VOC content can be reduced to less than 5% wt. %. For purposes of this application, "Residual organic compounds" (ROCs) are defined as compounds that burn off during thermogravimetric analysis, as defined above, between 150 degrees C. and 950 degrees C. Residual organic compounds include, but are not limited to, phenols, polyaromatic hydrocarbons, monoaromatic hydrocarbons, acids, alcohols, esters, ethers, ketones, sugars, alkanes and alkenes. Of the ROCs, those that burn off using thermogravimetric analysis between 150 degrees C. and 550 degrees are considered light organic compounds (volatiles or VOCs), and those that burn off between 550 degrees C. and 950 degrees C. are heavy residual organic compounds. It should be noted that there may be some inorganic compounds which also are burned off during TGA analysis in these temperature ranges, but these are generally a very low percentage of the total emission and can be disregarded in the vast majority of cases as slight variations. In any of these measurements, a gas chromatograph/mass spectrometer may be used if needed for higher degrees of precision.

Figure 13:
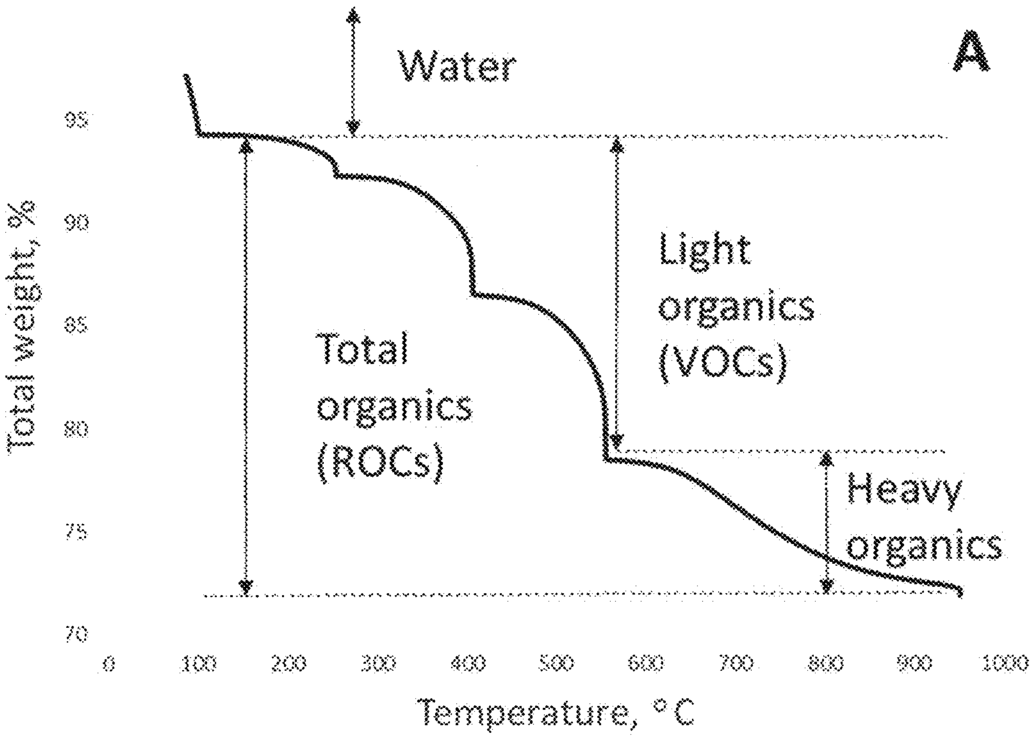
FIG. 13 is a Thermogravimetric Analysis (TGA) plot showing the measurement of water content, heavy organics and light organics in a sample.

The percent water, total organic compounds, total light organic compounds (volatiles or VOC) and total heavy organic compounds, as referenced in this application as contained in a biochar particle or particles in a sample may all be measured by thermogravimetric analysis. Thermogravimetric analysis is performed by a Hitachi STA 7200 analyzer or similar piece of equipment under nitrogen flow at the rate of 110 mL/min. The biochar samples are heated for predetermined periods of time, e.g., 20 minutes, at a variety of temperatures between 10° and 950° C. The sample weights are measured at the end of each dwell step and at the beginning and at the end of the experiment. Thermogravimetric analysis of a given sample indicating percentage water in a sample is determined by % mass loss measured between standard temperature and 150 degrees C. Thermogravimetric analysis of a given sample indicating percentage of residual organic compounds is measured by percentage mass loss sustained between 150 degrees C. and 950 degrees C. Thermogravimetric analysis of a given sample indicating percentage of light organic compounds (volatiles) is measured by percentage mass loss sustained between 150 degrees C. and 550 degrees C. Thermogravimetric analysis of a given sample indicating percentage of heavy organic compounds is measured by percentage mass loss sustained between 550 degrees C. and 950 degrees C. FIG. 13 is an example of a Thermogravimetric Analysis (TGA) plot outlining the above explanation and the measure of water, light organics and heavy organics.

As noted above, treatment can remove or neutralize heavy metals, transition metals, sodium and phytotoxic organics, polycyclic aromatic hydrocarbons, volatile organic compounds (VOCs), other phytotoxins, and even dioxins. Thus, by treating the biochar in accordance with the treatment processes set forth and described above, the resulting treated biochar has essentially all, and more preferably all, of their pore surfaces modified by the removal, neutralization or both, of one or more deleterious, harmful, or potentially harmful material that is present in the starting biochar material.

Dioxins may also be removed through the treatment processes of the present invention. Dioxins are released from combustion processes and thus are often found in raw biochar. Dioxins include polychlorinated dibenzo-p-dioxins (PCDDs) (i.e., 75 congeners (10 are specifically toxic)); polychlorinated dibenzofurans (PCDFs) (i.e., 135 congeners (7 are specifically toxic)) and polychlorinated biphenyls (PCBs) (Considered dioxin-like compounds (DLCs)).

Since some dioxins may be carcinogenic even at low levels of exposure over extended periods of time, the FDA views dioxins as a contaminant and has no tolerances or administrative levels in place for dioxins in animal feed. Dioxins in animal feed can cause health problems in the animals themselves. Additionally, the dioxins may accumulate in the fat of food-producing animals and thus consumption of animal derived foods (e.g. meat, eggs, milk) could be a major route of human exposure to dioxins. Thus, if biochar is used in animal applications, where the animals ingest the biochar, the ability to remove dioxins from the raw biochar prior to use is of particular significance.

Results have proven the removal of dioxins from raw biochar by applying the treatment process of the present invention. To demonstrate the removal of dioxins, samples of both raw biochar and biochar, treated within the parameters set forth above, were sent out for testing. The results revealed that the dioxins in the raw biochar were removed through treatment as the dioxins detected in the raw biochar sample were not detected in the treated biochar sample. Below is a chart comparing the test results of measured dioxins in the raw verses the treated biochar.

| Dioxins | Amount Detected in Raw Biochar Sample | Amount Detected in Treated Biochar Sample |
|---|---|---|
| Tetradioxins | 26.4 ng/Kg-dry | Not detectable |
| Pentadioxins | 5.86 ng/Kg-dry | Not detectable |
| Hexadioxins | 8.41 ng/Kg-dry | Not detectable |

A number of different dioxins exist, several of which are known to be toxic or undesirable for human consumption. Despite the test results above, it is possible that any number of dioxins could be present in raw biochar depending on the biomass or where the biomass is grown. It is shown, however, in the above testing, that the treatment process of the present invention can be used to eliminate dioxins present in raw biochar.

Seventeen tetra-octo dioxins and furan congeners are the basis for regulatory compliance. Other dioxins are much less toxic. Dioxins are generally regulated on toxic equivalents (TEQ) and are represented by the sum of values weighted by Toxic Equivalency $$TEQ = \sum [C_i] \times TEF_i \qquad \text{Factor (TEF)}$$

2,3,7,8-TCDD has a TEF of 1 (most toxic). TEQ is measured as ng/kg WHO-PCDD/F-TEQ//kg NDs are also evaluated. Two testing methods are generally used to determine TEQ values: EPA Method 8290 (for research and understanding at low levels (ppt-ppq); and EPA Method 1613B (for regulatory compliance). Both are based on high resolution gas chromatography (HRGC)/high resolution mass spectrometry (HRMS).

The required EU Feed Value is equal to or less than 0.75 ng/kg WHO-PCDD/F-TEQ//kg. Treated biochar, in accordance with the present invention, has shown to have TEQ dioxins less than 0.5 ng/kg WHO-PCDD/F-TEQ//kg, well below the requirement for EU Feed limits of 0.75 ng/kg WHO-PCDD/F-TEQ//kg. As further set forth above, treatment can reduce the amount of detectable dioxins from raw biochar such that the dioxins are not detectible in treated biochar. Two methods are used: EPA Method 8290 (for research and understanding at low levels (ppt-ppq); and EPA Method 1613B (for regulatory compliance). Both are based on high resolution gas chromatography (HRGC)/high resolution mass spectrometry (HRMS).

4. Pore Volume

Generally, a treated biochar sample has greater than 50% by volume of its porosity in macropores (pores greater than 300 nanometers). Further, results indicate that greater than 75% of pores in treated biochar are below 50,000 nanometers. Also, results indicate that greater than 50% by volume of treated biochar porosity are pores in the range of 500 nanometers and 100,000 nanometers. Bacterial sizes are typically 500 nanometers to several thousand nanometers. Bacteria and other microbes have been observed to fit and colonize in the pores of treated biochar, thus supporting the pore size test results.

Macropore volume is determined by mercury porosimetry, which measures the meso and/or macro porosity by applying pressure to a sample immersed in mercury at a pressure calibrated for the minimum pore diameter to be measured (for macroporosity this is 300 nanometers). This method can be used to measure pores in the range of 3 nm to 360,000 nm. Total volume of pores per volumetric unit of substance is measured using gas expansion method.

Depending upon the biomass from which the biochar is derived, mercury porosimetry testing has shown that washing under differential pressure, using the processes described above, can increase the number of both the smallest and larger pores in certain biochar (e.g., pine) and can increase the number of usable smaller pores. Treatment of biochar using either vacuum or surfactant does alter the percentage of total usable pores between 500 to 100,000 nanometers and further has varying impact on pores less than 50,000 nanometers and less than 10,000 nanometers.

Figure 14:
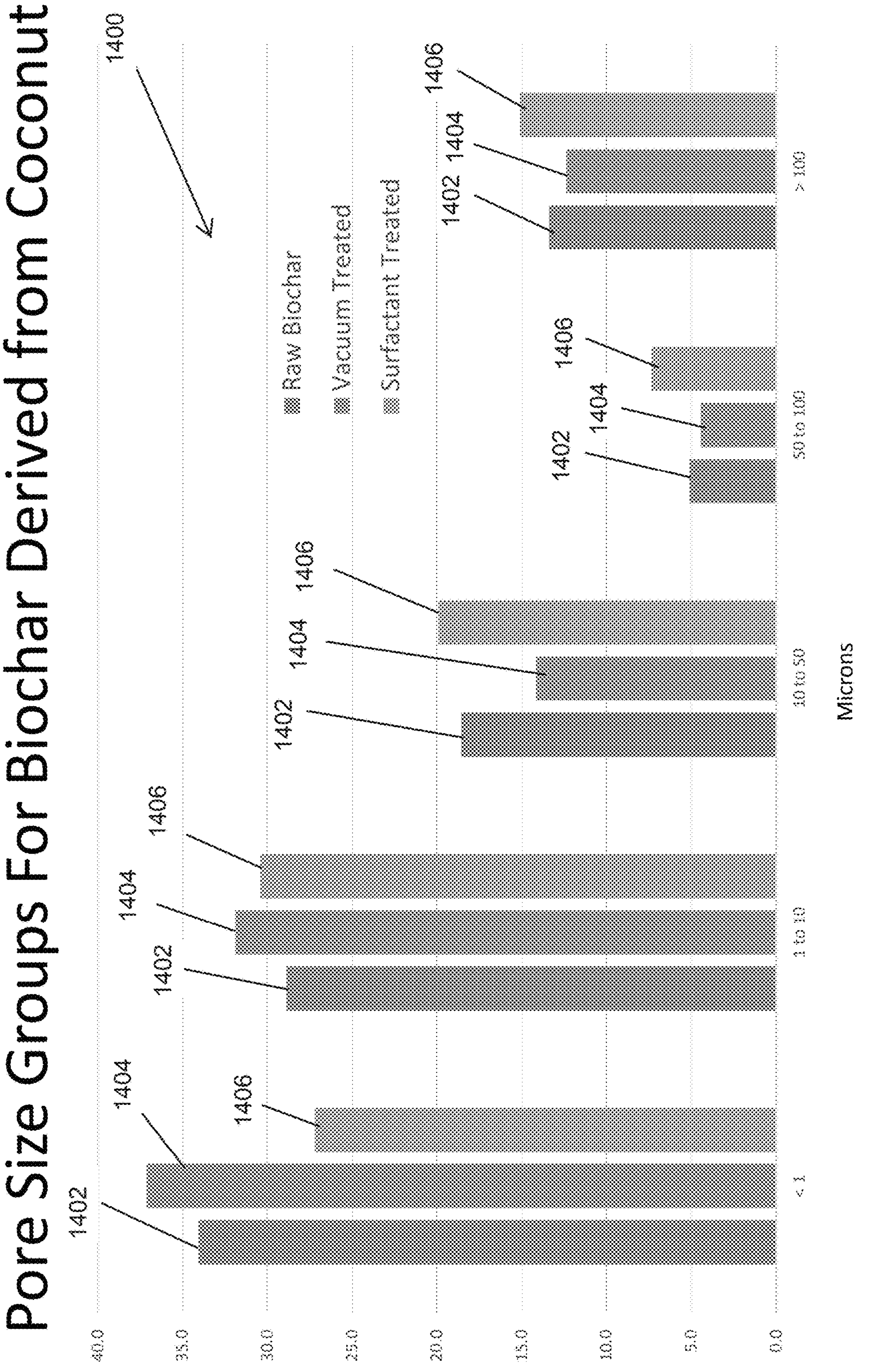
FIG. 14 is a chart showing the impact of treatment on pore sizes of biochar derived from coconut.

FIG. 14 is a chart 1400 showing the impact of treatment on pores sizes of biochar derived from coconut. The majority of the coconut based biochar pores are less than 10 microns. Many are less than 1 micron. Vacuum processing of the biochar results in small reduction of 10 to 50 micron pores, with increase of smaller pores on vacuum processing. The mercury porosimetry results of the raw biochar are represented by 1402 (first column in the group of three). The vacuum treated biochar is represented by 1404 (second column in the group of three) and the surfactant treated biochar is 1406 (third column in the group of three).

Figure 15:
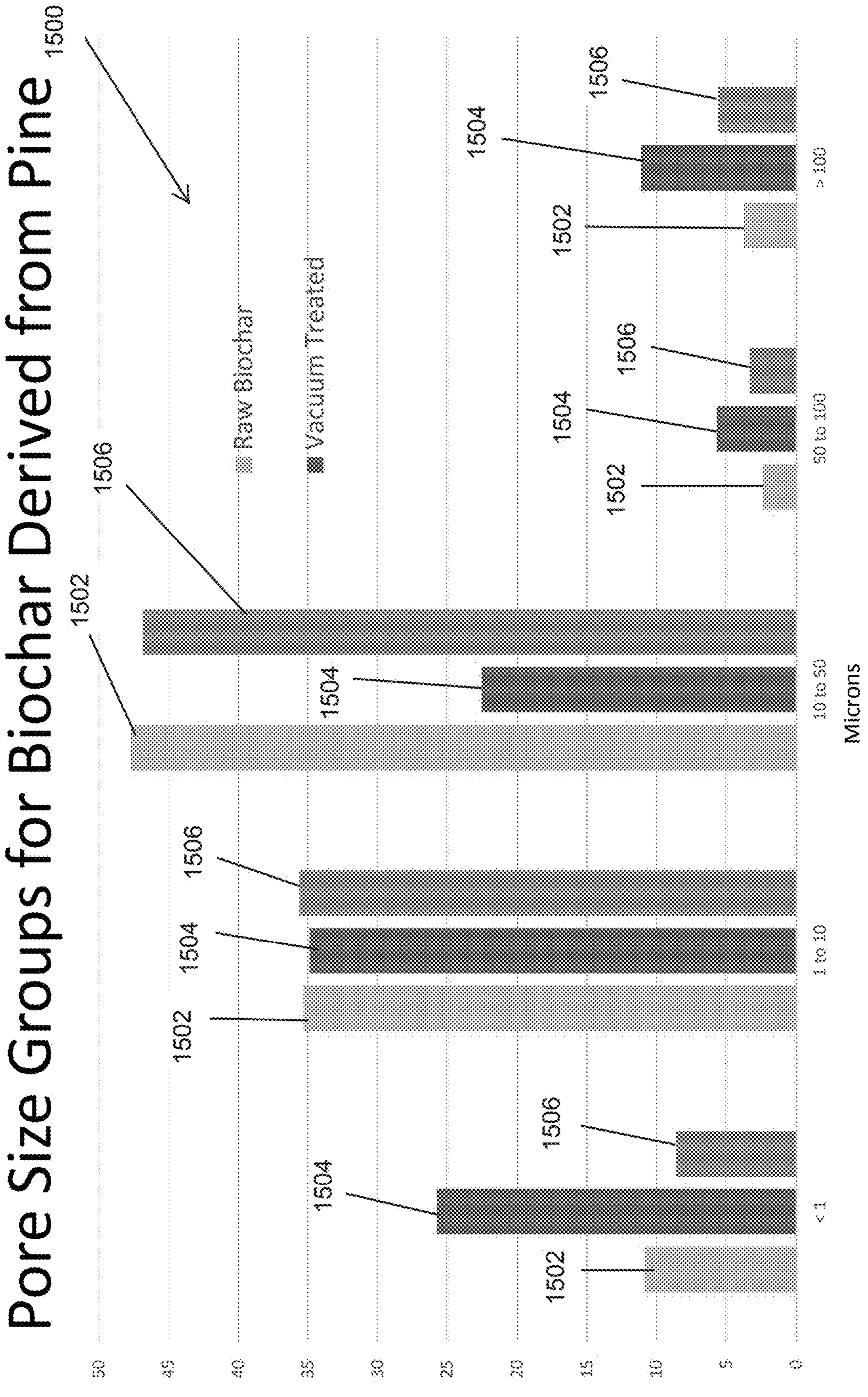
FIG. 15 is a chart showing the impact of treatment on pore sizes of biochar derived from pine.

FIG. 15 is a chart 1500 showing the impact of treatment on pores sizes of biochar derived from pine. The majority of the pine based biochar pores are 1 to 50 microns, which is a good range for micro-biologicals. Vacuum processing results in significant reduction of the 10 to 50 micron pores, with an increase of smallest and largest pores. The mercury porosimetry results of the raw biochar are represented by 1502 (first column in the group of three). The vacuum treated biochar is represented by 1504 (second column in the group of three) and the surfactant treated biochar is 3006 (third column in the group of three).

5. Electrical Conductivity

The electrical conductivity (EC) of a solid material-water mixture indicates the amount of salts present in the solid material. Salts are essential for plant growth. The EC measurement detects the amount of cations or anions in solution; the greater the amount of ions, the greater the EC. The ions generally associated with salinity are $Ca^{2+}$, $Mg^{2+}$, $K^+$, $Na^+$, $H^+$, $NO_3^-$, $SO_4^{2-}$, $Cl^-$, $HCO_3^-$, $OH^-$. Electrical conductivity testing of biochar was done following the method outlined in the USDA's Soil Quality Test Kit Guide and using a conventional EC meter. The biochar sample is mixed with DI water in a 1:1 biochar to water ratio on a volume basis. After thorough mixing, the EC (dS/m) is measured while the biochar particles are still suspended in solution. Treatment, as outlined in this disclosure can be used to adjust the ions in the char. Testing of treated biochar shows its EC is generally greater than 0.2 dS/m and sometimes greater than 0.5 dS/m.

6. Cation Exchange Capacity

One method for cation exchange capacity ("CEC") determination is the use of ammonium acetate buffered at pH 7.0 (see Schollenberger, C. J. and Dreibelbis, E R. 1930, *Analytical methods in base-exchange investigations on soils*, Soil Science, 30, 161-173). The material is saturated with 1M ammonium acetate, ($NH_4OAc$), followed by the release of the $NH_4^+$ ions and its measurement in meq/100 g (milliequivalents of charge per 100 g of dry soil) or cmolc/kg (centimoles of charge per kilogram of dry soil). Instead of ammonium acetate another method uses barium chloride according to Mehlich, 1938, *Use of triethanolamine acetate-barium hydroxide buffer for the determination of some base exchange properties and lime requirement of soil*, Soil Sci. Soc. Am. Proc. 29:374-378. 0.1 M $BaCl_2$ is used to saturate the exchange sites followed by replacement with either $MgSO_4$ or $MgCl_2$.

Indirect methods for CEC calculation involves the estimation of extracted $Ca_2^+$, $Mg_2^+$, $K^+$, and $Na^+$ in a standard soil test using Mehlich 3 and accounting for the exchangeable acidity (sum of $H^+$, $Al_3^+$, $Mn_2^+$, and $Fe_2^+$) if the pH is below 6.0 (see Mehlich, A. 1984, *Mehlich-3 soil test extractant: a modification of Mehlich-2 extractant*, Commun. Soil Sci. Plant Anal. 15(12): 1409-1416). When treated using the above methods, including but not limited by washing under a vacuum, treated biochars generally have a CEC greater than 5 millieq/l and some even have a CEC greater than 25 (millieq/l). To some extent, treatment can be used to adjust the CEC of a char.

7. Anion Exchange Capacity

Similar to CEC measurements, anion exchange capacity ("AEC") may be calculated directly or indirectly-saturated paste extraction of exchangeable anions, $Cl^-$, $NO_3^-$, $SO_4^{-2}$, and $PO_4^{3-}$ to calculate anion sum or the use of potassium bromide to saturate anions sites at different pHs and repeated washings with calcium chloride and final measurement of bromide (see Rhoades, J. D. 1982, *Soluble salts*, p. 167-179. In: A. L. Page et al. (ed.) Methods of soil analysis: Part 2: Chemical and microbiological properties; and Michael Lawrinenkoa and David A. Laird, 2015, *Anion exchange capacity of biochar*, Green Chem., 2015, 17, 4628-4636). When treated using the above methods, including but not limited by washing under a vacuum, treated biochars generally have an AEC greater than 5 millieq/l and some even have an AEC greater than 20 (millieq/l). To some extent, treatment can be used to adjust the CEC of a char.

8. Hydrophilicity/Hydrophobicity

The ability to control the hydrophilicity of the pores provides the ability to load the biochar particles with larger volumes of inoculant. The more hydrophilic the more the biochars can accept inoculant or infiltrate. Tests show that biochar treated in accordance with the above processes, using either vacuum or surfactant treatment processes increase the hydrophilicity of raw biochar. Two tests may be used to test the hydrophobicity/hydrophilicity of biochar: (i) the Molarity of Ethanol Drop ("MED") Test; and (ii) the Infiltrometer Test.

The MED test was originally developed by Doerr in 1998 and later modified by other researchers for various materials. The MED test is a timed penetration test that is noted to work well with biochar soil mixtures. For 100% biochar, penetration time of different mixtures of ethanol/water are noted to work better. Ethanol/Water mixtures verses surface tension dynes were correlated to determine whether treated biochar has increased hydrophilicity over raw biochar. Seven mixtures of ethanol and deionized water were used with a sorption time of 3 seconds on the biochar.

Seven solutions of deionized ("DI") water with the following respective percentages of ethanol: 3, 5, 11, 13, 18, 24 and 36, were made for testing. The test starts with a mixture having no DI. If the solution is soaked into the biochar in 3 seconds for the respective solution, it receives the corresponding Hydrophobicity Index value below.

| Ethanol % | Hydrophobicity Index | |
|---|---|---|
| 0: DI Water | 0 | Very Hydrophilic |
| 3% | 1 | |
| 5% | 2 | |
| 11% | 3 | |
| 13% | 4 | |
| 18% | 5 | |
| 24% | 6 | |
| 36% | 7 | Strongly hydrophobic |

To start the test the biochar ("material/substrate") is placed in convenient open container prepared for testing. Typically, materials to be tested are dried 110° C. overnight and cooled to room temperature. The test starts with a deionized water solution having no ethanol. Multiple drips of the solution are then laid onto the substrate surface from low height. If drops soak in less than 3 seconds, test records substrate as "0". If drops take longer than 3 seconds or don't soak in, go to test solution 1. Then, using test solution 1, multiple drops from dropper are laid onto the surface from low height. If drops soak into the substrate in less than 3 seconds, test records material as "1". If drops take longer than 3 seconds, or don't soak in, go to test solution 2. Then, using test solution 2, multiple drops from dropper laid onto the surface from low height. If drops soak into the substrate in less than 3 seconds, test records material as "2". If drops take longer than 3 seconds, or don't soak in, go to test solution 3. Then, using test solution 3, multiple drops from dropper laid onto the surface from low height. If drops soak into the substrate in less than 3 seconds, test records material as "3". If drops take longer than 3 seconds, or don't soak in, go to solution 4.

The process above is repeated, testing progressively higher numbered MED solutions until the tester finds the solution that soaks into the substrate in 3 seconds or less. The substrate is recorded as having that hydrophobicity index number that correlates to the solution number assigned to it (as set forth in the chart above).

Example test results using the MED test method is illustrated below.

| MATERIAL | HYDROPHOBICITY INDEX |
|---|---|
| Raw Biochars | 3 to 5 |
| Treated Biochars | 1 to 3 |

Another way to measure and confirm that treatment decreases hydrophobicity and increases hydrophilicity is by using a mini disk infiltrometer. For this test procedure, the bubble chamber of the infiltrometer is filled three quarters full with tap water for both water and ethanol sorptivity tests. Deionized or distilled water is not used. Once the upper chamber is full, the infiltrometer is inverted and the water reservoir on the reserve is filled with 80 mL. The infiltrometer is carefully set on the position of the end of the mariotte tube with respect to the porous disk to ensure a zero suction offset while the tube bubbles. If this dimension is changed accidentally, the end of the mariotte tube should be reset to 6 mm from the end of the plastic water reservoir tube. The bottom elastomer is then replaced, making sure the porous disk is firmly in place. If the infiltrometer is held vertically using a stand and clamp, no water should leak out.

The suction rate of 1 cm is set for all samples. If the surface of the sample is not smooth, a thin layer of fine biochar can be applied to the area directly underneath the infiltrometer stainless steel disk. This ensures good contact between the samples and the infiltrometer. Readings are then taken at 1 min intervals for both water and ethanol sorptivity test. To be accurate, 20 mL water or 95% ethanol needs to be infiltrated into the samples. Record time and water/ethanol volumes at the times are recorded.

The data is then processed to determine the results. The data is processed by the input of the volume levels and time to the corresponding volume column. The following equation is used to calculate the hydrophobicity index of R $$I = at + b\sqrt{t}$$

$$a: \text{Infiltration Rate, cm/s}$$

$$b: \text{Sorptivity, cm/s}^{1/2}$$

$$R = 1.95 * \frac{b_{ethanol}}{b_{water}}$$

Figure 16:
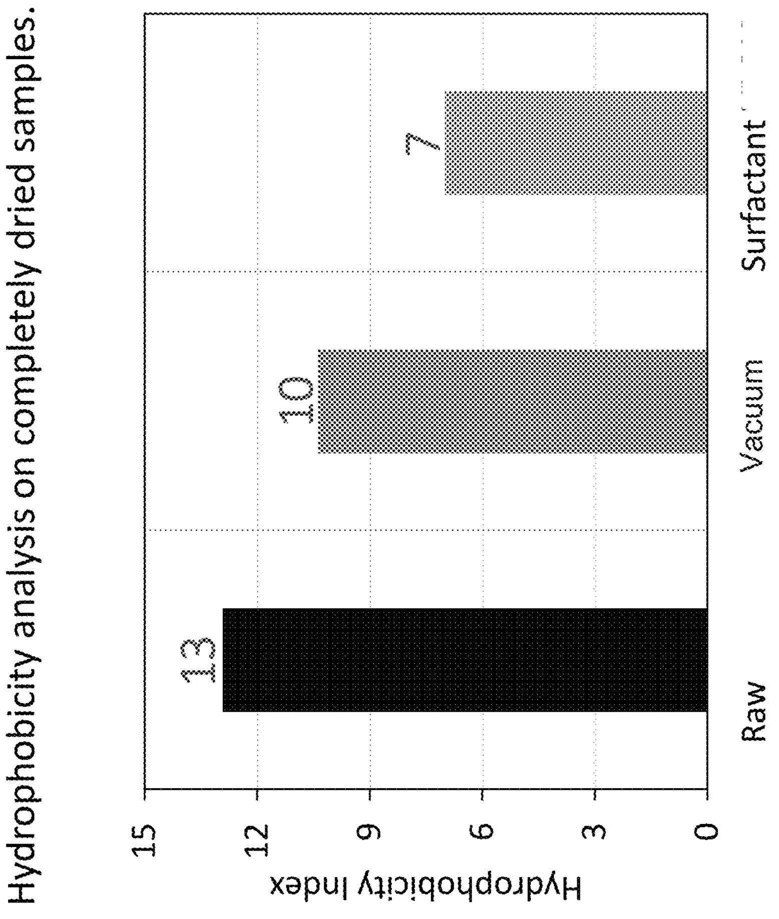
FIG. 16 is a chart showing the measured hydrophobicity index raw biochar, vacuum treated biochar and surfactant treated biochar.

FIG. 16 illustrates one example of the results of a hydrophobicity test performed on raw biochar, vacuum treated biochar and surfactant treated biochar. As illustrated, both the vacuum treated and surfactant treated biochar are more hydrophilic than the raw biochar based upon the lower Index rating. In accordance with the test data in FIG. 16, the hydrophobicity of raw biochar was reduced 23% by vacuum processing and 46% by surfactant addition.

As an example, raw biochar and treated biochar were tested with ethanol and water, five times for each. The results below show that the hydrophobicity index of the treated biochar is lower than the raw biochar. Thus, tests demonstrate that treating the biochar, using the methods set forth above, make the biochar less hydrophobic and more hydrophilic.

| MATERIAL | HYDROPHOBICITY INDEX |
|---|---|
| Dried Raw Biochar | 12.9 |
| Dried Vacuum Treated Biochar | 10.4 |
| Dried Surfactant Treated Biochar | 7.0 |

-continued

| MATERIAL | HYDROPHOBICITY INDEX |
|---|---|
| As Is Raw Biochar | 5.8 |
| As Is Vacuum Treated Biochar | 2.9 |

Further, through the treatment processes of the present invention, the biochar can also be infused with soil enhancing agents. By infusing liquid into the pore structure through the application of positive or negative pressure and/or a surfactant, alone or in combination, provides the ability to impregnate the macropores of the biochar with soil enhancing solutions and solids. The soil enhancing agent may include, but not be limited to, any of the following: water, water solutions of salts, inorganic and organic liquids of different polarities, liquid organic compounds or combinations of organic compounds and solvents, mineral and organic oils, slurries and suspensions, supercritical liquids, fertilizers, plant growth promoting rhizobacteria, free-living and nodule-forming nitrogen fixing bacteria, organic decomposers, nitrifying bacteria, phosphate solubilizing bacteria, biocontrol agents, bioremediation agents, saprotrophic fungi, ectomycorrhizae and endomycorrhizae, among others.

9. Impregnation and/or Inoculation with Infiltrates or Additives

In addition to mitigating or removing deleterious pore surface properties, by treating the pores of the biochar through a forced, assisted, accelerate or rapid infiltration process, such as those described above, the pore surface properties of the biochar can be enhanced. Such treatment processes may also permit subsequent processing, may modify the pore surface to provide predetermined properties to the biochar, and/or provide combinations and variations of these effects. For example, it may be desirable or otherwise advantageous to coat substantially all, or all of the biochar macropore and mesopore surfaces with a surface modifying agent or treatment to provide a predetermined feature to the biochar, e.g., surface charge and charge density, surface species and distribution, targeted nutrient addition, magnetic modifications, root growth facilitator, and water absorptivity and water retention properties.

By infusing liquids into the pores of biochar, it has been discovered that additives infused within the pores of the biochar provide a time release effect or steady flow of some beneficial substances to the environment, e.g. root zones of the plants, and also can improve and provide a more beneficial environment for microbes which may reside or take up residence within the pores of the biochar. In particular, additive infused biochars placed in the soil prior to or after planting can dramatically reduce the need for high frequency application of additives, minimize losses caused by leaching and runoff and/or reduce or eliminate the need for controlled release fertilizers. They can also be exceptionally beneficial in animal feed applications by providing an effective delivery mechanism for beneficial nutrients, pharmaceuticals, enzymes, microbes, or other substances.

For purposes of this application, "infusion" of a liquid or liquid solution into the pores of the biochar means the introduction of the liquid or liquid solution into the pores of the biochar by a means other than solely contacting the liquid or solution with the biochar, e.g., submersion. The infusion process, as described in this application in connection with the present invention, includes a mechanical, chemical or physical process that facilitates or assist with the penetration of liquid or solution into the pores of the biochar, which process may include, but not be limited to, positive and negative pressure changes, such as vacuum infusion, surfactant infusion, or infusion by movement of the liquid and/or biochar (e.g., centrifugal force and/or ultrasonic waves) or other method that facilitates, assists, forces or accelerates the liquid or solution into the pores of the biochar.

Figure 17:
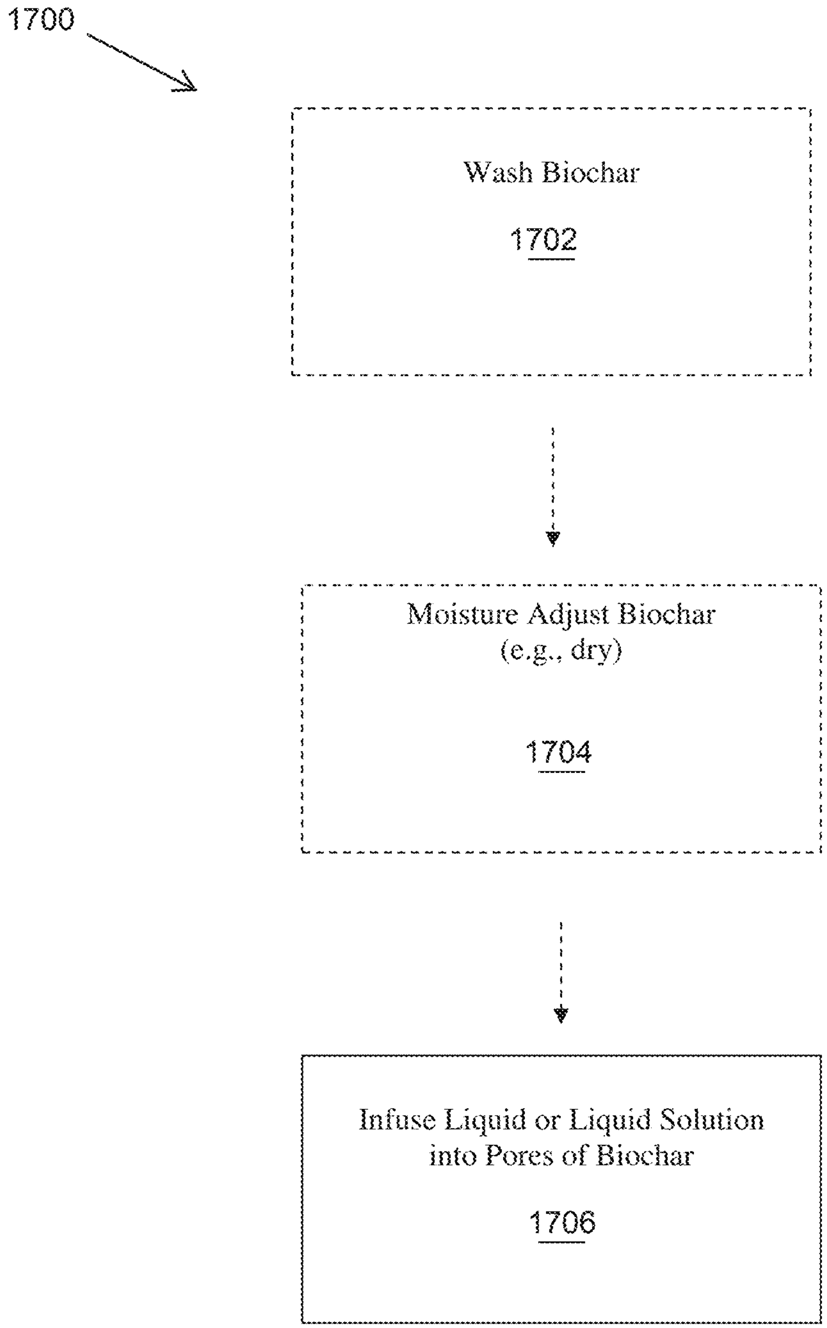
FIG. 17 is a flow diagram showing one example of a method for infusing biochar.

Prior to infusing the biochar, the biochar, as described in detail above, may be washed and/or moisture adjusted. FIG. 17 is a flow diagram 1700 of one example of a method for infusing biochar with an additive. Optionally, the biochar may first be washed or treated at step 1702, the wash may adjust the pH of the biochar, as described in more detail above, or may be used to remove elemental ash and other harmful organics that may be unsuitable for the desired infused additive. Optionally, the moisture content of the biochar may then be adjusted by drying the biochar at step 1704, also as described in further detail above, prior to infusion of the additive or inoculant at step 1706.

In summary, the infusion process may be performed with or without any washing, prior pH adjustment or moisture content adjustment. Optionally, the infusion process may be performed with the wash and/or the moisture adjustment step. All the processes may be completed alone or in the conjunction with one or more of the others.

Through the above process of infusing the additive into the pores of the biochar, the pores of the biochar may be filled by 25%, up to 100%, with an additive solution, as compared to 1-20% when the biochar is only submerged in the solution or washed with the solution for a period of less than twelve hours. Higher percentages may be achieved by washing and/or drying the pores of the biochar prior to infusion.

Data have been gathered from research conducted comparing the results of soaking or immersion of biochar in liquid versus vacuum impregnation of liquid into biochar. These data support the conclusion that vacuum impregnation provides greater benefits than simple soaking and results in a higher percentage volume of moisture on the surface, interstitially and in the pores of the biochar.

Figure 18:
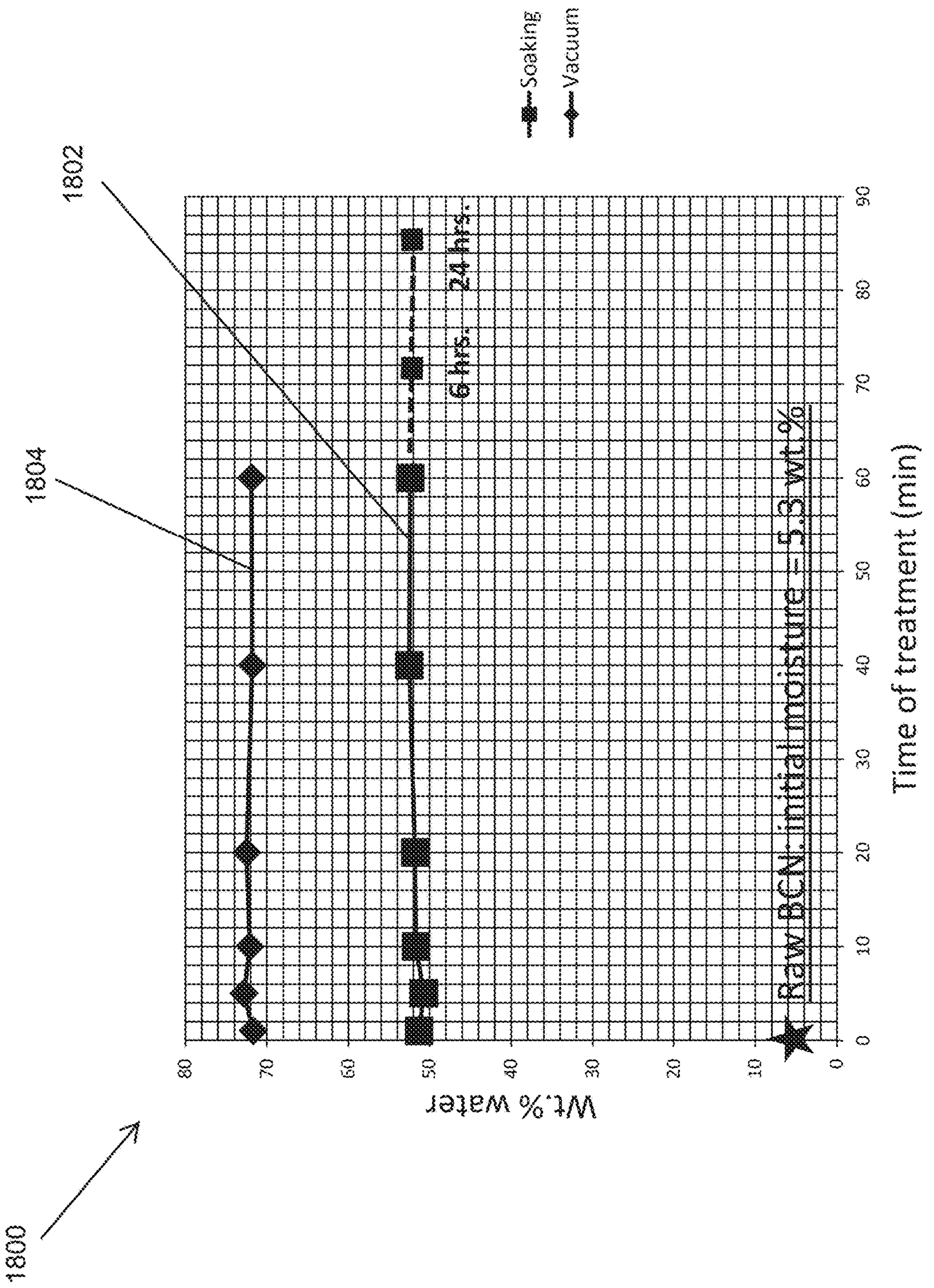
FIG. 18 illustrates the improved liquid content of biochar using vacuum impregnation as against soaking the biochar in liquid.

In one experiment, equal quantities of pine biochar were mixed with equal quantities of water, the first in a beaker, the second in a vacuum flask. The mixture in the beaker was continuously stirred for up to 24 hours, then samples of the suspended solid were taken, drained and analyzed for moisture content. The mixture in the vacuum flask was connected to a vacuum pump and negative pressure of 15" was applied. Samples of the treated solid were taken, drained and analyzed for moisture content. FIG. 18 is a chart illustrating the results of the experiment. The lower graph 1802 of the chart, which shows the results of soaking over time, shows a Wt. % of water of approximately 52%. The upper graph 1804 of the chart, which shows the results of vacuum impregnation over time, shows a Wt. % of water of approximately 72%.

Figure 19A:
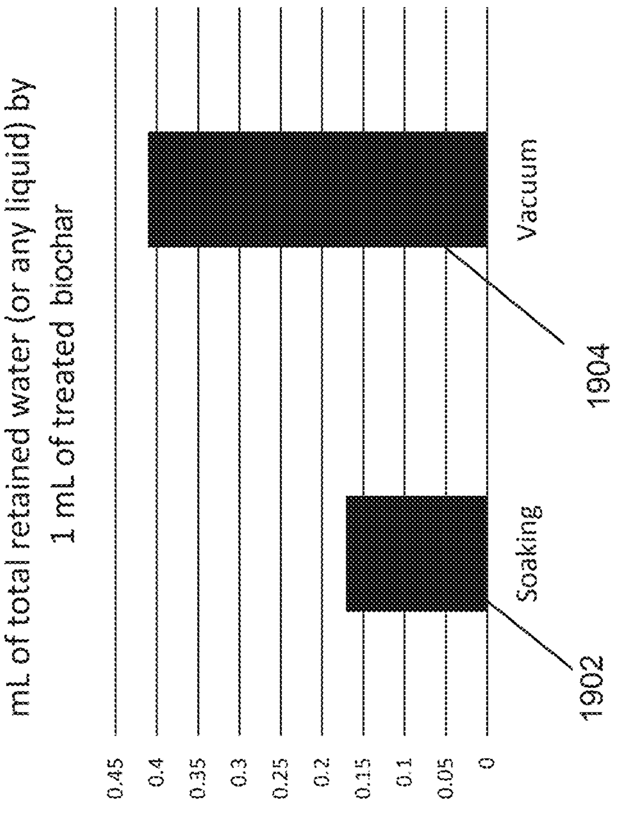
FIG. 19*a* is a chart comparing total retained water of treated biochar after soaking and after vacuum impregnation.
Figure 19B:
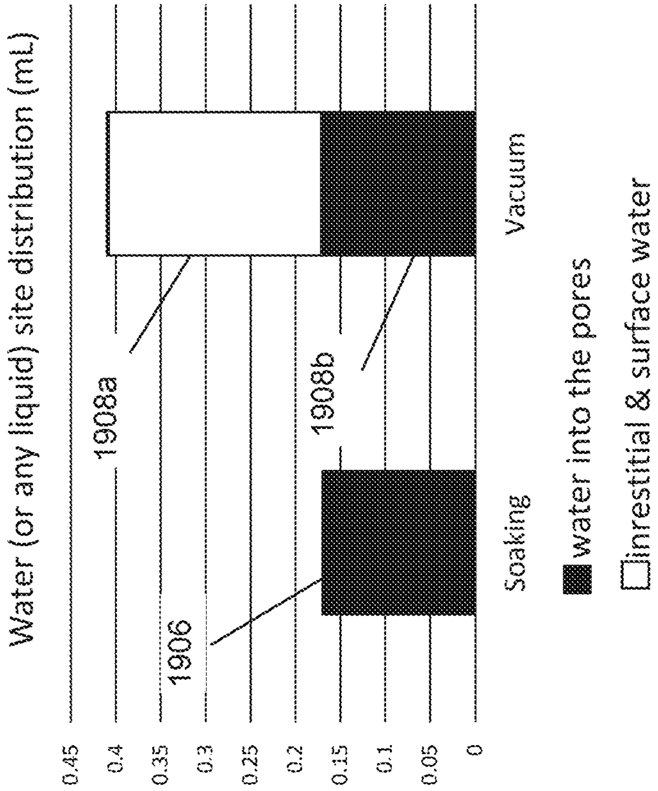
FIG. 19*b* is a chart comparing water on the surface, interstitially and in the pores of biochar after soaking and after vacuum impregnation.

FIGS. **19*a* and 19*b* show two charts that further illustrate that the total water and/or any other liquid content in processed biochar can be significantly increased using vacuum impregnation instead of soaking. FIG. 19*a* compares the mL of total water or other liquid by retained by 1 mL of treated biochar. The graph 1902 shows that approximately 0.17 mL of water or other liquid are retained through soaking, while the graph 1904 shows that approximately 0.42 mL of water or other liquid are retained as a result of vacuum impregnation. FIG. 19*b* shows that the retained water of a biochar subjected to soaking consists entirely of surface and interstitial water 1906, while the retained water of a biochar subjected to vacuum impregnation consists not only of surface and interstitial water 1908***a*, but also water impregnated in the pores of the biochar 1908*b*.

Figure 20:
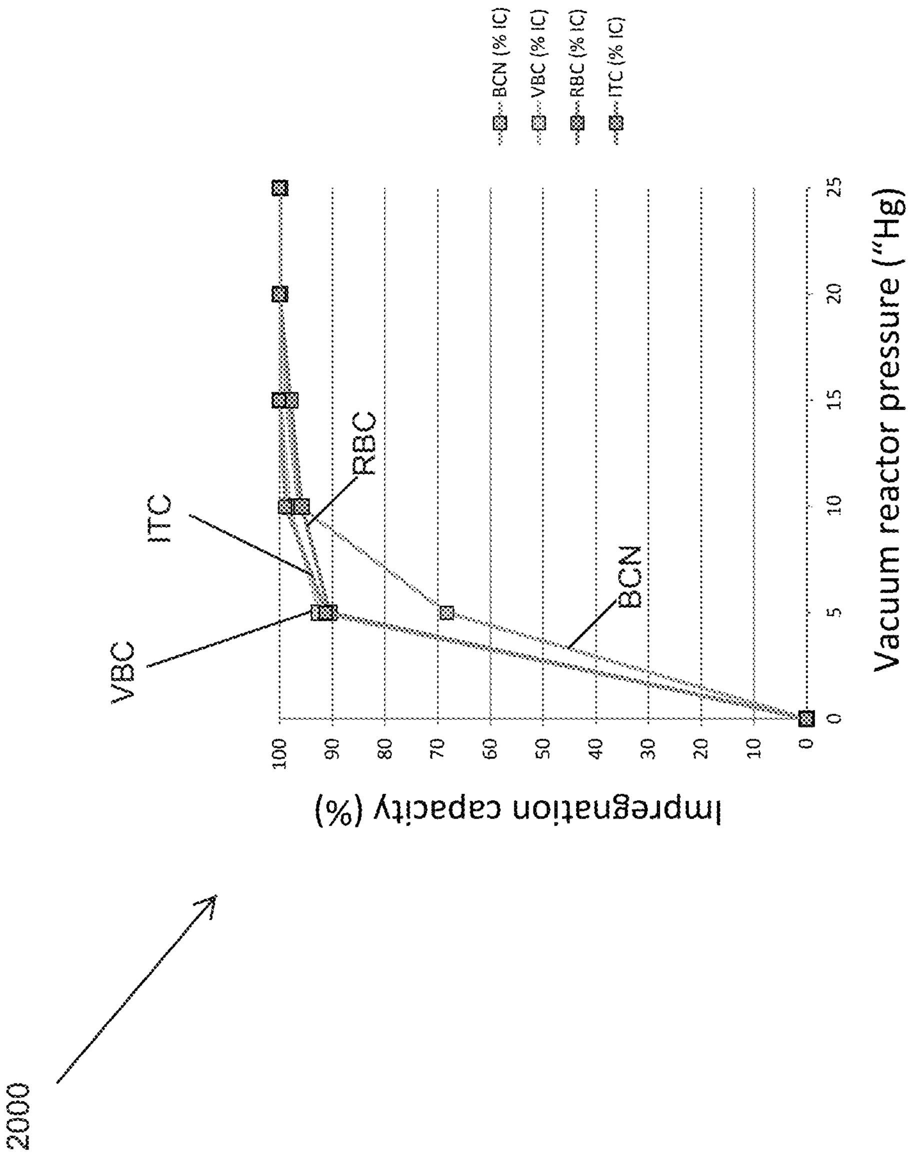
FIG. 20 illustrates how the amount of water or other liquid in the pores of vacuum processed biochars can be increased varied based upon the applied pressure.

In addition, as illustrated by FIG. 20, the amount of moisture content impregnated into the pores of vacuum processed biochars by varying the applied (negative) pressure during the treatment process. The graphs of four different biochars all show how the liquid content of the pours of each of them increase to 100% as the vacuum is increased.

The pores may be substantially filled or completely filled with additives to provide enhanced performance features to the biochar, such as increased plant growth, nutrient delivery, water retention, nutrient retention, disadvantageous species control, e.g., weeds, disease causing bacteria, insects, volunteer crops, etc. By infusing liquid deep into the pore structure through the application of positive or negative pressure, surfactant and/or ultrasonic waves, alone or in combination, provides the ability to impregnate the mesopores and macropores of the biochar with additives, that include, but are not limited to, soil enhancing solutions and solids. It should be noted that using these infusion techniques allows for impregnating the pores with additives that are more fragile. For example, since heating is not a requirement for these infusion techniques, microbes, chemicals, or compounds can be infused without risk of destroying the microbes or changing chemicals or compounds due to high temperatures. Also the process can be done at low temperatures to infuse chemicals that have low boiling points to keep them a liquid.

The additive may be a soil enhancing agent that includes, but is not be limited to, any of the following: water, water solutions of salts, inorganic and organic liquids of different polarities, liquid organic compounds or combinations of organic compounds and solvents, mineral and organic oils, slurries and suspensions, supercritical liquids, fertilizers, PGPB (including plant growth promoting rhizobacteria, free-living and nodule-forming nitrogen fixing bacteria, organic decomposers, nitrifying bacteria, and phosphate solubilizing bacteria), enzymes, biocontrol agents, bioremediation agents, saprotrophic fungi, ectomycorrhizae and endomycorrhizae, among others.

Fertilizers that may be infused into the biochar include, but are not limited to, the following sources of nitrogen, phosphorous, and potassium: urea, ammonium nitrate, calcium nitrate, sulfur, ammonium sulfate, monoammonium phosphate, ammonium polyphosphate, potassium sulfate, or potassium chloride.

Similar beneficial results are expected from other additives, such as: bio pesticides; herbicides; insecticides; nematicides; plant hormones; plant pheromones; organic or inorganic fungicides; algicides; antifouling agents; antimicrobials; attractants; biocides, disinfectants and sanitizers; miticides; microbial pesticides; molluscicides; bacteriacides; fumigants; ovicides; repellents; rodenticides, defoliants, desiccants; insect growth regulators; plant growth regulators; beneficial microbes; and, microbial nutrients or secondary signal activators, that may also be added to the biochar in a similar manner as a fertilizer. Additionally, beneficial macro- and micro-nutrients such as, calcium, magnesium, sulfur, boron, zinc, iron, manganese, molybdenum, copper and chloride may also be infused into the biochar in the form of a water solution or other solvent solution.

Examples of compounds, in addition to fertilizer, that may be infused into the pores of the biochar include, but are not limited to: phytohormones, such as, abscisic acid (ABA), auxins, cytokinins, gibberellins, brassinosteroies, salicylic acid, jasmonates, planet peptide hormones, polyamines, karrikins, strigolactones; 2,1,3-Benzothiadiazole (BTH), an inducer of systemic acquired resistance that confers broad spectrum disease resistance (including soil borne pathogens); signaling agents similar to BTH in mechanism or structure that protects against a broad range or specific plant pathogens; EPSPS inhibitors; synthetic auxins; photosystem I inhibitors photosystem II inhibitors; and HPPD inhibitors.

In one example, a 1000 ppm $NO_3^-$ N fertilizer solution is infused into the pores of the biochar. As discussed above, the method to infuse biochar with the fertilizer solution may be accomplished generally by placing the biochar in a vacuum infiltration tank or other sealable mixing vessel, chamber or tank. When using vacuum infiltration, a vacuum may be applied to the biochar and then the solution may be introduced into the tank. Alternatively, the solution and biochar may both be introduced into the tank and, once introduced, a vacuum is applied. Based upon the determined total pore volume of the biochar or the incipient wetness, the amount of solution to introduce into the tank necessary to fill the pore of the biochar can be determined. When infused in this manner, significantly more nutrients can be held in a given quantity of biochar versus direct contact of the biochar with the nutrients alone.

When using a surfactant, the biochar and additive solution may be added to a tank along with 0.01-20% of surfactant, but more preferably 1-5% of surfactant by volume of fertilizer solution. The surfactant or detergent aids in the penetration of the wash solution into the pores of the biochar. The same or similar equipment used in the vacuum infiltration process can be used in the surfactant treatment process. Although it is not necessary to apply a vacuum in the surfactant treatment process, the vacuum infiltration tank or any other mixing vessel, chamber or tank can be used. Again, while it is not necessary to apply a vacuum, a vacuum may be applied or the pressure in the vessel may be changed. Further, the surfactant can be added with or without heat or cooling either of the infiltrate, the biochar, the vessel itself, or any combination of the three.

The utility of infusing the biochar with an additive is that the pores in biochar create a protective "medium" for carrying said additive to the environment. As an example when the additive is a fertilizer the nutrient infused biochar provides a more constant supply of available nutrients to the soil and plants and continues to act beneficially, potentially sorbing more nutrients or nutrients in solution even after introduction to the soil. By infusing the nutrients in the pores of the biochar, immediate oversaturation of the soil with the nutrients is prevented and a time released effect is provided. This effect is illustrated in connection with FIGS. 18 and 19 below. As demonstrated in connection with FIGS. 18 & 19 below, biochars having pores infused with additives, using the infusion methods described above, have been shown to increase nutrient retention, increase crop yields and provide a steadier flow of fertilizer to the root zones of the plants.

Figure 21:
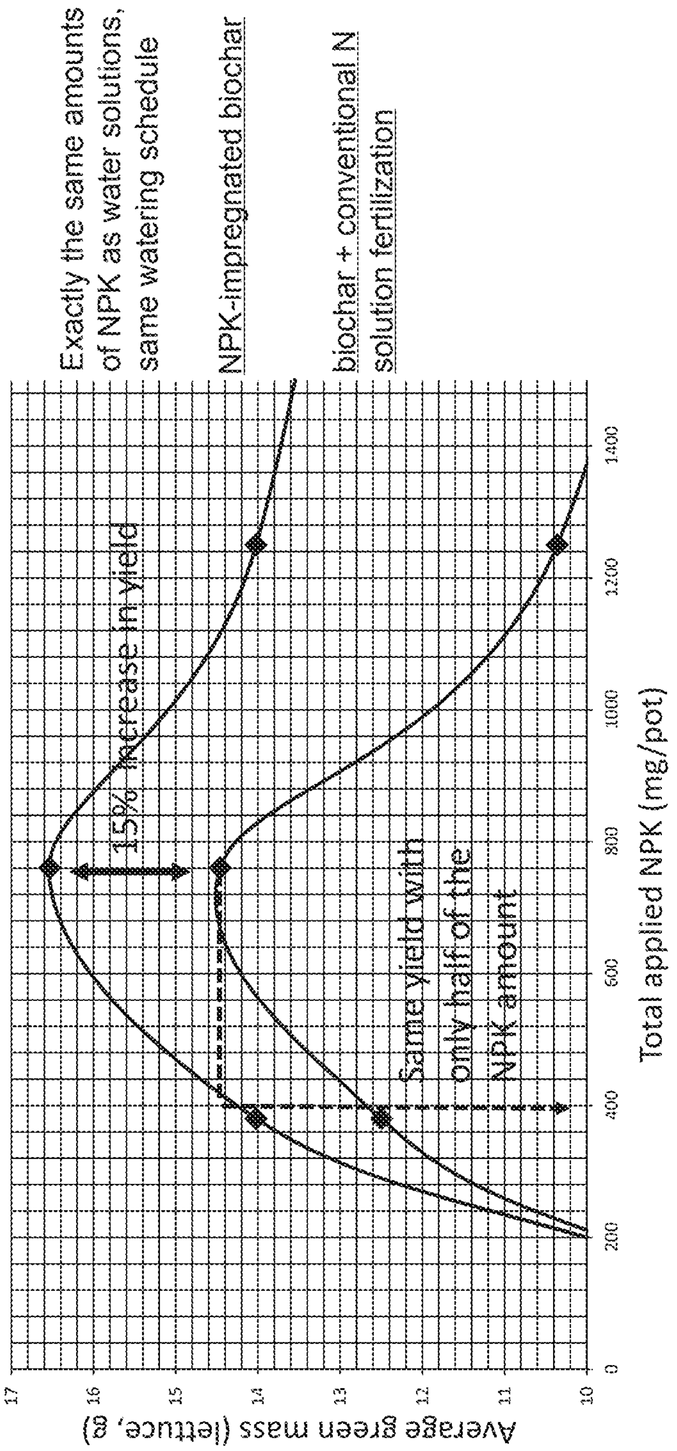
FIG. 21 illustrates the effects of NPK impregnation of biochar on lettuce yield.

FIG. 21 is a chart showing improved mass yield in lettuce with fertilizer infused biochar using vacuum impregnation. FIG. 21 compares the mass yield results of lettuce grown in different environments. One set of data measurements represents lettuce grown in soil over a certain set time period with certain, predetermined amounts of fertilizer infused into the biochar. A second set of data represents lettuce grown in soil over a certain set period of time with the same amount of unimpregnated biochar added at the beginning of the trial and certain predetermined amounts of NPK solution added to the soil over time. Growth comparisons were made between the same amount of fertilizer solution infused into the biochar as added directly to the soil, using the same watering schedule. As illustrated, the test results demonstrated a 15% yield increase in growth when infusing approximately 750 mg/pot of NPK into the biochar than when applying it directly to the soil. Similarly, the same mass yield of lettuce is achieved at 400 mg NPK/pot with infused biochar than at 750 mg/pot when adding the fertilizer solution directly to the soil.

Figure 22:
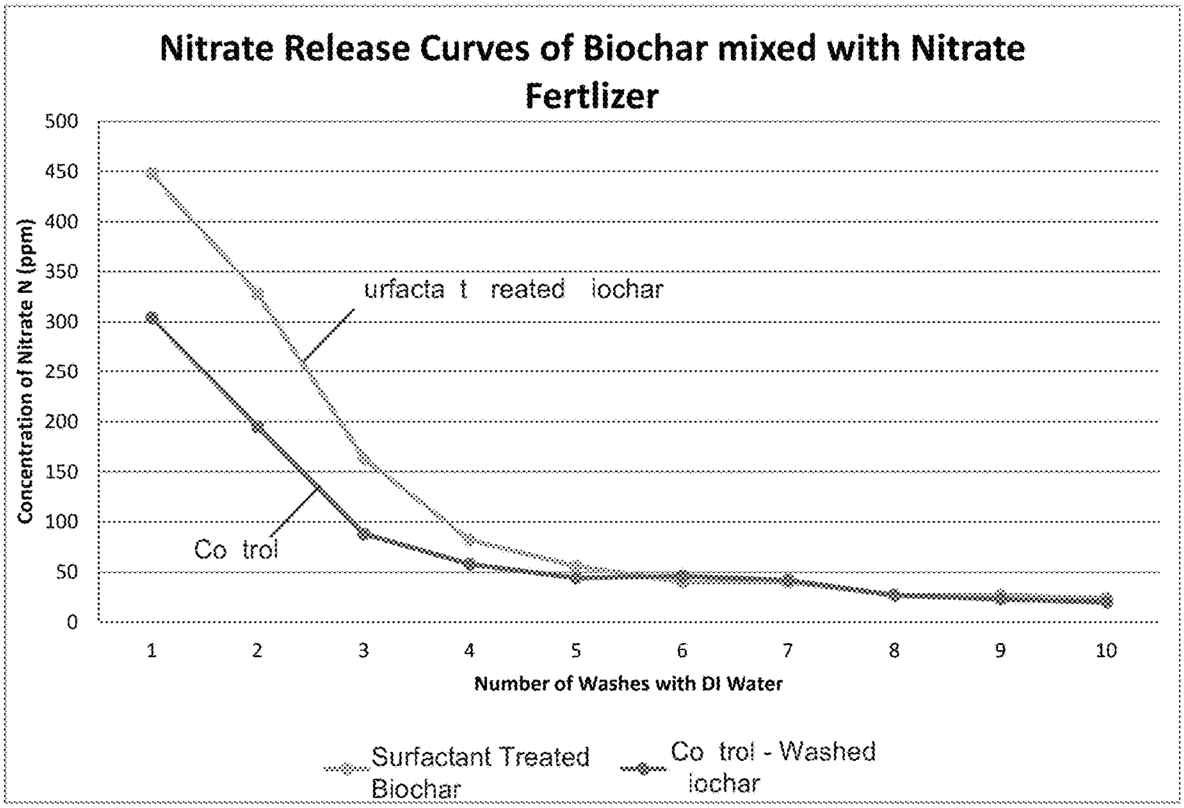
FIG. 22 is a chart showing nitrate release curves of treated biochars infused with nitrate fertilizer.

FIG. 22 is a chart illustrating the concentration of nitrate (N) found in distilled water after washing differentially treated biochar. In the illustrated example, two biochar samples (500 ml each) mixed with 1000 ppm $NO_3^-$ N fertilizer solution were washed with distilled water. The resulting wash was then tested for the presence of nitrate (N), measured in ppm. In one sample, the biochar was submerged in and mixed with the nutrient solution. In the other example, the biochar was mixed or washed with a nutrient solution augmented with 1% surfactant by volume (i.e., 1 ml of surfactant per 100 ml of fertilizer solution) in a tumbler. In both examples, the biochar was not dried completely before infusion with the $NO_3^-$ N fertilizer solution, but used as received with a moisture content of approximately 10-15%. In both examples, the biochar was mixed with solution and/or surfactant (in the case of a second sample) with a bench scale tumbler, rotating the drum for four (4) minutes without vacuum. The results demonstrate that the biochar treated with the 1% surfactant increases the efficiency of infiltrating nitrate fertilizer into biochar and then demonstrates the release of the nutrient over time. To yield the above data, the test was repeated six times for each treatment sample, with 10 washes for each sample per repeat test.

The above are only a few examples of how additive infused biochar may be produced for different uses. Those skilled in the art will recognize that there may be other mechanisms for infusing fertilizer or other soil additives into the pores of the biochar without departing from the scope of the invention. Those skilled in the art will further recognize that the present invention can be used on any type of soil application, including, but not limited to, the following: crops, turf grasses, potted plants, flowering plants, annuals, perennials, evergreens and seedlings, as will be further described below.

For example, in another implementation, additive infused biochar may be produced for use for consumption by animals and/or humans. Biochar may be infused in the same manner as described above with nutrients (such as carbohydrates, minerals, proteins, lipids), vitamins, drugs and/or other supplements (such as enzymes or hormones, to name a few), or a combination of any of the foregoing, for consumption by either humans and/or animals. Coloring, flavor agents and/or coating may also be infused into the pores of the biochar or applied to the surface. The foregoing may be included to enhance the performance of the substance in the digestive tract or to ease or facilitate the ingestion of the biochar.

D. Biochar as a Habitat for Microorganisms

Biotechnology, specifically the use of biological organisms, usually microorganisms, to address chemical, industrial, medical, or agricultural problems is a growing field with new applications being discovered daily. To date, much research has focused on identifying, developing, producing and deploying microbes for various uses. However, despite much work on the microbes themselves, relatively little work has been performed on how to carry, deliver, and encourage the successful establishment of these microbes in their targeted environment. Most current technology for microbial carriers in agriculture is based on technologies or products that are highly variable and, in many cases, lead to highly unpredictable performance of microbes in the field. For example, many commercial microbes in agricultural settings are delivered on peat, clay, or other carriers derived from natural sources, accompanied by limited engineering or process control.

Biochar have a proclivity to interact positively with many microbes relevant to plant health, animal health, and human public health applications. In fact, there has been a level of initial research focused on inoculating biochar with microbes and/or using biochar in conjunction with microbes or materials with microbes, e.g. compost. See co-owned U.S. Pat. No. 8,317,891 *Method for Enhancing Soil Growth Using Bio-char and Fischer et al., and Synergisms between compost and biochar for sustainable soil amelioration* 2012.

However, biochars, especially in raw form, often suffer from many characteristics which make their interaction with microbial organisms extremely unpredictable. Key among these undesirable characteristics is a high degree of variability. Because of this and other factors, biochar has been, to date, unused in large scale commercial biotechnology applications. There are several methods by which this variability can be ameliorated. At a high level, the methods to overcome these challenges fall into two categories: (i) making the biochar a more favorable habitat for the microbes-either by modifying its properties, adding materials beneficial to microbes, or removing materials deleterious to microbes, or (ii) inoculating, applying, or immobilizing the microbes on the biochar in ways that mitigate the underlying variability in the material. Both of these high-level methods can be used independently or in conjunction and have been shown to have a significant impact on the suitability of biochar in many biotechnology applications.

Before delving into the varying treatment methods that will turn the biochar into a microbial carrier or co-deploying with microbes, it is important to be able to view biochar as a habitat for microbes. Biochar, especially treated biochar, has many physical properties that make it interesting as a microbial habitat. The most obvious of these is its porosity (most biochars have a surface area of over 100 m2/g and total porosity of 0.10 cm3/cm3 or above). Furthermore, many biochars have significant water holding and nutrient retention characteristics which may be beneficial to microbes. Previous disclosure has outlined how these characteristics can be further improved with treatment, e.g., U.S. patent application Ser. No. 15/156,256, filed on May 16, 2016, and titled Enhanced Biochar.

However, recent data indicates that the Earth may be home to more than one trillion independent species of microbes (See Kenneth J. Locey and Jay T. Lennon, *Scaling laws predict global microbial diversity*, Proceedings of the National Academy of Science, vol. 113 no. 21. Clearly, each of these microbial species does not require an identical habitat. In fact, many have evolved in different conditions and thrive in different environments. Biochar, due to its organic origins, porosity, and amenability to treatment seems to be an extremely desirable base product to be used in the construction of microbial carriers or co-deployment of microbes. If the properties of the biochar can be made to match the properties expected by particular microbes, or groups of microbes, empirical data has shown that a much greater impact can be delivered in many applications—whether the targeted biochar is used as a carrier, substrate, co-deployed product, or merely is introduced into the same environment at a separate time. It stands to reason, as many real-world environments are composed of very complex microbial ecosystems, that giving certain microbes in these ecosystems a more favorable habitat, can ultimately help those microbes to become more successfully established, and potentially shift the entire ecosystem based on their improved ability to compete for resources. Clearly this is a very desirable characteristic when the successful deployment and establishment of a targeted microbe into a new environment is a desired outcome.

There are many properties of a habitat which may be important to certain microbes, but some of the most important are: pH, hydrophobicity or hydrophilicity, ability to hold moisture, ability to retain and exchange certain types of nutrients, ion exchange capacity (cationic and anionic), physical protection from predatory or competitive microbes or protozoa (usable and inhabitable porosity), presence or absence of nutrients, micronutrients, or sources of metabolic carbon, ability to host other symbiotic microbes or plant systems (such as plant root tissue), or others which may be important to various types or species of microbes. Ability to either enhance or suppress the availability of certain enzymes can also be an extremely important factor in building a viable habitat. This invention focuses on methods and systems that can be used to consistently produce biochar which has these targeted characteristics, methods that can be used to effectively create a particular formulation of biochar targeted to match a particular microbe or group of microbes, and techniques for deploying the desired microbes along with this targeted biochar, through inoculation, co-deployment, integrated growth/fermentation, or other methods.

By using treatment properties disclosed previously, proper feedstock selection, and control of the pyrolysis process, the following are some, but not all, of the properties that can be consistently targeted and controlled at production scales to improve the biochar for use with microbes or as a microbial carrier. Examples of those properties include (1) pH, (2) hydrophobicity, (3) sodium levels, (4) usable pore size distribution and usable pore volume, (5) particle size and distribution, (6) exterior and interior surface geometry, (7) nutrient exchange, (8) exterior and interior surface geometry, (9) useable carbon or energy source, (10) toxic materials or compounds, (11) surface structure/crystals/tortuosity, (12) compatibility with biofilm formations, and (13) enzyme activity.

1. pH

It is well known that various microbes prefer varying levels of acidity or alkalinity. For example, acidophiles have evolved to inhabit extremely acidic environments. Likewise, alkaliphiles prefer more basic (alkali) environments. It has been clearly shown that the methods outlined for treating biochars can product targeted pH values that can be sustained over long periods of time.

2. Hydrophobicity

There are several common sources of hydrophobicity in porous carbonaceous materials. One of them is the occurrence of hydrophobic organic compounds on the surface of the char—typically residual from the pyrolysis process. Targeted removal of these compounds is a method to improve the hydrophobicity of porous carbonaceous substances. These compounds can be removed in a non-selective way by increasing the pyrolysis temperature of the biomass to a level at which the compounds will disassociate with the material and become gaseous. This method, while useful, is very broad, and can also remove other desirable compounds as well as changing the surface chemistry of the residual carbon, increasing ash percentages, or reducing carbon yield by reacting and removing more carbon than is necessary. These compounds can also be selectively removed by the application of a targeted solvent using the mechanisms previously disclosed to infiltrate liquids into the pore volume of the material. This method is also effective, and has shown to be much more predictable in the removal of certain compounds. Since the vast majority of microbes rely heavily on water for both transport and life, the easy association of water with a material has a large bearing on its ability to sustain microbial life.

3. Sodium Levels

Differing types of microbes have varying proclivities for the presence of sodium. Some microbes *Halobacterium* spp., *Salinibacter ruber, Wallemia ichthyophaga* prefer high levels of salinity, while others prefer moderate or limited levels of sodium. Sodium can be removed from biochar by either simple washing, or more preferably and effectively, treatment methods which infuse a solvent (most commonly water, although others may be used) into the pores of the material. Sodium can be added, by using the same methods except instead of using a solvent, the liquid being washed with or infused is a solution high in sodium content. Additionally, since sodium usually manifests itself as a cation in solution, temporary or permanent adjustment of the cationic exchange capacity (CEC) of the material through treatment which impacts the ability of the material to exchange cations. Lowering the CEC of the material will in many cases reduce its ability to exchange sodium cations, while raising the CEC will typically enhance the ability of the material to exchange sodium cations, with exceptions occurring if other cations are present in quantities that cause them to preferentially exchange instead of the sodium cations present. Finally, differing biomass feedstock contains differing levels of sodium-selecting an appropriate feedstock prior to pyrolysis will result in a raw or untreated biochar with reasonably controlled levels of sodium. For example, pine wood, when pyrolyzed, results in a raw char with lower levels of sodium, while coconut shells result in char with higher levels of sodium after pyrolysis.

| ASH Composition | Untreated Coconut Shell Biochar | Untreated Pine Biochar #1 | Untreated Pine Biochar #2 |
|---|---|---|---|
| Ultimate Analysis - Moisture free results | | | |
| Ash | 6.7% | 9.2% | 3.6% |
| Ash Composition | | | |
| Sodium Oxide, as Na2O | 5.7 % | 1.2% | 0.8% |

Regardless, it should be clear that there are various methods available to produce final product with a targeted sodium level, making it suitable for various microbes depending on their preference for an environment with a certain sodium level.

4. Usable Pore Size Distribution and Usable Pore Volume

One very important quality of a microbial habitat is the availability of shelter from environmental or biological hazards. A few examples of environmental hazards are high temperature, UV radiation, or low moisture, while an example of a biological hazard is the existing of predatory multicellular microbes such as protozoa, including both flagellates and ciliates. In order for a particle or material to provide shelter for microbes, at least two conditions must be present: (i) The material must consist of pores or openings of a size which can be inhabited by the microbe in question (ii) but prevent the hazard from entering (e.g. pore size smaller than the size of predators, such as protozoa, or deep enough to be shaded from UV rays) and, (iii) the pores mentioned previously must be usable-namely, they should not be occupied by solid matter (clogged) and/or they should not contain substances that are toxic or undesirable for the microbe in question. In some cases, the pore size distribution of a biochar can be adjusted by the selection of the biomass feedstock to be pyrolyzed and the conditions of the pyrolysis process itself. For example, pine wood has a relatively narrow pore size distribution, with most pores falling in the range from 10-70 μm. Coconut shells, on the other hand, have a much wider size distribution, with many pores below 1 μm, and also a high percentage of porosity above 100 μm. It is theorized that materials with pores of a single size or where most pores are of similar size can potentially be good carriers or habitats for certain, targeted microbes, while materials consisting of broader ranges of pore sizes may be better habitats for communities, consortia or groups of microbes, where each microbe may prefer a slightly different pore size. Furthermore, the pore size of a material may also be controlled during the pyrolysis process by increasing temperature or performing "activation" or other steps common in activated carbon production to react or remove carbon, leaving larger pores, or exposing availability of pores that were once inaccessible from the exterior surface of the material. Adjusting the particle size of the material may also change the pore size distribution in at least two ways: (i) exposing pores that were not available or accessible previously, or (ii) destroying larger pores by fracturing, splitting, or dividing them. In many cases, raw biochar may contain a proper pore size distribution, but for one reason or another, the pores are not usable by the microbes in question. In other cases, the pore size distribution provided by the natural feedstock may be undesirable. Both properties may also be impacted through treatment of the raw biochar itself. Larger pores can be created using strong acids or other caustic substances either by simple washing or through forced or rapid infusion into the pores. Conversely, a material with fewer usable pores may be created by intentionally "clogging" or filling the larger pores with either solids, gums, or liquids designed to stay resident in the pores themselves. This treatment may be done in a controlled way to only partially fill the pores. For example, one could infuse a limited amount of heated liquid, such as a resin, that will become solid at normal atmospheric temperatures. If the volume of liquid used is less than the available pore volume of the material being infused, some of the porosity of the material will be left untreated and available for use. Most importantly, and most commonly, usable pore volume may be increased through the act of simply removing contaminants (physical or chemical) from the pores. Rapid infusion and extraction of liquids may be used to accomplish this. As discussed previously, appropriate solvents may be infused or extracted to remove chemical contaminants. Additionally, gasses or liquids may be driven into or out of the pores to force the removal of many solid obstructions, such as smaller particles of ash or simply smaller particles of raw biochar which may have become lodged in the pore in question. Regardless of the mechanism used, it has been shown that the available, uncontaminated, usable pore volume and pore size has a major role in determining the efficacy of biochars in microbial roles.

Figure 23:
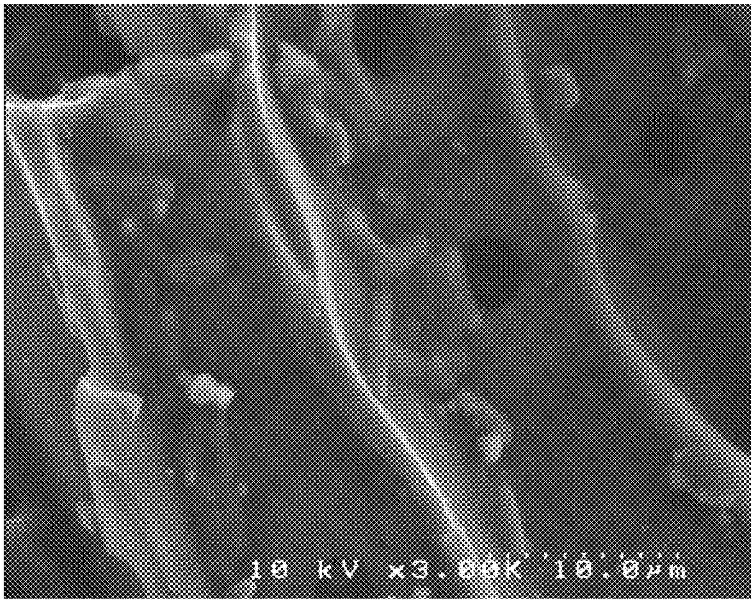
FIGS. 23 and 24 are images that show how different sized bacteria will fit in different biochar pore size structures.
Figure 24:
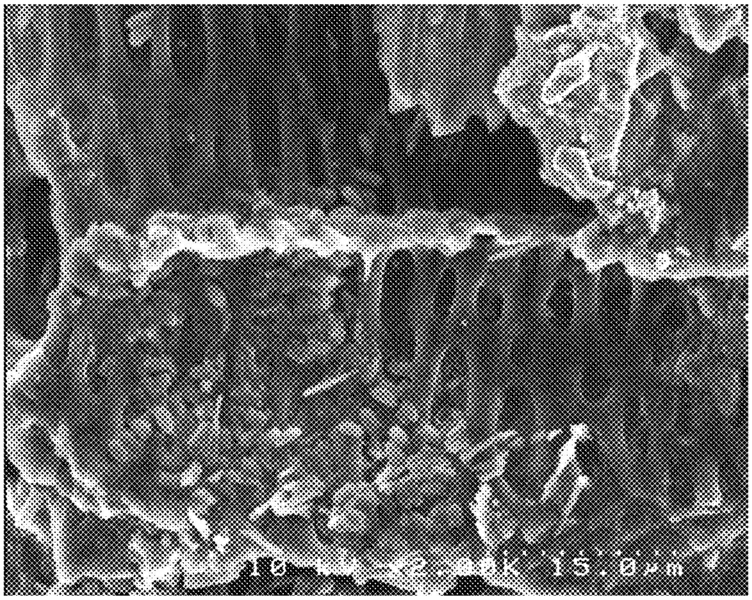

FIGS. 23 and 24 are images that show how different sized bacteria will fit in different biochar pore size structures. FIG. 23 is rod-shaped gram-positive bacteria, *Bacillus thuringiensis israelensis*, in a treated pine biochar, with pore openings of ~10-20 μm and bacteria of ~2-5 μm. FIG. 24 is rod-shaped gram-negative bacteria, *Serratia liquefaciens*, in a treated coconut shell biochar, with pore openings of ~2-10 μm and bacteria of ~1-2 μm.

Figure 25:
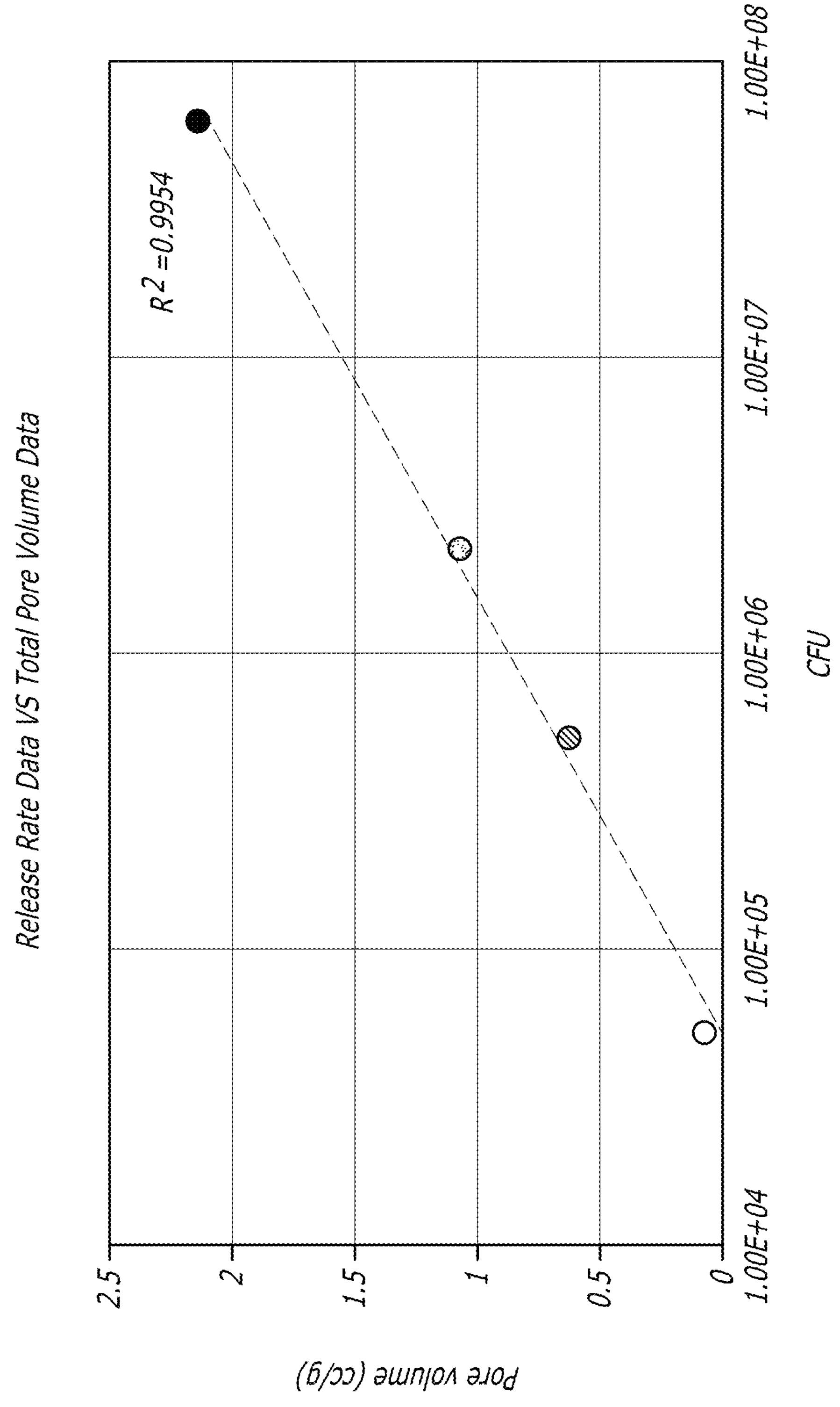
FIG. 25 illustrates release rate data verse total pore volume data for both coconut shell and pine based treated biochars inoculated with a releasable bacteria.

In addition, total pore volume in the size of 5-50 μm has been shown to correlate with microbial release rate after inoculation on treated biochar. FIG. 25 illustrates release rate data verse total pore volume data for both coconut shell and pine based treated biochars inoculated with a releasable bacteria. As illustrated in FIG. 25, the data was plotted in a graph, and clearly shows that as pore volume increases so does the release rate.

5. Exterior and Interior Surface Geometry

Two important properties of microbial carriers are: (i) their ability to release microbes from their surfaces and (ii) their ability to immobilize or stabilize microbes on their surfaces. Depending on the final application or use of the carrier, one or both of these properties may be desired. For example, for carriers designed to quickly release a microbe into a targeted domain such as a lake, river, or other waterway, the release characteristics of the material are paramount. For other applications, such as applications of certain symbiotic microbes in agriculture, rapid release may be undesirable, rather it may be important to sustain the microbes within the porosity of the material until plant tissue, such as root biomass, is nearby to provide nutrition for the microbes in question. The surface and pore geometry of the material used as a carrier can be critical to determine this behavior. For example, material with generally smooth, uniform surfaces will typically release many microbes much more effectively, while material with more rugged, varied, tortuous pore surfaces and geometry will typically retain and immobilize microbes more effectively. The biomass used in the production of the final material is one of the most important factors in surface geometry. However, even this quality can be altered through treatment. Specifically, smooth surfaces may be etched by implementing the treatment and infusion processes previously disclosed with strong acids, rendering them rougher. Conversely, rough surfaces may be treated with either organic or inorganic compounds to coat and remove contour. Mechanical means may also be used to affect changes in particle geometry. Many forms of charred material have relatively low crush strength and are relatively brittle. The method used to grind, or size particles can have a large impact on the geometry of the final particles. For example, particles milled using a ball mill or other type of grinding technology will typically have a smoother exterior geometry after the milling is complete and may lose a good amount of their porosity through the simple mechanical crushing of pores. However, particles sized using ultrasonic vibrations or even simple physical vibrations to shatter, rather than crush larger particles into smaller ones, will typically retain their geometry, or sometimes result in smaller particles with more rugged geometries than the particles at the beginning. It should be apparent to one skilled in the art that there are various mechanical mechanisms available to effect these changes, but the resulting particles can be tailored to meet a particular microbial release or immobilization outcome.

6, Particle Size and Distribution

It is well known that the particle size and particle size distribution of a material has a key impact on its formulation as a microbial carrier. In many cases, these factors are very different for porous carbonaceous materials than they are for other common microbial carriers. In standard carriers, typically the reduction of particle size is a method used to increase surface area, and thus the area available to support, immobilize, and carry microbes. However, in porous materials, specifically materials with a large volume of usable interior porosity, sometimes a reduction in particle size does not cause a large increase in the usable surface area-specifically because the interior surfaces of the material were already exposed, and reducing the size of the particle does not change that fact. This leads to a somewhat counterintuitive behavior in some cases in which the reduction of the particle size of a porous material actually degrades its performance as a microbial carrier, due to the phenomena that surfaces that were once sheltered inside the material are exposed as exterior surfaces when the material is split or crushed, making the material less desirable as a habitat for microbes that require shelter from the surrounding environment. Additionally, at times the actual distribution of particle sizes can be a key factor in performance. As a simple example, imagine an aggregated material which consists of only two particle sizes: 1 mm and 1 μm. Furthermore, imagine that 50% of the mass of the aggregate resided in the 1 mm particles with the remainder in the 1 μm particles. Lastly, imagine that the 1 mm particles were porous carbonaceous particles with an average pore size of approximately 50 μm. It should be clear that if this aggregate was placed in a container and agitated, that a good portion of the 1 μm particles would end up inhabiting the pore volume of the 1 mm particles, impacting their usability. In fact, this is the behavior that we see in practice. Therefore, for certain microbial applications, it is desirable to remove extremely small particles, often referred to as fines, from the aggregate. This has the additional benefit of reducing dust during application, which is particularly important in aerial applications, and reducing the level of surface runoff for applications in water, which also is important in certain microbial applications. The small particles may be removed through several methods such as sieving, blowing or aerodynamic removal, separation with either stationary or moving liquids (hydrostatic or hydrodynamic separation) of various viscosities, temperatures, flow rates, etc. However, at times, having a mixture of smaller and larger particles can be desirable. The most common cases are when communities of microbes are to be deployed, or the aggregate is to remain generally intact for a period of time (fermentation applications, long term storage applications, or preparation for other formulation uses such as palletization), in which case, the interparticle void space is also an important factor and can be optimized for a particular microbe or set of microbes by providing a range of particle sizes and geometries.

7. Nutrient Exchange

The ability of a material to hold or exchange nutrients is an incredibly important characteristic, not only for microbial, but also for general agricultural applications. There are two primary mechanisms that porous carbonaceous materials can exchange nutrients: (i) sorption or retention of the nutrients on the interior and exterior surfaces of the material, and (ii) retention of the nutrients either in suspension or solution in liquid or gasses residing in the pore volume of the material. Both mechanisms are very useful, but also very different in function. Surface sorption or retention is driven by two main properties, among others: (i) ion exchange capacity of the material and. (ii) reactivity or electrical charge of compounds present on or coating the surfaces of the material. Retention of nutrients in solution or suspension are impacted by other, different characteristics of the material, such as hydrophilicity, oil sorption capacity, usable pore volume and pore size distribution, and interior pore geometry and tortuosity. The surface retention of nutrients can be targeted by selecting the feedstock biomass (some materials render a char after pyrolysis with vastly differing ionic exchange capacities (CBC and ABC) than others). It can also be impacted by adjusting pyrolysis conditions. Higher pyrolysis temperatures tend to reduce CEC and nutrient adsorption capability. See Gai, Xiapu et al. "Effects of Feedstock and Pyrolysis Temperature on Biochar Adsorption of Ammonium and Nitrate." Ed. Jonathan A. Coles. *PLoS ONE* 9.12 (2014): e113888. *PMC*. Web. 19 Nov. 2016. In addition, the surface retention of nutrients can be impacted by treating the surfaces of the material with substances targeted towards adjusting the ionic exchange characteristics. For example, using the previously disclosed treatment methods to infuse $H_2O_2$ into the pores of the carbonaceous material and then evaporating the liquid can increase the cationic exchange properties of the material.

Furthermore, another way to exchange nutrients more efficiently is to use the pore volume rather than, or in addition to, the pore surfaces—namely keeping the nutrients in solution or liquid or gaseous form and placing them in the volume of the pores rather than attempting to sorb them on the surfaces of the material. This can be an incredibly useful technique not only for plant life and soil health, but also for microbes. The food sources can vary from simple to complex such as glucose, molasses, yeast extract, kelp meal, or bacteria media (e.g. MacConkey, Tryptic Soy, Luria-Bertani). When using the pore volume to exchange nutrients in this way, it should be clear that a wide variety of nutrients may be used, and targeted combinations of pore volume, size, and nutrition can be produced to assist in the delivery, establishment, or successful colonization of targeted microorganisms or groups of microorganisms. It should be clear by this point that merely immersing the biochar or porous carbonaceous material in a liquid nutrient broth may be partially effective in filling the pore volume or coating the pore surfaces with these nutrients and should be considered within the scope of this invention, however using the treatment techniques outlined in this and related disclosures is much more effective at both coating the surfaces and infusing nutrition into the pore volume of the material itself. Since many microbes rely on liquid for mobility, placing liquid into the pore volume of the material is in many cases a prerequisite for successfully infusing, carrying, or delivering microbes.

8. Usable Carbon or Energy Sources

Related to the ability to improve nutrient exchange is the ability to treat the pore volume, pore surfaces, exterior surfaces, or any combination of these with not only custom broths or growth media, but also other forms of carbon known to be beneficial to microbes and plant life. Some examples of this are carbohydrates (simple and complex), humic substances, plant macro and micronutrients such as nitrogen (in many forms, such as ammonium and nitrates), phosphorous, potassium, iron, magnesium, calcium, and sulfur and trace elements such as manganese, cobalt, zinc, copper, molybdenum. These nutrients may either be infused in liquid or gaseous form, or even as a suspended solid in liquid. The liquid may be left in the pores, or may be removed. If removed through evaporation, nutrients in solution or suspended solids may be left behind, while if removed by mechanical or physical means, a portion of the liquid may be left behind as well as some solids. It should be noted that the various forms of removal have differing advantages and disadvantages and that many energy sources may be added either at the same time or in sequence, with one, or many, removal steps in between treatment or infusion steps.

9. Toxic Materials or Compounds

The selective addition or removal of materials or substances known to be toxic to a certain microbe or lifeform is a key step in preparation of biochar for use as a microbial habitat or carrier. It has been shown, that through treatment, potentially toxic compounds can be removed with much greater effectiveness than through simple pyrolysis alone. Some examples of the potentially deleterious compounds that may be removed are: volatile organic compounds (VOCs), monoaromatics, polycyclic aromatic hydrocarbons (PAHs), heavy metals, and chlorinated compounds (e.g. dioxins and furans). A proven approach to remove these substances is to wash the exterior surfaces with and/or rapidly infuse a solvent into the pore volume of the material targeted to remove these substances. Following the infusion with either mechanical extraction, drying, or other methods to remove the solvent, laden with the substances in question, from the pores and interparticle spaces is a desirable, but not strictly necessary step to further reduce the levels of toxicity. For example, the following data shows removal of dioxins using the treatment process of the present invention.

| | Raw coconut shell biochar | Treated coconut shell biochar | Raw pine biochar | Treated pine biochar |
|---|---|---|---|---|
| TEQ ng/kg (method 8290A) | 0.7 | 0.4 | 9.6 | 0.4 |

Another approach for some toxic compounds (benzene as one example) is, rather than removing the compounds in question, to react them in place with other compounds to neutralize the toxicant. This approach can be used either with washing, or forced/assisted infusion, and in these cases a removal step is less necessary—although it still can be used to prepare the material for another, subsequent phase of treatment.

Much attention is given to the removal of toxic compounds, but it should be also be noted that at times, it can be extremely beneficial to actually add or treat the material with toxic compounds. A primary example of this is sterilization, or preparation for selective infusion. Even after pyrolysis, residual biological life has been found to potentially establish itself in biochars given the right conditions. Treating, washing, or infusing the material with antiseptics such as methanol, ethanol, or other antibacterial or antiviral substances can be a key step in removing contamination and preparing the material for use in microbial applications. A variation on this approach is to infuse, treat, or wash the material with a selectively toxic compound, such as a targeted antibiotic or pharmaceutical targeted towards interrupting the lifecycle of a specific set of microorganisms or organisms, thereby giving other microbes, either through infusion or merely contact in situ the opportunity to establish. Some examples of this treatment would be the use of antifungals such as cycloheximide to suppress fungal growth and provide an environment more well suited toward the establishment of bacteria. As has been stated previously, the methods may be used alone, or in combination with one another. Specifically, a toxic compound such as ethanol, may be infused, removed, and then steps may be taken to remove other toxic compounds, followed by steps to add carbon sources or growth media.

10. Surface Structures/Crystals/Tortuosity

The physical surface and pore structure of the material is critically important to its suitability as a microbial habitat. There are many factors that contribute to the surface structure of the material. The most notable of these factors is the biomass used to produce the carbonaceous material—the cellular structure of the biomass dictates the basic shape of many of the pores. For example, pyrolyzed coconut shells typically have less surface area, and a more diverse distribution of pore sizes than pyrolyzed pine wood, which, when pyrolyzed at the same temperature, has greater surface area, but a more uniform (less diverse) pore size distribution. Tortuosity, or the amount of curvature in a given path through a selected pore volume is also an extremely important characteristic of engineered porous carbonaceous materials.

Figure 26:
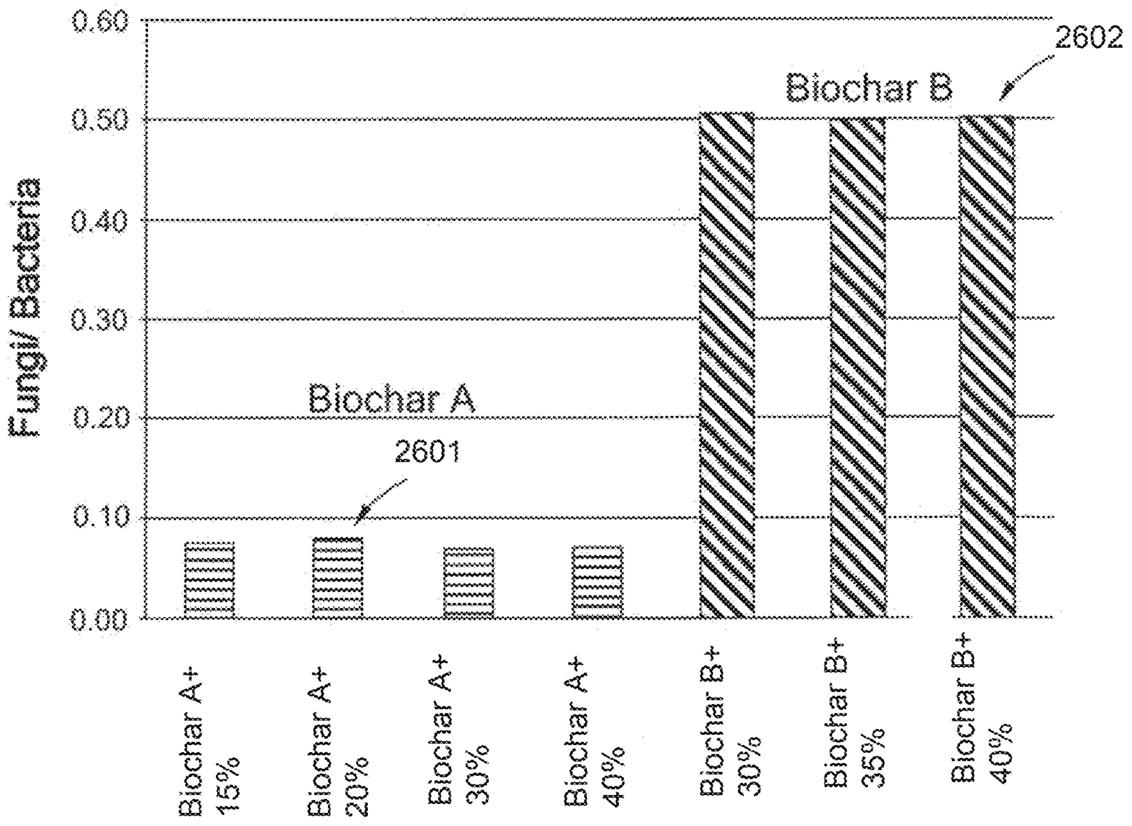
FIG. 26 is a chart comparing examples of biochars.

FIG. 26 shows the total fungi/bacteria ratio for two biochars derived from different biochar starting materials, e.g., feedstocks. Each biochar was loaded with different levels of moisture, and the total fungi/bacteria ratio was monitored during the first week. Biochar A 2301 showed a constant total fungi/bacteria ratio of 0.08 across moisture levels rang 5000 ng from 15% to 40%, while Biochar B 2302 showed a constant total fungi/bacteria ratio of 0.50 for moisture levels ranging from 30% to 40%. It is theorized that, a fungi/bacteria ratio between 0.05 and 0.60 is an effective prescription for a stable biochar composition. This composition allows a commercially viable product, which has sufficient shelf life that it can be delivered to storage houses waiting for the proper planting window.

It is theorized that the difference in the observed total fungi/total bacteria ratios of may also be explainable by the structures of the biochars. Biochar's having an open pore structure, e.g., more interconnected pores, promotes more bacteria formation; while closed pores, e.g., relatively non-connected nature of the pores, tends to promote fungi formation. Biochars with differing microbial communities may be beneficial for specific applications in commercial agriculture. Thus, custom or tailored loading of the microbial population may be a desired implementation of the present invention.

Figure 27A:
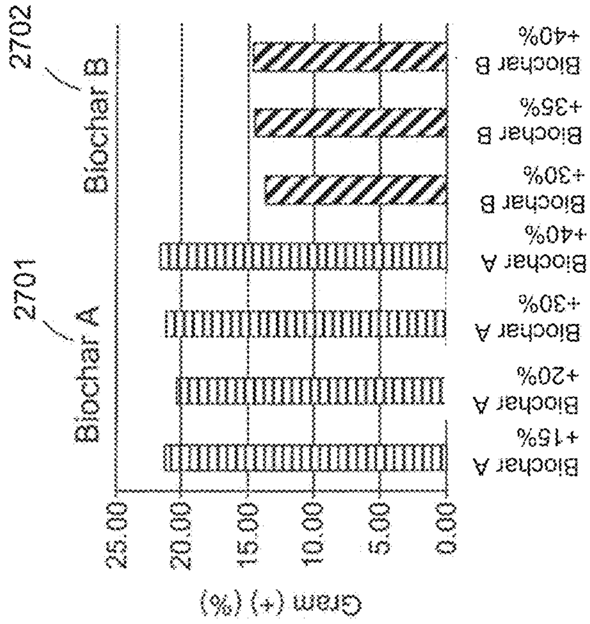
FIGS. 27*a*, 27*b*, 27*c* are charts comparing different examples of biochars.
Figure 27B:
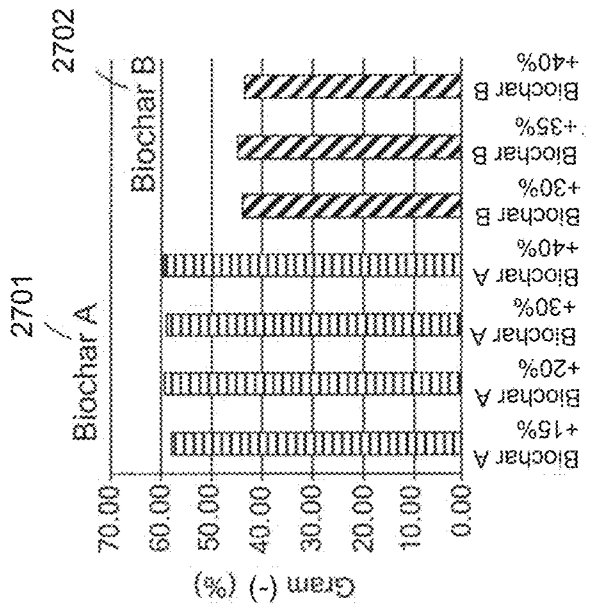
Figure 27C:
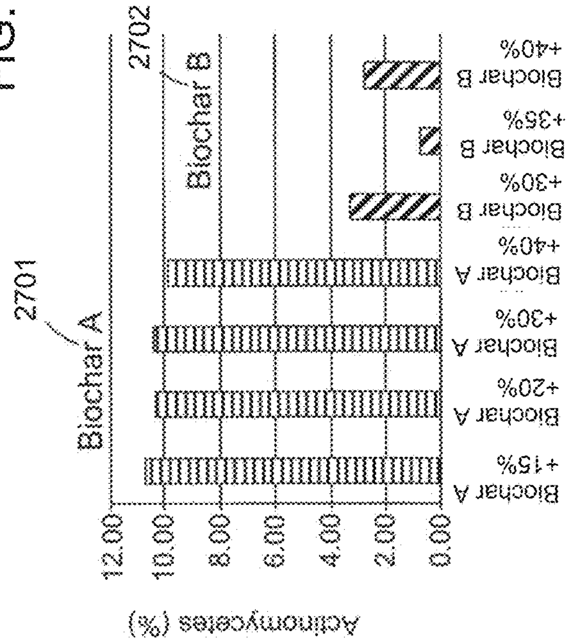

For example, as shown in FIGS. 27*a*, 27*b* and 27*c*, Biochar A 2701 shows that it has a greater population of, i.e., is inhabited by, more gram negative, gram positive and actinomycetes than Biochar B 2702. Thus, for example, Biochar A would be more applicable for use with certain agricultural crops in which Plant Growth Promoting Bacteria (PGPB) species in the actinomycetes, gram (−) pseudomonas, and bacillus groups are used for nutrient utilization and uptake.

It should be noted that both pyrolysis and post-treatment can be used to further modify the shape of these pores and structures. Pyrolyzing at higher temperatures, injecting select gasses or liquids during pyrolysis, or both typically will increase the pore volume and surface area of the material in question. Steam is the most readily available gas to cause this effect, but hydrogen sulfide, carbon dioxide, carbon monoxide, as well as other reactive gasses can be used. Prior art has clearly shown that the surface area of a biochar changes based on feedstock and pyrolysis temperature. Post treatment focused on a forced infusion of a strong acid, or other reactive substance into the pore space of the carbonaceous material can also be used to modify the pore size and pore volume of material by removing or breaking down the carbon matrix which forms the structure of the biochar, or other porous carbonaceous material. Acid etching or infusion can also be used to make smoother surfaces rougher. Rough surfaces can be very useful in the attachment and immobilization of microbes. Smooth surfaces can be useful for the easy release of carried microbes. Coating the surface area with materials such as starches is a technique to make rough surfaces smoother. Ultrasound, with or without a transmission media (gel, liquid, oil, or other) can also be used to rupture interpore divisions and create more pore space. Flash gasification, either at atmospheric pressure, or under negative or positive pressure, of liquid infused into the pores by the methods previously disclosed can also be used to crack, disrupt, or fracture solid material separating adjacent pores.

While much attention is given to modifying the pore structure by removing carbonaceous material, it should be noted that the pore structure can also be modified by the coating, forced infusion, and/or addition of materials which will bond to the carbon and consume pore volume, smooth surfaces, add tortuosity, change the exterior surfaces, or all of these. In the most simple form, it should be clear that materials may be added to coat surfaces or fill pore volume either through forced infusion, simple contact, or other means. However, if the material is infused or even simply contacted with a super saturated solution of a substance that will crystalize, such as sucrose, sodium chloride, or other common or uncommon substances known to form crystals. It should be noted that the crystals or substances used to create them do not need to be water soluble, and in fact in many cases it is desirable if they are not. The crystals may also be composed of nutrients or substances which may be beneficial to microbial or plant life. Examples of this are sucrose and monoammonium phosphate, both known for their ability to easily crystalize and be beneficial for microbial and plant life respectively. By adding material or even growing crystals on the carbon, a hybrid material is formed which can have many properties that are exceptionally useful for the delivery and establishment of microbial systems. Crystallization is also way to add tortuosity to a carbonaceous material and typically is much more effective in this aspect than coating with solids alone.

11. Compatibility with Biofilm Formation

Biofilms can be an important factor in the survival of a microbe in extreme or challenging conditions. Bacterial communities can shift their morphology to increase nutritional access and decrease predation. One such modification is that the bacteria may attach to surfaces, such as those found in biochar, in a densely compacted community. In this compacted form, they may form an extracellular polymeric substance (EPS) matrix called a biofilm. These communities can contain hundreds of different species which find shelter under the protective EPS coating from predatory protozoa, pathogens, contaminants, and other environmental stressors. In some cases, usually related to public health or healthcare, biofilms are undesirable as they typically allow pathogenic microbes to survive exposure to antiseptics, antibiotics, predatory microbes such as protozoa, or other agents which may eliminate them or negatively impact their prospects for survival. But in agricultural settings, encouraging target biofilm establishment could lead to improved microbe survival and thus improved agricultural or crop benefits.

As outlined in the article titled *The Effect of Environmental Conditions on Biofilm Formation of Burkholderia psudomallei Clinical Isolates*, it can be seen that certain bacteria require certain environmental factors, among them surface pH, for the creation of biofilms, See Ramli, et al., *The Effect of Environmental Conditions on Biofilm Formation of Burkholderia psudomallei Clinical Isolates* (Sep. 6, 2012). It is believed that other surface characteristics (rugged vs. smooth surfaces, surface charge, and more), along with moisture levels and relative humidity also play a large role in biofilm formation.

But for certain microbes requiring deployment into environments known to present survival challenges, optimizing a delivery material to encourage the formation of these protective biofilms can provide the targeted microbes with a significant advantage. Also, many vegetable and short cycle row crops such as tomatoes, lettuce, and celery form mutualistic relationships with bacteria that lead to the formation of biofilms on root hairs that function not only in nutrient uptake but also in plant pathogen resistance.

As outlined in previous disclosure, treatment of raw biochar can be used to adjust the surface pH to a level suitable for biofilm formation. Similarly, adjusting the humidity by selectively leaving a measured or controlled amount of water resident in the pore volume of the material can also provide benefit. Lastly, the techniques outlines for modifying the physical surface properties of the material either by smoothing or roughening, can be key factors also.

It should be clear that these factors can also be reversed to create an environment that is unsuitable for biofilm formation in applications where the formation of biofilms on the carrier is not desirable—e.g. delivery or applications where quick release of microbes from the carrier is important.

12. Surface Charge

The surface charge of a porous carbonaceous material can be crucially important in the association and establishment of targeted microbes with or on the material. For example, most bacteria have a net negative surface charge and in certain conditions a specific bacterium may favor attachment to positively charged surfaces. In some biological applications, this attachment may be preferred, in others, attachment may not be preferred. However, modifying the surface charge of the material is clearly a way to impact the suitability for attachment of certain microbes. There are many ways in which the surface charge of a carbonaceous material may be changed or modified. One way to accomplish this is by treating the surface area of the material with a solution containing a metal, such as Mn, Zn, Fe, or Ca. This can be performed either by doping the material with these metals prior to or during pyrolysis, or more preferably, by using a forced infusion or treatment technique after pyrolysis to deposit these substances on the interior and/or exterior surfaces of the carbonaceous material. By controlling the amount and or types of substances infused, the surface charge of the material can be modified by encouraging loading of $O_2^-$ or other anions, or conversely, $N^+$, $NH_2^+$, or other cations. This modification of surface charge can have a profound impact on the ability of certain microorganism to be immobilized on the interior and exterior surfaces of the material.

Another application of surface charge can be found by temporarily charging the carbonaceous material during inoculation with microbes. Carbon is used as a cathode or anode in many industrial applications. Because of its unique electrical properties, carbon, or more specifically porous carbonaceous materials, may be given a temporary surface charge by the application of a difference in electrical potential. One application of this mechanism is to create a temporarily positively charged surface to encourage microbial attachment. Then, while the charge is maintained, allowing the microbes to attach themselves to and colonize the carrier. Once the colonization is complete, the charge can be released and the carrier, laden with microbes can either be deployed as is, or can undergo further treatment to stabilize the microbes such as lyophilization, or freeze drying.

13. Enzyme Activity

For some types of microbes, enzyme activity, or the presence of certain enzymes is every bit as important as the availability of energy or nutrition. Enzymes can be critical in the ability of microbes to metabolize nutrition, which in turn can be a key element of reproduction, survival, and effective deployment. There are six main types of enzymes: hydrolases, isomerases, ligases, lyases, oxidoreductases, and transferases. These enzymes can be important in microbial applications. Through treatment or even simple contact, enzymes, like nutrients and energy sources, can be deposited on the surfaces or within the pore volume of porous carbonaceous materials, either as solids, or in solution/suspension, ensuring the enzymes are not degraded through the process. However, forced infusion of enzymes through the treatment processes previously outlined allows for much greater storage capacity and much greater levels of contact with the interior surfaces of the biochar, and as such, is preferable to simple contact. In some cases, the carbonaceous material can be used to deliver enzymes alone into an environment where both a habitat and enzymes are needed to promote or encourage the growth of certain indigenous microbes.

Another important aspect of enzyme activity is that some bacteria make extra-cellular enzymes which could be bound by the biochar or either reduce or even stop biochemical reactions. Thus, in certain situations when application is appropriate the carbonaceous material can be used to inhibit or make certain enzymes ineffective. For example, if the biochar is being used as a carrier for food or certain chemicals that are vulnerable to breakdown by enzymatic degradation and these specific enzymes would be bound by the biochar, then using the carbonaceous material as the carrier would provide for greater shelf-life and viability of the product versus traditional carriers.

14. Sterilization

In many cases, it is desirable to remove potential unwanted microbes from the surfaces and pore volume of the material through sterilization. At outlined above, infusion with antiseptics or antibiotics are a way to accomplish this. Boiling, or more preferably, forced infusion of steam is also a technique that can be used to remove resident microbial life. Heating to a temperature above 100 degrees C., and preferably between 100 and 150 degrees C. is also effective for removing some microbial life. Heating may be required for ideally 30 minutes or more, depending on volume, method, and extent (temperature, radiation). Autoclaving can also be used 30 minutes, 121 degrees C., 20 psig. For applications requiring a high level of sterility, gamma irradiation can be used, with dosages adjusted for the level of sterility needed in ranges of 5 to 10 kGy or even 50 to 100 kGy or even higher dosage levels. For all sterilization methods, the extent of treatment required will depend on the volume of material and the required level of sterilization. In general, sterilization, using heat, should be done for at least 30 minutes, but should be adjusted as needed.

At this point, it should be clear that all of these properties can be controlled and modified to create a treated, controlled biochar that is suitable for use as a microbial carrier, delivery system, habitat, fermentation substrate, or environmental (soil, water or other) enhancement. By controlling these properties and producing a material matched to the application and the microbe(s) in question, effectiveness can be dramatically improved over both traditional biological carriers, and many forms of raw, untreated, uncontrolled biochar. Furthermore, varying materials, with varying properties, may be aggregated to provide delivery systems or habitats targeted towards consortia, communities, or groups of microbes.

E. Inoculating, Applying, or Immobilizing the Microbes on the Biochar

Typically, the prior art teaches either placing biochar on soils alone or combining the biochar with compost and using this mixture as a soil amendment. The nature of the microbial population in this compost mixture is poorly disclosed by the prior art. Thus using more targeted methods to get the desired microbes into the suitable habitat created by the raw biochar, or more preferably treated or controlled biochar is desired. The following are some but not all, methods and systems that can be used to inoculate, deploy, or otherwise associate microbial life with a treated or untreated biochar:

1. Co-Deployment

This method focuses on deploying the microbes at the same time as the biochar. This can be done either by deploying the biochar into the environment first, followed by microbes or by reversing the order, or even deploying the two components simultaneously. An example of this would be the deployment of a commercial brady rhizobium inoculant simultaneously with the introduction of a treated biochar into the soil media. The system here is the combination use of a biochar and microbes in the environment, and more preferably a char treated to have suitable properties for a target microbe or group of microbes which it is used with in a targeted application for a specified purpose, for example a symbiotic crop of said microbe(s).

Figure 28:
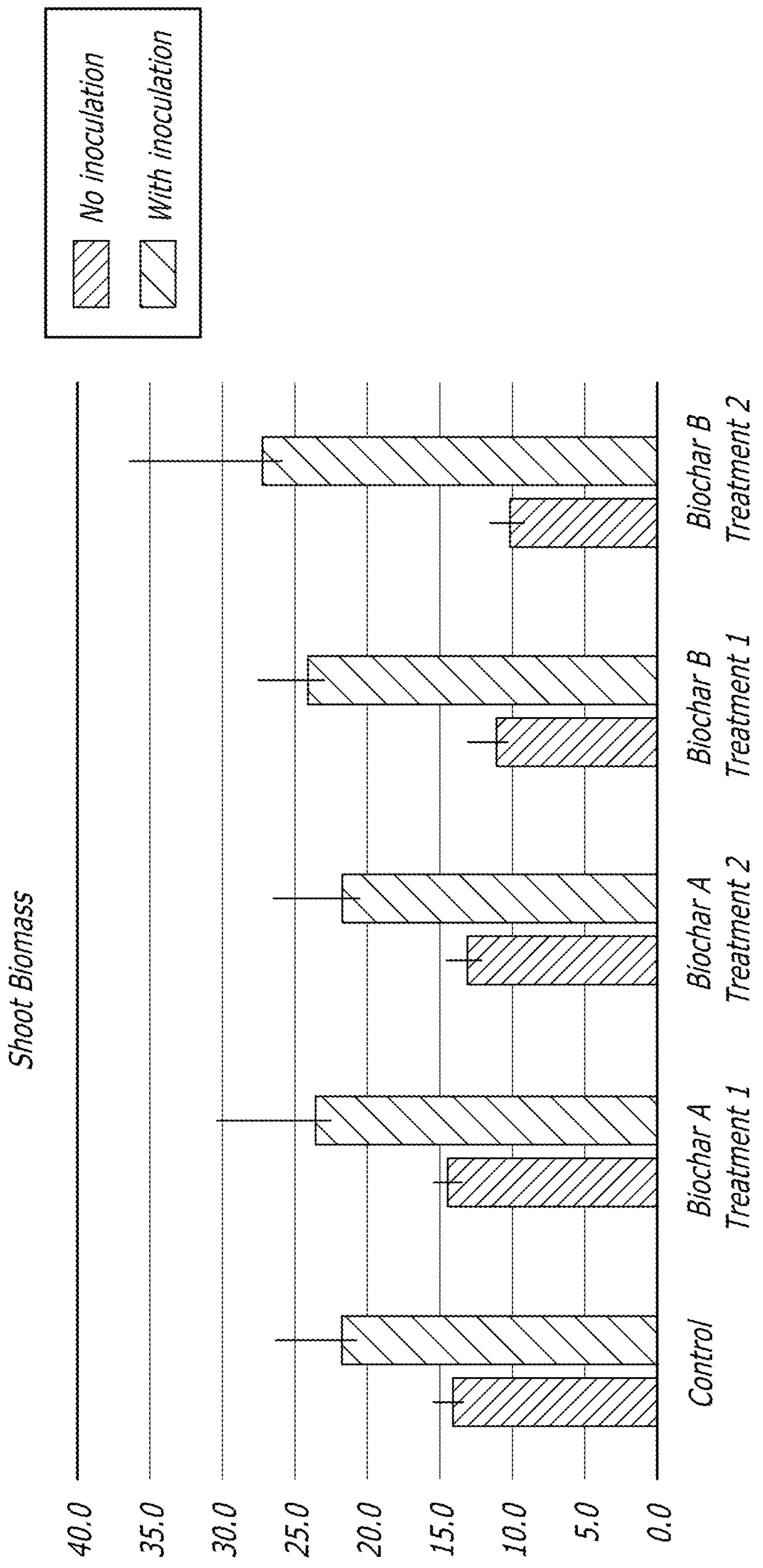
FIG. 28 is a chart comparing shoot biomass when the biochar added to a soilless mix containing soybean seeds is treated with microbial product containing *Bradyrhizobium japonicum*. and when it is untreated.

In one experiment, various biochar feedstocks with various post-treatments were added to a soilless mix containing soybean seeds that had been treated with a commercial microbial product containing *Bradyrhizobium japonicum*. and compared to both a control with microbe inoculant and one without. Some of the treated biochars co-deployed with the inoculant increased seed germination rates, one by 29%. Others increased nodulation measured at 10 weeks, one more than doubled the number of nodules. The use of the microbial inoculant increased shoot biomass in all treatments. FIG. 28 is a chart comparing shoot biomass when the biochar added to a soilless mix containing soybean seeds is treated with microbial product containing *Bradyrhizobium japonicum*. and when it is untreated. As illustrated in FIG. 28, shoot biomass increased with the biochar was treated.

Figure 29:
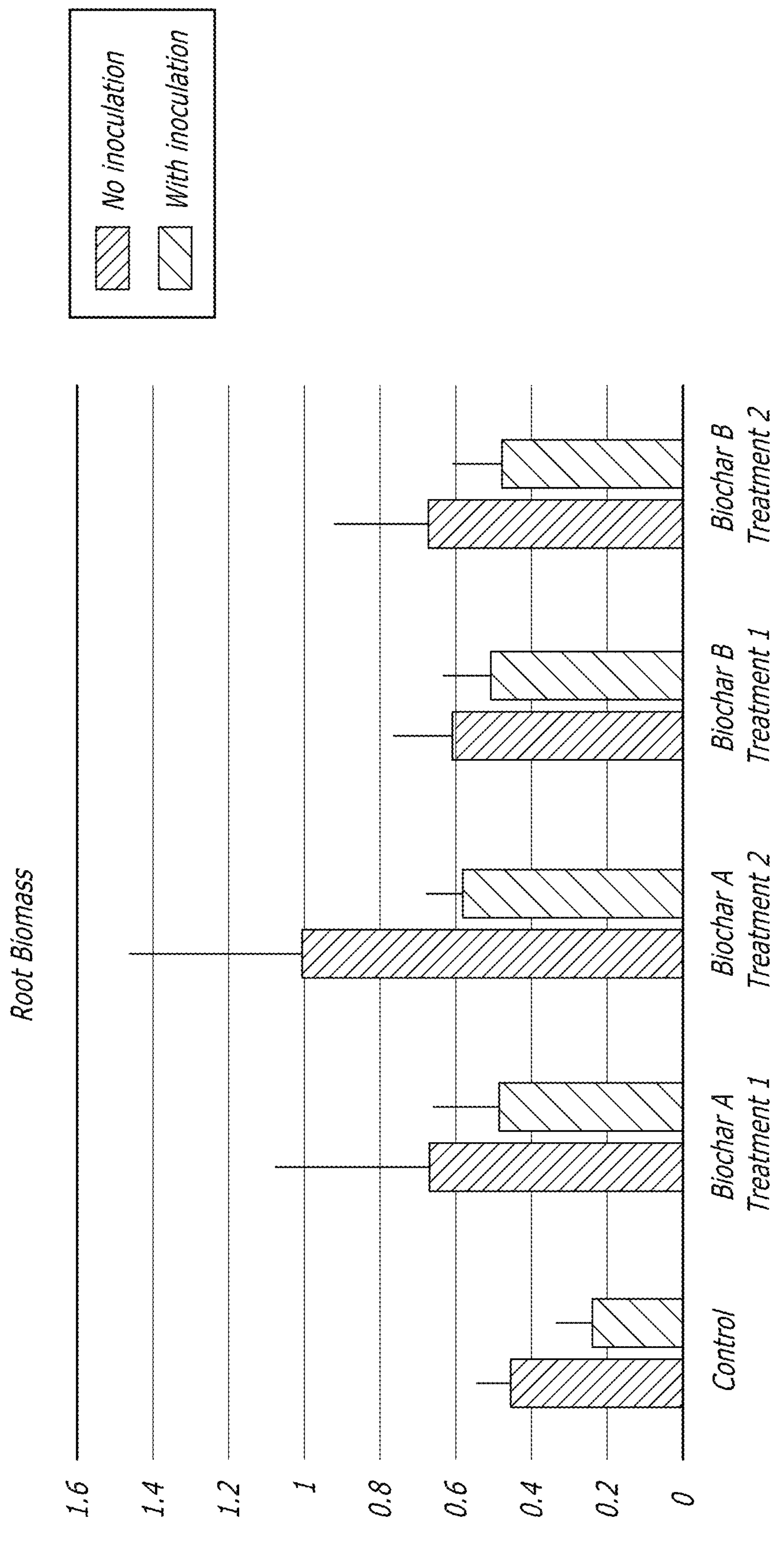
FIG. 29 shows the comparison of root biomass in a treated verses an untreated environment.

FIG. 29 shows the comparison of root biomass in a microbial inoculated environment versus one without inoculation. As illustrated in FIG. 29, when inoculated, root biomass decreased with the inoculant alone yet increased with the use of all the treated biochars with or without inoculant.

Figure 30:
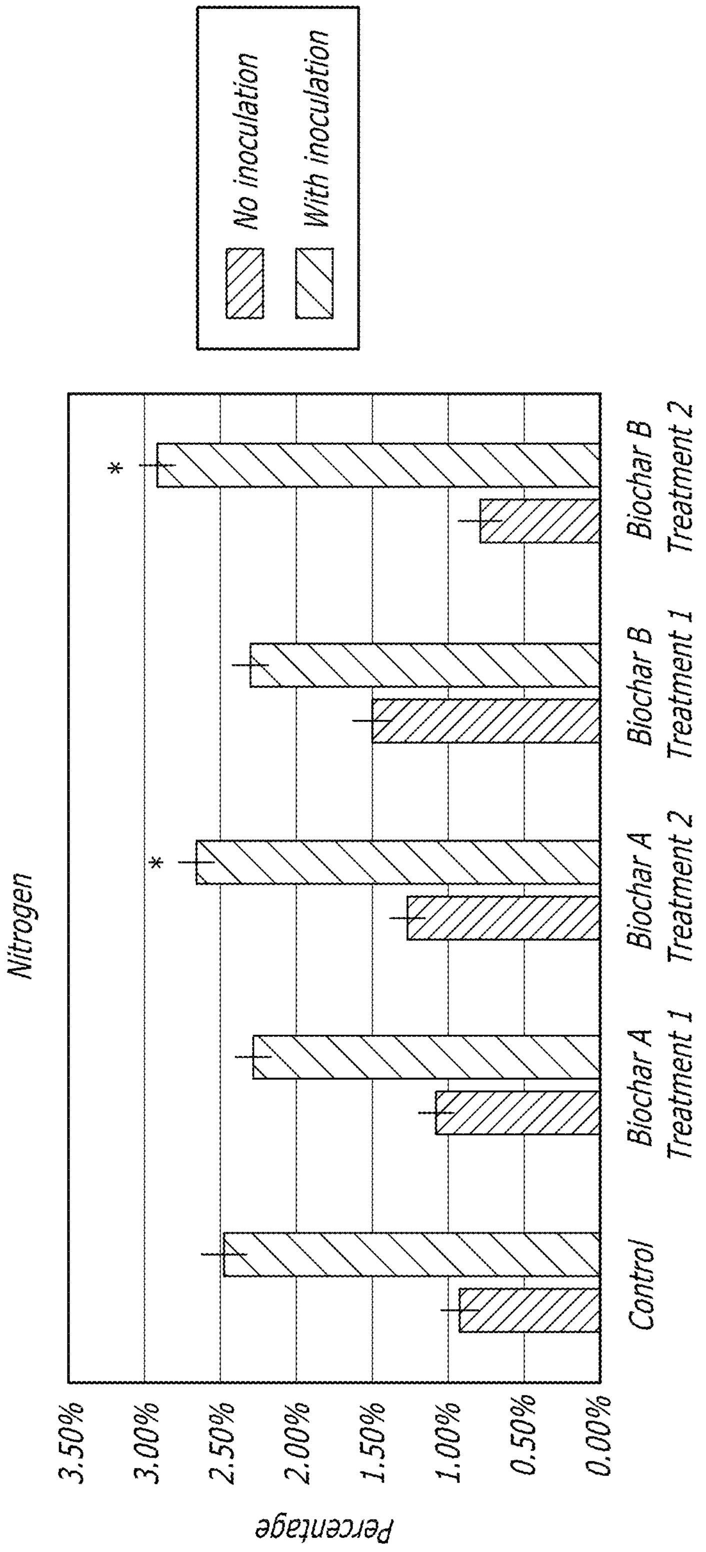
FIG. 30 is a chart comparing the nitrogen levels when the biochar is inoculated with the rhizobial inoculant verses when it is not inoculated.

In addition leaf tissue analysis was done which showed some of the treated biochars co-deployed with the rhizobial inoculant showed a significant increase in nitrogen uptake. FIG. 30 is a chart comparing the nitrogen levels when the biochar is inoculated with the rhizobial inoculant verses when it is not inoculated. Statistical significance in the chart in FIG. 30 is marked with a star. In all cases, nitrogen levels increase with inoculation.

As outlined in these results, the addition of a treated biochar suitable for co-deployment with this particular microbe increased nodulation, increased nitrogen fixation/availability, and resulted in substantially increased root mass. It should be noted that to demonstrate the differing performance of varying formulations, two formulations were tested, each showing different interactions with the microbe in question, along with significant variations in performance. This is just one example to demonstrate the invention of how the specific combination of biochar feedstock, biochar treatment, co-deployed microbe, and application (this case plant species) can lead to improved microbial effectiveness and thus improved results (this case plant vigor), versus no treatment, applying the microbe alone, or applying the biochar alone. Another example of co-deployment benefit could be using a biochar that has strong absorption properties in combination with fertilizer (or infused with fertilizer) and microbes in an agricultural setting. The biochar properties that help retain and then slowly release nutrients and ions will also help the targeted microbe population to establish and grow without being impacted by the high levels of fertilizer salts or nutrients which can often impede and sometimes kill the microbes being deployed.

2. Basic Inoculation

A more advanced method of inoculation centers on mixing the microbe or microbes in question with the treated or untreated biochar before deployment. In some cases, the biochar in question can be treated, produced, or controlled to assist with this deployment, making this case slightly different than merely inoculating a microbe on untreated biochar. In one form, microbes suspended in liquid (either water, growth media, or other liquids) are deposited on the biochar and mixed together until both materials are well integrated and then the material is deployed as a granular solid. It has been shown that materials that have been treated to be more hydrophilic typically accept this inoculation more readily than hydrophobic materials-demonstrating yet another way in which the treatment of biochar can enhance performance. In another form of basic inoculation, the biochar is delivered in suspension in the liquid also carrying the microbes. This biochar/liquid/microbe slurry is then deployed as a liquid. In this form, sizing the biochar particles in such a way that their surface properties and porosity is maintained is a key element of effectiveness. Additionally, ensuring that the pores are treated to allow easy association of both liquid and microbes with the surfaces of the biochar is important. An example of a basic inoculation method of biochar for a bacteria in lab scale is as follows:

1) Isolate *Pseudomonas protegens* on a plate with 1.5% w/v Tryptic Soy Broth solidified with 1.5% w/v agar and incubate at 30° C. for 12 h
2) Take an isolated colony of *Pseudomonas protegens* and grow up in a 1.5% w/v TSB solution (90 ml) along with 10 g sterile biochar (sterilized at 110 C in small batches for 15-20 min) and combine both in a sterile 250 ml Erlenmeyer flask
3) Shake contents of flask at 150 rpm at 30° C. for 12 h, or greater
4) Transfer contents of flask into a sterilized ultracentrifuge tube (250 ml) and spin at 10,000×g for 10 min
5) Carefully remove supernatant liquid fraction by filtering through a Whatman No 4 filter with a vacuum filtration system to separate out the bulk liquid from biochar.

After basic inoculation, the material and the microbes may be deployed immediately, stored for future use, or stabilized using technology such as lyophilization.

3. Assisted Inoculation

Figure 31:
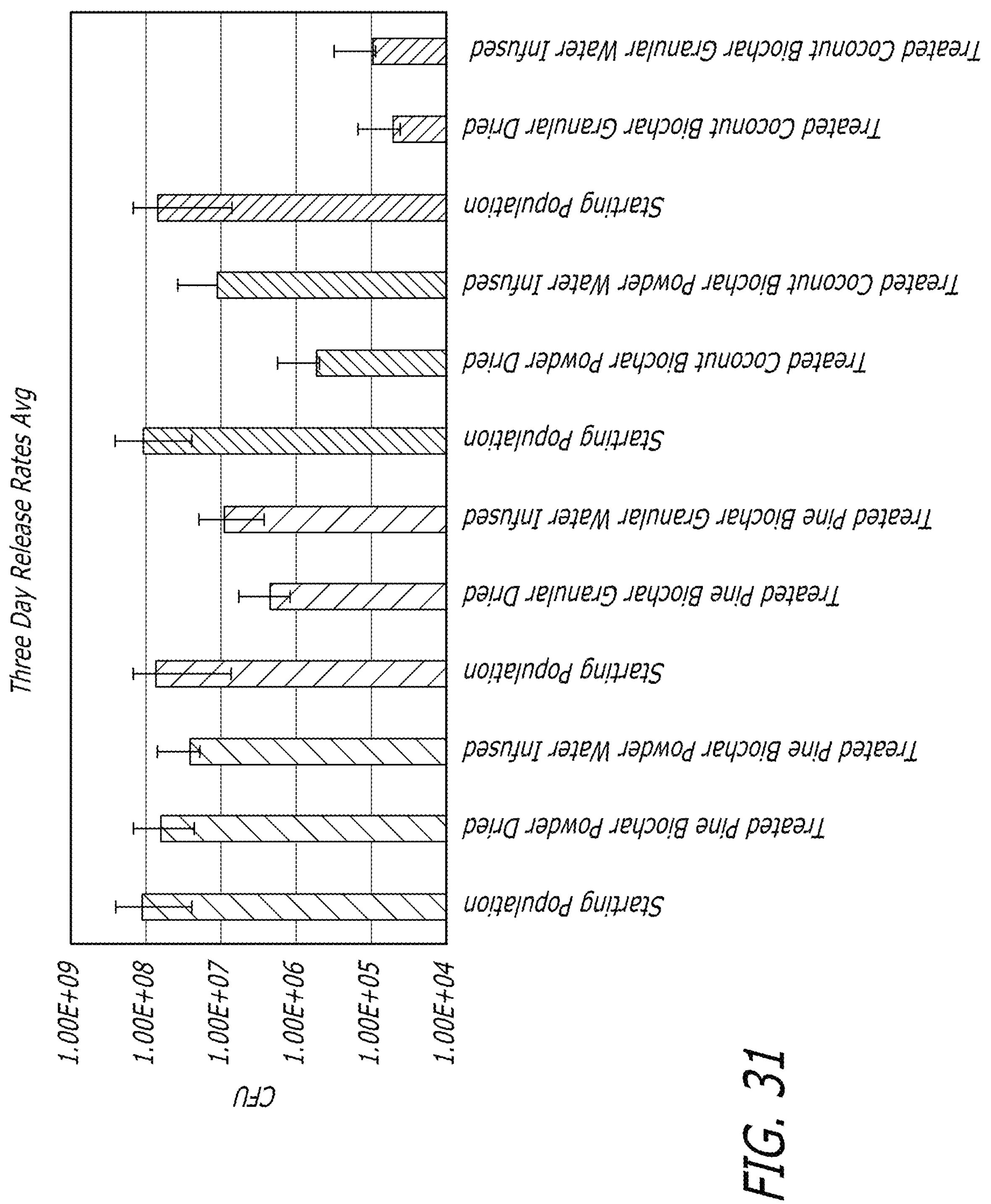
FIG. 31 illustrates the three day release rates of water infused biochar compared to other types of biochar.

Another form of inoculation, which appears to have greater efficacy with some microbial systems, is assisted inoculation. Assisted inoculation involves providing mechanical, chemical, or biological assistance to move the targeted microbe either into the pore volume of the carrier or onto interior surfaces of the material that normally may not be accessible. Realizing that many microbes require liquid, and preferably water, for mobility, the most straightforward method of assisted inoculation requires infiltrating the pore volume of the material with water prior to contact with the targeted microbes. This water infusion can be done using the treatment methods described previously in this disclosure. It has been shown that, with certain microbes, making this change alone will have a positive impact on the ability of microbes to associate with and infiltrate the material. In one experiment, it was shown that water infusion improved release rate on both a treated pine biochar with granular particles and with a coconut biochar powder. FIG. 31 illustrates the three-day release rates of water infused biochar compared to other types of biochar. As illustrated, results vary depending upon the biomass.

Changes can also be made in the media to reduce surface tension and increase flowability through the addition of a surfactant to the water, either into the liquid used to carry the microbes, or into the pores of the material itself, through simple contact, or preferably forced infusion.

Additionally, the microbes themselves may be assisted into the pores using the treatment techniques previously outlined. Care needs to be taken to match the microbe to the technique used, but many microbes are capable of surviving vacuum infiltration if performed at relatively gentle, lower pressure differentials (+/−10% of standard temperature and pressure). Some microbes, and many spores however are capable of surviving vacuum infiltration even at relatively large pressure differentials (+/−50, 75, or even 90 or 95% or more variation from standard temperature and pressure). When this technique is used, a liquid mixture is constructed containing both liquid to be infused and the microbe or microbes in question. The liquid is then used as the "infiltrant" outlined in previous disclosure related to placing liquid into the pore volume of the material. The final material, infiltrated with microbes, may then be heated to incubate the microbes, cooled to slow development of the microbes or stabilize the microbes, or have other techniques applied such as lyophilization. The material may then be delivered in solid granular form, powdered, further sized downward by grinding or milling, upward by agglomerating, aggregating, or bonding, or suspended in a liquid carrier. A clear advantage to this assisted infusion approach is that the material can be processed or handled after inoculation with more microbial stability because the targeted microbes are inhabiting the interior pore volume of the material and are less prone to degradation due to contact with exterior surfaces, or other direct physical or environmental contact. This method may be applied repeatedly, with one or more microbes, and one to many moisture removal steps. It may also be combined with the other inoculation methods disclosed here either in whole or in part.

Figure 32A:
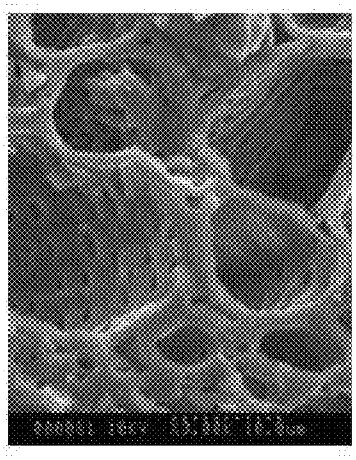
FIG. 32*a* is a SEM (10 KV×3.00K 10.0 μm) of pore morphology of raw biochar.
Figure 32B:
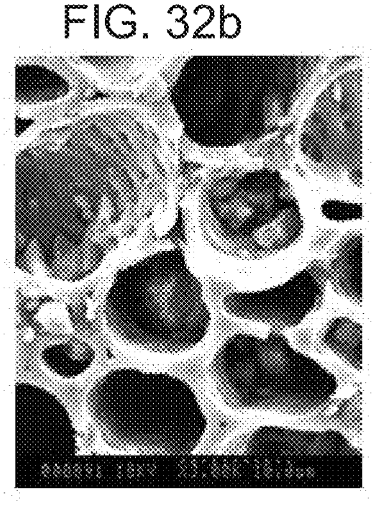
FIG. 32*b* is a SEM (10 KV×3.00K 10.0 μm) of pore morphology of raw biochar of FIG. 32*a* after it has been infused with microbial species.
Figure 32C:
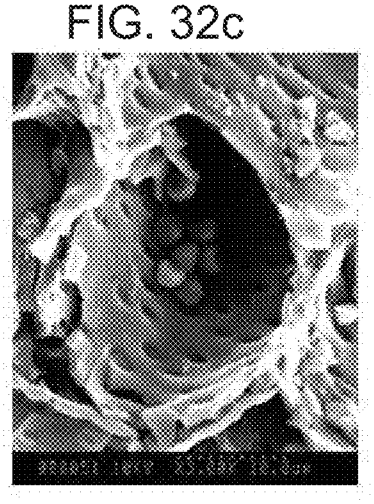
FIG. 32*c* is a SEM (10 KV×3.00K 10.0 μm) of a pore morphology of another example of raw biochar of FIG. 17*a* after it has been infused with microbial species.

FIGS. 32*a*, 32*b* and 32*c* show scanning electron microscopy (SEM) images of raw biochar compared to ones that have been processed by being infused under vacuum with bio-extract containing different microbial species.

FIG. 32*a* is a SEM (10 KV×3.00K 10.0 μm) of pore morphology of raw biochar. FIG. 32*b* is a SEM (10 KV×3.00K 10.0 μm) of pore morphology of raw biochar of FIG. 32*a* after it has been infused with microbial species. FIG. 32*c* is a SEM (10 KV×3.00K 10.0 μm) of a pore morphology of another example of raw biochar of FIG. 32*a* after it has been infused with microbial species. The images confirm the ability to incorporate different microbes into the pores of biochar by treatment. In turn, these beneficial microbes can interact with and enhance the performance of the environment they are deployed into, for example the plants' root systems when the inoculated biochar is mixed with the soil in the root zone.

Compared to a biochar that has immersed in a compost tea, which may have a relatively short, e.g., a few days for the life of the microbes, the impregnated populations of examples of the present treated biochars, are stable over substantially longer periods of time, e.g., at least an 8 week period and in some cases 1 year or more as measured by PLFA (Phospholipid-derived fatty acids) analysis. PLFA analysis extracts the fatty acid side chains of phospholipid bilayers and measures the quantity of these biomarkers using GC-MS. An estimate of the microbial community population can thus be determined through PLFA analysis. The microbial activity may also be inferred through PLFA analysis by monitoring the transformation of specific fatty acids. Thus, the impregnation of the biochar with a microbial population provides for extended life of the microbes by at least 5×, 10×, or more over simple contact or immersion. In fact, some microbes may be better suited to surfactant infiltration versus vacuum infiltration and vice versa and this may impact the shelf life, penetration, viability, or other characteristics of the microbes.

As used herein, unless stated otherwise, the stable shelf life of an example of a biochar product having a microbial population is the period of time over which the product can be stored in a warehouse, e.g., dry environment, temperature between 40° F.-90° F., with a less than 50% decrease in microbial population.

4. Integrated Growth/Deployable Substrate

With many microbes, especially fungi, it can be helpful to develop or "grow" the microbes on the material itself. With porous materials, rather than mechanically or chemically assisting the infiltration of the microbes, it can be beneficial to allow the microbes themselves to inhabit the pore volume of the material prior to deployment. In fact, with materials constructed to effectively immobilize microbes, this can be the most efficient technique to stabilize, store, and ultimately deploy the microbes in question.

An example of this method involves preparing the biochar material for the microbes, sometimes through thorough cleansing, other times through addition of either enzymes or energy sources needed by the microbe in question, preferably using the treatment techniques described previously in this disclosure. Once the material is prepared, the microbes are placed onto the material, or infused into the material and then incubated for a period of time. In the case of many microbial systems, the microbes themselves will inhabit the material and form close affiliations with available surfaces and pore volume. At this point, the material can be deployed with the microbes actively attached and affiliated. With many microbes, especially fungi, this is a preferred method of deployment and shows many advantages over co-deployment, or basic inoculation because of the tight integration of biological life with the material itself.

An example of an integrated growth inoculation method of biochar for a fungus in lab scale is as follows:

1) Make petri dishes containing corn meal agar (17 g/L), glucose (10 g/L), and yeast extract (1 g/L)
2) Inoculate plates with *Sordaria fimicola* and incubate between 22-30 C for at least 1 day to produce hyphae
3) Sterilize an inoculating loop and slice "plugs" of the hyphae and agar generating cubes that are agar and hyphal mass
4) Inoculate a sterile plate with a "plug" in the center of the plate, around perimeter have sterile biochar
5) Incubate plate for at least a day and remove biochar (that are now covered with grown over hyphae)]

It should be noted that because of this effect, biochars, and specifically treated biochars can also be extremely effective substrates for solid state fermentation-particularly when growth media or energy sources are added to the pore volume of the material. So, once incubation is ongoing, the material can either be removed, with the integrated microbes, and deployed, or it can be stabilized for long term storage, or it can be left in situ and used as a fermentation or growth substrate to develop or grow more microbes-especially those that require a solid to propagate and develop.

5. Media and/or Enzyme Infiltration

As mentioned previously, growth media, energy sources, enzymes, or other beneficial/necessary components for microbial growth may be infused into the pore volume or coated onto the surfaces of the material in question. This method can be combined with any of the other inoculation techniques disclosed here. It has been shown that with certain microbes and certain types of material, inoculation with growth media or enzymes can significant impact the effectiveness of the biochar material as a carrier.

6. Habitat Pre-Establishment (Enhanced Rhizosphere)

There are certain microbes which, because of symbiotic associations with host organisms, such as plants, prefer to develop in the vicinity of the organism, such as the active root or other plant tissue. An effective method for deploying these organisms can be to develop and deploy the plant/microbe/habitat (biochar) system together as a unit.

An example of this is germinating seed or transplanting a seedling or developing juvenile plant in the presence of treated or untreated biochar, and the targeted microbes. Biochar that has been treated to encourage hydrophilicity and neutral pH typically allows for easier affiliation of plant root tissue with the material. As this affiliation occurs, a habitat for symbiotic organisms is developed within the material itself due to the proximity of active plant tissue to microbes reliant on the tissue for energy. As this symbiosis continues, the number, activity, and colony size of the targeted microbes will continue to grow. At this point, the plant and biochar can be deployed together into the target environment, acting as a pre-established habitat and carrying the microbes along with them.

Another option is to develop and then remove the biochar from the "incubation" system either by stripping the biochar material from the symbiotic organism, such as the root mass, or by sieving or sifting the media used to grow the plant. At this point, the microbes can either be deployed directly or stabilized for storage.

Thus, through more controlled inoculation of the biochar particles, one can achieve a predetermined and controllable amount of a microbial community, e.g., population, into the soil. This integration of a microbial community with a biochar particle, and biochar batches provides the ability to have controlled addition, use and release of the microbes in the community. In agricultural applications, this integration can further enhance, promote and facilitate the growth of roots, e.g., micro-roots, in the biochar pores, e.g., pore morphology, pore volume.

Other methods than those listed above exist for integrating a microbial community with an untreated or previously infused biochar particle. Different manners and methods would be preferred depending on needs to minimize contamination, encourage biochar pore colonization/infiltration, minimize labor and cost and producing a uniform, or mostly uniform, product.

Other methods for integrating a microbial community with a biochar particle may include, but are not be limited to the following: while under vacuum, pulling the microbial solution through a treated biochar bed that is resting on a membrane filter; spraying a microbial solution on top of a treated biochar bed; lyophilizing a microbial solution and then blending said freeze dried solution with the treated biochar; again infusing, as defined previously, the treated biochar with a microbial solution; adding treated biochar to a growth medium, inoculating with the microbe, and incubating to allow the microbe to grow in said biochar containing medium; infusing, as defined previously, the biochar with a food source and then introducing the substrate infused biochar to a microbe and incubating to allow the microbes to grow; blending commercially available strains in dry form with treated biochar; adding the treated biochar to a microbial solution and then centrifuging at a high speed, potentially with a density gradient in order to promote the biochar to spin down with the microbes; densely packing a column with treated biochar and then gravity flowing a microbial solution through the column and possibly repeating this multiple times; or adding the microbe to a solution based binder that is well known to enter the treated biochar pores and then adding said solution to the treated biochar. In order to insure the proper microbial community the treated biochar may need to be sterilized prior to these methods for integrating a microbial community. All or parts of the above manners and methods may be combined to create greater efficacy. In addition, those skilled in the art will recognize that there may be additional manners or methods of infusing biochars with microbials, including those created by the combination of one or more of the manners and methods listed above, without departing from the scope of the present invention.

F. Using Microbial Inoculated Biochars

Thus, treated biochar can have a microbial community in its pores (macro-, meso-, and combinations and variations of these), on its pore surfaces, embedded in it, located on its surface, and combinations and variations of these. The microbial community can have several different types, e.g., species, of biologics, such as different types of bacteria or fungi, or it may have only a single type. For example, a preferred functional biochar, can have a preferred range for bacterial population of from about 50-5000000 micrograms/g biochar; and for fungi, from about 5 to 500000 micrograms/g biochar. A primary purpose in agricultural settings, among many purposes, in selecting the microbial population is looking toward a population that will initiate a healthy soil, e.g., one that is beneficial for, enhances or otherwise advance the desired growth of plants under particular environmental conditions. Two types of microbial infused biochars will be discussed further for agricultural settings: bacteria and fungi. However, the microbes may also be used in other applications, including but not limited to animal health, either directly or through interactions with other microbes in the animals' digestive tract and public health applications, such as microbial larvicides (e.g. *Bacillus thuringiensis* var. *israelensis* (Bti) and *Bacillus sphaericus* used to fight Malaria).

G. Bacteria Inoculated Biochars

PGPB include, for example, plant growth promoting rhizobacteria, free-living and nodule-forming nitrogen fixing bacteria, organic decomposers, nitrifying bacteria, phosphate solubilizing bacteria, biocontrol agents, bioremediation agents, archea, actinomycetes, thermophilic bacteria, purple sulfur bacteria, cyanobacteria, and combinations and variations of these.

PGPB may promote plant growth either by direct stimulation such as iron chelation, phosphate solubilization, nitrogen fixation and phytohormone production or by indirect stimulation, such as suppression of plant pathogens and induction of resistance in host plants against pathogens. In addition, some beneficial bacteria produce enzymes (including chitinases, cellulases, -1,3 glucanases, proteases, and lipases) that can lyse a portion of the cell walls of many pathogenic fungi. PGPB that synthesize one or more of these enzymes have been found to have biocontrol activity against a range of pathogenic fungi including *Botrytis cinerea, Sclerotium rolfsii, Fusarium oxysporum, Phytophthora* spp., *Rhizoctonia solani, Pythium ultimum.*

Currently the most economic conventional solid carrier used to deliver microbes is peat. A solid carrier allows for a relatively long shelf life and a more direct application to a plant's root system compared to a microbial liquid solution, which would be sprayed directly.

Figure 33:
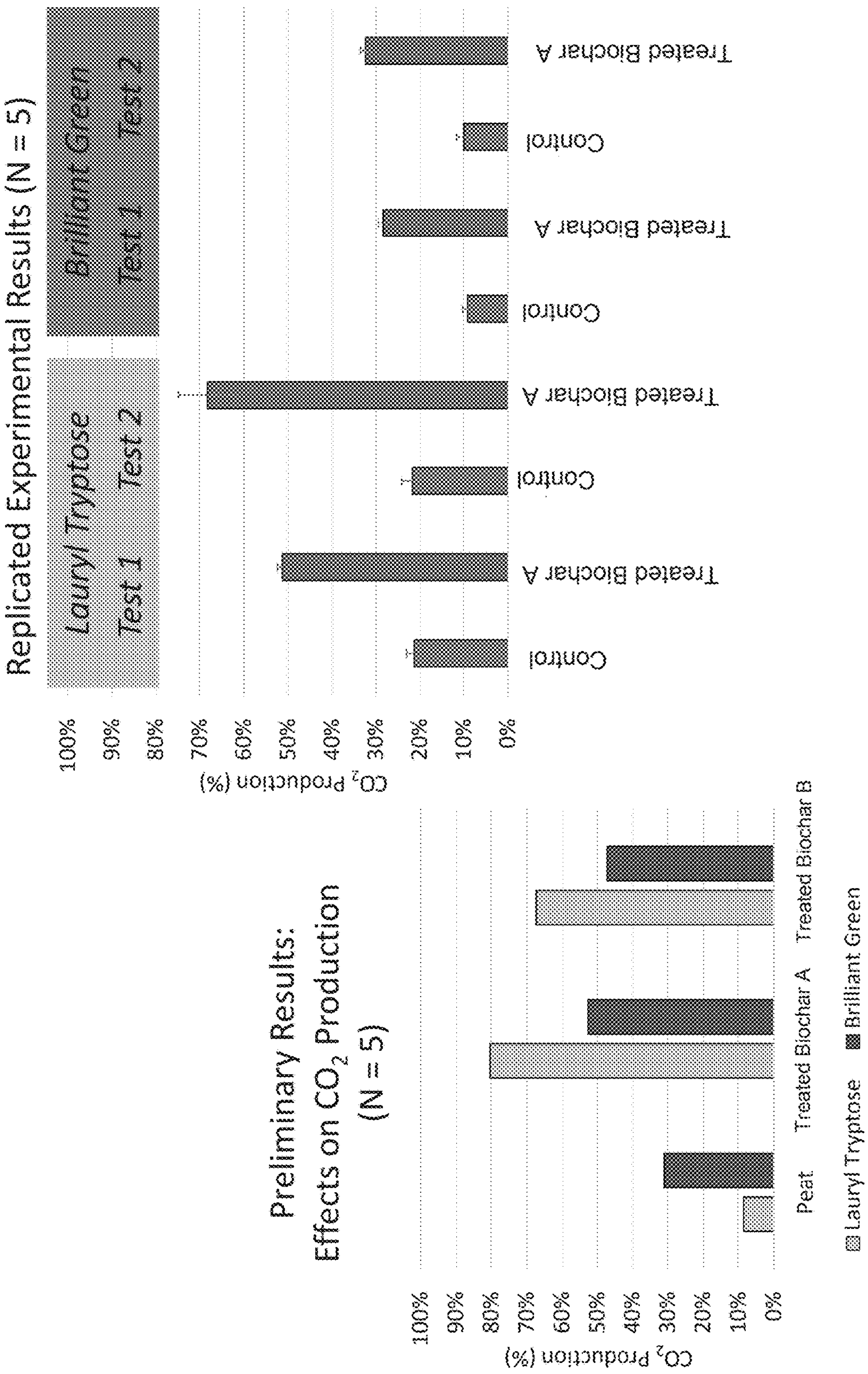
FIG. 33 contains charts illustrating improved results obtained through the use of biochars.

Research has shown a substantial increase in PGPB growth and distribution resulting from being infused in biochar. For example, data resulting from research conducted to compare the effects upon CO2 production (an indicator of bacterial growth) using peat and biochars show the beneficial effects of using various biochars in promoting PGPB growth. As illustrated in the left-hand chart in FIG. 33, peat results in CO2 production of between approximately 10% and 30% (depending upon the grown medium), whereas biochars result in CO2 production of approximately 48% and 80%. Replicated experimental results using different biochars confirm CO2 production of approximately 30% to 70% (depending on the grown medium), as compared to approximately 10% to 20% for the peat control.

Figure 34:
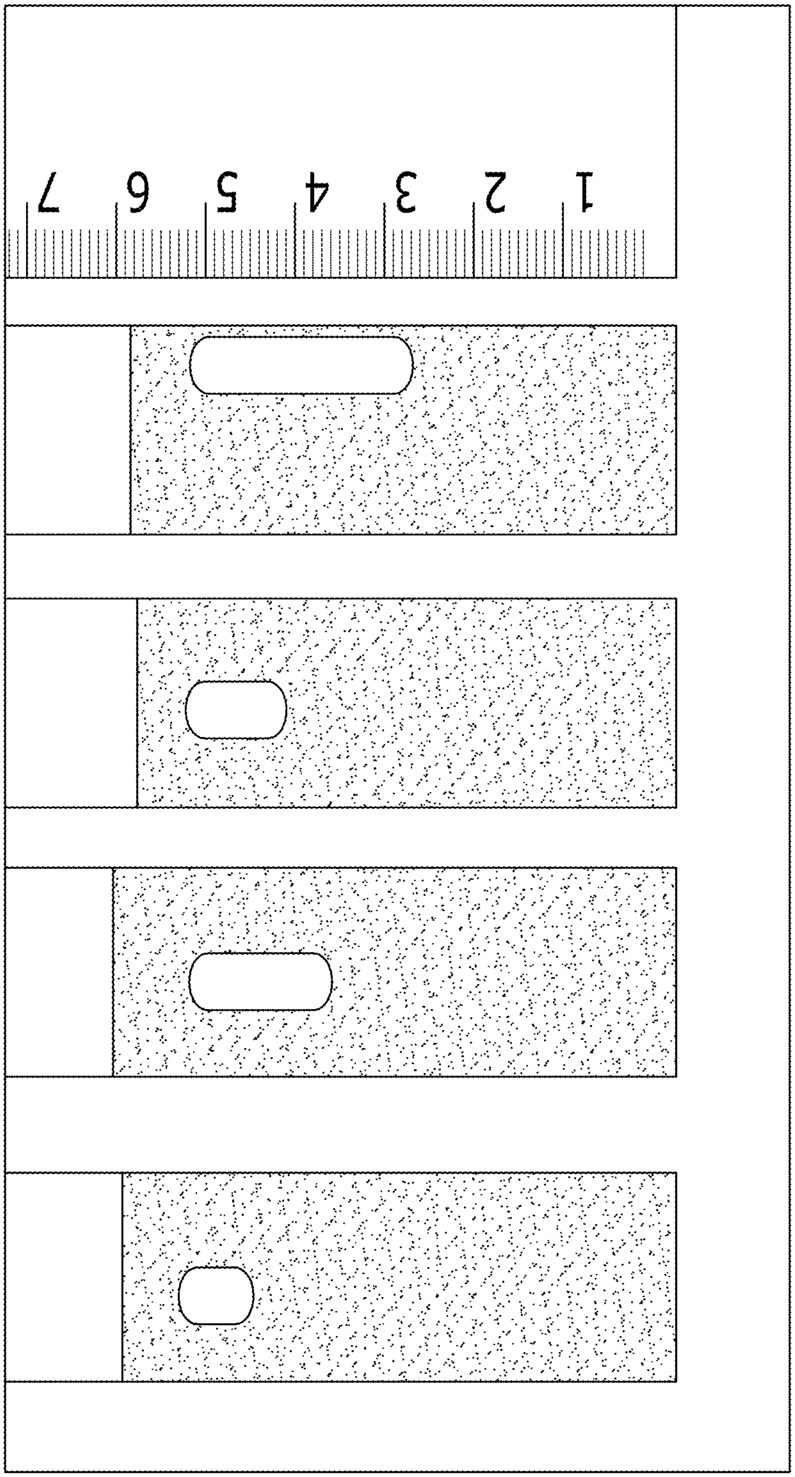
FIG. 34 is an example of carbon dioxide production captured as a continuous gas bubble in BGB (left two tubes) and LTB (right two tubes) growth medium.

The method developed for determining this CO2 production as an indicator of bacterial growth consists of the following. The substrate, here biochar or peat, is sterilized by heating at 110 C for 15 hours. A bacterial stock solution is then created, here Tryptic Soy Broth was solidified with agar at 1.5% w/v in petri plates to isolate the gram negative non-pathogenic organism *Escherichia coli* ATCC 51813 (15 h growth at 37° C.). Then an isolated colony is captured with an inoculating loop and suspend in 10 ml sterile buffer (phosphate buffer saline or equivalent) to create the bacterial stock solution. Lactose containing assays are then used, here, test tubes that contain 13 ml of either Lauryl Tryptose Broth (LTB) or Brilliant Green Broth (BGB) that also contain a Durham tube. A negative control is generated by adding 10 μL of sterile buffer to triplicate sets of LTB and BGB tubes. A positive control is generated by adding 10 μL of bacterial stock solution to triplicate sets of LTB and BGB tubes. A negative substrate is generated by adding 1.25 ml (~1% v/v) of sterile substrate to triplicate sets of LTB and BGB tubes. A positive substrate is generated by adding 1.25 ml (~1% v/v) of sterile substrate and 10 μL of bacterial stock solution to triplicate sets of LTB and BGB tubes. The tubes of the four treatments are then incubated statically in a test tube rack at 37° C. for at least 15 h. The tubes are then carefully observed and any gas bubbles captured by the Durham tube within respective LTB or BGB tubes are closely measured with a ruler. Small bubbles <0.2 mm should not be considered. A continuous bubble as shown in individual tubes in FIG. 34 are what are observed and quantified. FIG. 34 is an example of carbon dioxide production captured as a continuous gas bubble in BGB (left two tubes) and LTB (right two tubes) growth medium. The percent carbon dioxide production is then calculated by dividing the recorded bubble length by the total Durham tube length and multiplying by 100.

Further tests were conducted using the *Streptomyces lidicus* WYEC 108 bacterium found in one of the commercially available products sold under the Actinovate brand. Actinovate products are biofungicides that protect against many common foliar and soil-borne diseases found in outdoor crops, greenhouses and nurseries. The formulations are water-soluble.

Figure 35:
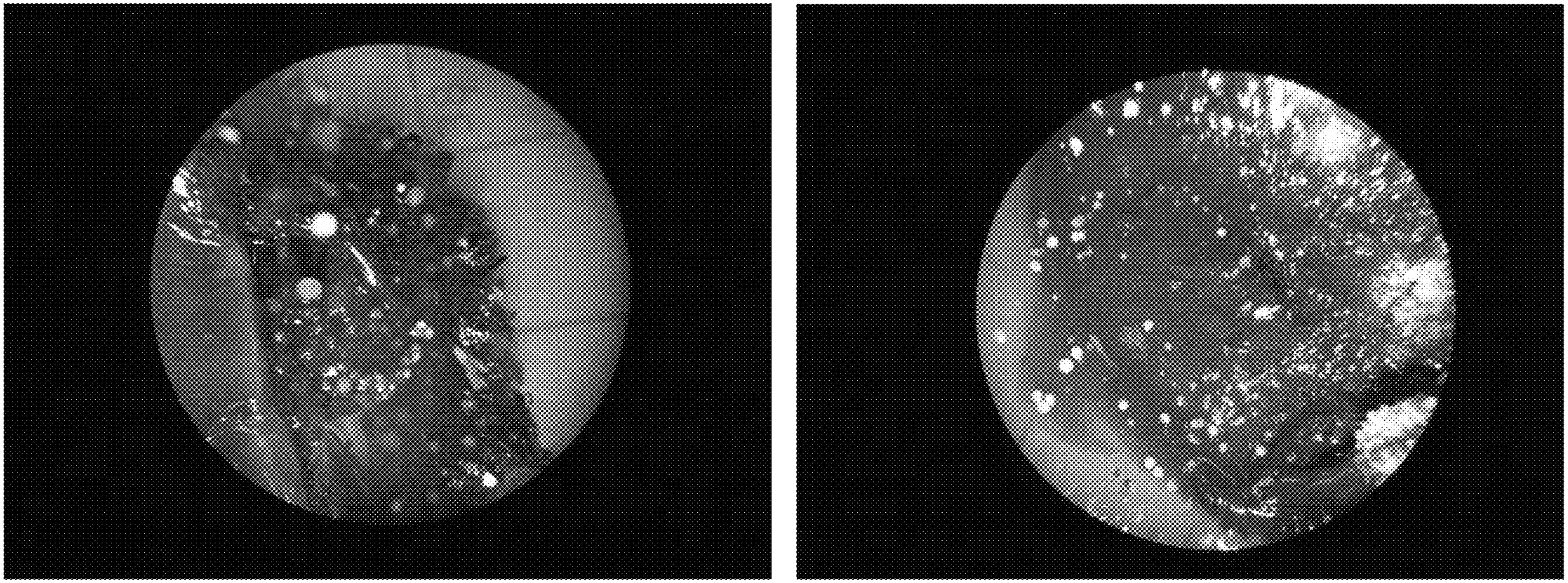
FIGS. 35 and 36 illustrate improved growth rates of colonies of *Streptomyces lydicus* using biochars.

FIG. 35 illustrates the effects upon the growth of *Streptomyces* lidicus using conventional peat versus biochars. In the test illustrated by the photograph on the left of FIG. 35, an Actinovate powder was blended with peat, placed in an inoculated media and incubated at 25° C. The photograph shows the distribution and density of white colonies after 3 days. In the test illustrated by the photograph on the right of FIG. 35, an Actinovate powder was blended with the treated biochar, placed in an inoculated media and incubated at 25° C. The photograph also shows the distribution and density of white colonies after 3 days, the distribution and density of which are significantly greater than those achieved with peat.

Figure 36:
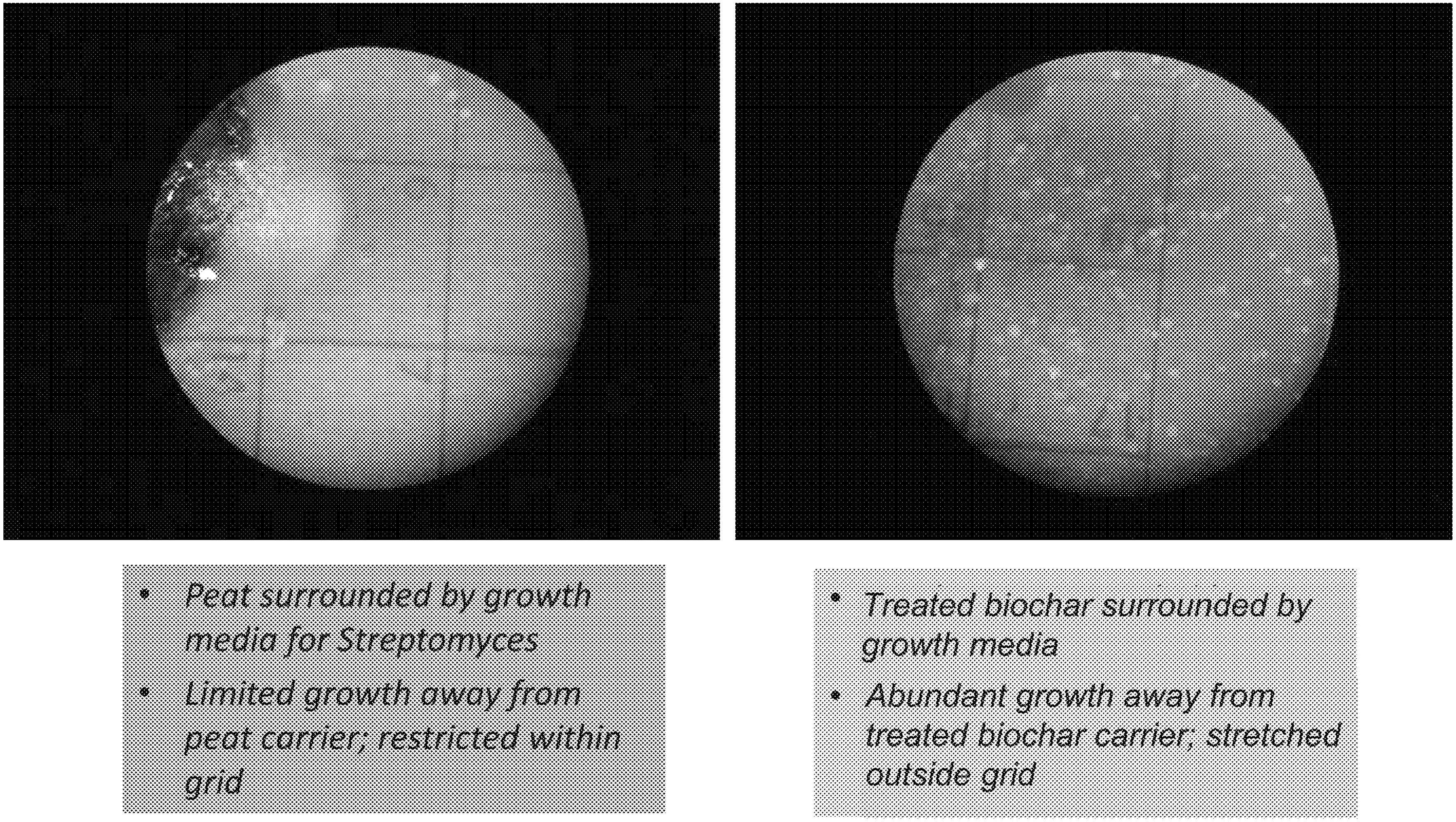

FIG. 36 further illustrates the improved growth of the Actinovate bacterium using biochar versus peat. The left photograph shows only limited and restricted growth away from the peat carrier. The right photograph shows abundant growth of the bacterium spread much farther out from the biochar carrier.

Another application of using biochar inoculated with bacteria would be in the biofuel industry, where methanotroph inoculated biochar could be used to create methanol. Methanotrophic bacteria are proteobacteria with diverse respiration capabilities, enzyme types, and carbon assimilation pathways. However, *Methylosinus trichosporium* OB3b is one of the few methanotrophs that can be manipulated by environmental conditioning to exclusively produce methanol from methane. *M. trichosporium* OB3b is one of the most well studied aerobic $C_1$ degraders and can be grown in either batch or continuous systems. As mentioned earlier, the large pore volume and surface area of biochar is suitable for bacterial colonization and should subsequently increase substrate access to enzyme activation sites. To improve the conversion rate, copper, nitrate, and phosphate should be included in the system. The use of biochar as a support material for the aerobic bioconversion of methane to methanol provides a pore distribution suitable for both adsorptions of methane and impregnation with bacteria. By providing biological and adsorptive functionality the biochar can intensify the bacteria in the biochar and increases the conversion rate.

In general, bacteria communicate via the distribution of signaling molecules which trigger a variety of behaviors like swarming (rapid surface colonization), nodulation (nitrogen fixation), and virulence. Biochars can bind signaling molecules and in particular it is believed can bind a major signaling molecule to their surface. This binding ability can be dependent upon many factors including on the pyrolysis temperature. This dependency on pyrolysis temperature and other factors can be overcome, mitigated, by the use of examples of the present vacuum infiltration techniques. For example, a signaling molecule that is involved in quorum sensing-multicellular-like cross-talk found in prokaryotes can be bound to the surface of biochars. Concentration of biochars required to bind the signaling molecule decreased as the surface area of biochars increased. These signaling molecules may be added to the surface of a biochar and may be used to manipulate the behavior of the bacteria. An example of such a use would be to bind the molecules which inhibit cell-to-cell communication and could be useful in hindering plant pathogens; using techniques in the present invention signaling molecules may be added to the surface of a biochar to engineer specific responses from various naturally occurring bacteria.

H. Fungi Inoculated Biochars

Beneficial fungi include, for example, saprotrophic fungi, biocontrol fungi, ectomycorrhizae, endomycorrhizae, ericoid mycorrhizae, and combinations and variations of these. It is further theorized that, in general, biochars with greater fungal development may be better suited for perennial crops such as grapes, almonds, blueberries, and strawberries in which symbiotic relationships with arbuscular mycorrhizal fungi (AMF) are favored over PGPBs. The presence of high concentrations of AMF spores in biochars can therefore rapidly promote fungal colonization of plant root hairs leading to extensive mycelial development. Increased plant root associations with mycelial filaments would consequently increase nutrient and water uptake.

Mycorrhizal fungi, including but not limited to Endomycorrhizae and Ectomycorrhizae, are known to be an important component of soil life. The mutualistic association between the fungi and the plant can be particularly helpful in improving plant survivability in nutrient-poor soils, plant resistance to diseases, e.g. microbial soil-borne pathogens, and plant resistance to contaminated soils, e.g. soils with high metal concentrations. Since mycorrhizal root systems significantly increase the absorbing area of plant roots, introducing mycorrhizal fungi may also reduce water and fertilizer requirements for plants.

Typically mycorrhizae are introduced into soil as a liquid formulation or as a solid in powder or granular form and contain dormant mycorrhizal spores and/or colonized root fragments. Often the most economic and efficient method is to treat the seeds themselves, but dealing with traditional liquid and powder inoculums to coat the seed can be difficult. In accordance with the present invention, inoculated biochar may be used to coat the seeds by, for example, using a starch binder on the seeds and then subjecting the seeds to inoculated biochar fines or powder. Another method is by placing the mycorrhizae inoculum in the soil near the seeding or established plant but is more costly and has delayed response as the plants initial roots form without a mycorrhizal system. This is because the dormant mycorrhizae are only activated when they come close enough to living roots which exude a signaling chemical. In addition if the phosphorus levels are high in the soil, e.g. greater than 70 ppm, the dormant mycorrhizae will not be activated until the phosphorus levels are reduced. Thus applying inoculant with or near fertilizers with readily available phosphorus levels can impede the desired mycorrhizal fungi growth. A third option is to dip plant roots into an inoculant solution prior to replanting, but this is costly as it is both labor and time intensive and only applicable to transplanting.

If the colonization of mycorrhizae can be quickened and the density of the mycorrhizae's hyphal network can be increased then the beneficial results of mycorrhizal root systems, e.g. increased growth, increased survivability, reduced water, and reduced fertilizer needs, can be realized sooner. Prior art shows that compost, compost teas, humates, and fish fertilizers can improve microbial activities and in more recent studies have shown physically combining arbuscular mycorrhizal fungi (AMF) inoculant with raw biochar has resulted in additional plant yield compared to each alone. See Hammer, et. al. *Biochar Increases Arbuscular Mycorrhizal Plant Growth Enhancement and Ameliorates Salinity Stress*, Applied Soil Ecology Vol 96, November 2015 (pg. 114-121).

An ideal carrier for the mycorrhizae would have moisture, air, a neutral pH, a surface for fungi to attach, and a space for the roots and fungi to meet. Thus a previously infused biochar created by the method disclosed above would be a better carrier than raw biochar alone. The infused biochar could be physically mixed with a solid mycorrhizal fungi inoculant or sprayed with a liquid mycorrhizal inoculant prior to or during application at seeding or to established plants. Additionally, the infused biochar and mycorrhizal fungi inoculant could be combined to form starter cubes, similar to Organo-Cubes, rockwool, oasis cubes, and peat pots.

The infused biochar could be further improved upon by initially infusing or further infusing the biochar with micronutrients for mycorrhizal fungi, for example but not limited to humic acid, molasses, or sugar. The growth nutrient infused biochar would further expedite the colonization of the mycorrhizal fungi when physically combined with the inoculant and applied to seeds or plants.

Another improvement to the infused biochar would be to initially infuse or further infuse the biochar with the signaling molecules of mycorrhizal fungi. The signaling molecule infused biochar would further expedite the colonization of the mycorrhizal fungi when physically combined with the inoculant and applied to seeds or plants, as it would bring the mycorrhizae out of dormancy quicker and thus establish the mycorrhizal root system quicker.

Another method for establishing and improving mycorrhizal fungi colonies would be by growing mycorrhizae into the infused biochar and then applying the mycorrhizal fungi inoculated biochar to seeds or plants. Similar to a sand culture (Ojala and Jarrell 1980, a bed of infused biochar is treated with a recycled inoculated nutrient solution by passing it through the bed multiple times.

I. Batch Treatment/Bulk Production

As demonstrated above, the treatment processes described above are particularly well suited for large scale production of biochar. The processes and biochars of the present invention provides a unique capability to select starting materials and pyrolysis techniques solely on the basis of obtaining a particular structure, e.g., pore size, density, pore volume, amount of open pores, interconnectivity, tortuosity, etc. Thus, these starting materials and processes can be selected without regard to adverse, harmful, phytotoxic side effects that may come from the materials and processes. This is possible, because the infiltration steps have the capability of mitigating, removing or otherwise address those adverse side effects. In this manner, a truly custom biochar can be made, with any adverse side effects of the material selection and pyrolysis process being mitigated in later processing steps.

Further, the processes are capable of treating a large, potentially variable, batch of biochar to provide the same, generally uniform, predetermined customized characteristics for which treatment was designed to achieve, e.g., pH adjustment. Treatment can result in treated biochar batches in which 50% to 70% to 80% to 99% of the biochar particles in the batch have same modified or customized characteristic, e.g., deleterious pore surface materials mitigated, pore surface modified to provide beneficial surface, pore volume containing beneficial additives.

Accordingly, the ability to produce large quantities of biochar having a high level of consistency, predictability and uniformity, provides numerous advantages in both large and small agricultural applications, among other things. For example, the ability to provide large quantities of biochar having predetermined and generally uniform properties will find applications in large scale agriculture applications. Thus, treated biochar batches from about 100 lbs up to 50,000+lbs and between may have treated biochar particles with predetermined, uniform properties.

As the treated biochar batches are made up of individual biochar particles, when referring to uniformity of such batches it is understood that these batches are made up of tens and hundreds of thousands of particles. Uniformity is thus based upon a sampling and testing method that statistically establishes a level of certainty that the particles in the batch have the desired uniformity.

Thus, when referring to a treated batch of biochar as being "completely uniform" or having "complete uniformity" it means that at least about 99% of all particles in the batch have at least one or more property or feature that is the same. Same being within appropriately set tolerances for said property. When a treated batch of biochar is referred to as "substantially uniform" or having "substantial uniformity" it means that at least about 95% of all particles in the batch have at least one or more property or feature that is the same. When a treated batch of biochar is referred to as "essentially uniform" or having "essential uniformity" it means that at least about 80% of all particles in the batch have at least one or more property or feature that is the same. The batches can have less than 25%, 20% to 80%, and 80% or more particles in the batch that have at least one or more property or feature that is the same. Further, the batches can have less than 25%, 20% to 80%, and 80% or more particles in the batch that have at one, two, three, four, or all properties or features that are the same.

J. Aggregate Biochar Particles

It has been discovered that the same benefits can be achieved through the production and application of biochar aggregate particles as biochar particles that have not been aggregated. The creation of biochar aggregate particles, however, allows for easier product distribution for in various applications including industrial agricultural equipment, and provides a highly beneficial use for the biochar dust and fines, which are generally discarded. In this same manner, biochar aggregate particles may be produced for use for consumption by animals or use in composting.

The biochar, prior to being formed into a solid aggregate (e.g., through agglomeration, extrusion, or pelletization), may be raw or treated, as described above. If the biochar is treated, not only can various characteristics including pH be adjusted as needed, but fertilizers, nutrients, vitamins, supplements, microbes or other additives may be infused into the biochar prior to aggregation. (as further described below). However, regardless of whether the biochar is raw or treated, the present application for biochar aggregate particles can be utilized for both.

Figure 37A:
FIG. 37*a* is an image of biochar aggregate particles of the present invention made in the form pellets.
Figure 37B:
FIG. 37*b* is an image of biochar aggregate particles of the present invention made in the form an extrudates.
Figure 37C:
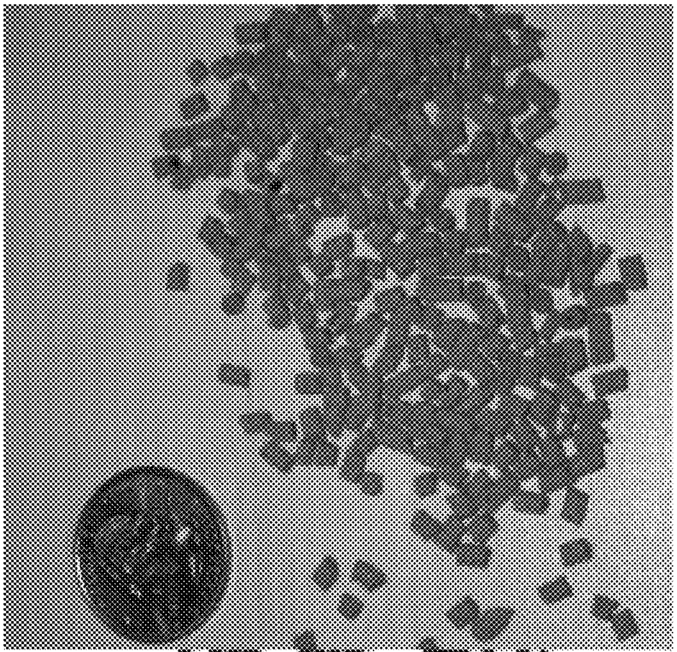
FIG. 37*c* is an image of the biochar aggregate particles made in the form of biochar sulfur prills.

There are various types of aggregation methods and resulting aggregate particles. FIGS. 37*a*, 37*b* and 37*c* shows three resulting aggregate examples. FIG. 37*a* shows pellets, FIG. 37*b* shows extrudates and FIG. 37*c* shows biochar sulfate prills.

Figure 38:
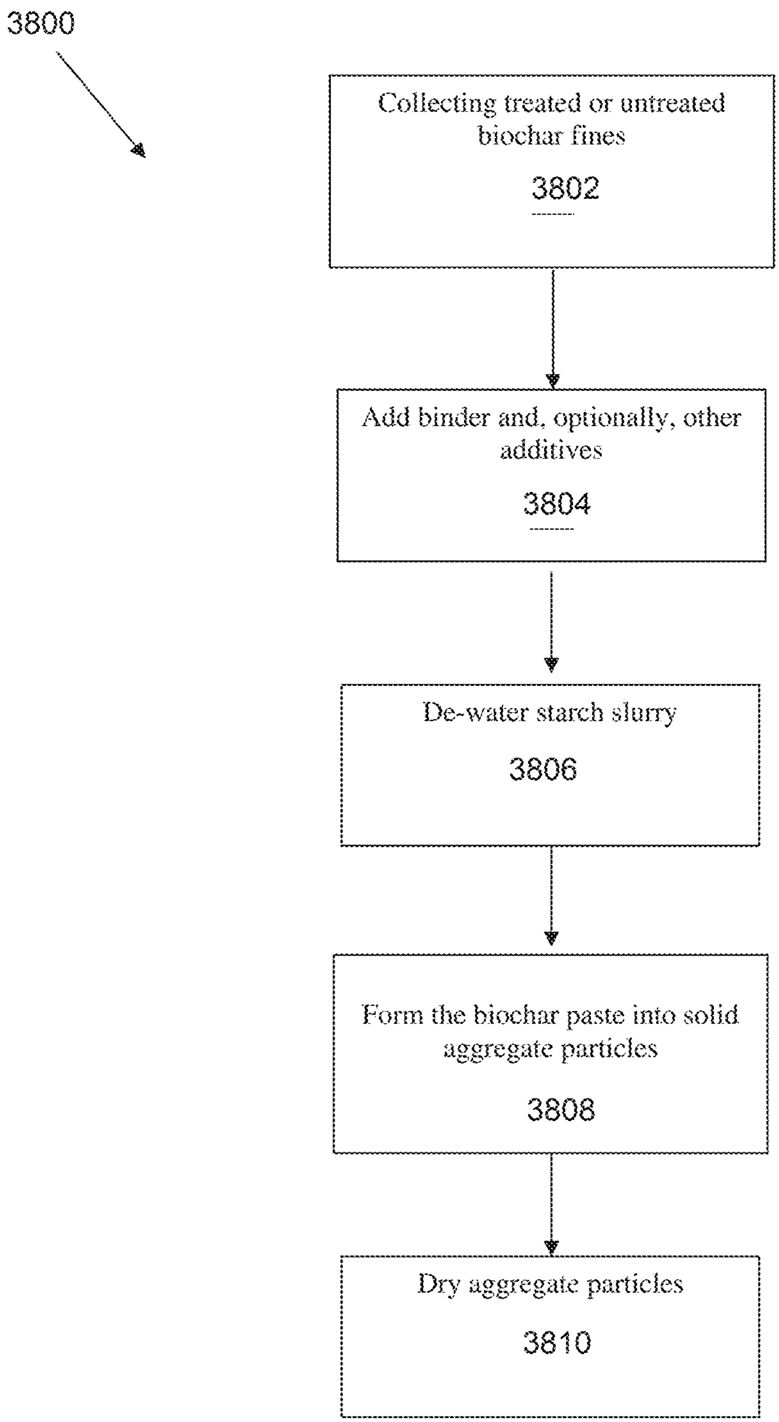
FIG. 38 is a flow diagram of one example of a method for producing biochar aggregate particles.

As an example, one method to produce biochar aggregate particles is depicted in the flow diagram shown in FIG. 38. The flow diagram 3800 of FIG. 38 is an example of one method that may be used for producing biochar aggregate particles. In general, the method of producing biochar aggregate particles from biochar may be accomplished by first collecting the treated or untreated biochar fines at step 3802. The fines may be collected by washing the biochar media, which may cause the biochar fines and dust to be placed in suspension in the liquid solution used to wash and/or treat the biochar. The biochar fines can also be produced by grinding, crushing, sieving, or otherwise resizing biochar of a larger particle size to one better suited for extrusion, compression, coagulation, or other forms of pelletization.

For example, the biochar fines may be separated from larger biochar particles by dry-sieving to remove the fine particles followed by wet-sieving with deionized water to remove fine fractions that remained. To separate particles of 0.5 mm or less of equivalent diameter, both the dry-sieving and wet-sieving may be carried out with a US size 35 mesh sieve. Biochar fines or dust may also be created by mechanical means such as grinding cutting or crushing the raw or treated biochar particles. These mechanically created small particles can be separated as set forth above through sieving or may be collected by washing or treating the material and using the resulting solution (the "biochar extract" or "extracted treating solution") to recover the smaller particles. The recovery of small biochar particles from the extracted treating solution can be accomplished by using chemical or physical means of separation or even a combination of multiple chemical and physical separation methods or steps.

While the biochar particles or fines may be treated in advance of collection, it is also possible to treat them once collected or as part of the collection process. Optionally, other physical and chemical properties may be adjusted during the treating step, as needed, or may be adjusted prior to, or during the fines collection process. For example, the biochar fines may be collected during treatment of the biochar media (e.g., to adjust the pH). The fines may then be collected in the treating solution by adding a flocculent and/or coagulant to the treating liquid, which creates a biochar slurry (the "flocculent slurry").

Given the application, it may be necessary to de-water the flocculent slurry before further treatment, as part of the collection process. The flocculent slurry is de-watered, typically using a belt filter press to create a biochar paste. Those skilled in the art will recognize that other de-watering systems, besides a belt filter press may be used to de-water the biochar slurry and that mechanisms other than a flocculent, such as filtration, settling, or other separation technology, may be used to separate the biochar from the minerals, inorganic compounds, and other substances found in the slurry that remain in the washing or treating solution.

Once the biochar fines are collected, a binder is then added to the biochar particles at step 3804. The binder solution used to coagulate the fines may be prepared by mixing a starch, polymer, lignin, clay, or other binder with water or appropriate solvents. The addition of the binder solution creates a biochar slurry or a paste (the "binder slurry"). The binder solution may be prepared by mixing, for example, enough corn starch with deionized $H_2O$ to create a solution. For example, the starch may be approximately 2% by weight, but may range from 0.5% to 10% by weight. Those skilled in the art will recognize that another material, besides corn starch may be used as a binder. Additionally, other binders may be used with the restriction that they must be appropriate for the application they will be used in. So for example, they may not be toxic in the quantities used in agriculture or animal feed and must be suitable for introduction into whatever application without profound ill effect. Some examples of other generally non-toxic binders that may be used are gelatins, cellulose, sugars, or combinations thereof. While the above describes adding the binder after the flocculent slurry is dewatered, the binder may also be added to the flocculent slurry before de-watering.

Like the flocculent slurry, the binder slurry is also de-watered before further treatment, step 3806. The binder slurry may be de-watered using a belt filter press to create a biochar paste. Those skilled in the art will recognize that other de-watering systems, besides a belt filter press may be used to de-water the biochar.

Optionally, other growth or beneficial additives may also be added to the slurry at step 3706. The binder and the growth additives may be added together or at separate stages, before or after the de-watering step 3806, with or without de-watering between, depending upon the application, the binder and the additives. In either event, the biochar is de-watered at step 3806 prior to further treatment.

Such growth enhancing additives may include, but are not limited to, fertilizers and beneficial microbes that can withstand the biochar aggregation process. For certain additives, the temperature of the process may need to be adjusted to avoid, for example, the denaturing of the proteins. Such additives can be added to the biochar particles (either with or after de-watering the starch slurry) through mixing. If a fertilizer is desired, the fertilizer may be pulverized to prepare for addition. The fertilizer may be pulverized to an average particle size of <1 mm before dispensing. Liquid fertilizers may also be used in solution. For example, 1000 ppm $NO3^-$ N fertilizer solution may be used. Examples of fertilizers that may be added to the paste, include, but are not limited to the following: ammonium nitrate, ammonium sulfate, monoammonium phosphate, ammonium polyphosphate, Cal-Mag fertilizers or micronutrient fertilizers. Other additives, such as fungicides, insecticides, nematicides, plant hormones, beneficial microbial spores, secondary signal activators, vitamins, medications, supplements, or sensory enhancers may also be added to the paste in a similar manner as a fertilizer, the inclusion of which does not depart from the scope of the invention. Additionally, beneficial macro- and micro-nutrients such as nitrogen, phosphorous, potassium, calcium, magnesium, sulfur, boron, zinc, iron, manganese, molybdenum, copper and chloride can be added to the mixture at this time.

Examples of compounds, in addition to fertilizer, that may be blended with, infused into the pores of or coated on the surface of the biochar include, but are not limited to: 2,1,3-Benzothiadiazole (BTH), an inducer of systemic acquired resistance that confers broad spectrum disease resistance (including soil borne pathogens); signaling agents similar to BTH in mechanism or structure that protects against a broad range or specific plant pathogens; biopesticides; herbicides; and fungicides.

As noted above, all the above additives may also be added at various steps in the described processes, including with the flocculant or coagulant, with the binder, or prior to the creation of the slurry or biochar paste. Such additives may be added through a pre-treatment process, such as those treatment processes described above (e.g., vacuum infiltration or surfactant treatment), or other treatment processes that result in the infusion of liquids and/or vapors into the pores of the biochar. It may also be possible to contact the biochar aggregate particles, once they are produced, with additives. Such contact or coating after production of the biochar aggregate particles is within the scope of the present invention.

Once de-watered, at step 3806, the biochar particles become a thicker slurry or paste (the "biochar paste"). The biochar paste, now including a binder and possibly other additives, is then formed into solid shapes, at step 3808 and then dried, at step 3810. To form the biochar paste into solids, alternative forms of processing may be used. For example, the paste may be passed through an extruder, a pelletizer, a briquetter, a granulator and/or other heating, cooling, dehydration, or pressure system capable of forming the paste into solid shapes. Alternatively, the biochar may be mixed with the binder, both in a dry form, and then fed into the equipment used to form the solid shaped biochar aggregates while adding moisture and/or other additives.

In one example of an implementation, the biochar paste is shaped through an extruder that is heated at a temperature of 25-120° C. in order to adequately activate the starch or other binder. The extruder may be specifically set depending on the appointed application to produce an extrudate size, ranging from 1 to 5 mm in diameter. At step 3810, the resulting extrudates are dried using a hot air, tunnel oven dryer, or other dryer known to the art. For some application, e.g., when microbes are added to or inoculated into the biochar particles, it may not be desirable to use heat to activate the binder. Alternatively, lipids or other binders that bind at cold temperatures may be used, with the substitution of cooling equipment in place of heating equipment to activate said binder.

The biochar aggregate particles from the extruder may be cut into predetermined specific sized particles, which may take the form of pellets. The steps of extruding and cutting may be performed together by the extruder, or separately, again depending upon the application and equipment capabilities. In addition larger extrudates can be formed creating a biochar spike, which can be applied by pushing them into soil near existing plants or trees.

In one example of an implementation, the biochar aggregate particles may be created from pyrolyzed wood or cellulosic biomass, as described above. The resulting biochar fines or dust are then removed from the other biochar particles at step 3802. As part of the collection process, the fines may optionally be washed with a treatment solution, as described in detail above. The treatment solution may, for example, be added to neutralize the biochar pH levels, as needed, depending upon the pH of the biochar fines. A neutralized biochar slurry is then exposed to a de-watering station and a flocculent is added to coagulate the fines or dust for de-watering. To dewater the flocculent slurry, a belt filter press or other equipment known to the art may be used. Once dewatered, a starch or another suitable binder is added to the biochar particles, at step 3804. Other additives may also be added to the biochar particles during this step. The biochar particles are again de-watered at step 3806 and the slurry becomes a thicker slurry or paste. The de-watered biochar paste may then be formed into aggregate solids at step 3808, by, for example, the use of an extruder. The aggregate particles are then dried using a hot air, tunnel oven dryer, or other dryer known to the art, at step 3810. The aggregate particles could also be freeze dried (e.g., lyophilized) and/or allowed to air dry, at step 3810. Such drying can be done before or after the biochar paste is subjected to a forming processes.

Treatment of biochar fines or dust is optional, but may be desired for pH adjustment and/or removal of elemental ash and other harmful organics or materials, as described in more detail above. Depending on the chemical properties of the biochar dust or fines, either water or acidic acid can be used to adjust the pH to neutral levels, and obtain a neutralized biochar slurry. The wash may also contain a surfactant or detergent to aid in the penetration of the wash solution into the pores of the char. Those skilled in the art will recognize that other pH adjusting agents, besides acidic acid may be used to neutralize the biochar pH levels. Additionally, other binders may be used with the restriction that they must be suitable for introduction into their particular application, for example not phytotoxic for use in soil or toxic to animals or humans for use in animal feed or maintenance. Some examples of these other pH adjustment agents include, but are not limited to gypsum, sulfur, lime, or combinations thereof. As set forth earlier, treatment can be performed on the fines or on the larger biochar media from which the fines are collected.

The above illustrated example details only one method of how biochar aggregate particles may be produced. As noted above, alternate forming processes may also be used besides passing the biochar paste through an extruder, such as a pelletizer, a briquetter, a granulator and/or other heat, cold, evaporation and/or pressure system capable of forming the paste into solid shapes.

Further, in another implementation, raw or treated biochar fines and/or larger biochar particles may be dried and ground to a smaller particle size or powder. The biochar powder can then be mixed with a binder in a rotary drum to create reasonably uniform spherical biochar aggregate particles.

Further, in another implementation, the biomass, prior to pyrolysis, may be formed into solids shape aggregates, such as pellets, by equipment designed to create pellets, granules and/or briquettes. Further, these pellets may be stabilized by mixing a dry binder or a binder solution with biomass prior to pelletizing to improve the mechanical stability of the formed pellet. These binders may include but are not limited to starches, polymers, clays, or lignins. By shaping the biomass prior to pyrolysis, the biomass may retain the solid shape. Depending upon the biomass, the biomass aggregate may need to be treated prior to pyrolysis to maintain the original shape with, for example, a binder solution. Wet formed, or solution treated pellets may require drying before handling and pyrolysis. This drying may be done using hot air, a tunnel oven dryer, or other dryer known to the art.

Figures 39A, 39B, 39C, 39D, 39E, 39F:
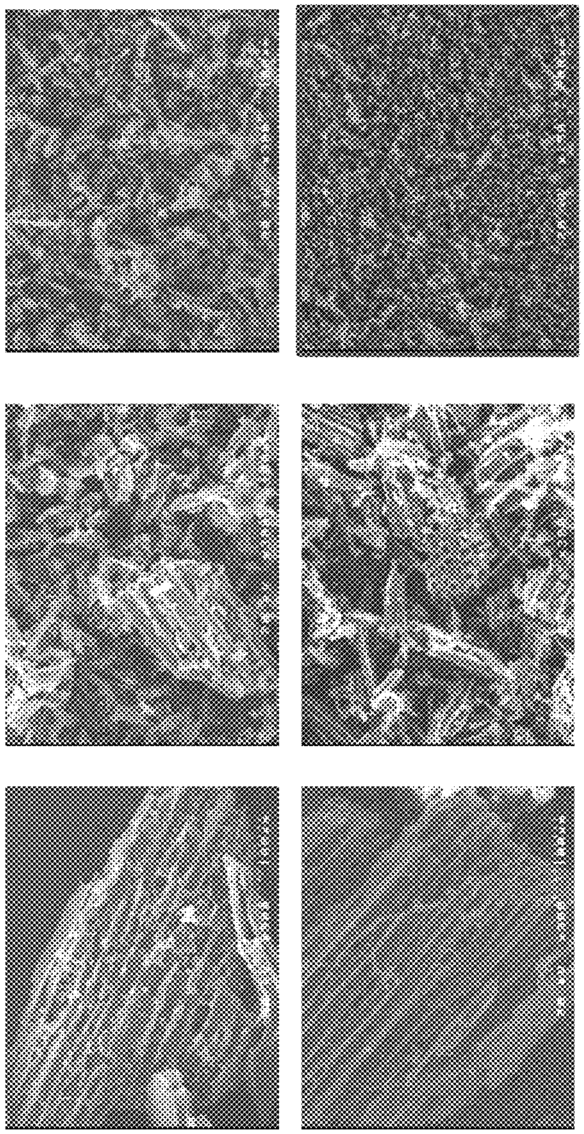
FIGS. 39*a-f* illustrates the effects of size and grinding on particle structure of a biochar derived from a first biomass.
Figure 41A:
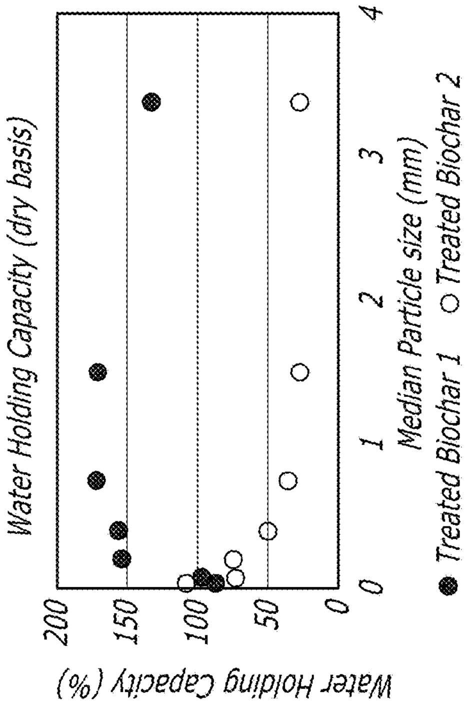
FIG. 41*a* shows the effect of size fraction on water holding capacity of two different biomass based treated biochars.
Figure 41B:
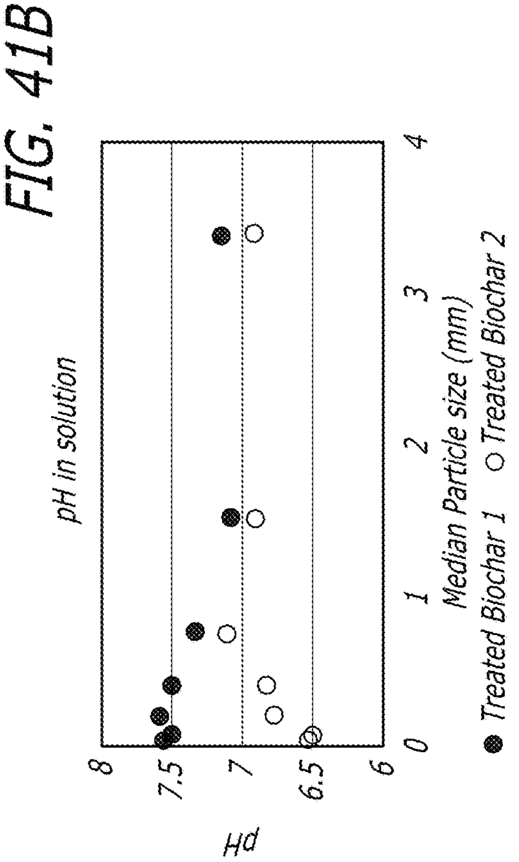
FIG. 41*b* shows the effect of size fraction on pH of two different biomass based treated biochars.
Figure 41C:
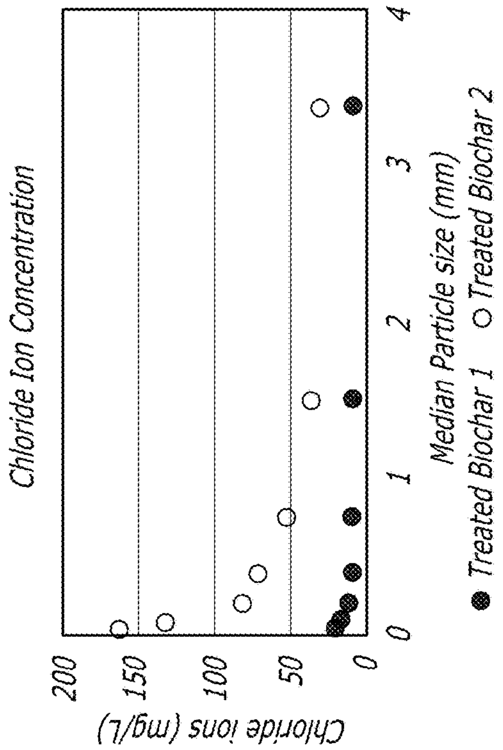
FIG. 41*c* shows the effect of size fraction on Cl− concentration of two different biomass based treated biochars.
Figure 41D:
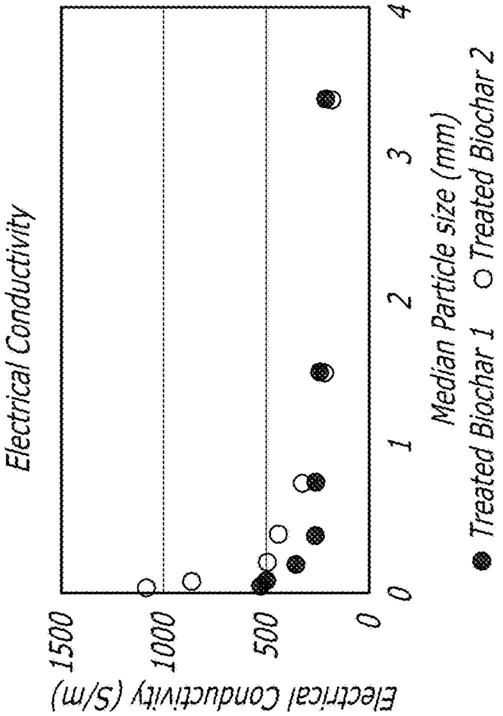
FIG. 41*d* shows the effect of size fraction on electrical conductivity of two different biomass based treated biochars.

In creating biochar aggregates, it is critical to determine the proper biochar particle size and the proper method to use to create said particles for the biochar aggregate production. Setting the correct size limits and method will ensure the aggregates maintain the physical and chemical characteristics that make the specific biochar effective in the target application. FIGS. 39 and 40 show SEM photos from two different biomass based treated biochars. FIG. 39 shows the effect of size and grinding on particle structure for three different particle size ranges: 0.1-0.3 mm, 0.05-1 mm, and <0.05 mm. These particles were collected using two different methods: (i) sieving the as is treated biochar and (ii) grinding the as is treated biochar and then sieving. FIG. 39 shows one treated biochar ("treated biochar 1") and FIG. 40 shows a second treated biochar ("treated biochar 2"). In the treated biochar 1 SEM photos (FIGS. 39*a, b, c, d, e* and *f*), it is clear that the two methods of collection show no substantial difference in pore structure. It is also clear that the particle structure is destroyed once the particle sizes are less than 0.05 mm. In the treated biochar 2 SEM photos (FIGS. 40*a, b, c, d, e* and *f*), a different observation is noted, when the material is just sieved to 0.3-0.5 mm range, the biochar particle has retained its porous structure, but when the as is treated biochar 2 is ground using a medium grind or a fine grind and then sieved to 0.3-0.5 mm range, then the porous structures have been mostly destroyed. FIGS. 40*d*, 40*e* and 40*f* are zoomed images of FIGS. 40*a*, 40*b* and 40*c*.

In addition, various particle size ranges from the two treated biochars were further tested to see how biochar characteristics changed with particle size. FIGS. 41 *a, b, c* and *d* show the effect of size fraction on four properties, water holding capacity, pH, Cl-concentration, and electrical conductivity of two different biomass based treated biochars. For treated biochar 1, these properties, except pH, were stable across particle sizes except when the particles were smaller than 0.1 mm. This is likely due to the loss of pore structure somewhere below 0.1 mm for this treated biochar. For treated biochar 2, some properties, electrical conductivity and chloride concentration, seemed to correlate to particle size in a similar way to that of treated biochar 1. But decreasing particle size of treated biochar 2 had the opposite effect on water holding capacity and pH versus treated biochar 1.

These observations show how particle size and the method used to create them can have significant impact on both the pore structure of the particles and the biochars properties. Thus an aggregate's properties and effectiveness can be maintained, adjusted, or harmed based on the method for creating and collecting sized biochar particles in addition to the method of aggregation and may differ based on the biochar feedstock and pyrolysis method.

Further in another implementation, the biomass may be sized prior to pyrolysis so that the aggregate can be made with the as is biochar particles or treated biochar particles without additional sizing. Eliminating the need to size the biochar further, may help to maintain the biochar properties when aggregating as biochar pore structures that are susceptible to being destroyed during sizing post pyrolysis will not be harmed using this method.

As noted above, the biochar aggregate particles can be created with either raw biochar or treated biochar that is treated in the manner or method further described below. Biochar aggregate particles can be applied through a wide range of devices, including agricultural equipment including but not limited to broadcast spreaders, drop spreaders and/or hand distribution means. The application of biochar aggregate particles can be used for trees, row crops, vines, turf grasses, potted plants, flowering plants, annuals, perennials, evergreens and seedlings. The biochar aggregate particles may also be applied to animal pens, bedding, and/or other areas where animal waste is present to reduce odor and emission of unpleasant or undesirable vapors. Furthermore it may be applied to compost piles to reduce odor, emissions, and temperature or even to areas where fertilizer or pesticide runoff is occurring to slow or inhibit leaching and runoff. The aggregates may also be integrated with animal feed and/or other substances beneficial to animal health, either whole (biochar pellets mixed with separate feed pellets to form an aggregate, for example), or with animal feed or other beneficial substances mixed into the biochar slurry or paste prior to extrusion. Biochar aggregate particles may be incorporated into or around the root zone of a plant. As most trees, rows, and specialty crops extract greater than 90% of their water from the first twenty-four inches below the soil surface, the above applications will generally be effective incorporating the biochar around the root zone from the top surface of the soil and up to a depth of 24" below the top surface of the soil, depending on the plant type and species, or alternatively, within a 24" radius surrounding the roots regardless of root depth or proximity from the top surface of the soil. When the plant roots are closer to the surface, the incorporation of the biochar within the top 2-6" inches of the soil surface may also be effective. Greater depths are more beneficial for plants having larger root zones, such as trees.

Biochar aggregates are particularly useful, when they will be put into an application that requires mixing with other solid granular products. This is because the aggregates can be designed and created to be similar in shape, size, or density to that which it will be mixed with. When the aggregates are physically similar to the material particles they will be mixed with then the final mixture will stay more uniformly mixed and have better flow properties. When a specific rate of each material in the mixture is needed, say in agriculture or animal feed, then a uniform mixture is critical to ensure the soil or animal consistently gets the correct rate.

K. Biochars for Use In Composting

In addition to the use of treated biochar in connection with agriculture and animal applications for human consumption, treated biochar can also be used throughout the world, in numerous composting applications. The biochar used in composting applications can be all treated biochar, in accordance with the treatment processes set forth above, or may be mixed with raw, untreated biochar.

Figure 42:
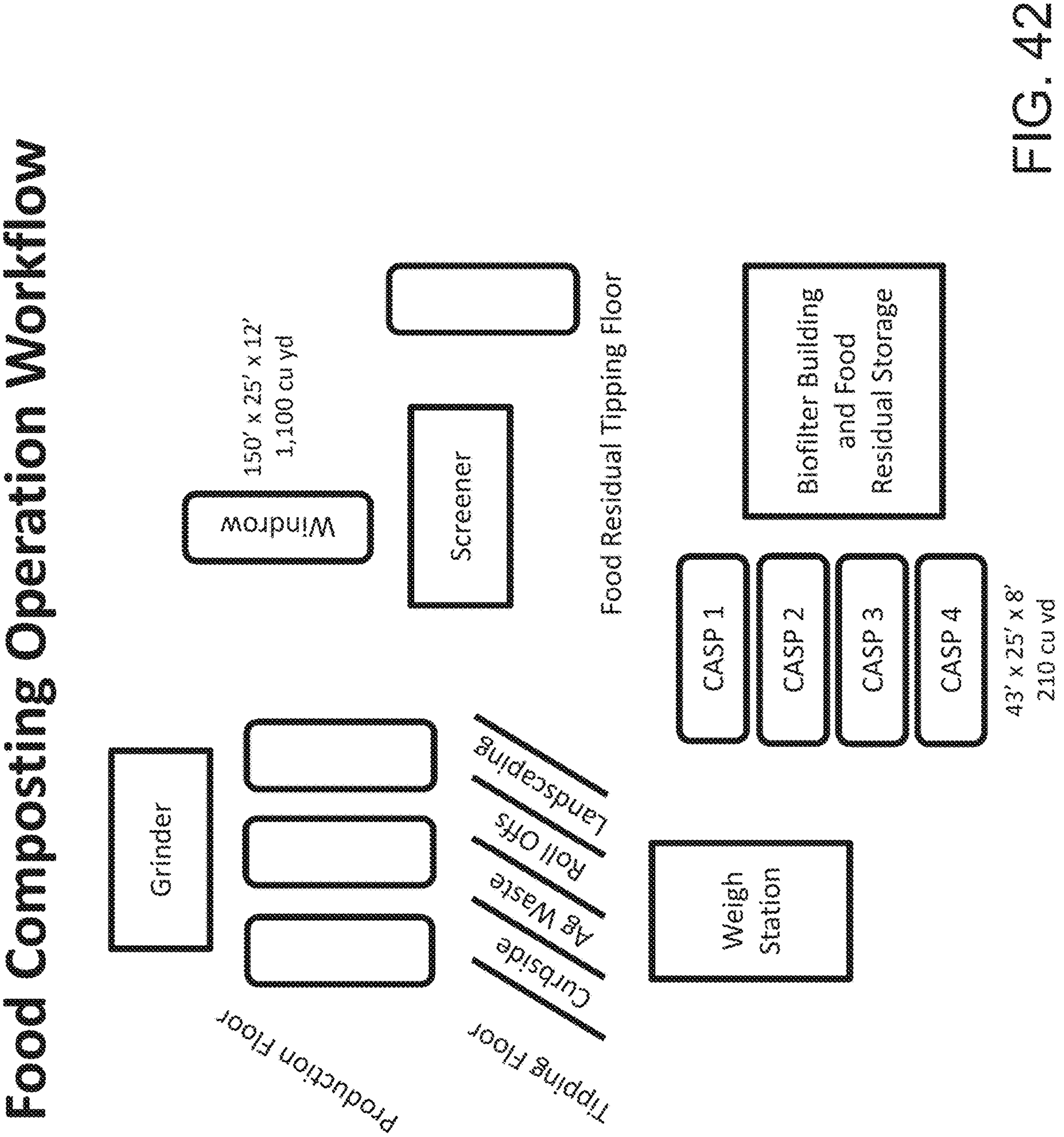
FIG. 42 is a diagram illustrating one example of the workflow for a food composting operation.

FIG. 42 is a diagram illustrating one example of the work flow for a commercial food composting operation. As illustrated in the diagram, compost material is first dropped at a weigh station, where clients are paid various rates for the compost materials. The materials then released to a tipping floor and segmented by types. Green waste/woods are cleaned and ground down on the production floor. Foods are slowly received and stored. Screening of green waste/woods creates various sized inputs. Stored food is blended with green waste/woods via screening to remove inerts from food.

When composted using covered aerated static piles ("CASP"), piles of the materials are placed over porous pipes. Tarps are laid over the pipes. Negative pressure aerates the piles and pulls odor into a biofilter. The CASPs run for approximately 30 days. When the piles are composted using woodrow (mechanical turning), the piles are kept in the woodrow for approximately 15 days.

Biochar can be applied to composting environments to allow for the control of temperature, moisture, pH levels, odors and bacterial cultures. As illustrated below, applying biochar in composting environments has been shown to significantly reduce water loss, control temperatures, reduce odors and control acidic pH issues. The present treatment processes for biochar allow for the capability of custom-manufacturing biochar for use in composting for a particular climate, environment, geographical area, or by more precisely controlling key characteristics of the biochar.

The method of the present invention for applying biochar to composts includes blending low, affordable rates of treated biochar (1%-5% v/v) with feedstock high in food residuals (40% v/v). Treated biochar may also be blended with other materials, such as raw and/or processed biochar, processed differently than the treatment processes described above, and with compost having other compositions than feedstock high in food residuals. Blending various rates of treated biochar, by itself, or with raw and/or processed biochar, in various composting environments may produce different desired results.

Figure 43:
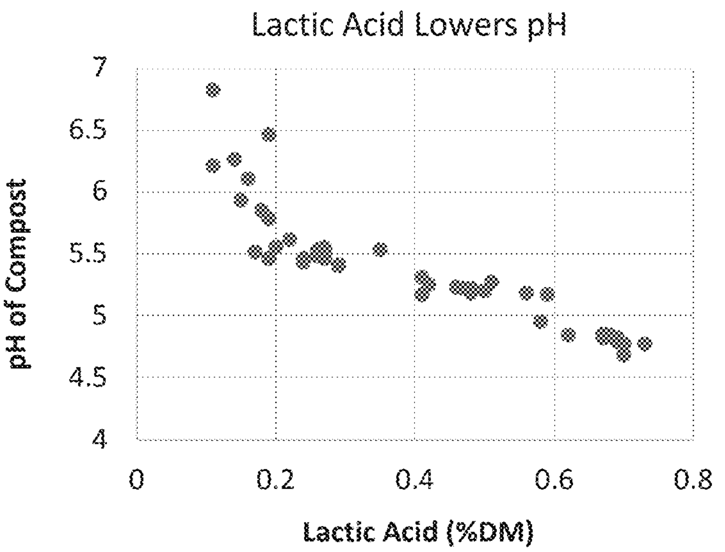
FIG. 43 is a chart showing the pH of compost as the percent of lactic acid increases.
Figure 44:
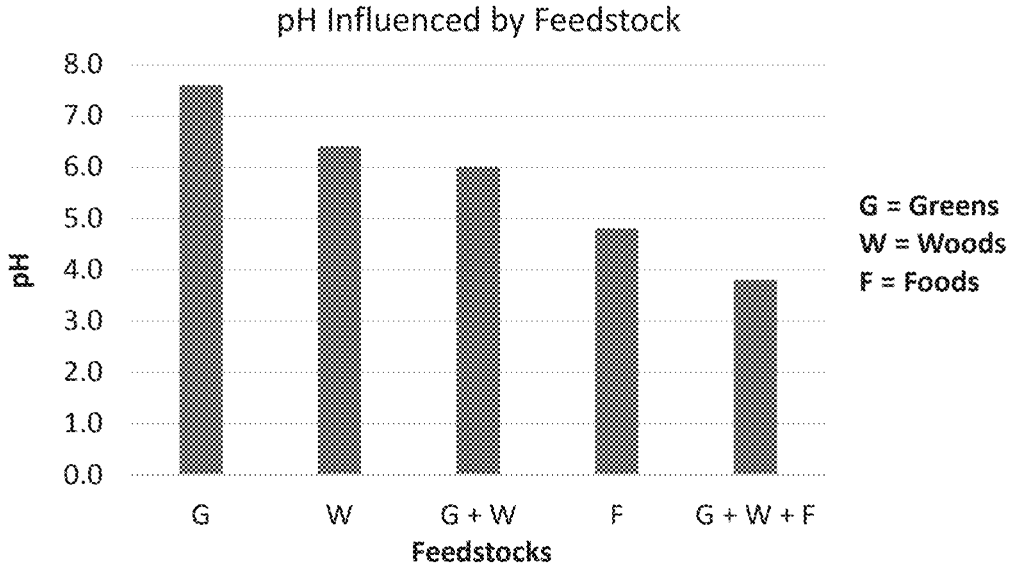
FIG. 44 is a chart showing how pH is influenced in compost when mixing greens, woods and foods.

One of the recurring problems in composting environments is to control the acidity levels and the lowering of pH in the compost. Food residuals contain high levels of organic acids like lactic acid. Low pH shifts the microbial community to more acid tolerant microbes that stimulate a feedback loop wherein lactobacilli produce more lactic acid. FIG. 43 is a chart showing the pH of compost as the percent of lactic acid increases. As illustrated in FIG. 43, the more lactic acid by percent, the lower the pH in compost. FIG. 43 shows the general pH of compost materials, before commencing the composting process. FIG. 44 demonstrates how pH is influenced in compost when mixing green wastes, woods and foods. As illustrated, the addition of foods and woods to compost lower the pH of the compost. Green waste provides the highest pH, while the combination of foods, green waste and wood, produce the lowest pH.

In composting, different microbial communities degrade the organic acids to raise the pH. Generally, the starting point for feedstock composting is a pH of ≥6.0. In CASP methods, feedstock compost may remain acidic to a pH of ≤5.0. Acidic compost is not ideal for plant nutrient uptake or other uses of the compost. Raising the pH in the compost is desired for a number of reasons.

Adding treated biochar to compost has been shown to increase aeration and lower and/or control the temperatures in the compost, leading to higher, less acidic pH levels. Lower temperatures are critical in the early stages of composting to stimulate the mesophilic ("cool-loving") microbes to outcompete the thermophilic ("heat-loving") microbes inherent to food residuals. Lactic acid bacteria are thermophiles that generally reduce the pH levels in compost. Adding treated biochar to compost appears to reduce lactic acid bacteria and generally increase the pH levels in compost. Despite lower temperatures, pathogen reduction still occurs. These reduced composting temperatures also means less air and water will be required.

Figure 45:
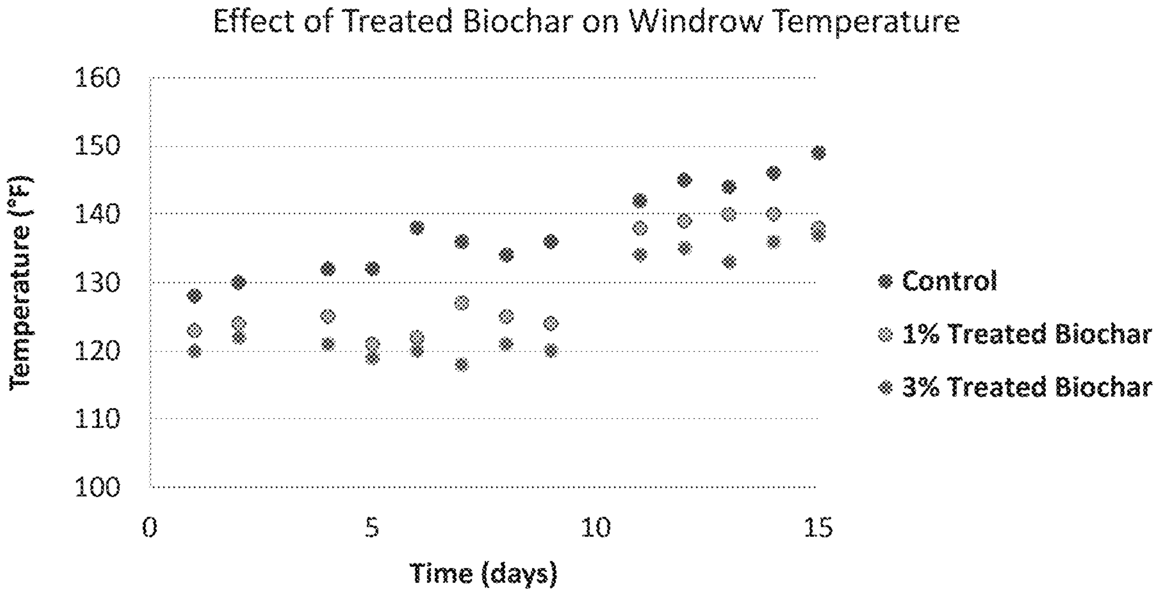
FIG. 45 is a chart showing the impact on composting temperatures when treated biochar is added to compost.

FIG. 45 is a chart showing the impact on composting temperatures when 1% and 3% treated biochar are added to the compost (control). The control represents the compost with 0% added biochar. As shown by FIG. 45, adding treated biochar to compost in a windrow environment generally decreases the temperature in the compost. It was shown that adding 1-3% treated biochar to the compost in a windrow environment generally lowered the temperature in the compost between 5-20° F.

Figure 46:
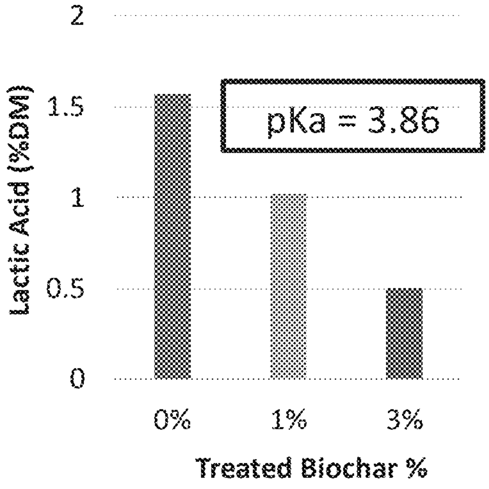
FIG. 46 is a chart showing the decrease of lactic acid production in compost by adding treated biochar.

FIG. 46 is a chart showing the decrease of lactic acid production in compost by adding treated biochar. As shown by FIG. 46, adding treated biochar to compost in a windrow environment generally decreases the lactic acid in the compost. The addition of 1% treated biochar in the compost reduced the lactic acid by 0.5-0.6% DM and the addition of 3% treated biochar in the compost reduced the lactic acid by as much as 1.0-1.1% DM. The control compost is represented by 0% added treated biochar.

Figure 47:
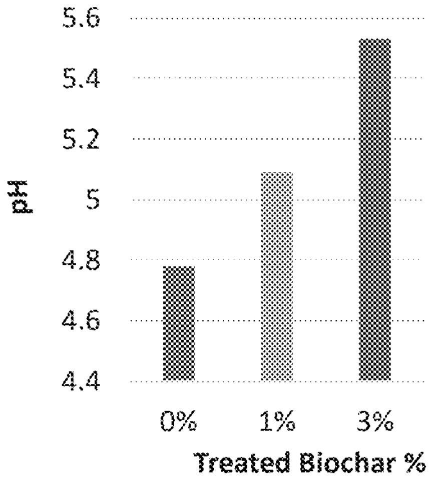
FIG. 47 is a chart showing the increase in pH in compost by adding treated biochar.

FIG. 47 is a chart showing the increase in pH in compost by adding treated biochar. As shown by FIG. 47, adding treated biochar to compost in a windrow environment generally increases the pH level in the compost. The addition of 1% treated biochar in the compost increased the basicity from between 4.7-4.8 pH to approximately 5.1 pH. The addition of 3% treated biochar in the compost increased the basicity from between 4.7-4.8 pH to approximately 5.3 pH. The control compost is represented by 0% added treated biochar.

Figure 48:
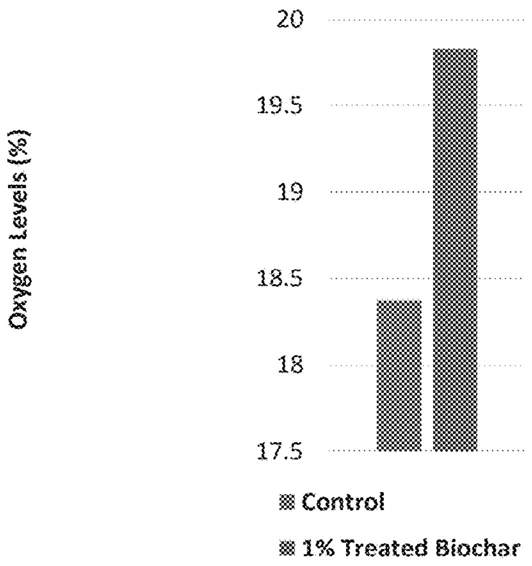
FIG. 48 is a chart showing the increase in oxygen levels in compost by adding treated biochar.

FIG. 48 is a chart showing the increase in oxygen levels in compost by adding treated biochar. As shown by FIG. 48, adding treated biochar to compost in a windrow environment generally increases the oxygen level in the compost. The addition of 1% treated biochar in the compost increased the oxygen level from approximately 18.4% to approximately 19.8%. The control compost is represented by 0% added treated biochar. The increased oxygen levels show the increased aeration in the compost and may explain the lowered temperatures also observed.

Figure 49:
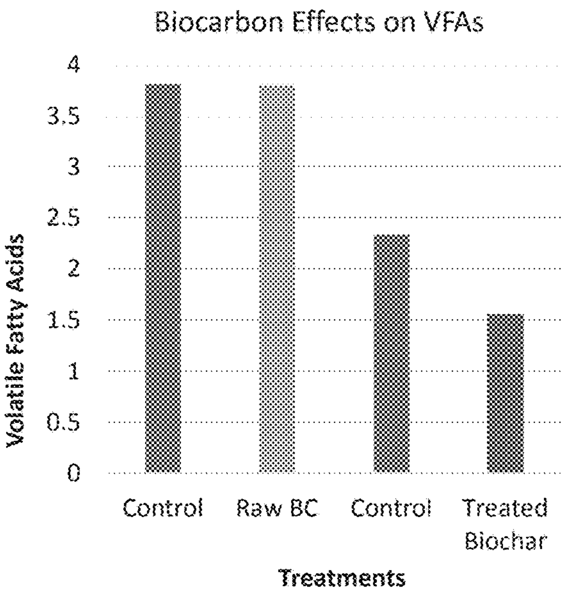
FIG. 49 is a chart showing the impact of the addition of both raw and treated biochar in a CASP compost environment to volatile fatty acids (VFAs).
Figure 50:
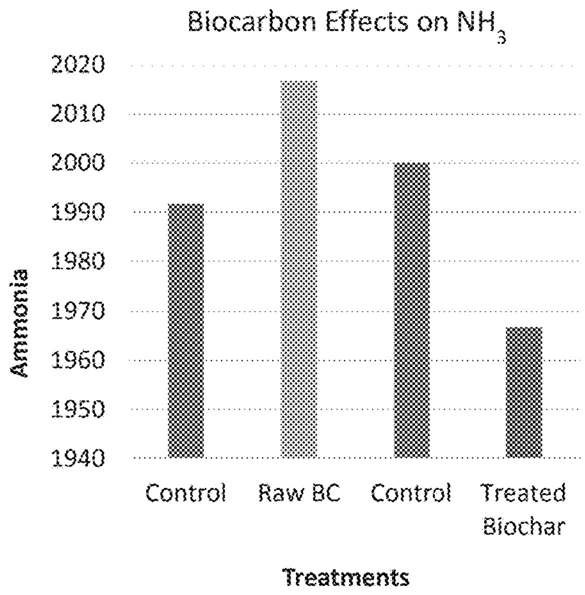
FIG. 50 is a chart showing the impact of the addition of both raw and treated biochar in a CASP compost environment to $NH_3$ levels.

FIGS. 49 and 50 show the impact of the addition of both raw and treated biochar in a CASP compost environment to volatile fatty acids (VFAs) and ammonia ($NH_3$) levels, respectively. When comparing raw biochar to treated biochar in CASP environments, it was generally shown that raw biochar has no effect on volatile fatty acids (VFAs) and increases $NH_3$ levels. Treated biochar on the other hand was shown to reduce both VFAs and $NH_3$ levels and indicative of reducing air emissions. VFAs and $NH_3$ levels are known to be odor indicating compounds. Reducing the amount of VFAs and $NH_3$ levels in the compost should indicate a reduction in the odor produced by the compost. Additionally, if $NH_3$ levels are reduced, then the nitrogen is more likely staying in the form of ammonium (NH4) and eventually turning into nitrates, which improves the quality of the resulting compost product.

As shown by FIG. 49, adding treated biochar to compost in a CASP environment generally decreases VFAs while the addition of raw biochar has no visible effect. The control compost has 0% added biochar. As shown by FIG. 50, adding treated biochar to compost in a CASP environment generally decreases $NH_3$ while the addition of raw biocarbon increases $NH_3$. The control compost has 0% added biochar.

Figure 51:
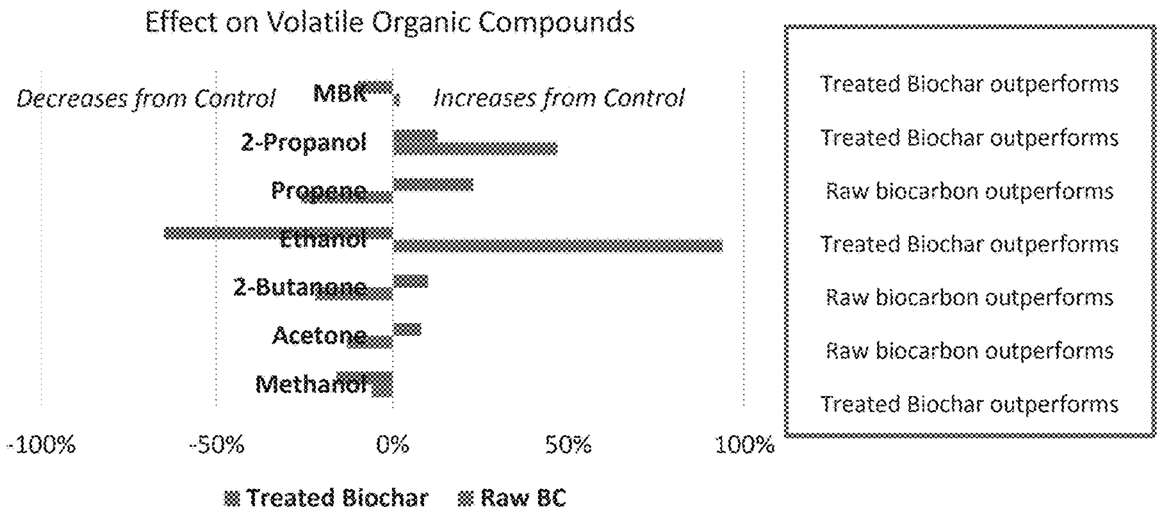
FIG. 51 is a chart showing the impact on volatile organic compounds ("VOCs") by adding treated and raw biochar to CASP compost.

FIG. 51 is a chart showing the impact on volatile organic compounds ("VOC") by adding treated and raw biochar to CASP compost. As shown, the addition of raw or treated biochar has variable effects on VOCs and can increase or decrease volatile organic compounds. The measurements were taken from negative pressure system of compost from a CASP environment tapped into a summa canister to capture gases generated by the compost. The addition of treated biochar to compost, compared to the control compost (0% biochar added), decreased the percentage of methyl-iso-butyl ketone (MBK), ethanol and methanol, while it increased the percentage of 2-propanol, propene, 2-butanone and acetone. The addition of raw biochar, compared to the control compost, decreased the percentage of propene, 2-butanone, acetone and methanol, while it increased the percentage of MBK and 2-propanol.

Figure 52:
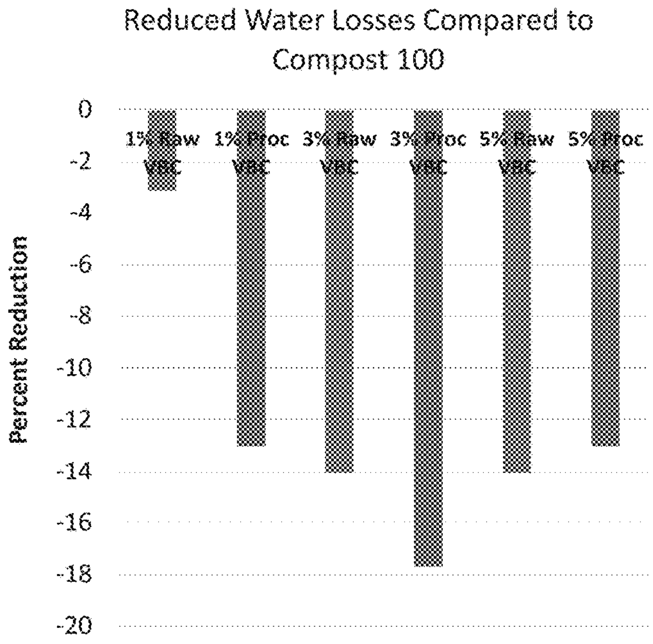
FIG. 52 is a chart shows a test of evaporative water loss from control compost against blended treatments with raw or processed biochars at 1, 3 and 5% by volume.

FIG. 52 is a chart shows a test of evaporative water loss from control compost (Control 100) against blended treatments with raw or processed biochars at 1, 3 and 5% by volume. Treated biochar at 1 or 3% outperformed raw treatments by as much as 10%. Treated biochar added to control compost at 3% v/v showed a dramatic 17.5% reduction in evaporative loss. The control compost in FIG. 52 is without raw and/or treated biochar. As shown, the evaporative loss of water in compost decreased as much as 10% if the compost is mixed with 1-3% processed biochar. Mixing the compost with 3% treated biochar has shown to maintain moisture levels in the compost essential for a climate similar to California.

Figure 53:
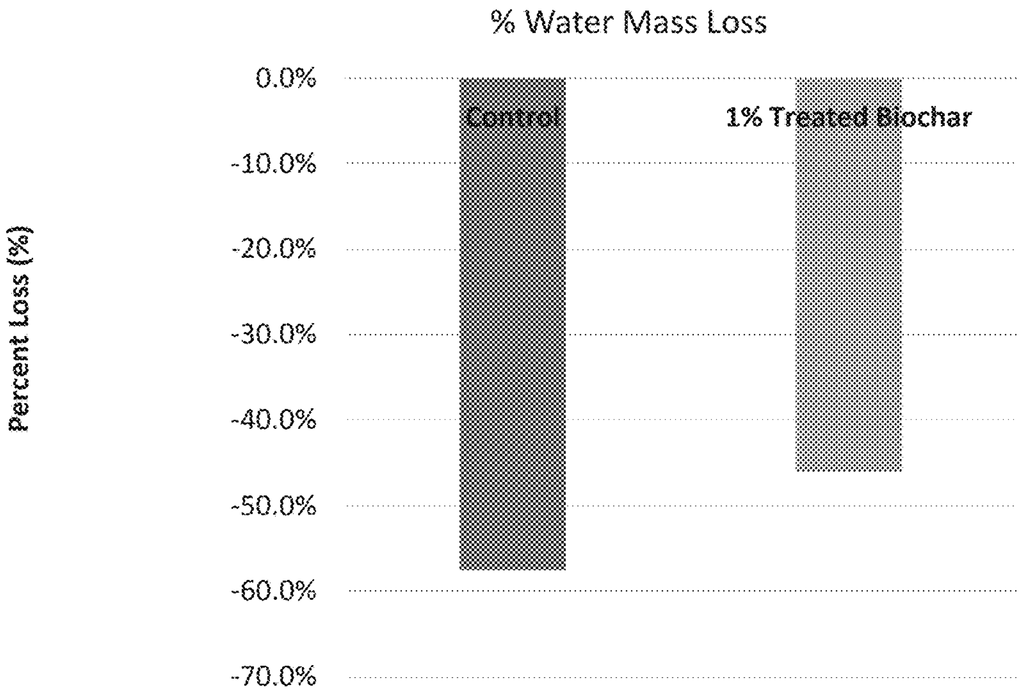
FIG. 53 is a chart showing the effect that the addition of treated biochar has on percent mass water loss in a CASP compost environment.

FIG. 53 is a chart showing the effect that the addition of treated biochar has on percent mass water loss in a CASP compost environment. Mass was determined by pile volume and bulk density. As shown in FIG. 53, adding % treated biochar to the piles of control compost reduced the water mass loss by 10%. The control compost in FIG. 53 is without raw and/or processed biochar.

All biochar treatments of compost have shown reductions in water loss and mixing various levels of treated biochar into the compost can assist to control essential moisture levels for various climates and assist in optimizing the composting process. Similar effects are seen windrow compost environments. As treated biochar controls the pile temperatures (see FIG. 45), despite the lower temperatures pathogen reduction still occurs. Lower pile temperature can reduce water demand up to 1,000 gallons of water added every 3-4 days.

Figure 54:
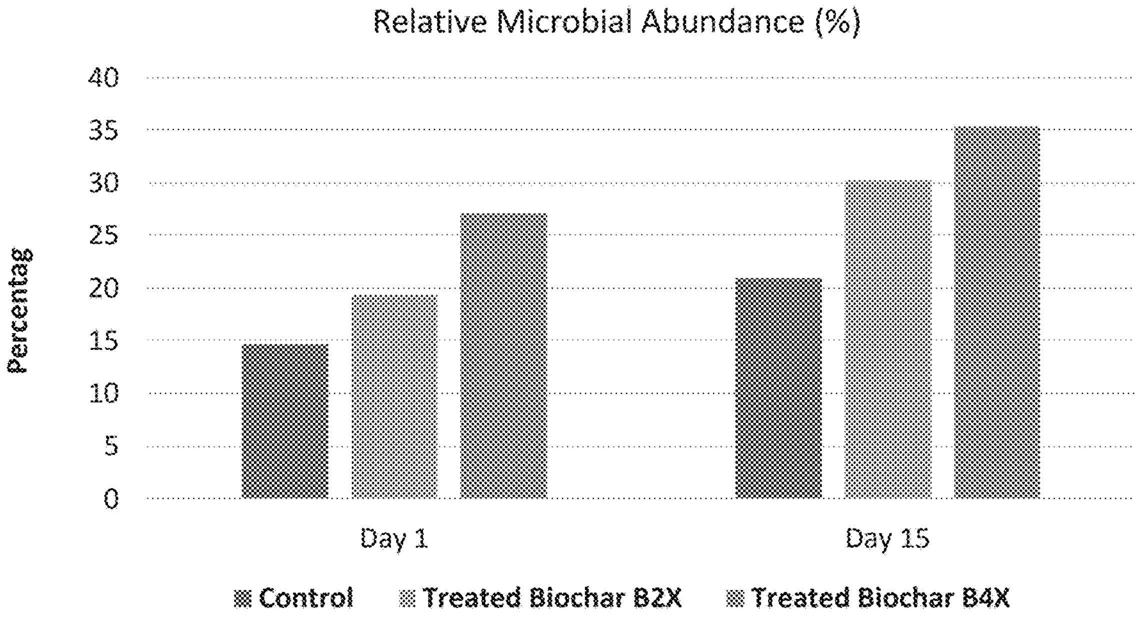
FIG. 54 is a chart showing in impact of the addition of the inoculated biochar to compost on microbial abundance.
Figure 55:
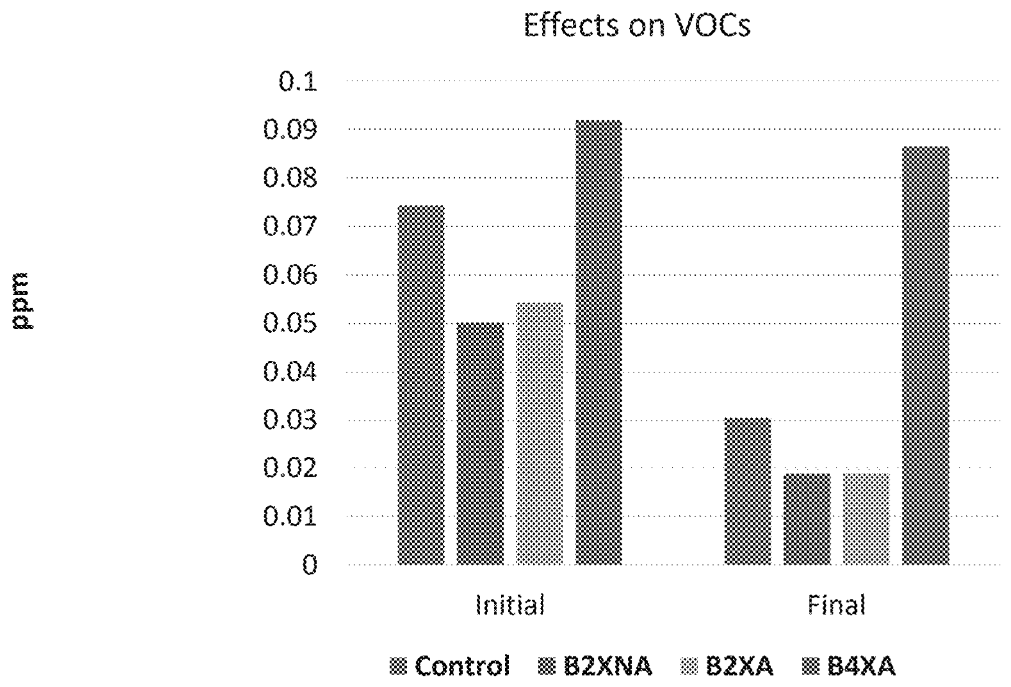
FIG. 55 is a chart showing in impact of the addition of the inoculated biochar to compost on VOCs.
Figure 56:
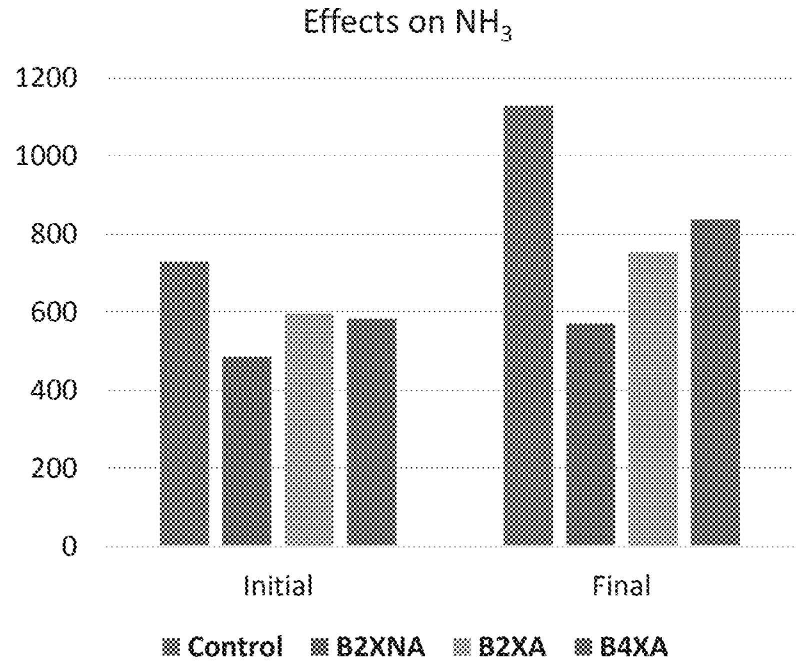
FIG. 56 is a chart showing in impact of the addition of the inoculated biochar to compost on $NH_3$.

FIGS. 54, 55 and 56 all demonstrate the impact of inoculating the biochar with specialized microbes. In all cases, the compost includes 2.6% biochar. The biochar added to the control is raw biochar. The biochar B2XNA and B2XA are inoculated with bacillus. *Bacillus* spp. was chosen for their ability to form endospores that allow the microbes to survive harsh temperature found during composting. Relative Percent Abundance of *Bacillus* spp. is as follows: *Bacillus licheniformis* (25%); *Bacillus szutsauensis* (5%); *Bacillus amyloliquefaciens* (15%); *Bacillus subtilis* (18%); *Bacillus velezensis* (26%); and *Bacillus pumilus* (33%). The types of *Bacillus* used were selected for the following purposes: nutrient cycling (*B. licheniformis* and *B. subtilis*), nitrogen fixation (*B. pumilus*), biocontrol of plant pathogens (*B. velezensis* and *B. subtilis*), and plant growth promotion (*B. pumilus* and *B. subtilis*). B2XA was pH adjusted, whereas B2XNA was not pH adjusted. B4XA is inoculated with twice as much bacillus as the B2XA and was also pH adjusted.

FIG. 54 is a chart showing in impact of the addition of the inoculated biochar to compost on microbial abundance. FIG. 55 is a chart showing in impact of the addition of the inoculated biochar to compost on VOCs. FIG. 56 is a chart showing in impact of the addition of the inoculated biochar to compost on $NH_3$.

FIG. 54 shows that compost piles having 2.6% inoculated biochar had elevated populations of gram positive bacteria. As illustrated, compost piles mixed with biochar inoculated with bacteria are shown to have elevated populations of gram positive bacteria. This suggests that thermotolerant endospore forming bacterial inoculated into biocarbon can survive native competition in composting systems and may have a positive effect on the composting process.

Regarding FIG. 55, it was generally determined that inoculated biocarbon decreases VOC levels. However, inoculated biochar, B4XA, treatment of biocarbon increased the VOC levels, possibly due to elevated bacillus populations.

Regarding FIG. 56, it was generally determined that inoculated biocarbon decreases $NH_3$ levels.

In general, in the application of biochar to compost, it was shown that treated biochar is able to raise the pH levels in composting with food waste, improves aeration, lowers temperature of compost piles, and can reduce odor indicating compounds like ammonia, VFAs and other volatile organics. Compared to raw biochar, treated biochar outperforms with the control of most of the odor indicating compounds and, at lower doses, with the ability to reduce evaporative loss. Treated biochar helps reduce overall water loss that occurs during composting and helps reduce water inputs regarding temperature control.

In addition to the composting benefits seen by adding treated biochar, the value of the resulting compost is also increased. Since the treated biochar helped retain nitrogen during the composting (as seen by reduced NH3), the compost itself will have higher nutrients when applied in agriculture usage. Also, the treated biochar remains in the compost and continues to display the benefits outlined in this invention, including but not limited to water and nutrient retention. Thus when the resulting compost is used in agriculture the compost will show similar improvement trends as when treated biochar itself is applied.

In another implementation or this invention, treated biochar could be added directly to animal bedding to control odors. Then once used, the bedding could be recycled via composting and still get the benefits of the treated biochar in composting. And finally the resulting compost which still has treated biochar could be used in agriculture and still continue to provide additional benefits to plants as well.

L. Biochar Suspended Solution

In many instances, treatments can be made to the biochar to allow better affiliation of root tissue with the material—these treatments can include modification of physical or chemical properties as just described, but they can also involve infusion of the biochar with rooting hormones, biologicals, nutritionals, or other materials which promote plant root development.

It has been discovered that these same benefits can be imparted to agricultural growth through the production and application of biochar suspended solutions as described below. The creation of biochar suspended solutions prevents the potential for wind to blow biochar dust or fines, thus reducing biochar losses and allowing more uniform application and distribution. Furthermore, the biochar suspended solution, being wet, allows for greater penetration through the soil and allows for more accessibility for the roots of plants to garner the biochar's advantageous physical/chemical properties.

Further, biochar may be more effectively applied if the biochar is in suspension in solution. The biochar, prior to being put in suspension in solution, may be raw or treated, as described above. If the biochar is treated, not only can the pH be adjusted as needed, as discussed above, but also fertilizers, microbes, and host of other additives may be infused in the biochar prior to suspension in solution (as further described below). However, regardless of whether the biochar is raw or treated, the present application for the suspension of biochar in solution can be utilized for both.

Figure 57:
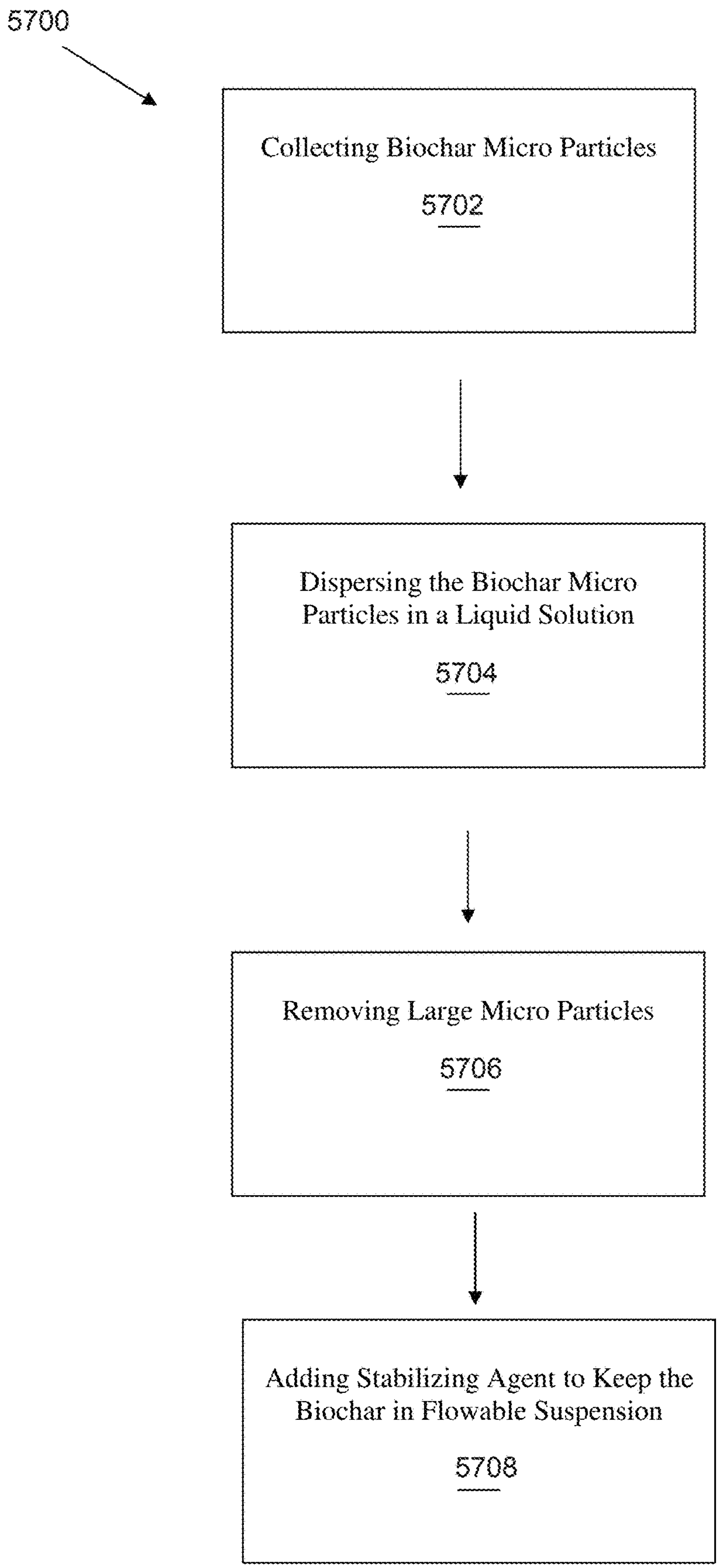
FIG. 57 is a flow diagram of one example of a method for producing a suspended biochar solution.

FIG. 57 is a flow diagram of an example of a method that may be used for producing biochar solutions. For purposes of this application, "biochar solution" or "biochar suspended solution" shall mean biochar that has been added or suspended in a liquid, alone or in combination with other additives. In general, the method of producing liquid products containing biochar may be accomplished by sufficiently de-sizing the biochar to pass through nozzles and/or mesh screens, dispersing the biochar in solution, such as water, and adding xanthan gum and/or other additives to keep the biochar in suspension, in solution.

At step 5702, biochar particles, either treated or raw, are collected for use in solution. The biochar particles may be collected in any number of ways, including but not limited to: (i) flow from a centrifuge effluent, (ii) from biochar granular product, or (ii) a combination of both a centrifuge effluent and granulated product. In all cases, the collected biochar may be passed to a media mill, air impingement, burr grinder, or other grinding, milling, or particle sizing equipment for production of smaller particles. The media mill or other similar equipment (e.g., attritor mill) allows for the de-sizing of the biochar product through dry and/or wet grinding. Micro particles may also be collected directly by traditional desizing equipment, including but not limited to hammer mills and grinders. Those skilled in the art will recognize that other desizing equipment, such as impellers, ultrasonic mechanisms, vibrators, shakers, or other devices besides hammer mills and grinders may be used to produce and collect biochar micro particles. Flocculants such as polyacrylamide can also be used at levels of 1000 ppm or less to collect the micro particles and to create a biochar micro particle cake. The residual amount of flocculant left in the micro particle cake will vary depending on the amount of flocculant that leaves with the liquid. Those skilled in the art will recognize that other flocculants, besides polyacrylamide may be used to clump the biochar particles together and other agents besides flocculants may be used to separate the solid micro particles from liquid for storing, transporting, or other purposes. Differences or variation in liquid or gas flow speed, rate, or pressure may also be used to sort particles based on their hydrodynamic or aerodynamic properties.

At step 5704, the biochar micro particles may then be dispersed in a liquid solution to create a biocarbon solution having a biochar solid content of approximately 1-75%, most desirable ranges between 15-70%. The liquid solution may include, but not be limited to, water, deionized water, liquid fertilizer and/or any combination thereof. Other liquid and/or solid additives may also be included in solution without departing from the scope of the invention. Once mixed in solution, the resulting biochar solution may then be passed through nozzles and mesh screens to remove any large biochar particles from the solution, at step 5706. Filters, such as nozzles and screen may be used to filter particles of sizes greater than about 0.2 mm. For example, mesh screens ranging from 0.2 mm-7.0 mm in size may be used to filter undesired larger particle sizes from solution. For example, a 15 mesh screen having 1.0 mm-1.2 mm openings may be used to filter undesired larger particle sizes from solution. Those skilled in the art will also recognize that the step of filtering out the larger particles may alternatively occur prior to or during the collection process (at step 5702).

To best hold the biochar in suspension, biochar micro particle sizes of about 0.5 mm or less may be desired or may depend on the method of application. For example, if applying biochar suspended solution with irrigation equipment, less than 0.05 mm, 0.025 mm, 0.01 mm, or even less may be desired, whereas less than 1 mm, 0.5 mm, 0.2 mm, or even less than 0.1 mm may be desired if applying biochar suspended solution with varying types of fertilizer equipment.

The following table shows the particle size distribution and physical characteristics of particles when held in suspension to support the efficacy of using biochar held in suspension compared to other mixtures such as solutions and colloids:

TABLE 18-2

"Laboratory 18.0: Colloids and Suspensions - Introduction."

| Characteristic | Solution | Colloid | Suspension |
|---|---|---|---|
| Type of particle | Individual molecules or ions | Very large individual molecules or aggregates of tens to thousands of smaller molecules | Very large aggregates of molecules |
| Particle Size | <1 nm | ~1 nm to ~200 nm | >100 nm |
| Separation by Gravity? | No | No (usually, otherwise, very slowly | Yes |
| Separation by Centrifugation | No | Yes, for more massive dispersed particles | Yes |
| Captured by Filter paper? | No | No | Yes |
| Captured by membrane? | No | Yes (usually) | Yes |
| Percipitatable by flocculation? | No | Yes | Yes |
| Exhibits Tyndall Effect? | No | Yes | Yes |
| Affects Colligative Properties? | Yes | No | No |

http://makezine.com/laboratory-18-colloids-and-suspensi/.

It should be noted that the pH of the biochar solution can affect how much biochar particles will stay in solution and the viscosity of said solution. Thus it may be beneficial to add an acid or base before, during, or after these steps. For example, lowering the viscosity of the solution by adding a base to the solution prior to wet milling will allow for more efficient milling and result in a higher amount of solids fit for the solution, i.e. less particles will be removed during the large particle removal step. Then, after the wet milling an acid could be added to bring the pH back down and provide the viscous stability to ensure the particles stay and solution instead of settling.

At step 5708, a stabilizing agent may then be added to keep the biochar in flowable suspension and prevent it from settling. The stabilizing agent can include xanthan gum at about. 0.1% to 0.7% by weight to the solution or it can vary depending on the solids already in solution, the percentage of solids in solution and/or the particle size of the biochar used to create the solution. Alternative natural or synthetic agents with pseudoplastic rheology capable of suspending biocarbon particles in solution may also be added at this step such as alkali swellable acrylic thickeners, inorganic substances, surfactants or other water born thickeners. Isothiazolin type preservatives could also be added to prevent biological degradation of the xanthan gum. For example, 50 ppm of active Kathon™ LX 1.5% biocide may be added to protect the xanthan gum. Those skilled in the art will recognize that other preservatives may be used to prevent biological degradation of the xanthan gum. Those skilled in the art will also recognize that the step of adding stabilizing agents may alternatively occur prior to, during, or after the collection process (at step 5702).

For example, the stabilizing agent could be added prior to the creation of the suspended biochar solution by mixing or spraying the agents on dry biochar particles either prior or post micro particle collection process. In fact, they could even be added or infuse into the biochar during the treatment processes. This could allow for the production, transport, and/or sale of a dry or semi-dry biochar product that could then be turned into a solution after production, for example at the time of sale or just prior to application at say the farm where it will be applied. Similarly, the process of adjusting the density of the biochar can be combined with the process of adding stabilizing agents or thickeners.

Depending on the thickener or stabilizing agent used at step 5708, a preservative may also be added to ensure an optimal product with long shelf life. Choosing the right preservative is important as the biochar itself can absorb certain preservatives and thus allow unwanted microbiological growth in the solution over time. Potential preservatives that may be used are polymeric preservatives such as poly quats or formaldehyde emitter preservatives. Chlorine based preservatives are not generally used as the biochar can degrade chlorine in a short amount of time. Another option to avoid biochar solution degradation is to choose a stabilizing agent that will not rot or encourage microbiological growth in the solution. One example of this is clay based thickeners such as Attagel and Veegum. An exception to this would be cases in which microbial agents are to be inoculated on or suspended with the biochar itself. A third option is to not create the solution until right before it will be used, for example at the time of sale or at the time of application. The shorter shelf-life reduces chances of solution degradation.

Optionally, growth enhancing additives, including but not limited to, fertilizers, liquid micronutrients, liquid manure, liquefied compost or compost "tea", compost extract and beneficial microbes can be added to the biochar solution. These additives may be added either prior, during, or after the suspended biochar solution is created. For example, the additive may be infused into the biochar prior to creating the solution using vacuum infiltration or a surfactant as further described above. Alternatively, or in addition to infusing the biochar with additives, additives may be included with the biochar solution described above prior, during or after creation of the biochar solution.

For example, fertilizers may be pulverized to an average particle size of <1 mm and included with the solid biochar or added to solution. Liquid fertilizers may also be used in solution. For example, 1000 ppm $NO3^-$ N fertilizer solution may be used. Examples of fertilizers that may be added to the solution, include, but are not limited to the following: ammonium nitrate, ammonium sulfate, monoammonium phosphate, ammonium polyphosphate, Cal-Mag fertilizers or micronutrient fertilizers. Other additives, such as fungicides, insecticides, nematicides, plant hormones, beneficial microbial spores, or secondary signal activators, may also be added to the solution in a similar manner as a fertilizer, the inclusion of which does not depart from the scope of the invention. Additionally, beneficial macro- and micro-nutrients such as nitrogen, phosphorous, potassium, calcium, magnesium, sulfur, boron, zinc, iron, manganese, molybdenum, copper and chloride can be added to the suspended biochar solution. As set forth above, in addition to adding these to solution, such additives can be infused into the biochar prior to creating the solution.

Examples of compounds, in addition to fertilizer, that may be mixed with the biochar solution or infused into the biochar prior to creating the solution include, but are not limited to: 2,1,3-Benzothiadiazole (BTH), an inducer of systemic acquired resistance that confers broad spectrum disease resistance (including soil borne pathogens); signaling agents similar to BTH in mechanism or structure that protects against a broad range or specific plant pathogens; biopesticides; herbicides; and fungicides.

Those skilled in the art will recognize that there are many other mechanisms and processes that may be used to produce biochar solutions without departing from the scope of the invention. Those skilled in the art will further recognize that the present invention can be used on any type of soil application, including, but not limited to, the following: crops, turf grasses, potted plants, flowering plants, annuals, perennials, evergreens and seedlings. Further, it should be noted that the above described steps to create the solution can be performed in any order, or steps may be repeated during the process.

By putting the biochar solution, as taught above, a variety of equipment may be used for the application of the suspended biochar solution. The ability to uniformly apply the biochar solution is also enhanced by allowing the use of pumps, sprays and various other types of equipment capable of handling liquid dispersion. For example, Sprayers, booms, and misting heads can be an efficient way to apply the biochar solution to a large area, while backpacks or hose sprayers can be sufficient for smaller applications. Aside from spraying applications, biochar solution may also be pumped through the ground to eliminate the potential for wind erosion while allowing for faster infiltration into the soil. Furthermore, biochar solution can be used in connection with a variety of equipment used for hydroseeding, manure spreading (either solid or liquid), foliar spraying, irrigation, or other liquid application technologies. As there are so many different options to apply biochar suspended solutions or solution, much time and expense can be saved.

In addition, the use of a biochar suspended solution can allow for more efficient and focused applications to ensure the biochar treatment stays in the root zone, or is deployed in the vicinity of juvenile or developing root tissue, thus reducing the amount of biochar needed on a cubic yard per acre basis. For example, if the biochar solution is put through irrigation tape that is laid directly in a row crop bed the biochar will only be treating the root zones of said crop in the beds and not the row crop furrows nor above or below the root zone in the bed. Not only does this lessen the cost by reducing the amount of biochar needed it also can lessen the cost of the application method itself as it can be applied using the same equipment that may already be available for irrigation and liquid fertilizer application.

The application of the biochar solution can be used for trees, row crops, vines, turf grasses, potted plants, flowering plants, annuals, perennials, evergreens and seedlings. The biochar solution may be incorporated into or around the root zone of a plant at ratios of between 1:999 to 1:1. However, an application does not necessarily need to be restricted or limited to these ratios. Biochar can be added to soil at a concentration of 0.01% up to 99% depending upon the application, plant type and plant size. As most trees, rows, and specialty crops extract greater than 90% of their water from the first twenty-four inches below the soil surface, the above applications will generally be effective incorporating the biochar around the root zone from the top surface of the soil and up to a depth of 24" below the top surface of the soil, depending on the plant type and species, or alternatively, within a 24" radius surrounding the roots regardless of root depth or proximity from the top surface of the soil. When the plant roots are closer to the surface, the incorporation of the biochar within the top 2-6" inches of the soil surface may also be effective. Greater depths are more beneficial for plants having larger root zones, such as trees.

The biochar suspended solution may also be applied to animal pens, bedding, and/or other areas where animal waste is present to reduce odor and emission of unpleasant or undesirable vapors. Furthermore it may be applied to compost piles to reduce odor, emissions, and temperature or even to areas where fertilizer or pesticide runoff is occurring to slow or inhibit leaching and runoff. In some instances, it may even be mixed with animal feed, fed to animals directly as a liquid, or used in aquaculture applications.

Biochar solution may also be utilized and applied through irrigation equipment for both low flow and high flow irrigation systems. For the purpose of this application, "low flow system" includes but is not limited to micro sprays, drip emitters, and drip lines and "high flow systems" includes but is not limited to fixed sprays, rotors, bubblers, and soaker hoses. Although the utilization of the chemical and physical properties of biochar for optimal plant growth would ideally be most effective when applied to plants during their peak growing cycle, all of the applications discussed above can be applied at any time during the different stages of plant growth or ground preparation as needed. Similarly, the methods of application can be repeated as many times as needed from year to year depending on factors not limited to plant type, climate, soil properties, topography, and light. In summary, when any type of liquid is applied to the plants such as water or liquid fertilizer, the suspended biochar solution can be added to the liquid in order to provide further soil enhancement characteristics.

An alternative method for creating a biochar solution is to instead make a biochar slurry using a process similar to hydromulching or hydroseeding. With this method the size reduction step can be reduced or eliminated since the process is typically applicable for larger particle sizes in which the resulting slurry is applied through pumps and sprays. For this application method typically the granular biochar will be mixed with water, fiber mulch, and optionally a tackifier at time of application and then sprayed to area needed. In addition, it can be mixed with fertilizer, seeds, or other additives including dyes to help aid in uniform distribution. Typical hydroseeding and hydromulching equipment may be used and generally include a tank mounted truck that is equipped with a special pump and continuous agitation system. The pump then pushes the slurry though a hose and nozzle for application. To create a biochar slurry for this application the fiber mulch is usually a cellulose based material which can be made from shredded waste paper sources and can include dyes, binders, or other additives. The optional tackifier can include but is not limited to guar gum, xanthan gum, plantago gum, methyl cellulose, pectin, lignin, seedmeals, such as camelina or lesquerella, polysaccharide gums, or starches, such as corn starch. The addition of a tackifier increases the biochar slurry's effectiveness especially when applied on a slope, on an area that is erosion prone, or other areas that would cause concern of the biochar application being washed away due to rain or irrigation. If the slurry is to be made significantly prior to application then a preservative would likely be needed as well to ensure a longer shelf life. Otherwise the biochar, fiber, and tackifier can be mixed dry and then turned into a slurry just prior to application or even onsite, similarly to current practices of hydromulching and hydroseeding. This biochar slurry may be particularly useful in turf and landscape applications where hydroseeding or hydromulching is already being used. In the case of turf particularly, it could be either mixed with grass seeds prior to application or applied immediately prior to the hydroseeding application. A process similar to this can be used for mixing the biochar with manure to create a manure slurry, either in lagoons, or at any point prior to application of the manure.

M. Animal Applications

Generally, treated biochar of the present inventions can be used with numerous animal species, large and small scale farming, and in a variety of animal management applications and systems, and combinations and variations of these. In fact, this particular solution provides the capability to custom-manufacture biochar for a particular species, physiology, nutritional need, pathogen susceptibility, illness, environment, geographical area or other application by more precisely controlling key characteristics.

The fundamental benefit of treated biochar use in animal applications is the fact that deleterious characteristics can be adjusted and toxic materials left over from the biomass and its pyrolysis can be removed. For example, pH can be adjusted, and undesirable ash, inorganic compounds, toxins or heavy metals, and organic compounds such as acids, esters, ethers, ketones, alcohols, sugars, phenyls, alkanes, alkenes, phenols, polychlorinated biphenyls or poly or mono aromatic hydrocarbons, can be removed. As described previously, one major concern with charcoals or raw biochars used in animal applications is the potential for dioxins which are released from combustion processes and are an example of toxic material that the treatment of the present invention can remove. Thus, a treated biochar can be used in animal applications where ingestion may be possible such as bedding, or specifically as a feed additive, whether it be for general purpose such as color, manure odor control, or roughage replacement or as a technical additive as a binding agent or carrier as it can be made without toxins, specifically dioxins, consistently with various feedstocks and various pyrolysis methods without risk of harm to the animals or humans that consume the animal products/meat from said animals.

Through the use of detoxified treated biochars, the other benefits of biochar qualities can be realized in applications related to the care, maintenance and feeding of animals. These benefits can include increase in animals' uptake of foodstuffs and the energy contained within them; reduction in the amount of nutrients lost into excrement and manure; detoxification of the animal and enrichment of the beneficial microbes in the digestive track that are key to maintaining an animal's metabolism and helping it to resist dangerous pathogens; reduction in methane production; better odor control of stalls, pens, cages, lagoons and other animal enclosures; and any combination and variation of these and other benefits. The results are increased growth rates for animals consuming treated biochar, as well as better overall health of the animals that consume it, greater efficiencies in animal care and maintenance, and improved odor. As an additional benefit, manure produced by an animal that consumes biochar contains biochar, making this manure better for agricultural purposes than ordinary manure.

For animal applications, in the same way that biochars are known to bind organic contaminants in soil environments due to hydrophobic-hydrophobic interactions, treated biochar may bind organic toxins as they pass through an animal's digestive system, for example, when cattle are suffering from botulism or diarrhea. Another toxin binding application could be with commercial farm pollinating bee hives. Bee species have been on the decline in the US and this year, the first species of bee in the continental US was placed on the endangered species list. Bee species' decline appears to be in part due to fungicides, and insecticides, including neonicotinoids, leading to bees becoming more susceptible to disease. See Pettis et al., *Crop Pollination Exposes Honey Bees to Pesticides Which Alters Their Susceptibility to the Gut Pathogen Nosema ceranae*, PLOS, Jul. 24, 2013

Adding small particle treated biochar to a commercial hive feed patty, which generally consist of sugar and protein and may have additional vitamins or probiotics, may allow the insects to ingest said treated biochar and allow for it to help bind the pesticide toxins and help lessen their sub-lethal effects to keep the bees more resistant to pathogens even when they have been and continue to be exposed to these pesticides.

Figure 58:
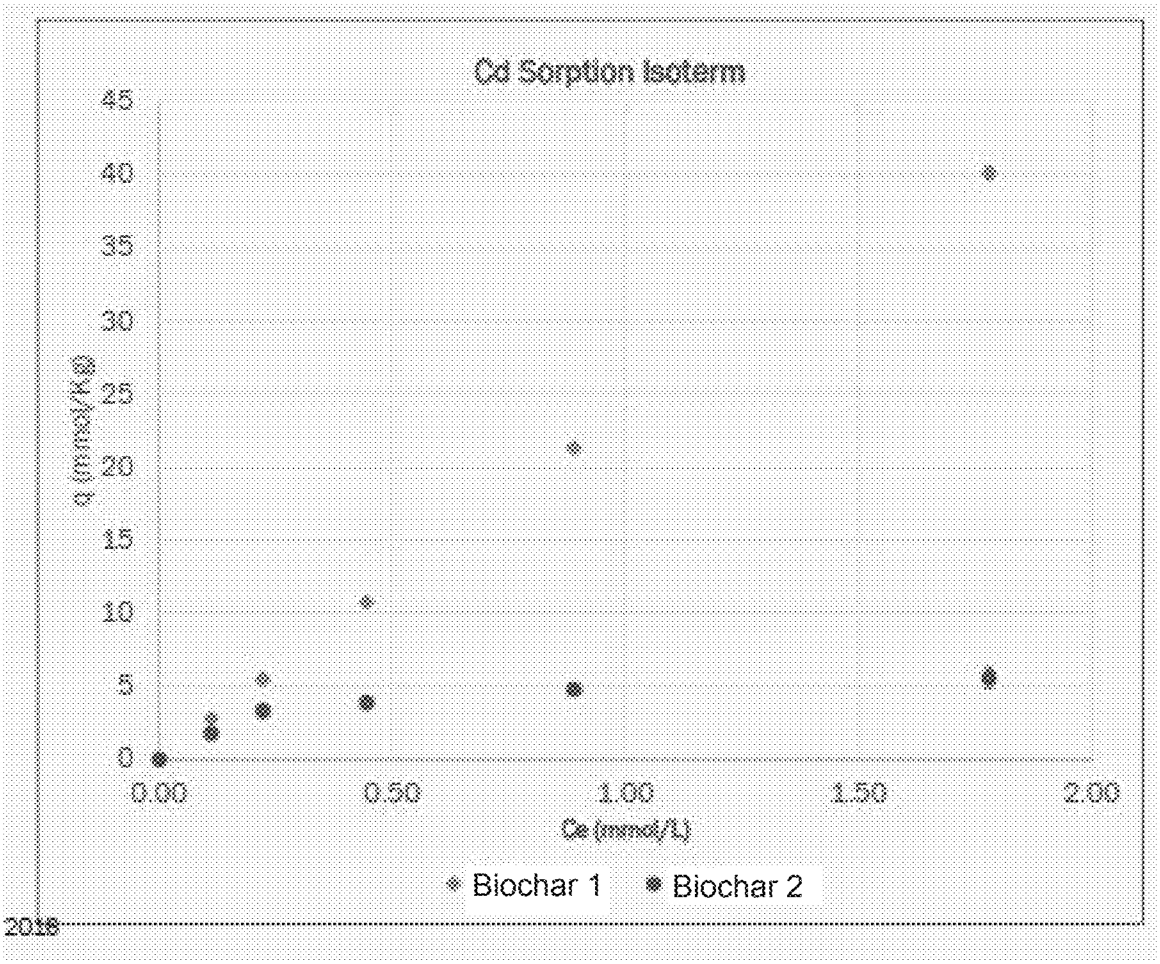
FIG. 58 is chart illustrating biochar capacity to absorb Cadmium.

In another example, biochars were shown to absorb Cadmium, a heavy metal, but the absorption capacity was depended on the biochar properties including the biomass feedstock type. FIG. 58 is chart illustrating biochar capacity to absorb Cadmium. Thus a specific treated biochar formulation can be developed for each toxin binding animal application to ensure optimum results for the specific toxin(s) of concern.

Another application is to use the treated biochar as bedding in order to reduce odors, absorb ammonia, and absorb toxins and thus lead to an environment that will lead to healthier animals and also lead to a better secondary product of quality manure by reduced nutrient leaching. A bedding trial was conducted with broiler chickens. After decaking the houses, the test houses had treated biochar spread evenly over the entire house at various rates while one was left as a control. The flock produced over the two sets of trials was above normal. After the first trial, manure samples were tested from each house for nutrient content and estimated 1$^{st}$ year availability of said nutrients. The estimated manure value was then calculated off of the estimated 1$^{st}$ year availability. Results showed higher value for the bedding with treated biochar, as seen in table below:

| | 1st Year Availability (lbs/ton) | |
|---|---|---|
| | Control | With Treated Biochar |
| Total N | 37 | 35 |
| P (P2O5) | 31 | 34 |
| K (K2O) | 56 | 61 |
| Total Est. Value | $56.40 | $58.90 |

As was discussed previously, mixing treated biochar in while composting can reduce odors, these same mechanisms can be used to reduce odors when treated biochar is mixed with animal bedding, manure, swine lagoons, etc.

Typically, the prior art teaches mixing raw biochar with animal feed without 'precharging' with nutrients, microbes, etc. Through impregnation of the biochar particles, one can achieve a predetermined and controllable amount of a particular nutrient, medication, foodstuff, microbial community, etc. being ingested by the animal. Once in the rumen, data indicates that these infused additives will also be released more slowly over time, yielding yet another benefit over additives mixed directly into the feed. This integration of a beneficial additive with a biochar particle and biochar batches provides the ability to have controlled addition, use and release of the additive or additives. This integration may further enhances, promotes and facilitate animal growth and health, aid in digestion and digestibility of food, improvement hygiene, increase intestinal health, reduces the amount of nutrients lost into excrement and manure and reduces methane discharge.

Enhancing treated biochar with an additive, including infusing liquids into the pores of biochar, can provide additional benefits in animal applications, by making it an effective delivery mechanism for beneficial nutrients, pharmaceuticals, enzymes, microbes, or other substances. Additionally a sensory enhancer, such as a smell or flavor (e.g. salt), could be infused to increase the animal's desire to ingest said biochar.

The additive may include, but not be limited to, water, water solutions of salts, inorganic and organic liquids of different polarities, liquid organic compounds or combinations of organic compounds and solvents, vitamins, supplements and/or medications, nutrients, minerals, oils, amino acids, fatty acids, supercritical liquids, growth promotants, proteins and enzymes, phytogenics, carbohydrates, antimicrobial additives and sensory additives (e.g, flavor enhancers salt or sweeteners or smell enhancers), among others, to provide nutrition, promote the overall health of the animal, and increase the animal's desire to ingest said biochar. Vitamins, supplements, minerals, nutritional and/or medications may be used to prevent, treat or cure animal illnesses and diseases and/or control the nutritional value of the animals overall diet.

For example, dietary supplementation with certain nutrients (e.g., arginine, glutamine, zinc, and conjugated linoleic acid) can regulate gene expression and key metabolic pathways to improve fertility, pregnancy outcome, immune function, neonatal survival and growth, feed efficiency, and meat quality. Such additives in the biochar can help provide the proper balance of protein, energy, vitamins and nutritionally important minerals in animal diets. Additionally, for poultry, the additive may include, for example, coccidiostats and/or histomonostats, which are both shown to control the health of the poultry. The present invention can be used to help correct deficiencies in basal diets (e.g., corn- and soybean meal-based diets for swine; milk replacers for calves and lambs; and available forage for ruminants).

The treated biochar can also have a microbial community infused in its pores (macro-, meso-, and combinations and variations of these), on its pore surfaces, embedded in it, located on its surface, and combinations and variations of these. The microbial community can have several different types, e.g., species, of biologics, such as different types of bacteria or fungi, or it may have only a single type. A primary purpose, among many purposes, in selecting the microbial population is looking toward a population that will promote animal health either directly or through interactions with other microbes in the animals digestive tract. These types of beneficial microbes are essential to a functional gastrointestinal tract and immune system in many types of animals, serving many functional roles, including degradation of ingesta, pathogen exclusion, production of short-chain fatty acids, compound detoxification, vitamin supplementation, and immunodevelopment. Beneficial bacteria include *Lactobacillus acidophilus* LA1 (which decreases adhesion of diarrheagenic *Escherichia coli* to Caco-2 cells by 85% and prevents invasion of the same cells by *E. coli* (95%), Yersinia pseudo-tuberculosis (64%) and *Salmonella enterica* serovar *Typhimurium*) and *Lactobacillus rhamnosus* GG to prevent *E. coli* O157:H7-induced lesions in Caco-2 cells.

Further, biochar may be impregnated with probiotic bacteria to treat diseases in farm-raised fish. Infectious diseases pose one of the most significant threats to successful aquaculture. The maintenance of large numbers of fish crowded together in a small area provides an environment conducive for the development and spread of infectious diseases. In this crowded, relatively unnatural environment, fish are stressed and more susceptible to disease. Moreover, the water environment, and limited water flow, facilitates the spread of pathogens within crowded populations. There is thus an urgent need in aquaculture to develop microbial control strategies, since disease outbreaks are recognized as important constraints to aquaculture production and trade and since the development of antibiotic resistance has become a matter of growing concern. One alternative disease control relies on the use of probiotic bacteria as microbial control agents. Another implementation of the invention therefore involves the impregnation of biochar for consumption by aquatic animals as a treatment or preventative for disease.

Additionally, biochar may be infused with bacteria which prove helpful in methane reduction. An example of this is to infuse the biochar with methanotrophic bacteria (bacteria which are able to metabolize methane as a source of carbon and energy). Bacteria which metabolize methane are useful in two regards-they can reduce the environmental methane emissions from the rumen and they (the bacteria) also serve as nutrition for the animal itself, leading to increased weight gain. Infusing biocarbon with microbes such as these can lead to methane reduction in cattle applications that exceeds the methane reduction of solely untreated biochar itself.

Additive infused biochars may be mixed with the animals regular feeds or may be included within a salt or mineral block and made available for animals to self-feed or self-administer the additives.

While this application focuses mainly on applications of infused biochars in connection with farm-raised animals, those skilled in the art will also recognize that the invention could also be applied more generally for veterinary purposes for many types of animals other than livestock, poultry, fish or horses, including pets, as well as in a wide variety of environments and contexts, for example, for zoo or aquarium animals or for other penned or caged animals, insects such as bees, or for wild animals.

Furthermore, the treated or additive infused biochar can be sized, agglomerated, or suspended in solution to optimize its use in a specific animal application. For example, if using as a feed additive with smaller animals or very young animals, small particles will be required and being able to suspend these small particles in a solution will make for an easier application.

In addition, if the treated or additive infused biochar is being used to deliver its specific benefit in a targeted location in the animals' digestive tract, it can be mixed with an additive or coated to allow for a slower release or a targeted release in said location. So, for example if the additive or biochar is being targeted for use in the intestines or after rumens a specific coating substance and thickness can be chosen so as to degrade at the required specified rate leading to the biochar or additive being available after the stomach or rumens. This could be specifically useful for getting beneficial microbes to targeted organs in the digestive tract. If the microbe is infused into the pores to a significant depth of at least approximately 10 to 20 microns, then both the biochar structure itself and a coating could be used to protect the microbe through harsh conditions, such as stomach acid, prior to getting to the targeted organ location.

Treated biochar and additive infused treated biochar can be used in promoting growth and health in livestock (dairy and beef cattle, sheep, goats and swine); poultry; farm-raised wild animals (e.g. bison, deer and elk); farm-raised fish and other aquatic animals; horses and other members of the horse family; for controlling levels of certain pathogens, e.g. *salmonella* in poultry; for veterinary uses, such as delivery systems for medications, supplements and/or vitamins; for maintenance and welfare of zoo animals or other caged, penned or contained animals; for pets; for zoos and aquaria; for wild animals; for insects, such as bees, and for combinations and variations of these.

Treated biochars and practices and methods provide for healthier animals, increase food intake efficiency, promote better digestion and reduce methane emissions, and combinations and variations of these, and other features that relate to the increased holding, retention and time discharge features of the present biochars and processes.

Treated biochar may also be used in other applications, for example, such mixing with manure in holding ponds to potentially reduce gaseous nitrogen losses, soil remediation (for example absorption and capture of pesticide, contaminates, heavy metals, or other undesirable, disadvantageous soil components), ground water remediation, other bioremediations, storm water runoff remediation, mine remediation and mercury remediation.

In summary, the treatment processes of the present information may be used to clean the pores of the biochar, ridding the pores of dioxins or other detrimental substances, or infiltrating the pores of biochar with a variety of substances, for a number of purposes, including but not limited to, infiltrating the pores of biochar with nutrients, vitamins, drugs, microbes, and/or other supplements, or a combination of any of the foregoing, for consumption by animals. The treated biochar may also be applied to animal pens, bedding, and/or other areas where animal waste is present to reduce odor and emission of unpleasant or undesirable vapors. Furthermore it may be applied to compost piles to reduce odor, emissions, and temperature to enable the use of the food waste and animal feed in composting. Biochar can also be applied to areas where fertilizer or pesticide runoff is occurring to slow or inhibit leaching and runoff. The biochar may also be treated with additives which make it easier to dispense or apply, such as non-toxic oils, anti-clumping/binding additives, surface drying agents, or other materials.

While the above teaches a treatment process for biochar that increases the amount of additives that can be retained within the pores of the biochar, it is within the scope of the present invention to contact raw or treated biochar with additives (e.g. by submersion) for purposes of creating a delivery system for additives useful for animal health and consumption.

N. Extraction of Residual Compounds.

As described previously, the treatment methods of this invention can be used to remove residual compounds, including but not limited to heavy metals, transition metals, inorganic mineral compounds, and residual organic compounds (ROCs), both volatile organic compounds (VOCs) and heavy ROCs. Some residual compounds may be deleterious in certain applications, including, but not limited to, polyaromatic hydrocarbons, polychlorinated biphenyls, dioxins, phenols, benzaldehydes, and furans. This treatment method may also extract compounds that are desirable for use in certain applications, for example in agriculture or animal applications. Some beneficial compounds that could be extracted include, but are not limited to, macronutrients, secondary nutrients, micronutrients, vitamins, organic compounds that microbes feed on, or signaling chemicals. Thus extraction, and in particular the treatment described previously, can be used to clean the biochar of certain undesirable compounds or to collect desirable compounds, or to do both.

However, the treatment method described previously, is just one example of the extraction methods disclosed in this invention. In the simplest terms, the invention is a set of methods that extract or remove some amount of residual compounds from a biochar. Of particular interest is the removal of organic compounds from the biochar, but it is not the only one. Other potential compounds could include inorganic compounds such as ash or minerals. The extraction method can be selected to remove specific targeted compounds, specific groups of compounds, or a broad range of compounds from the biochar. The purpose of the extraction or removal can be to improve the biochar, to collect some or all of the removed compounds, or a combination of both improving the biochar and collecting removed compounds. In some cases, an extraction may remove a broad range of compounds and then the extract material could be refined or distilled to collect the desired compound or group of compounds. This refined extract could then be used as its own product, disposed of, or be reincorporated into the biochar product. Alternatively, the resulting non-purified extract could also be used as its own product, disposed of, or be reincorporated into the biochar product.

1. Biochar Selection for Extraction

Figure 59:
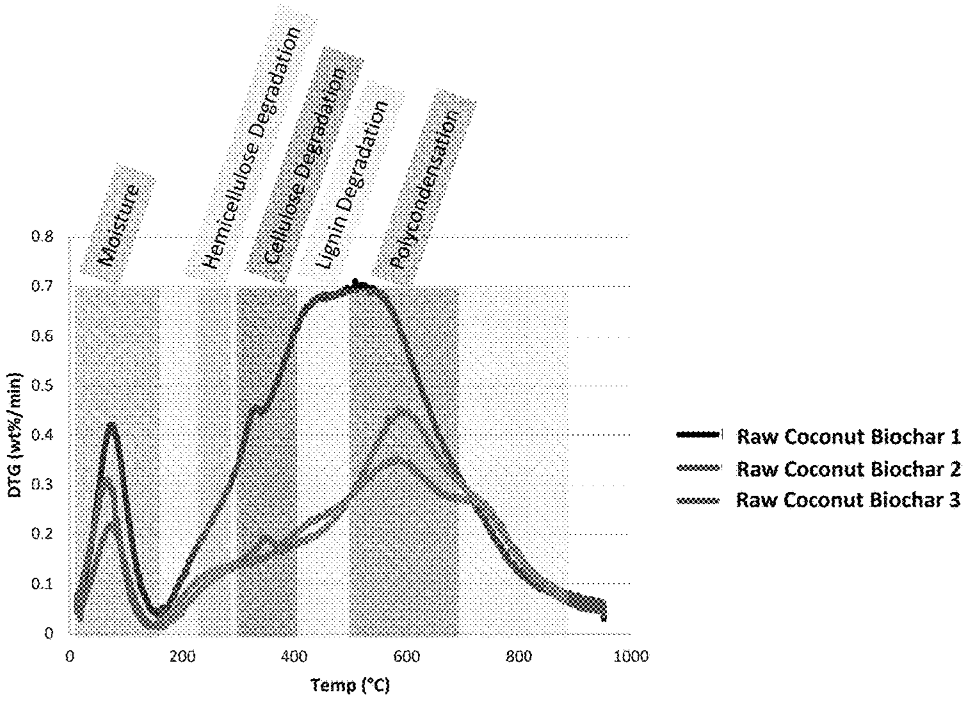
FIG. 59 is an example of a Thermogravimetric Analysis (TGA) plot which shows how the type and amount of residual organic compounds can vary for biochars from the same source.

It is understood in the field of pyrolysis that various residual organic compounds found in biochars are derived from certain compounds in the original biomass. In addition, it is understood that due to the energy needed to convert the biomass compounds to these residual compounds, the pyrolysis method and conditions, including temperature and residence time, will also impact the amount and type of residual organic compounds left in the biochar. FIG. 59 is an example of a Thermogravimetric Analysis (TGA) plot which show how the type and amount of residual organic compounds can vary for biochars from the same source, in this case coconut shells. As depicted in the figure and consistent with ranges presented by Yang, et. al in "Characteristics of hemicellulose, cellulose, and lignin pyrolysis" (Fuel 86, 2007), compounds that are released at 220-315° C. are due to hemicellulose degradation, those released at 315-400° C.

are from cellulose, and those from lignin range from 160-900° C. As Brebu and Vasile point out in "Thermal Degradation of Lignin-A Review" (Cellulose Chemistry and Technology, 2009), lignin degradation is complex and requires both consecutive reactions and competing reactions. Some lignin decomposition reactions will occur at relatively low temperatures, but the main decomposition reactions will occur around 400° C. Secondary decomposition reactions of lignin intermediates will occur at temperatures above 600° C. In addition, competing cross-linking reactions occur, so the degradation process will include both polymerization and depolymerization reactions. In FIG. 59, polycondensation reactions are estimated to occur primarily at 500-700° C.

Figure 60:
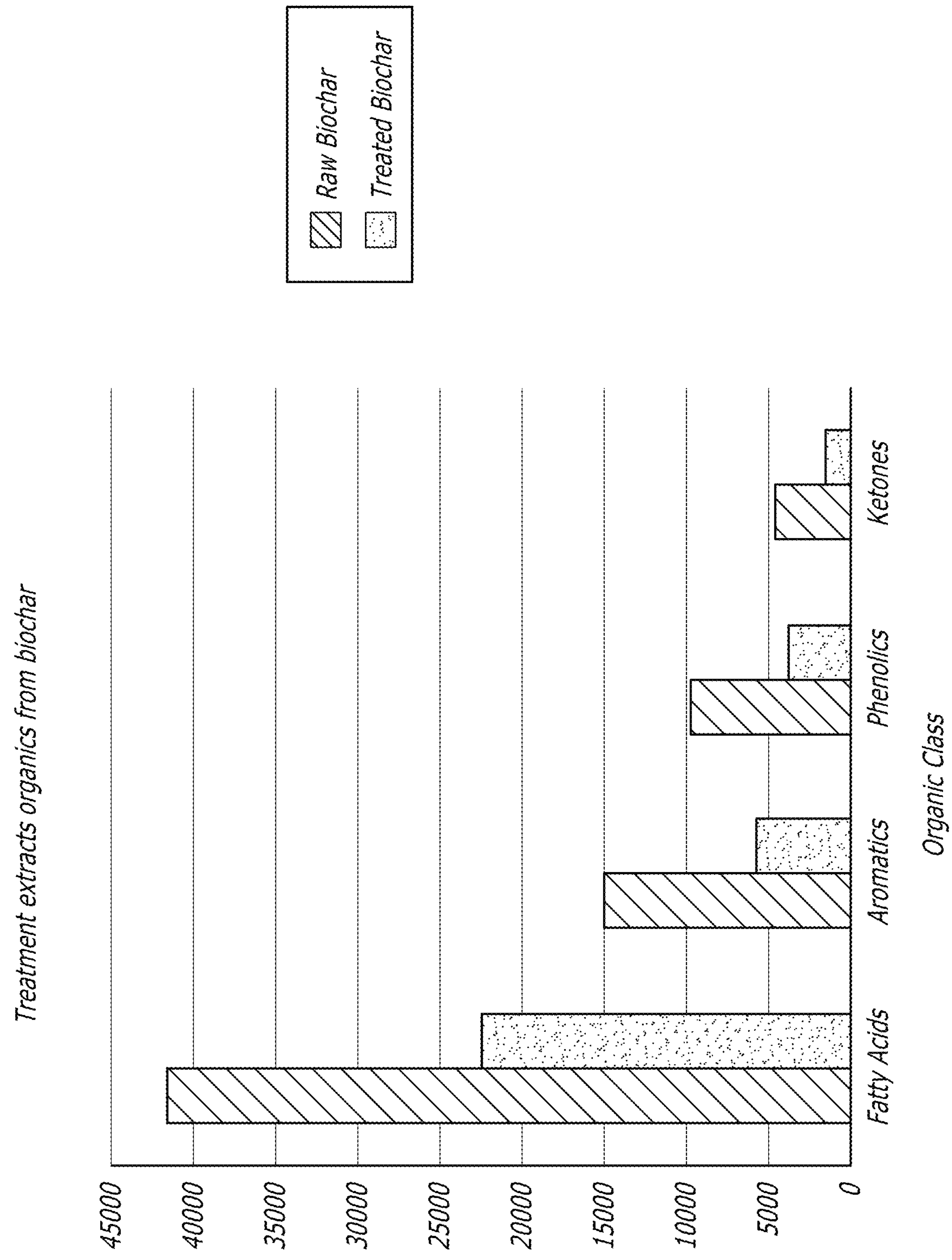
FIG. 60 is a chart showing the results of treating raw biochar vs. treated biochar using the treatment process of the present invention to extract semivolatile residual organic compounds in the biochar.

A sample of raw biochar and treated biochar from the same feedstock were tested using EPA method 8270 to understand what types of semi-volatile residual organic compounds were in the biochar and to what extent they were extracted through the treatment process disclosed previously. The biochar samples were ground prior to analysis and prepared using EPA method 3550. The identified compounds were then grouped into classes: fatty acids, aromatics, phenolics, and ketones. The results are depicted in FIG. 60. The treatment process successfully extracted a significant amount of the organics in all four classes from the biochar, as shown in the reduced organic levels in the treated biochar versus the raw biochar.

Figure 61:
FIG. 61 illustrates the concentrated extracts using acetone as the solvent from a variety of raw biochars sourced from coconut and pine.

FIG. 61 shows the resulting concentrated extracts using acetone as the extraction liquid from a variety of raw biochars sourced from coconut and pine feedstocks. The color and opacity of the various extracts again shows how, depending on biochar feedstock and pyrolysis method, different types and amounts of compounds will be extracted from the biochars using the same extraction method.

Figure 62:
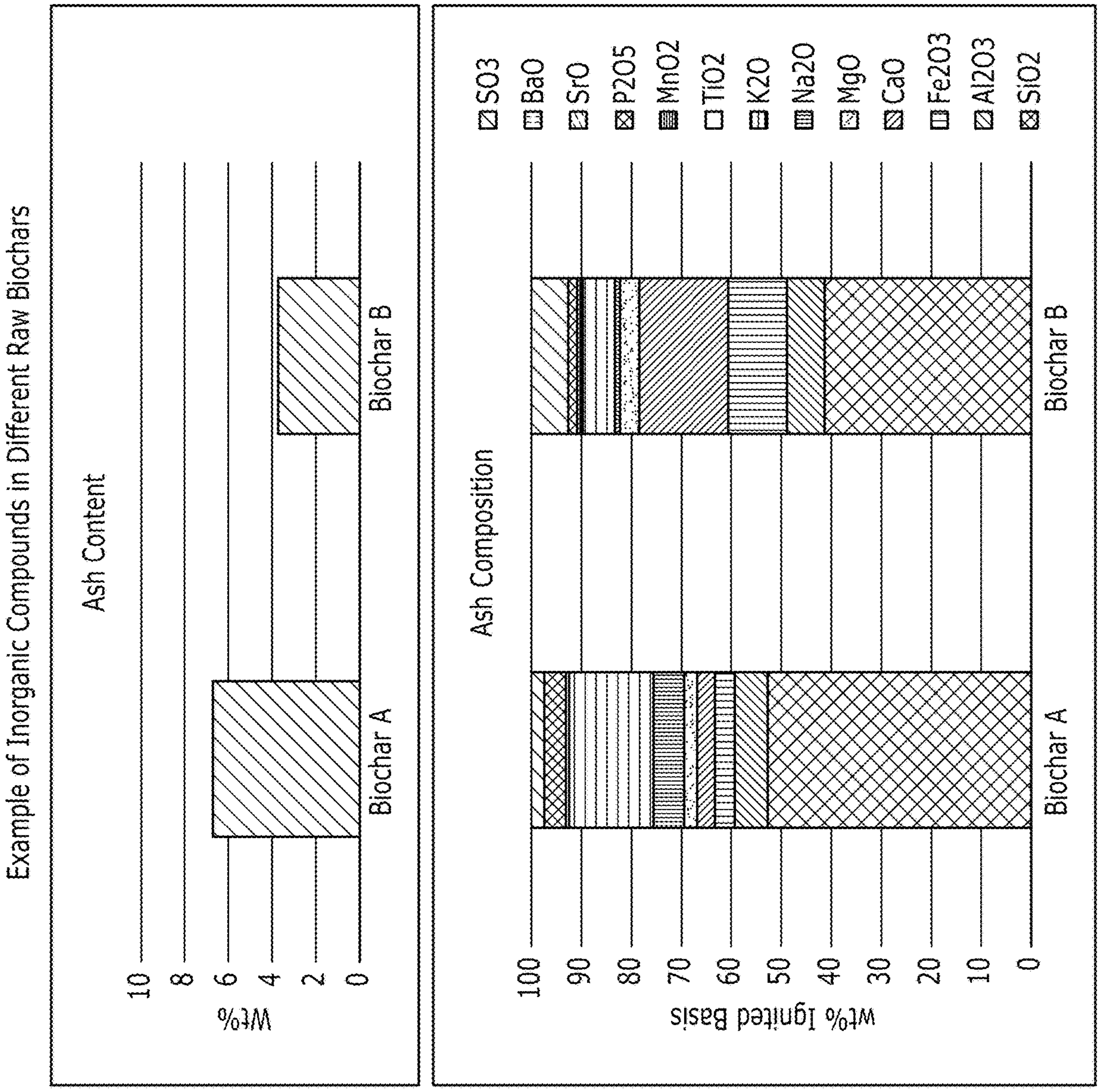
FIG. 62 is a chart showing the compositional analysis of the resulting ash from two different raw biochars, from different feedstocks.

Feedstock and pyrolysis conditions will also determine the amounts of compounds other than ROCs in the biochar and how available they are for extraction. These other compounds include heavy metals, transition metals, and inorganic mineral compounds. When it comes to non-organic compounds, growing conditions will also impact the types and amounts in the biochar. For example, if a biomass feedstock is grown in soil with high levels of heavy metals the resulting biochar may have a higher concentration of those metals than the biochar created from the same biomass and pyrolysis conditions that was grown in non-contaminated soil. Another example would be chloride levels when a resultant biochar's feedstock was grown with high salinity irrigation or soil versus resulting biochar from FIG. 62 shows compositional analysis using ASTM C311/XRF of the resulting ash following proximate analysis using ASTM E1534-93 (ashing temperature of 600° C.) from two different raw biochars, from different feedstocks. Ash composition results are in wt % after ignition. The total amount of inorganics (ash) in raw biochar A is more than 1.5 times the amount in biochar B. In addition, when looking at the composition of those inorganics there are significant differences between the two biochars, for example, there is a much higher percentage of potassium in Biochar A's ash versus that of Biochar B and there is a much higher percentage of iron and calcium in Biochar B's ash versus that of Biochar A. This data is shown as example only that the biochars themselves will have an impact on the amount and types of non-organic compounds available to be extracted, if desirable.

In addition to feedstock selection and pyrolysis conditions, the biomass and biochar particle size can also impact the resulting extract. Generally speaking, smaller particles that have been pyrolyzed with larger particles will have been pyrolyzed to a further extent thus the residual compound types or quantities in biochar fines may be significantly different than those in the larger particles. Thus, physically removing fines or small particles could extract residual compounds. Furthermore, segregating the biochar by particle size prior to extraction will in many cases result in different composition of the extracts vs. leaving the various particles mixed together. It should be noted that grinding biochar after pyrolysis to gain a desired particle size distribution yields a different result than sizing the particles before pyrolysis. This is because sizing before pyrolysis impacts the level of pyrolysis of the particles (typically less pyrolysis for the larger particles) and sizing after impacts the accessibility of various compounds by exposing new externally accessible surface area from which to extract materials. It is desirable in such cases to use biochar particles having particle sizes and distributions ranging from about 0.01 μm to about 10 mm. For example, particle sizes between 10 μm and 500 μm can be selected to improve extraction efficiency. By way of another example, particle sizes between 0.5 mm and 5 mm can be selected to improve separation after extraction. For a specific extraction more consistent particle sizes in a smaller range may be beneficial to get more consistent extraction and separation properties, such that 70% distribution around the mean particle size is 20% of the mean particle size. So, for example if average particle size is 100 μm, then 70% distribution around the mean would equate to plus or minus 20% of 10 μm, or in other words 70% of particles would be between 80 and 120 μm. By way of another example, if average particle size is 1 mm, then 70% of particles would be in the range of 0.8 mm and 1.2 mm.

Another variable of raw biochar that can impact what compounds are in the biochar will be the age and storage conditions of the biochar. Biochar aging is a known variable in biochar characteristics, which has been studied previously (e.g. by Mia, et. al in "Long-Term Aging of Biochar" (Advances in Agronomy Vol 141, 2017). Natural aging, a physiochemical process due to oxidation, can change a raw biochar's structure and surface chemistry which also impacts other biochar properties such as sorption or ion exchange capacity. Thus, the age of the raw biochar or storage conditions that would promote or inhibit oxidation, may impact an extraction method's efficacy in removing targeted compounds, or in some cases even the types and quantity of extractable compounds present.

2. Extraction Methods

Figure 63:
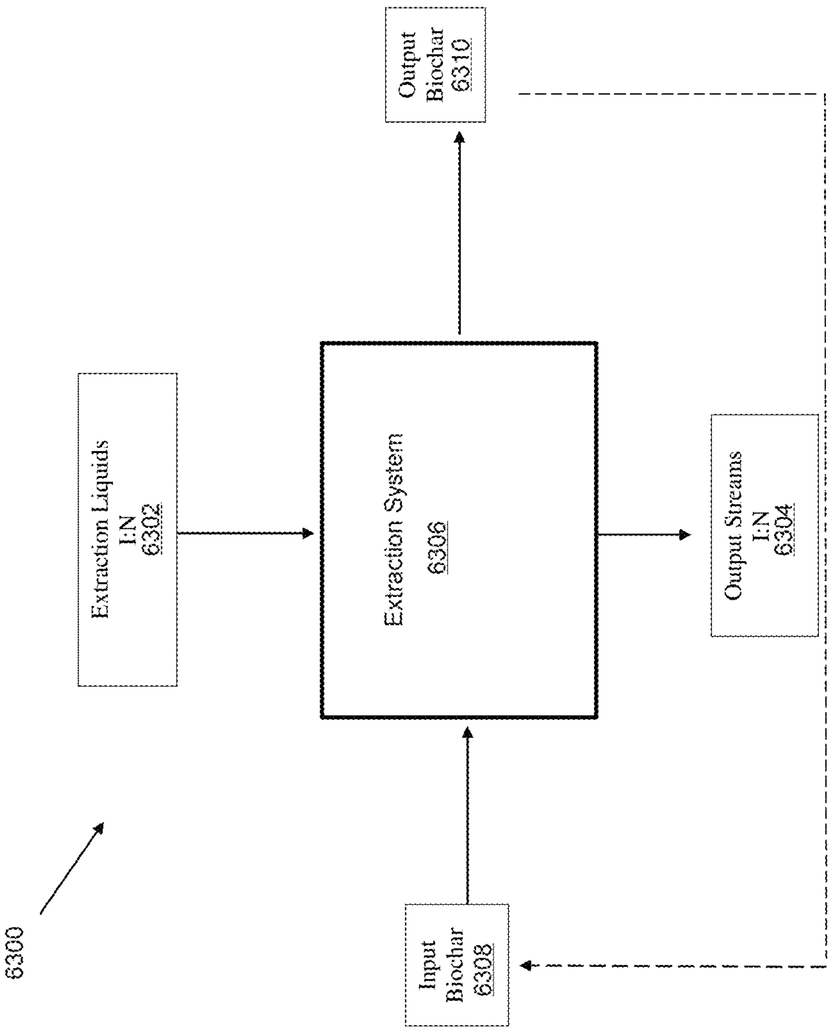
FIG. 63 is a flow chart illustrating that there can be from 1 to N extraction liquids and from 1 to N output streams resulting from a single stage of the treatment process of the present invention.
Figure 64:
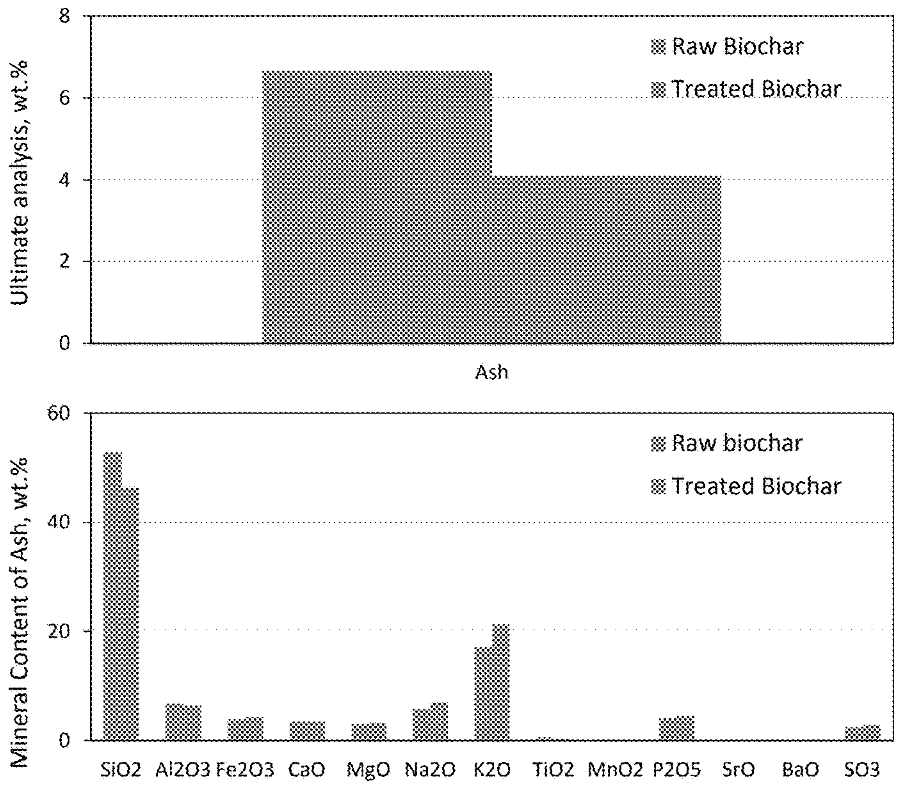
FIG. 64 shows the results of biochar material before and after treatment to remove organic compounds.

Of equal import, as illustrated by the flow chart 6300 shown in FIG. 63, is that there can be from 1 to N extraction liquids 6302, and from 1 to N output streams 6304 resulting from the extraction or treatment process system 6306 which includes the input of biochar 6308. These output streams 6104 could be segregated by time, temperature, pressure, solubility, reaction, or even physical or hydrodynamic properties. The extraction system 6306 can be one tank or vessel or it could be a multi-vessel system. The various extraction liquids 6302 may also be introduced at the same time, through the same or multiple openings in varying locations in the treatment system, 6306, or may be introduced at different times in alignment with temperature or pressure changes, or even reactivity/reaction times occurring in the treatment system 6306. The same treatment system 6306 may be used for multiple treatments without removing the biochar 6308. It should also be noted that the output streams 6304 can contain any (or all) of solid, liquid, or gaseous products. As further shown in the figure, after a round of extraction, the remaining biochar 6310 can be removed and then sent to another stage directly or reintroduced into the same treatment system 6306. The remaining biochar 6310 can also be treated, and then sent to another stage of extraction.

In addition, the extraction can be done at any time after the biochar is created and can be one step of many in the production of a biochar or a biochar extract product. By way of example, this means an extraction step can be done before, after, or as the treatment method described previously or the biochar can be sized, agglomerated, or slurried before, during, or after an extraction step or the biochar can be inoculated with a microbe before, during, or after an extraction step.

Various materials or media can be used to extract compounds from biochar. Water is likely the easiest material to use for extraction but any material or technique that will remove the compounds from the biochar can be used. The material could remove the compound through physical or chemical means. For example, using a liquid material, such as water, that the residual compound dissolves in and then removing the liquid is one mechanism for extraction, but that same liquid material may also physically suspend particles and thus when the liquid is removed those solid particles are also removed. These suspended solid particles could either be the residual compound itself, like an ash, or they could be biochar fines that have the residual compounds in them. To restate from previous discussion, the time at which the material is sized can have a dramatic impact on the composition of the extract. The liquid with solid particles could then be filtered to purify these solid residual compounds from the liquid. If the fines contain the residual compound within them, instead of being the residual compounds themselves, then they could be further extracted using any of the methods described herewith in. FIG. 62 shows the results of biochar material before and post treatment and demonstrates inorganic removal through treatment where the extraction mechanism is generally physical.

Some other materials that work well to remove residual compounds by means of physical or chemical mechanisms from the biochar are steam, supercritical fluids, or solvents. Depending on the extent and targeted residual organic compounds a solvent extraction may perform better than water. Typical solvents to use for removal of residual organic compounds would be water, acidic solutions, alkaline solutions, acetone, acetonitrile, ethyl acetate, organic acids, ethanol, methanol or other polar solvents, hexane or other non-polar organic solvents, ethers, chloroform, furans, ketones, phenolics and dichloromethane.

Various conditions can be applied during the extraction to improve the extent or selectivity of the extraction. One variable that can be adjusted is pressure. The method of extraction can be done under vacuum, at elevated pressures, at atmospheric pressure, or under a pressure gradient, pulse, or variation. The pressure or change of pressure can allow the extraction media to diffuse further into the biochar pores, release gases from internal pores or fine particulates within pores, and thus increase the quantity of compounds captured by the extraction media. Another variable is temperature. The method of extraction can be done at standard temperature, elevated temperatures, or under a temperature gradient, or variation. Since solubility is dependent on temperature, adjusting the temperature can also be used to selectively extract compounds or to adjust the extent of extraction, either increasing or reducing the compounds removed in the extraction media. A third variable is time, the amount of time the extraction liquid is in contact with the biochar will impact the selectivity and extent of extraction of compounds, by both time the extraction material has to contact all surfaces of the biochar and the time after the extraction liquid is in contact that the compounds have to be extracted for example by reaction rate or diffusion rate into the liquid. The material used to perform the extraction may be in solid, liquid, gaseous, or supercritical form, with each form having advantages and disadvantages in performing the extraction. The material targeted for extraction from the biochar may also be in solid, liquid, gaseous, or in rare instances supercritical form. Mating the proper technique, with the proper extraction material, to gain a desired extract is a primary focus of this invention.

Figure 65:
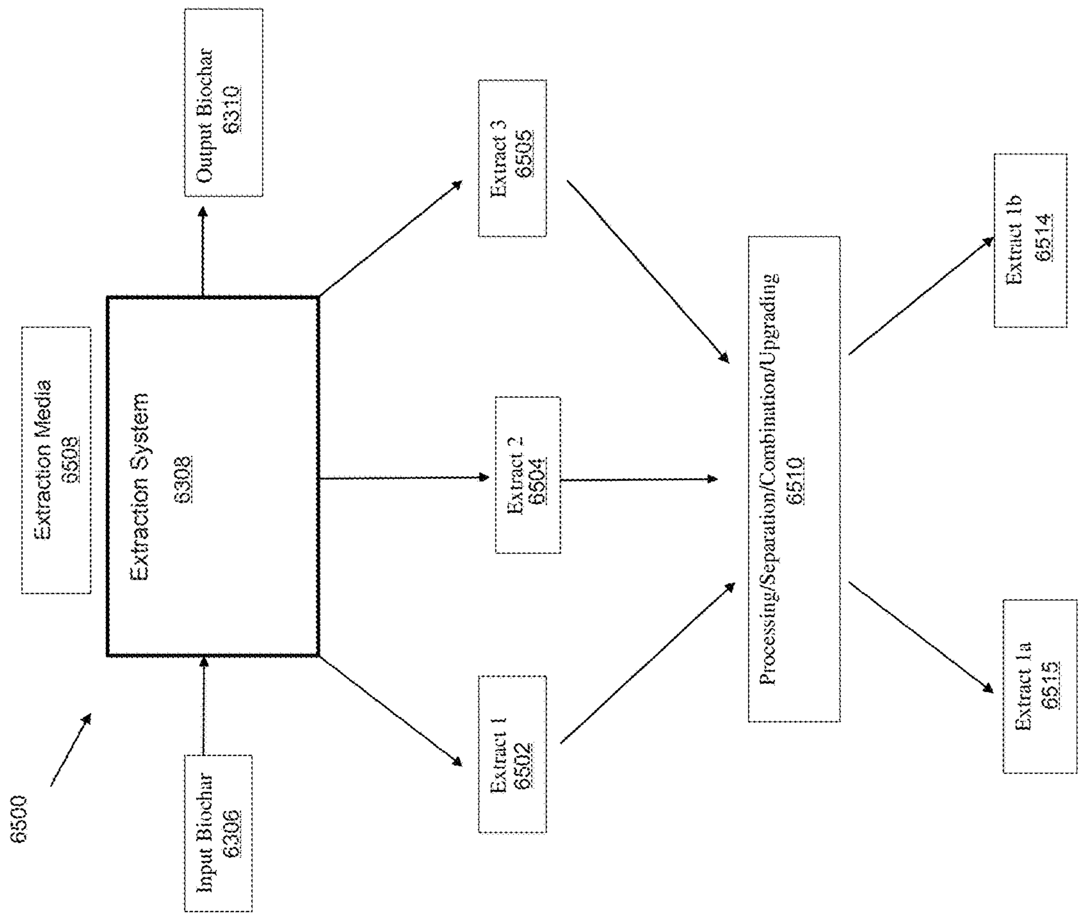
FIG. 65 is a flow chart illustrating how multiple extracts may be generated from the same input material using the treatment process of the present invention.

As illustrated by the flow chart 6500 shown in FIG. 65, multiple extracts 6502, 6504, 6506 may be generated from the same extraction media 6508, representing different compositions. For example, using water as the extraction medium and a treatment tank as the extraction system, the pressure in the treatment tank 6308 can be lowered to allow the extraction liquid 6508 to infiltrate a percentage of the pore volume of the input biochar 6306, contacting a larger amount of surface area than would be possible without the pressure change, then the pressure can be returned to atmospheric, followed by water laden with water soluble compounds taken from the output biochar 6310 being removed from the treatment tank 6308 as a first extract 6502. Then, the temperature in the treatment tank 6308 or the temperature of the extraction water can be raised to over 100° C., and a second extract 6504 comprising primarily steam, but also containing other gaseous compounds that volatilize or transition to vapor state at 100° C. or below may be removed as a separate extract. It should be noted that an extract does not need to be in liquid form. As shown in the figure, the gaseous extract 6504 can be routed to further stages for processing, separation, combination, or upgrading at step 6510 independent of whether it remains a gas or is condensed into liquid form. At times, it may be advantageous to leave a particular extract in its native form rather than going through a phase change. At other times, a phase change may be desired. Furthermore, each of the extracts 6502, 6504, 6506 can be subjected to a further separation process at step 6510 after the actual extraction has taken place to create additional extracts 6512, 6514. Some ways to adjust the contents of an extract are variations in extraction material, temperature, level, type, frequency, or direction of agitation, type of pressure variation (either static or dynamic), or other factors.

In some cases, the initial extraction media itself may need to be removed, for example if it in itself is phytotoxic, and the desired compounds may need to be separated from that media and furthermore may need to be mixed, suspended, or dissolved in a different media. The separation process at step 6510 used to create extracts 6512, 6514 shown in FIG. 65 can involve filtration, hydrodynamic sorting, centrifugal sorting (centrifuging), chromatography, distillation, freezing, condensation, liquid-liquid extraction, solid-phase extraction, scrubbing, adsorption, flotation, decantation, flocculation, biodegradation, oxidation, ozonation, UV treatment, membrane processes, enzymatic treatment, precipitation, melting, separation using electrical charge attraction, repulsion, or by charging the extracted liquids, solids, or gasses, directly, as well as other generally accepted methods for separating materials in mixtures, solutions, or aggregates.

Figure 66:
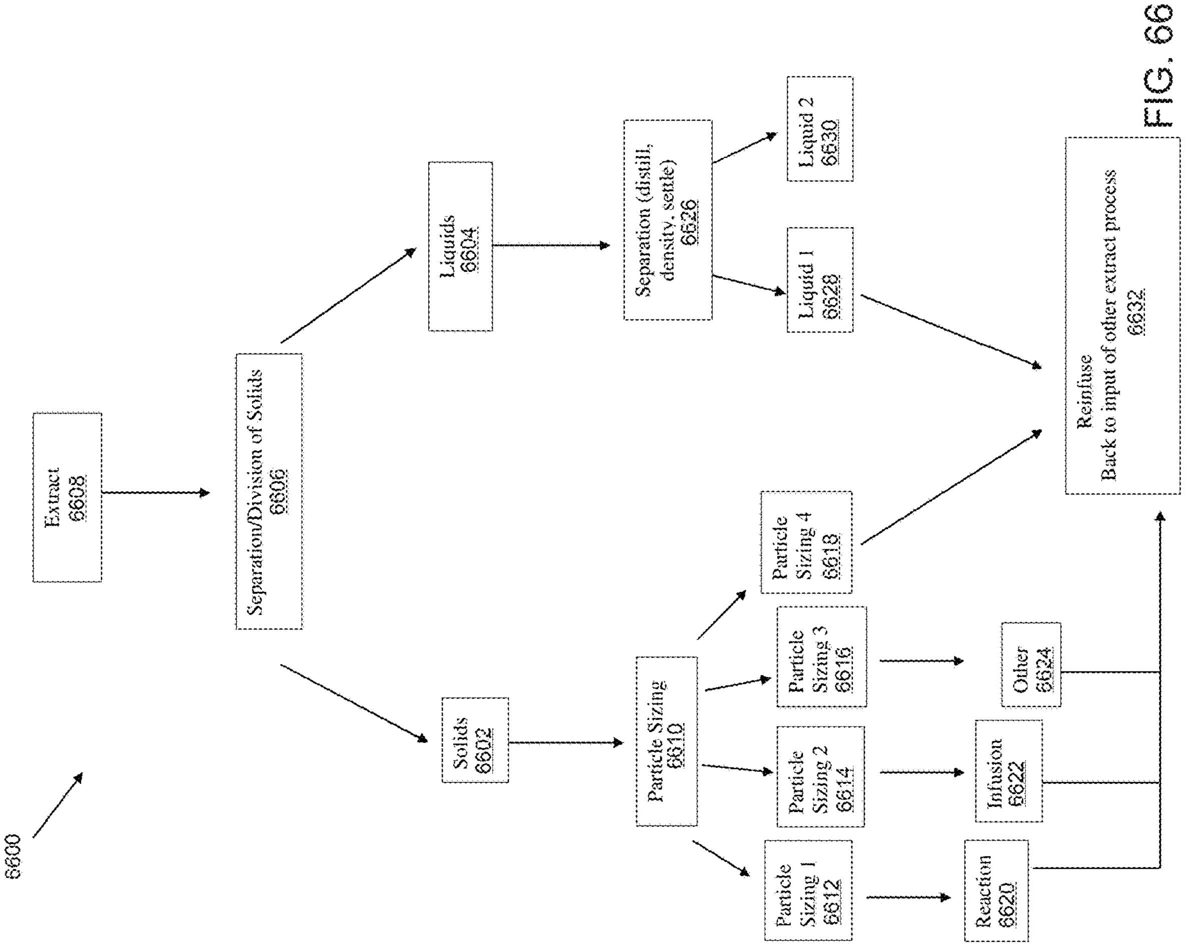
FIG. 66 is a flow chart illustrating how solids and the liquids may also be separated from the extract resulting from the treatment process of the present invention.

As shown in FIG. 66, solids 6602 and liquids 6604 may also be subjected to a process of separation/division at step 6606 from the input extract 6608. The solids 6602 can be treated in multiple ways, and routed to separate parts of the process, for example, sizing by particle size at step 6610, the resulting particles of like size segregated 6612, 6614, 6616, 6618, and then subjected to additional treatment, e.g. further reaction at step 6620, infusion at step 6622 with, for example, microbes, or other treatment at step 6624, such as suspension into a slurry or agglomeration into granules. Similarly, the liquids 6604 can also be separated using a process of distillation, solvent extraction, settling, density or viscosity separation, or other methods at step 6626. The separated liquids 6628, 6630 can then be moved to other parts of the process, used as an extract, disposed of, or recombined with one or more of the solids or other liquids produced in other parts of the process at step 6632. Infusion at step 6622 with microbes, that is, using microbes to change the state of the material into more advantageous forms, is also a valid and efficacious form of treatment. Microbes may be used to upgrade, solubilize, or modify organic or inorganic compounds found on the interior or exterior surfaces of the biochar. Microbes may also be used in some cases to modify the apparent or functional surface chemistry of the material by occupying exchange sites or by eroding or consuming residual surface compounds which impact the biochar's localized surface charge, availability of free electrons, pH, ion exchange capacity, or other common measurements of surface physical or chemical performance.

In addition to methods of separation for purification, the extracts can also be concentrated through evaporative, condensation, and/or crystallization methods. Some examples of industrial equipment for concentration process are flooded evaporators, rising/falling film evaporators, forced circulation evaporators, vacuum evaporators, multiple effect evaporators, and plate evaporators. In some cases, the extraction media could be fully evaporated off and the remaining material could be resuspended or dissolved in a different media, such as water. This additional concentration step is often needed to make a commercially viable product when the desirable compound is in a low concentration in the extract stream, for example less than 20 wt %, less than 10 wt %, less than 1 wt %, in the ppm range, or in the ppb range. One example of application for this additional concentration step is if the resulting extract product is for seed treatment. Seed treatments can be done upstream, i.e. during seed production or in seed batch treatments prior to planting, or downstream, i.e. during the planting the treatment is applied to the seeds in furrow. By way of example, typical corn seed treatment rates for bio-stimulant or biocontrol products for upstream applications are about 1-2 fl oz per 100 lb seeds (<0.0005 mL/seed) and downstream applications are about 0.5-1 fl oz per 1000 ft-row (<0.05 mL/seed). Thus, removing the non-active liquid solvent from the stream is critical to getting a higher rate of application of the desirable material onto the seed at these very low application rates.

Figure 67:
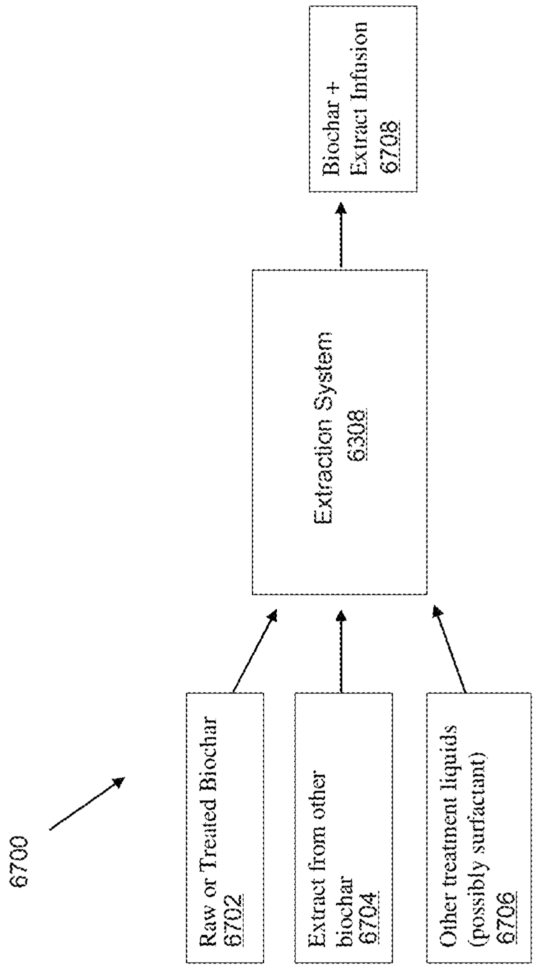
FIG. 67 is a flow chart illustrating how raw or treated biochar can also be combined, reinfused, or treated with extracts from other biochars.
Figure 68B:
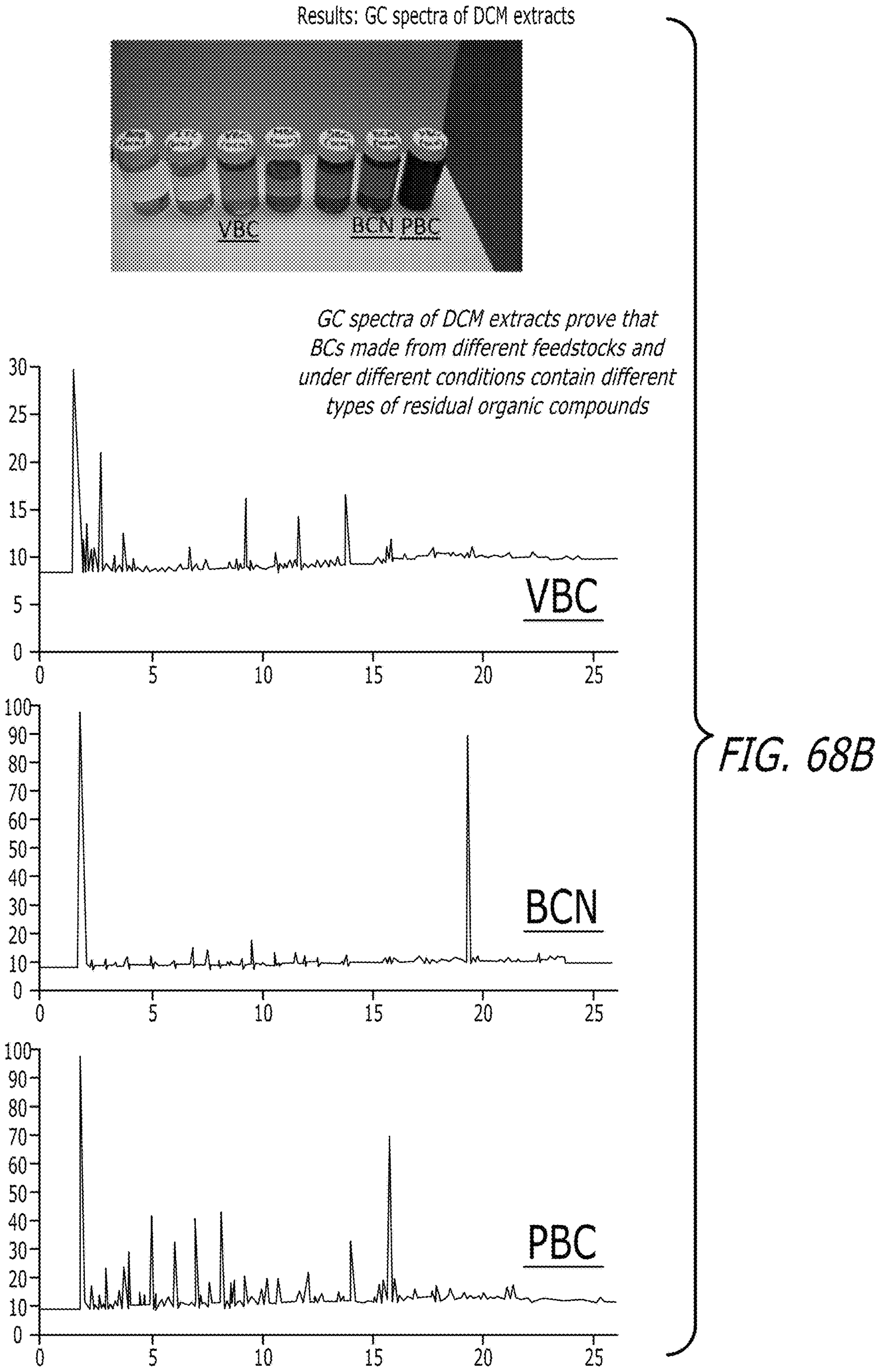

As shown in the flow chart 6700 of FIG. 67, raw or treated biochar 6702 can also be combined, reinfused, or treated in the treatment tank 6308 with extracts from other biochars 6704 or other liquids such as a surfactant 6706, thus in some cases imparting some of the properties of the other biochar to the inoculated material. As shown by example in FIGS. 68*a-e*, a phytotoxic biochar can become harmless and a harmless biochar can become phytotoxic when the residual organic compounds are extracted from each of the biochars and then reinfused into the other biochar. In other words, a biochar known to be phytotoxic can have the phytotoxic materials extracted. When this extract is reinfused into the pores of a second (previously non-phytotoxic) biochar, the second biochar can be proven to be phytotoxic, while the first biochar has been rendered non-phytotoxic. It should be noted that when the reinfusion takes place that it can occur with one or more extracts, either directly extracted, or treated/upgraded/amended with intermediate processing steps, in solid, liquid, gaseous, or supercritical forms. The reinfusion can be performed using any of the treatment processes described earlier in this application, to include simple soaking, but preferably a method such as vacuum, surfactant, ultrasound, or other that allows for greater, deeper, more rapid penetration of the extract into the pores of the newly targeted biochar. This example is an extreme one as one of the biochar extracts is clearly harmful, but it demonstrates that the residual organic and inorganic compounds are different between biochars and can have varying impacts. Thus, using this method, compound, hybrid biochars can be created that share some of the properties of multiple raw biochars. Or, more importantly, previously unattainable forms of biochar can be developed by extracting materials from multiple other biochars, upgrading the extracts, and then reinfusing them at step 6708. After infusion, the upgraded biochar can be further treated, upgraded, modified, or processed in accordance with the methods outlined above, which address treating or processing raw or treated biochar.

Figure 69:
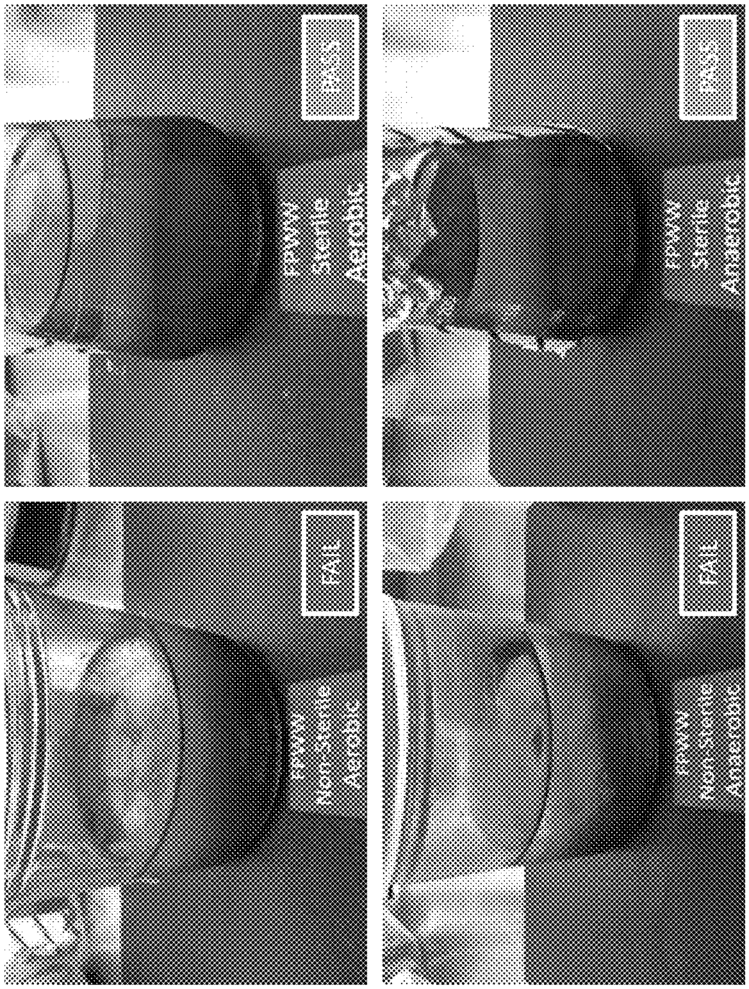
FIG. 69 shows the visual results of a lab test done to see the difference in microbial growth of a biochar extract during storage when sterilized at 121° C. and 21 psi for 45 minutes or not and when the extract was stored aerobically or anaerobically.

Some of the properties that cause a biochar extract to be a beneficial and a commercially viable product can also lead to product shelf-life concerns. For example, if the beneficial compounds in the extract are a nutrient for plants or microbes, then the extract stream could also grow microbial life after production prior to use. Thus, an additional sterilization step may be needed prior to, during, or post extraction and/or the final extract may need to be properly packaged and stored to ensure extract product has a long shelf-life. FIG. 69 shows the visual results of a lab test done to see the difference in microbial growth of a biochar extract during storage when sterilized at 121° C. and 21 psi for 45 minutes or not and when the extract was stored aerobically or anaerobically. The samples were stored for 12 days at 30° C. to induce quicker growth. The samples were then visually rated a pass or fail based on turbidity, surface growth, and discoloration. As seen in the figures, the sterilization step would be vital on this extract for a commercial product. The sterilization step may be in combination with other steps, for example during treatment, inoculation, purification, or concentration if the extract stream reaches sterilization conditions based on temperature and pressure. Sterilization could also be done using Ultra-violet light, radiation, or chemical methods.

To demonstrate other examples of extraction methods and their impact on resulting biochar extracts, two different lab methods were tested with different extraction media (solvents) to see impact on the biochar extracts created. The first method was a simple soak and filter method. The biochar was placed in a flask with a liquid solvent and allowed to stand for a set amount of time and then the material in the flask was filtered to remove the solid biochars leaving a liquid extract. The second method was using a Soxhlet extractor, which consists of a boiler and a reflux that continually circulates the solvent through a solid material to continuously extract compounds from the solid material for collection in the solvent using a siphon. This method is particularly useful when desired compounds have limited solubility in the solvent.

With both methods, the extract could be considered final for testing or additional steps could be made to separate the solvent from the extracted compounds, typically through a rotary evaporator, and then to dissolve or suspend the extracted compounds back into a set volume of a different solvent to create a final extract for testing. This final solution could be made with the same volume of solvent as the original solvent used to keep similar concentrations, or a different amount of solvent to increase or decrease the resulting extract's concentrations.

Figure 70:
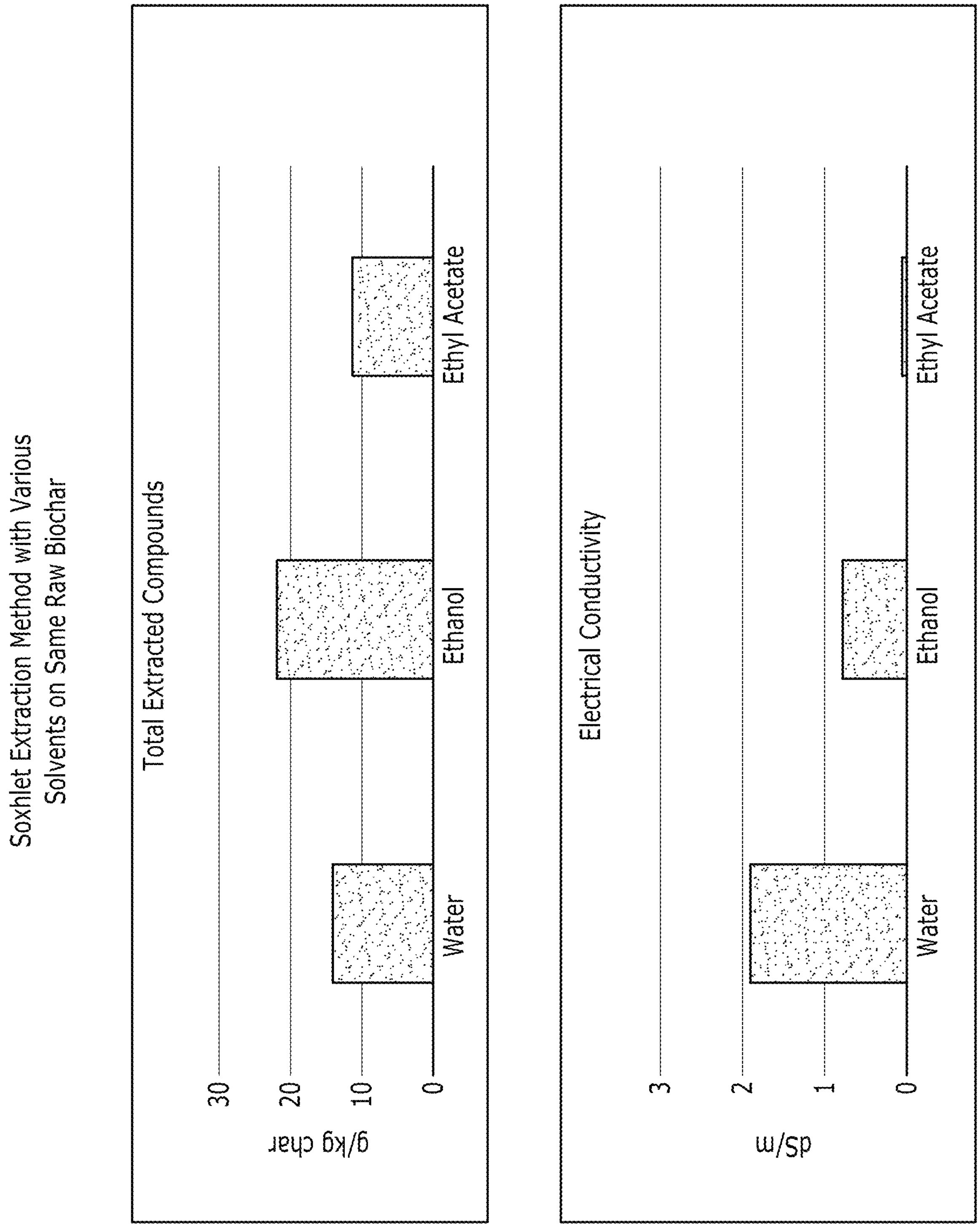
FIG. 70 show analysis results of Soxhlet extracts from the same biochar using three different solvents: water, ethanol, and ethyl acetate.
Figure 71:
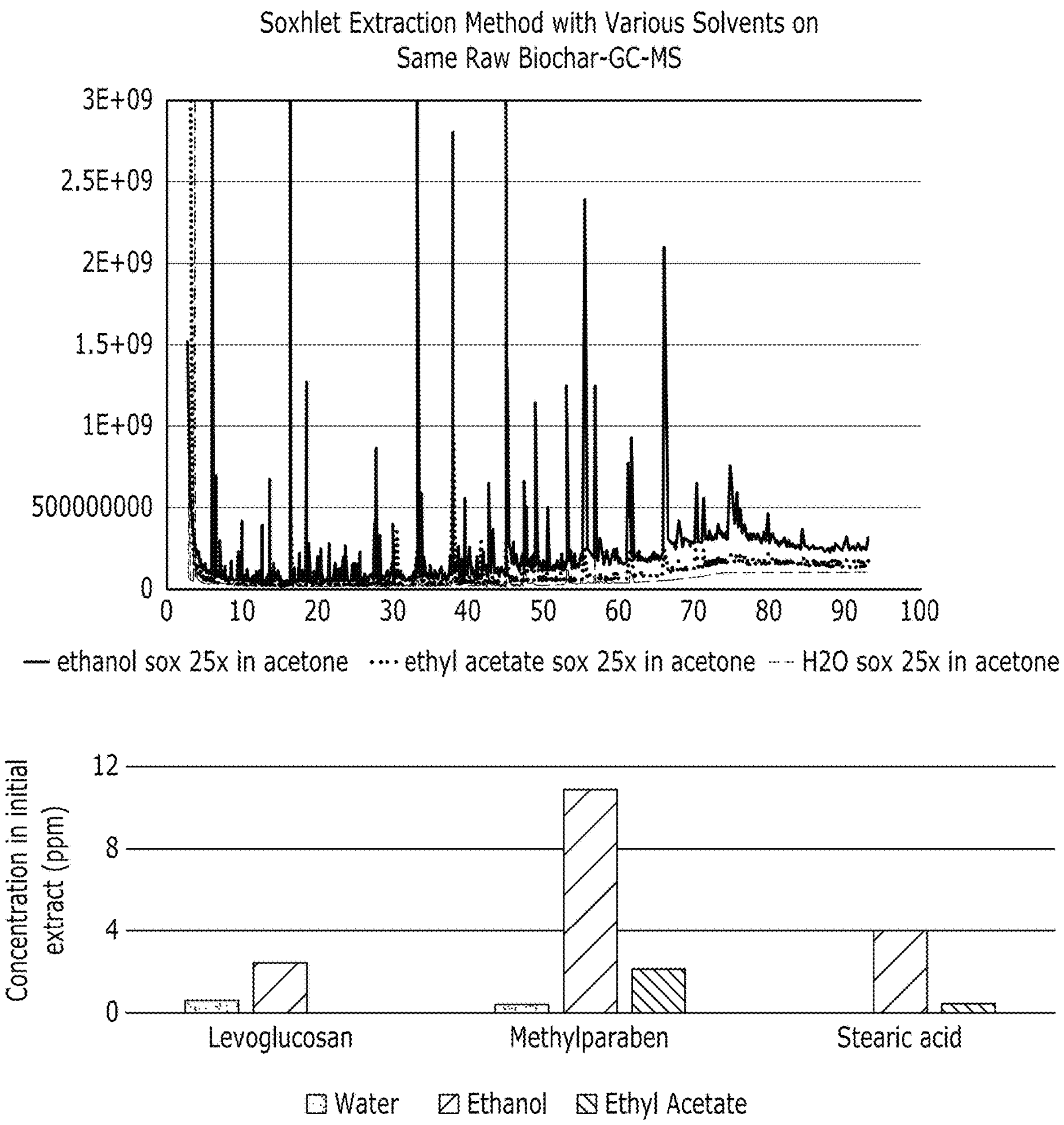
FIG. 71 shows how the extraction efficiencies varied by solvent.
Figure 72:
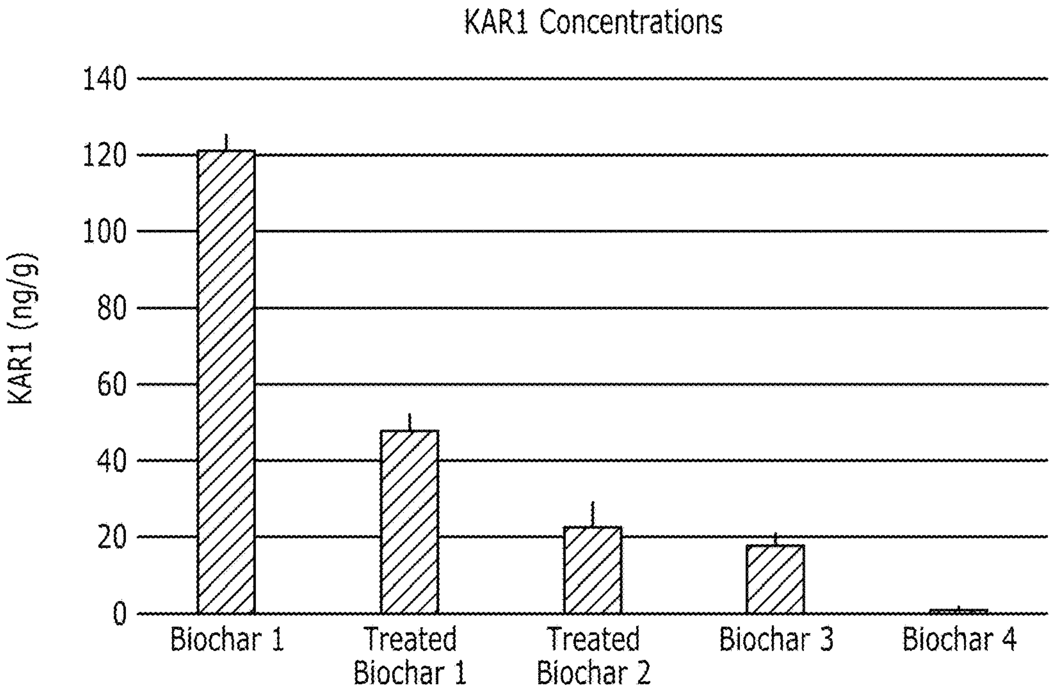
FIG. 72 is a chart quantifying the amount of $KAR_1$ concentrations in various sources of biochar.

FIG. 70 and FIG. 71 show analysis results of Soxhlet extracts from the same biochar using three different solvents: water, ethanol, and ethyl acetate. The overall total amount of extracted compounds was highest with ethanol, followed by water and then ethyl acetate. Not surprisingly, the water, alcohol, and organic solvent also had different extraction efficiencies and selectivity for different types of compounds. Based on the electrical conductivity of the three extracts, the water extracted the most minerals, ethanol extracted some, and ethyl acetate extracted almost none. The GC-MS spectra of the three extracts also showed different compounds and amounts for the three different solvents. As way of example, three representative compounds identified and quantified by the GC-MS are depicted in FIG. 71 to show how the extraction efficiencies varied by solvent. Levoglucosan, an anyhdrosugar, had the highest concentration in the ethanol extract, followed by the water, and it was not identified in the ethyl acetate extract. Methylparaben, a phenolic, also had its highest concentration in the ethanol extract, but the ethyl acetate extract had the second highest concentration and the water had the lowest concentration. The highest concentration of stearic acid, a fatty acid, was also seen in the ethanol extract, but a small amount was seen in the ethyl acetate extract, and it was not detected in the water extract.

Because different biochars have different types and amounts of residual compounds and because different extracting methods and media will have different extraction efficiencies for each residual compound, biochars and extraction systems can be designed for the desired compound or set of compounds. In many cases, additional extraction or purification steps may be warranted. For example, in some cases it could be desirable to extract as many compounds as possible from the biochar to leave a relatively clean biochar, devoid of most residual compounds, and then take the initial extract and do another extraction step to selectively choose a subset of compounds from the first extract. In other cases, it could be more desirable to use a more selective extraction method and solvent, so much of the residual compounds remain on the biochar. Or in even other cases it could be more desirable to use a more selective extraction method and solvent as a first extraction method, and then do a secondary extraction step on the remaining biochar either with a different selective extraction method and media or with a broad efficient extraction method and media.

3. Composition of Extract

As set forth above, of particular interest is both (i) the extraction of organic compounds from the biochar that have been shown to promote seed germination and early plant development and/or (ii) maximizing the amount of organic compounds that are shown to promote seed germination and early plant development in the biochar (for use as is or for extraction purposes). For purposes of this application, the organic compounds that can be used to promote seed germination or plant development or microbial interactions may be referred to as "soluble signaling compounds." As demonstrated and explained further below, the amount of signaling compounds in a biochar can be controlled with (i) the selection of biomass from which the biochar is created, (ii) the pyrolysis parameters and processes, and/or (iii) the types of post treatment processing used. Through these choices, the amount of soluble signaling compounds found in the biochar can be optimized. Of particular interest is maximizing the amounts of soluble signaling compounds in the resulting biochar and/or extracting them from the biochar.

As background, two groups of soluble signaling compounds have been isolated from the smoke of burning plant material and have been shown to increase seed germination and early plant development: (i) Cyanohydrins, such as glyceronitrile and (ii) Butenolides. Butenolides are similar in functionality as strigolactones, which are a phytohormone that help to control plant development through shoot branching and cell elongation and act as a signaling compound in plant-microbial interactions. While the entire class of cyanohydrins, butenolides, and strigolactones are of interest, within the class of butenolides, karrikins are of particular interest. The karrikin family consists of $KAR_1$, $KAR_2$, $KAR_3$, and $KAR_4$. $KAR_1$ is 3-methyl-2H-furo[2,3-c]pyran-2-one, a two-ring structure comprised of a pyran ring and a lactone ring. Karrikins, which are easily dissolved in organic solvents, and to lesser degree in water, have been shown to be effective at concentrations as small as $10^{-10}$ M, similar to phytohormones. See Flematti et al, *Burning vegetation produces cyanohydrins that liberate cyanide and stimulate seed germination*, Nat Commun. 2011 Jun. 21; 2:360 and Flematti et al, *A compound from smoke that promotes seed germination*, Science 305, 977 (2004).

Recent research has identified the presence of karrikins in biochar and has quantified karrikinolide in several systematically prepared biochars and associated this amount with species specific increases in seed germination and plant size resulting from the use of biochar in the growth media. See Kochanek et al., *Karrikin Identified in Biochars Indicate Post-Fire Chemical Cues Can Influence Community Diversity and Plant Development*, Aug. 18, 2016, PLOS Tenth Anniversary Journal. Until now, no data has been collected demonstrating levels over 10 ng/g of $KAR_1$ in biochar. It has been recently determined and discovered that through the selection of biomass, in combination with varying pyrolysis processes and parameters, higher levels of soluble signaling compounds can be achieved in biochar than previously identified, which can be maintained in the biochar or extracted from the biochar for use in the promotion of seed germination and early plant development.

Given this research, it has been proven that the amount of soluble signaling compounds can be maximized by biomass selection and pyrolysis processes and parameters. For example, FIG. 70 is a chart quantifying the amount of $KAR_1$ concentrations in various sources of biochar. Biochar 1, which is a raw biochar, has the highest concentrations of $KAR_1$ at 121 ng/g of char. Treated Biochar 1 is from the same exact biochar source as Biochar 1, but has undergone pressure/vacuum treatment, as set forth above, and showed the second highest level of $KAR_1$ at 47 ng/g of char. Thus, the pressure/vacuum treatment processing described above removed about 61% of $KAR_1$ from the biochar. However, the concentration levels of $KAR_1$ on both Biochar 1 and Treated Biochar 1 are orders of magnitude greater than that of the highest published data on biochar KAR1 levels of 0.8 ng/g of biochar. See Kochanek et al., *Karrikin Identified in Biochars Indicate Post-Fire Chemical Cues Can Influence Community Diversity and Plant Development*, Aug. 18, 2016, PLOS Tenth Anniversary Journal. Treated Biochar 2, at 22 ng/g of char, showed about half the amount of KAR1 than Treated Biochar 1, even though they are from the same type of biomass and went through the same pressure/vacuum treatment processing. Thus, the difference most likely lies in the pyrolysis conditions. Biochar 3 and Biochar 4 are both raw biochars derived from the same type of biomass source, which is a different type of biomass than that of Biochars 1 and 2. Their levels of $KAR_1$ are significantly lower than that of raw Biochar 1, pointing to feedstock impact on karrikin levels. However, Biochar 3's KAR1 level of 17 ng/g of char is still significantly more than that of the published data, whereas Biochar 4's KAR1 level of 0.5 ng/g, falls in about the middle of published data, again pointing to the impact of pyrolysis conditions on resulting biochar karrikin levels. Accordingly, current tests show that not only do the pyrolysis methods, processes and parameters impact the concentration of the karrikins in the biochar, but also the source material/biomass also plays a significant role in the availability of the karrikins to the biochar. Further, post treatment processes, such as subjecting the biochar to a treating liquid under a vacuum can also remove or extract the karrikins, or other soluble signaling compounds from the biochar. Whereas, a surfactant post treatment process would allow for the benefits described previously while maintaining the highest levels of karrikins in the biochar.

Figure 73:
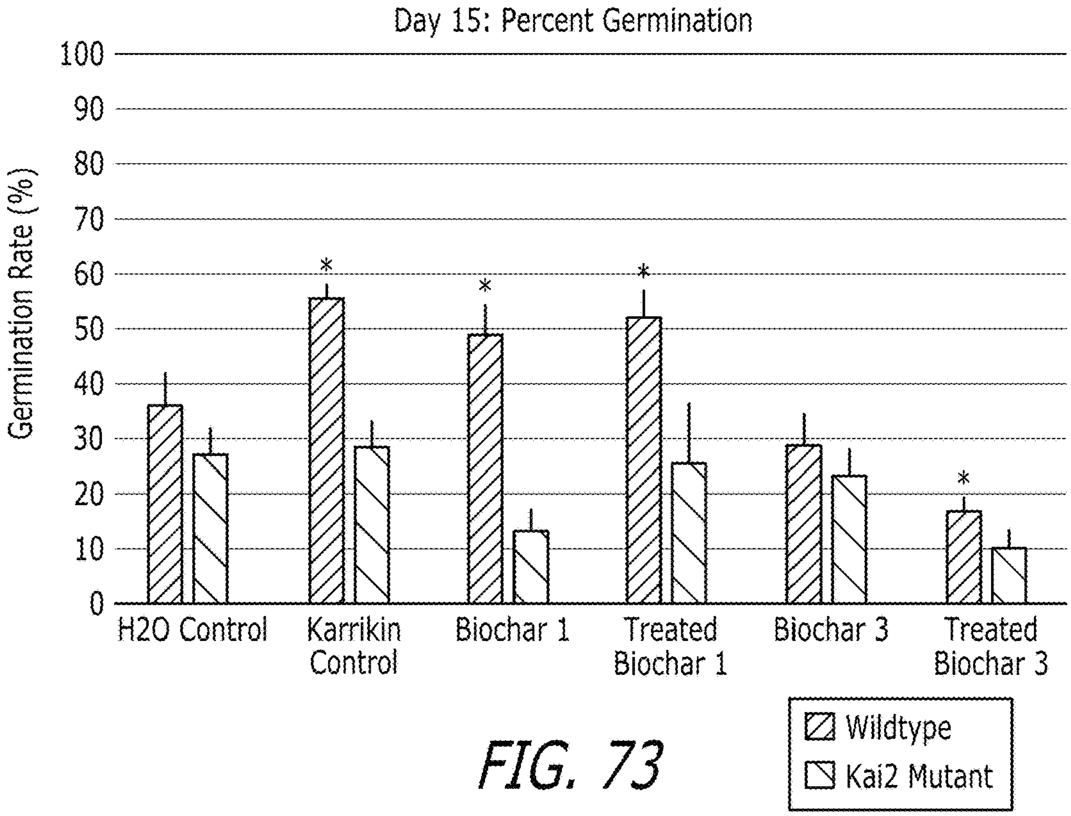
FIG. 73 is a chart that shows seed germination rates of Arabidopsis seeds after 15 days in different media.

FIG. 73 is a chart that shows seed germination rates of *Arabidopsis thaliana* seeds after 15 days in different media. Two types of *Arabidopsis* seeds were used a wild variety and a KAI2 mutant variety. Karrikin molecules are known to interact with KAI2 receptor proteins in the Karrikin pathway to impact germination and early stage plant growth. The KAI2 mutant seeds had T-DNA insertion mutations in the KAI2 gene to block the karrikin mediated signal transduction pathway. In other words, the KAI2 mutants' germination and early growth cannot be impacted by karrikins whereas the wild variety still has the signaling pathway available and thus growth and early germination can be impacted by karrikins. As expected, the synthetic karrikin positive control increased wildtype seed germination by 54% ($p<0.01$) over the water control but did not impact germination in the KAI2 mutant seeds. Biochar 1 and Treated Biochar 1 showed similar results to the karrikin control, increasing wildtype seed germination by 35% and 43% over water controls ($p<0.05$), but not increasing KAI2 mutant seed germination rate. There was no significant difference in seed germination rates between wildtype and kai2 seeds with Biochar 3 or Treated Biochar 3, which are derived from a different biomass type than Biochar 1 and Treated Biochar 1. In summary, proper concentrations of karrikins on Biochar 1 and Treated Biochar 1 increase seed germination rates in seeds where the karrikin-mediated signal transduction pathway is present.

Karrikins can be extracted from the biochar and the presence and concentration of the karrikins in the extract can be determined by using gas chromatography-mass spectrometry (GC-MS). Flematti et al., Identification of Alkyl Substituted 2H-Furo[2,3-c]pyran-2-ones as Germination Stimulants Present in Smoke, 2009, Journal of Agricultural and Food Chemistry presented a scan of KAR1 through GC-MS which can be used as a benchmark or control to determine the presence of the $KAR_1$ in the tested biochar extracts. As discussed previously, biochar extracts can be created by using a solvent, such as water, acetone, acetonitrile, dichloromethane, ethanol, ethyl acetate, or hydrochloric acid, to extract compounds from the biochar.

It is desirable to have Karrikin levels in biochar extract greater than 1 ppt, more preferably greater than 0.005 ppb, even more preferably greater than 0.05 ppm, or even more preferably greater than 0.5 ppb. In fact, having concentrations greater than 1 ppb or even greater than 1 ppm could also be desirable. This is because in application the extract can be diluted to get to the right application rate to see the desired effect.

Figure 74:
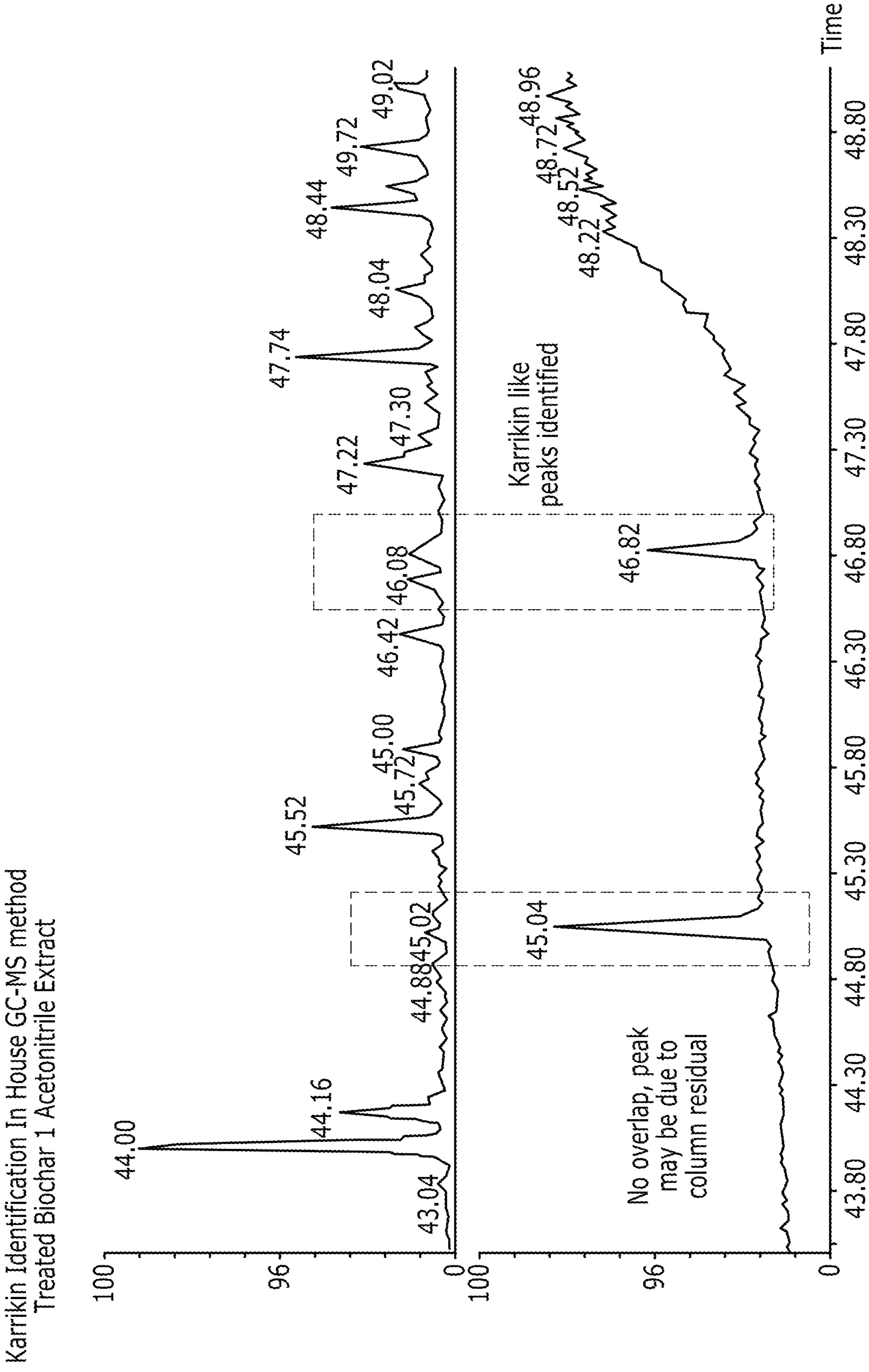
FIG. 74 is a scan of the biochar extract taken through GC-MS in the area of interest for showing the presence of karrikins, alongside the scan in the same region of $KAR_1$ in water.
Figure 75:
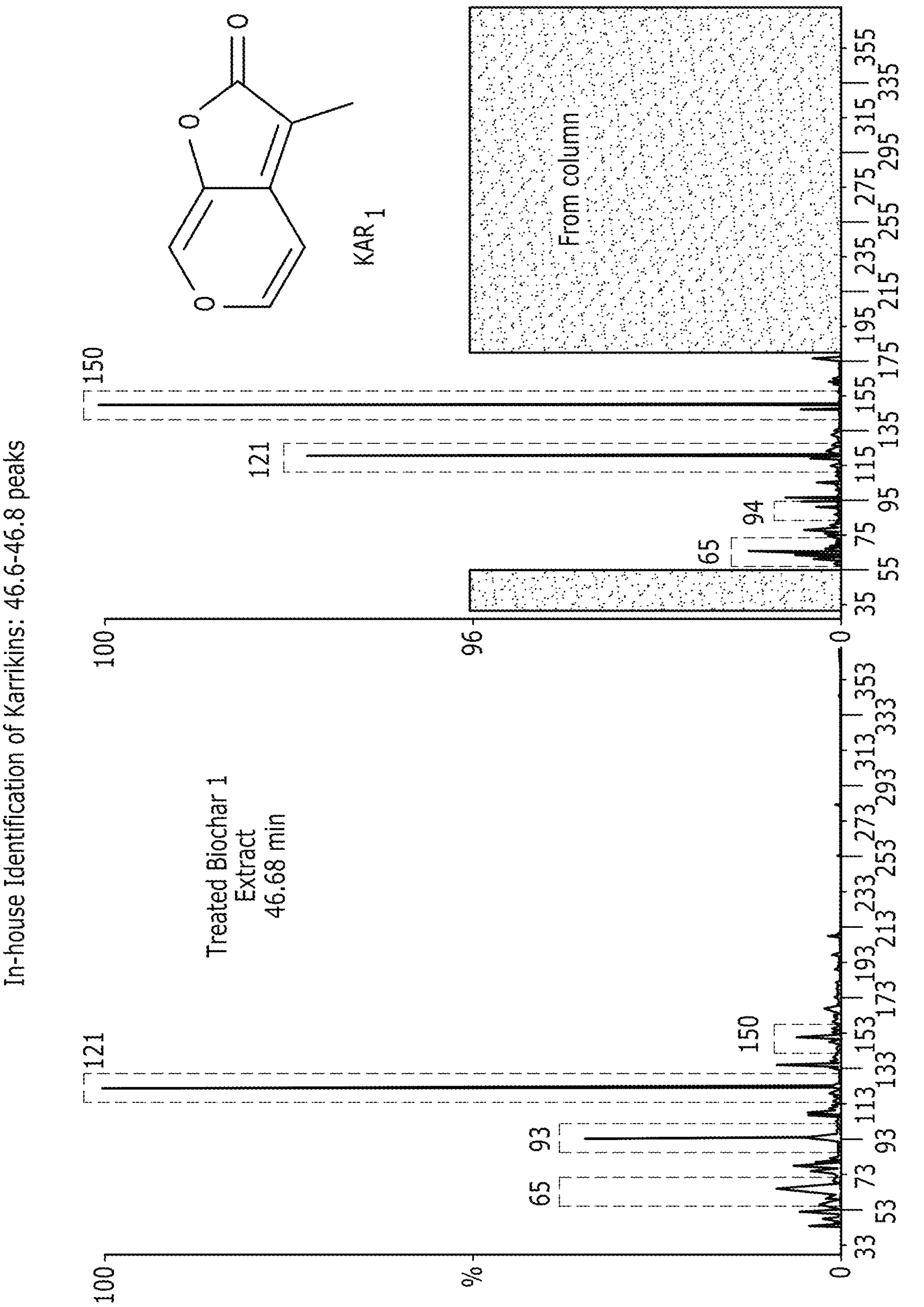
FIG. 75 compares the peaks of $KAR_1$ and the treated biochar at 46.68 min.
Figure 76:
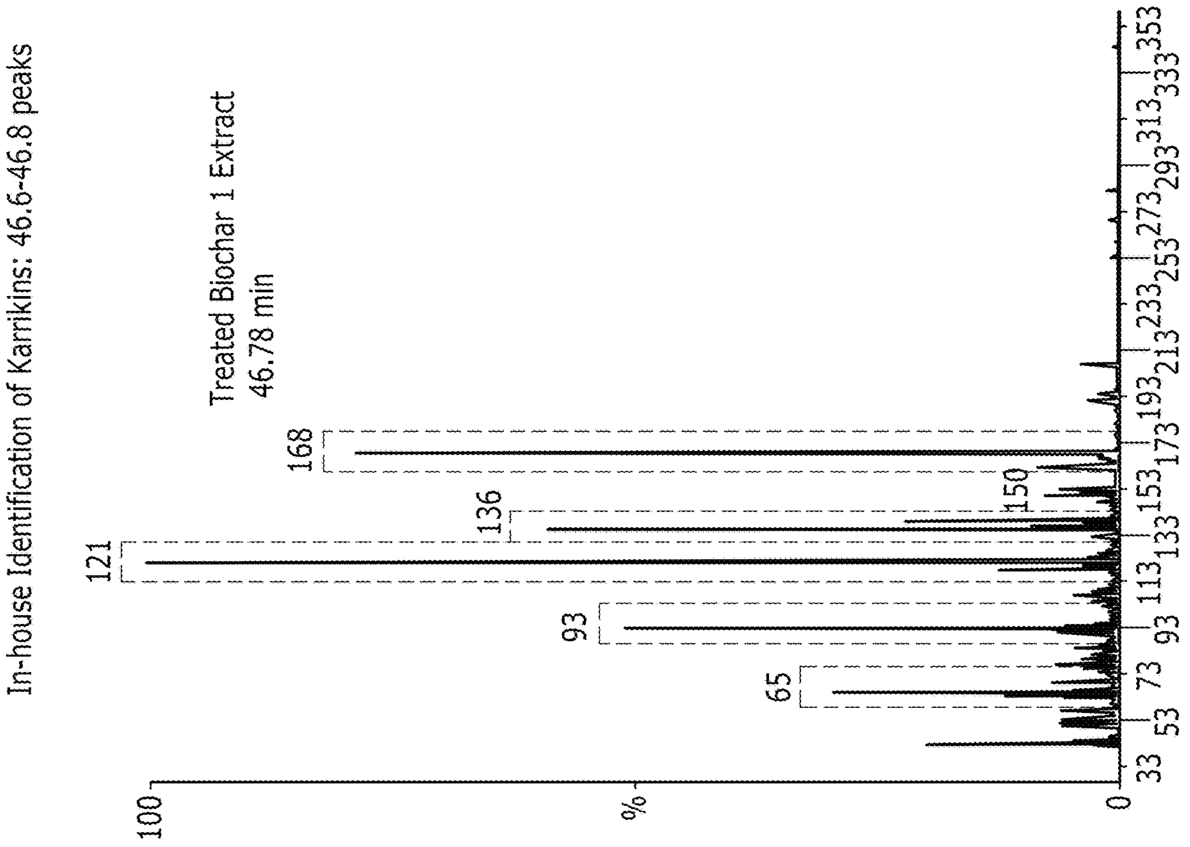
FIG. 76 illustrates the peaks of the treated biochar at 46.78 min.
Figure 76:
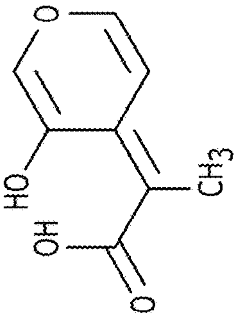
Figure 77:
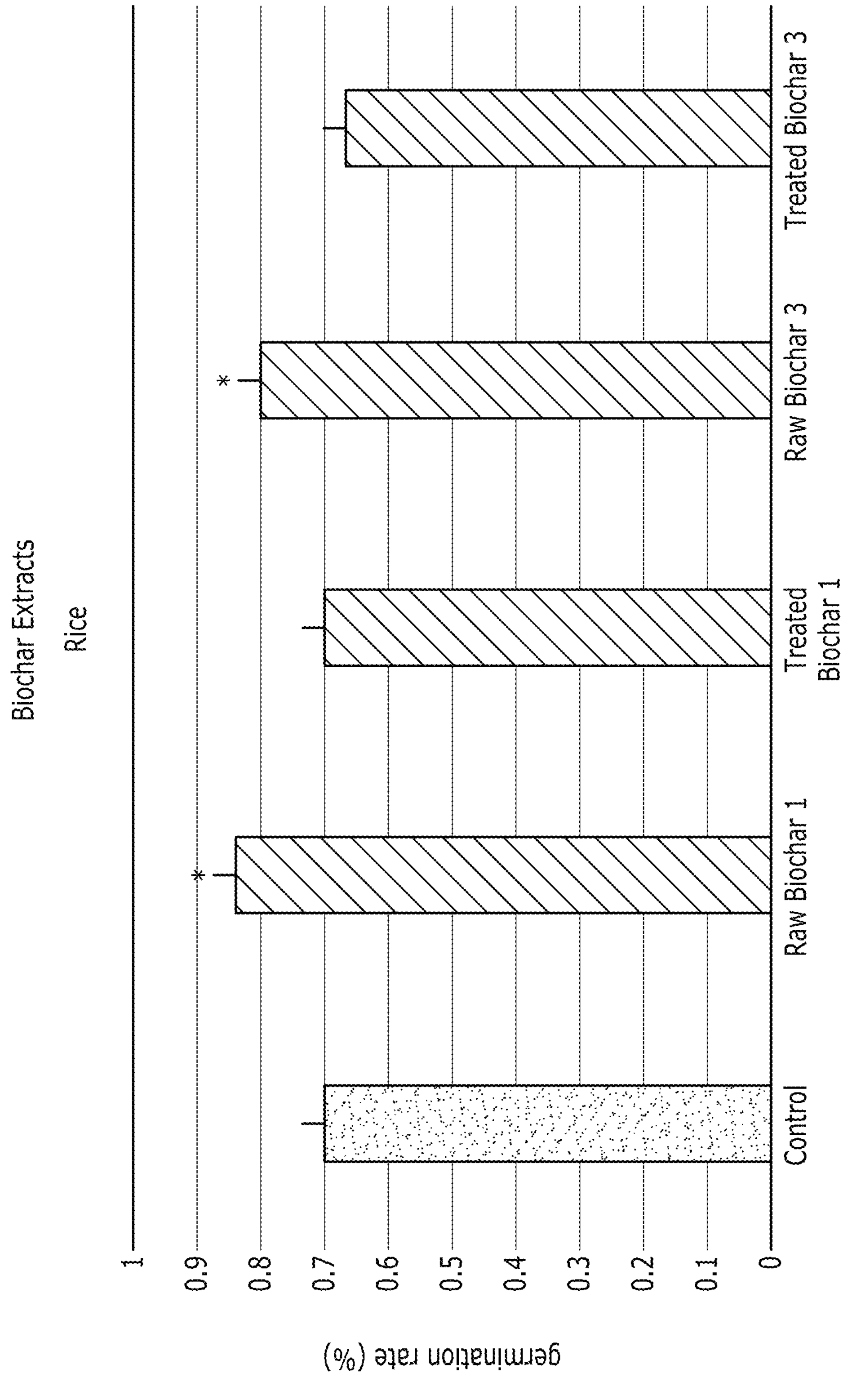
FIG. 77 is a chart showing the test results of the use of the raw and treated biochar extracts on tall fescue at Day 5.

FIG. 74 shows two GC-MS spectra in the region of interest for identifying the presence of karrikins. The top spectra chart is that of an acetonitrile biochar extract from Treated Biochar 1, which as previously discussed was shown to have a large amount of $KAR_1$ but had been reduced by post-pyrolysis treatment processes. The bottom spectra is a positive control reference of 4 ppm of $KAR_1$ in water. In this figure, it is seen that karrikin-like peaks are identified in the extract of the treated biochar. FIG. 75 compares the peaks of the $KAR_1$ reference and the Treated Biochar 1 at 46.68 min and FIG. 76 illustrates the MS peaks at 46.78 min. Peaks in both FIGS. 74 and 75 are consistent with karrikins or karrikin derivatives Extracts from raw and treated biochars were then tested to determine the impact of the extract on seed germinations rates in rice and corn. FIG. 77 shows the test results of the use of the raw and treated biochar extracts on rice at Day 4. The extracts from Raw Biochar 1 and Raw Biochar 3 are both from different sources of biomass and both increase seed germination rates by 19 and 14 percent at Day 4, respectively, over the control.

Figure 78:
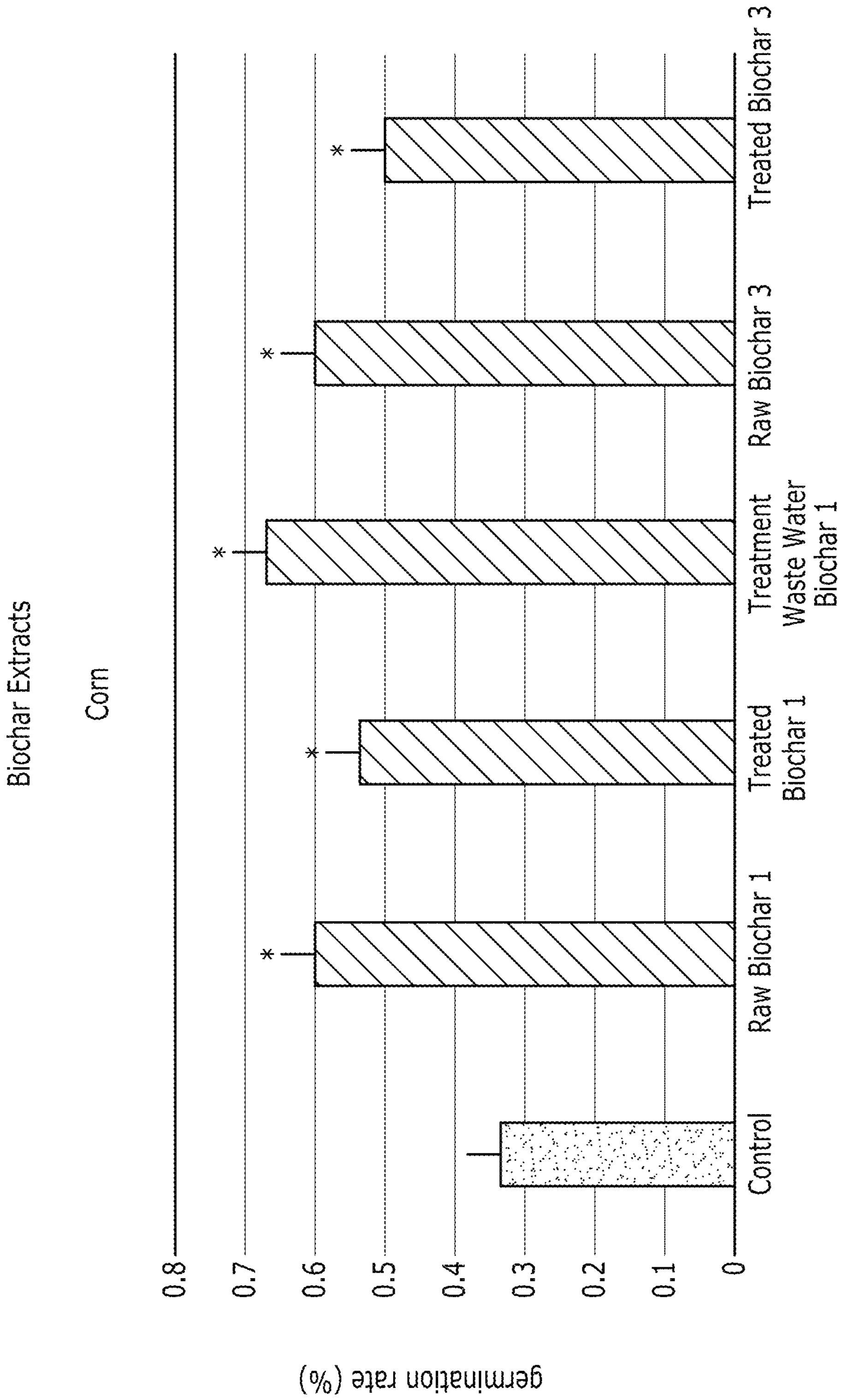
FIG. 78 is a chart showing the test results of the use of the raw and treated biochar extracts on corn at Day 3.

FIG. 78 shows the test results of the use of the raw and treated biochar extracts on corn at Day 3. FIG. 78 also show additional test results using the treating waste water extracted from the vacuum treatment process of Treated Biochar 1. As shown, extracts from the Raw Biochar 1 and Raw Biochar 3, which are both from different sources of biomass, along with the treating waste water from Treated Biochar 1, significantly increase corn seed germination by more than 50% over the control at Day 3. Treated Biochar 1 and Treated Biochar 3 also show a statistical increase in germination rate over the control but to a somewhat lesser extent than their raw counterparts. While FIG. 78 illustrates the test using the extracts on corn, it is worth noting that testing has also demonstrated that Treated Biochar 1 and Treated Biochar 3, prior to any solvent extraction, also increases rice seed germination rates by 14 and 33 percent over the control at Day 2.

The conclusions drawn for the tests shown and described in connection with FIGS. 77 and 78 are that extracts from Raw Biochars 1 and 3 seem to increase rice and corn seed germination more than the extracts from the vacuum Treated Biochars 1 and 3. The waste water from the Treated Biochar 1, a type of extraction, also shows a high increase in corn seed germination at Day 3. This appears to correlate well with results presented previously on KAR1 levels and the corresponding *Arabidopsis* Wild and KAI2 Mutant tests.

Figure 79:
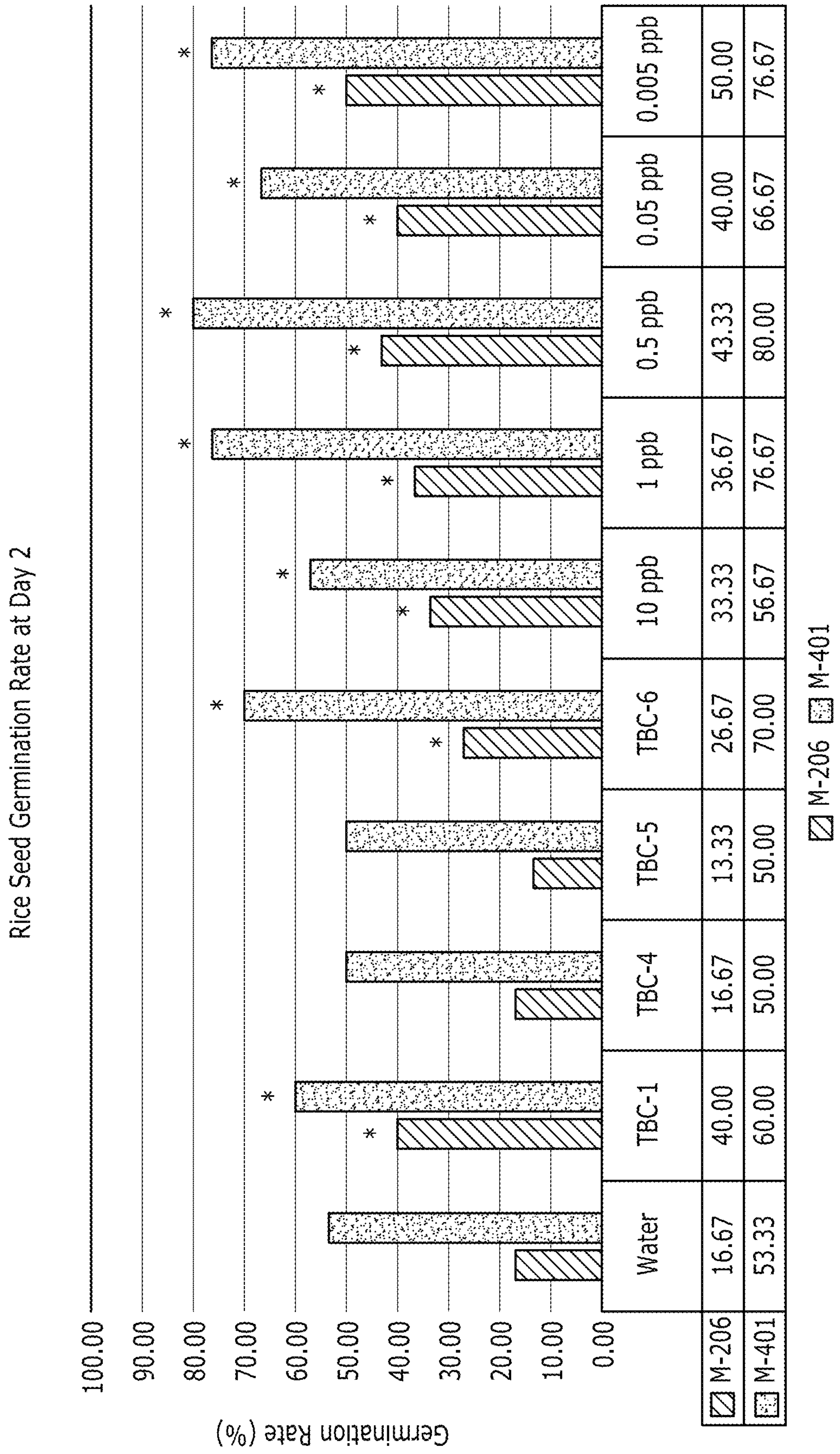
FIG. 79 is a seed germination assay on two types of rice measuring the seed germination rate of the seeds at Day 2.
Figure 80:
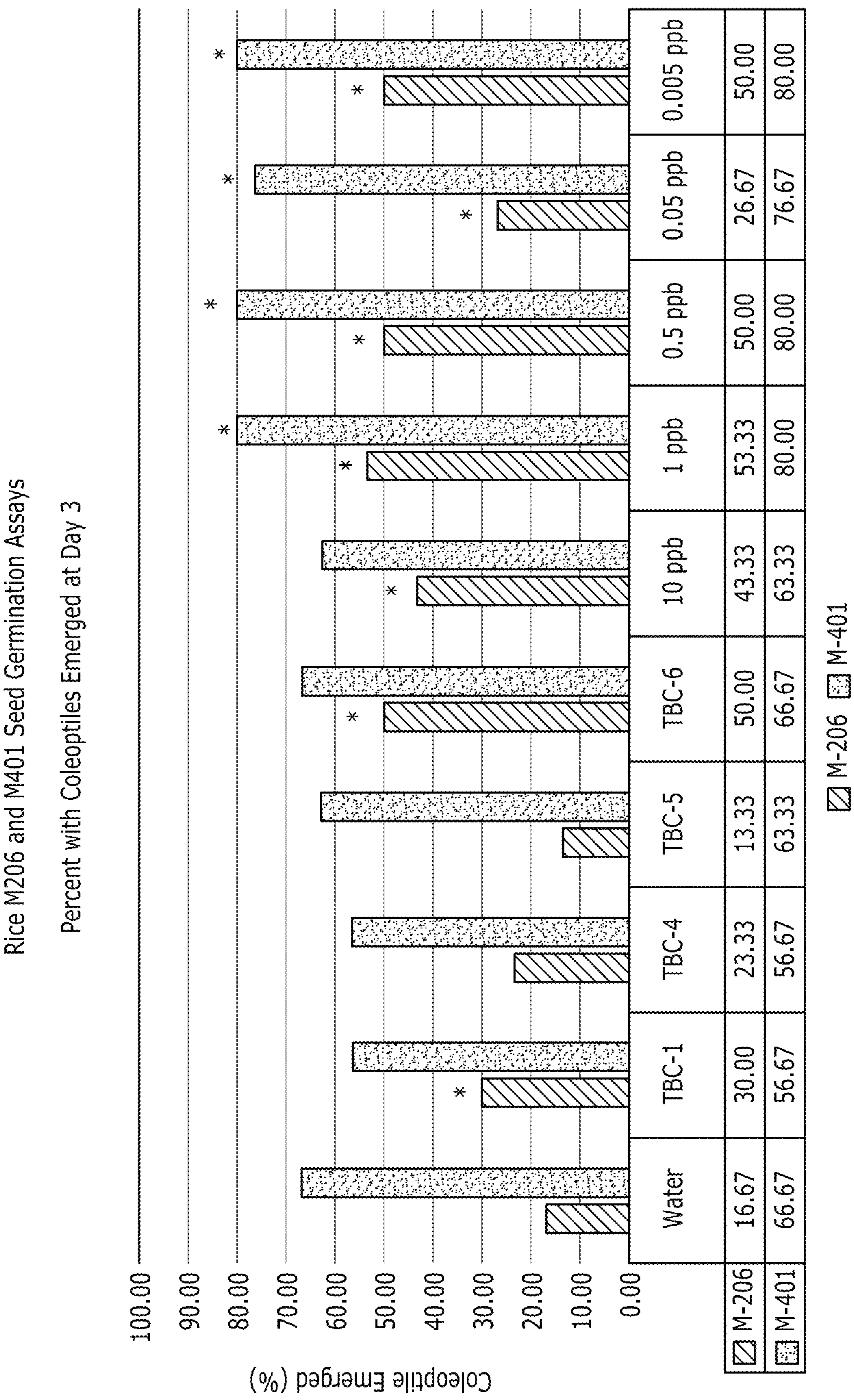
FIG. 80 illustrates seed germination assay of FIG. 80 measuring the percentage with coleoptiles emerged at Day 3.

Post-treatment processes in general, as well as the type of post-treatment processes specifically described previously, in conjunction with the type of biochar, based on feedstock and pyrolysis conditions, may also impact the efficacy or the concentration of available karrikins, or other soluble signaling compounds that impact seed germination and early plant development. FIG. 78 depicts the germination rate of two types of rice seeds at Day 2. FIG. 80 illustrates the same seed germination assay of FIG. 79 but measures the percentage with coleoptiles emerged at Day 3.

The media used to germinate the seeds included a water control, treated biochar 1 (TBC-1), treated biochar 4 (TBC-4), treated biochar 5 (TBC-5) and treated biochar 6 (TBC-6), along with reference karrikin ($KAR_1$) controls at various ppb levels (10, 1, 0.5, 0.05 and 0.005) in water. TBC-1 and TBC-5 are derived from raw Biochar 1. TBC-4 and TBC-6 are derived from raw biochar 4, a different biomass feedstock than TBC-1. TBC-1, 4 and 5 were all vacuum treated, as described more fully above. TBC-6 is an agglomerate that includes raw Biochar 4 that has been treated with surfactant.

Both tests demonstrate that TBC-1 and TBC-6 significantly increase both types of rice seed germination and significantly increase the rate of coleoptile emergence in the M206 seeds. Accordingly, biochars derived from different biomass, if treated differently through post treatment processes, can change the amount of available signaling compounds, including karrikins. As demonstrated, TBC-1 can significantly increase germination rates of M-206, with most similar results to that of the karrikin solution at 0.05 ppb. TBC-6's germination results were most like that of the 10 ppb karrikin solution. When looking at M-206 on day 3 coleoptile emergence, TBC-1 was still closest to the 0.05 ppb and TBC-6 was closest to 0.5 ppb but still also similar to the 10 ppb. As shown in FIG. 70, the concentration of $KAR_1$ on TBC-1, is approximately 50 ppb, whereas the concentration of $KAR_1$ on raw Biochar 4 (which was included in TBC-6) is approximately 0.5 ppb. One potential cause for this unexpected difference in performance and karrikin level is that, not only does the post-treatment method impact the absolute amount of karrikins in the biochar, it may also impact the availability of said karrikins to impact seed germination and early growth. Comparing to reference karrikin samples, it appears the amount of $KAR_1$ available for the rice seed to impact germination and early growth may be similar between TBC-1 & TBC-6, despite TBC-1 having significantly higher levels of $KAR_1$. Accordingly, a surfactant treatment may help increase the availability of $KAR_1$ to the seed during treatment.

Another potential cause for the unexpected difference in performance and karrikin level in the test is that the signaling compounds, such as karrikins, are competing with germination-inhibiting compounds. These inhibiting compounds could be phytotoxic compounds or potentially even related butenolides such as 3,4,5-trimethylfuran-2(5H)-one, which prior art has identified and isolated from plant-derived smoke and found to both reduce germination and reduce the beneficial effects of the signaling compound, 3-methyl-2H-furo[2,3-c]pyran-2-one (Light, et. al in "Butenolides from Plant-Derived Smoke: Natural Plant-Growth Regulators with Antagonistic Actions on Seed Germination" Journal of Natural Products, 2010). Since inhibitor compounds will also be impacted by how the biochar is made and post-processed, the levels of inhibitor compounds in the various biochars tested may also vary and thus cause some biochars with signaling compounds not to perform as expected.

A third potential cause is that signaling compounds and inhibitor compounds might have concentration or quantity thresholds. For example, at a certain level a signaling compound changes from a positive influence in germination and early growth to a negative influence. By way of a different example the threshold could be similar to an activation level, where no impact is seen until a certain level of compound is reached or where once a certain level is achieved no further impact is seen as the level of compound increases.

Figure 81:
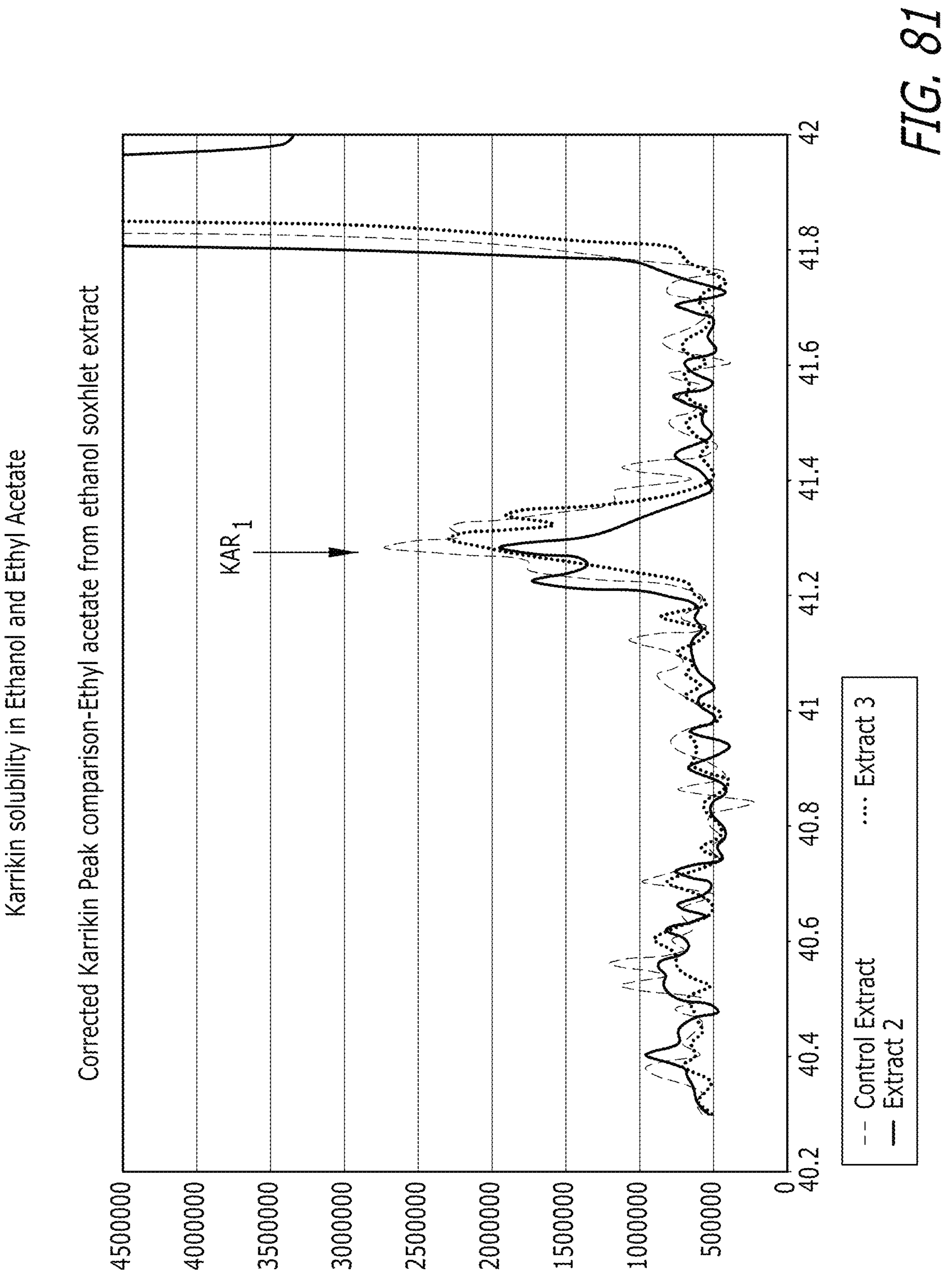
FIG. 81 is a chart showing that KAR1 is soluble and extractable with all three extract methods tested.

To better understand extraction of signaling compounds and also the interactions between signaling compounds and inhibitor compounds in extracts further testing was completed. First to better understand how $KAR_1$ could be extracted and isolated from biochar, Biochar 1, previously shown to have high levels of $KAR_1$, was used to make three different extracts. The control extract was made using the Soxhlet extractor with Ethanol as the solvent and then concentrated 25× by rotary evaporation. The second extract was made from the control extract by removing the ethanol using a rotary evaporator and then resolubilizing the extracted compounds in ethyl acetate, at a 10× concentration level. It should be noted that when depicting results for this extract they were multiplied by 2.5 to normalize the concentration to that of solutions 1 and 3. The third extract was made from the control extract by removing the ethanol using a rotary evaporator and then resolubilizing in water and then as a final step liquid-liquid extracted into ethyl acetate, at a 25× concentration. These three extracts were then run on CG-MS with mass specific selective ion analysis to identify $KAR_1$. For GC-MS testing, the control extract was also rotary evaporated and resolubilized in acetone at a 25× concentration. The three spectra are depicted in FIG. 81 and show that KAR1 is soluble and extractable with all three extract methods tested. In addition, the KAR1 levels continued to equate to 75-150 ng/g of biochar.

Figure 82:
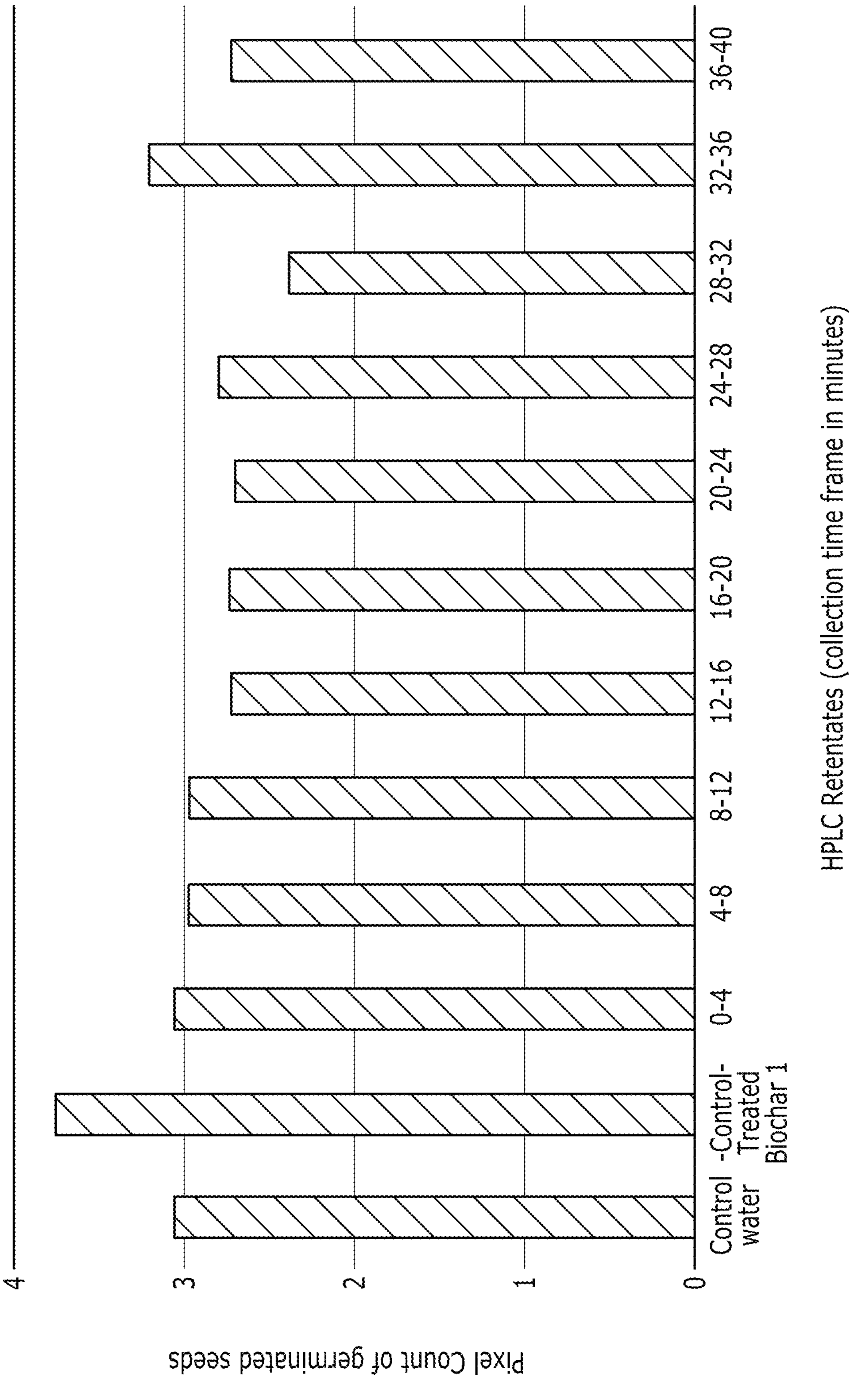
FIG. 82 is a chart showing the pixel court of germinated seed on Day 4 grown with HPLC fractioned ethanol extract of biochar 1.
Figure 83:
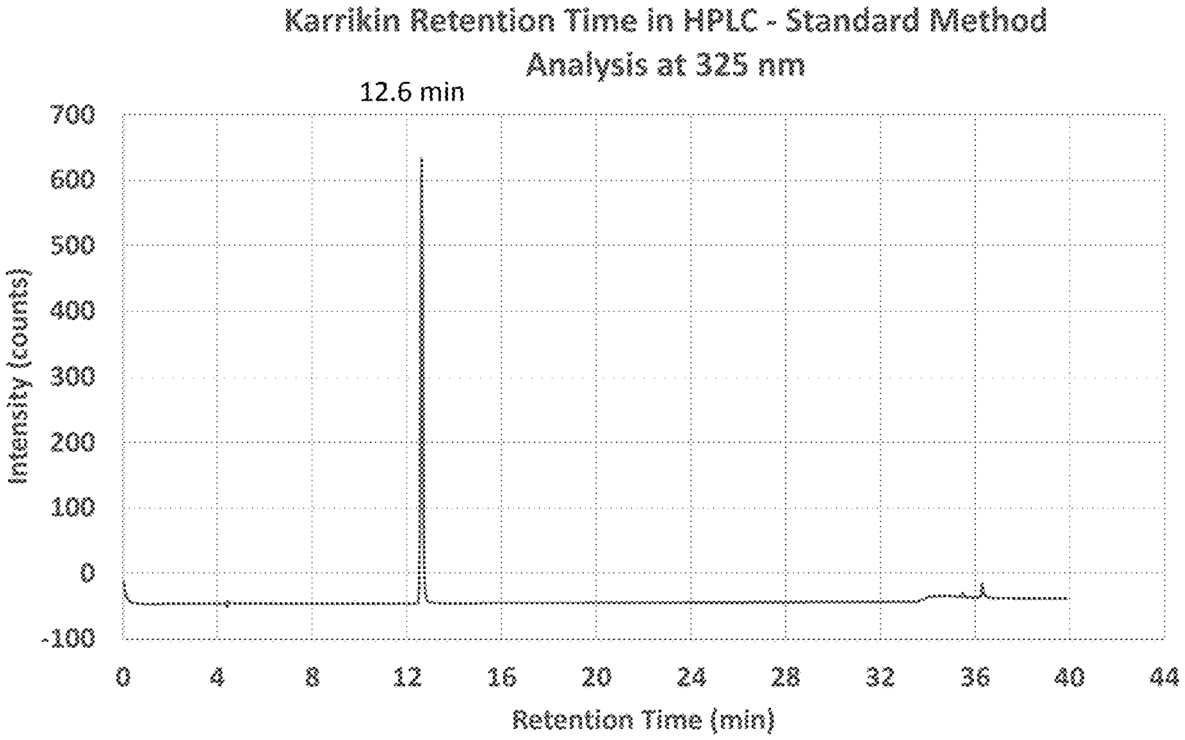
FIG. 83 is a chart showing standard reference $KAR_1$ on the HPLC analysis at 325 nm.
Figure 84:
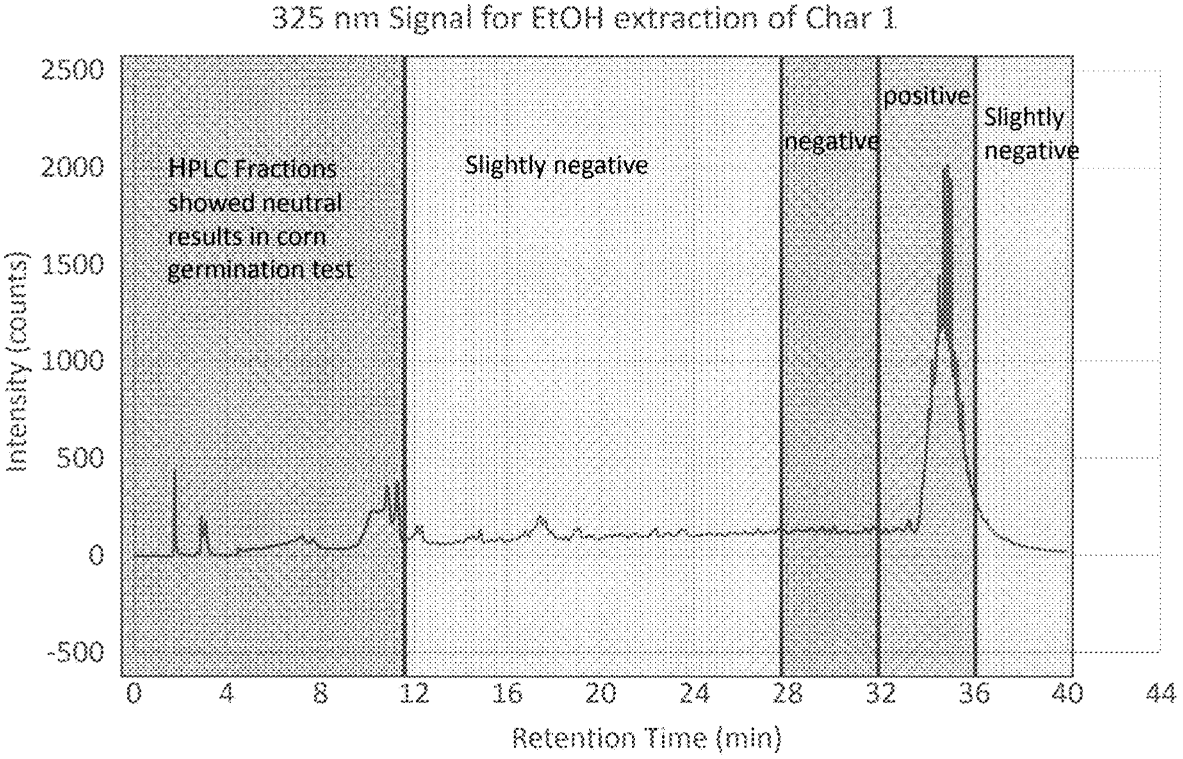
FIG. 84 is a chart showing the HPLC analysis at 325 nm for the extract of biochar 1.
Figure 85:
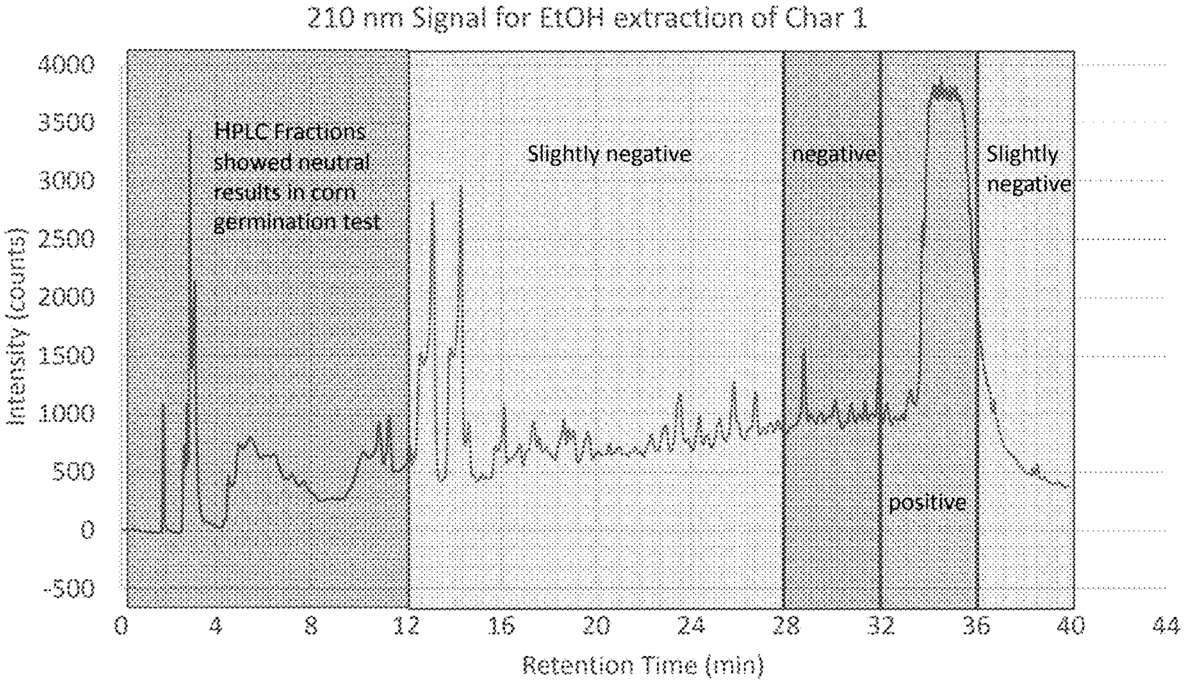
FIG. 85 is a chart showing HPLC analysis at 210 nm for the EtOH extraction of biochar 1.
Figure 86B:
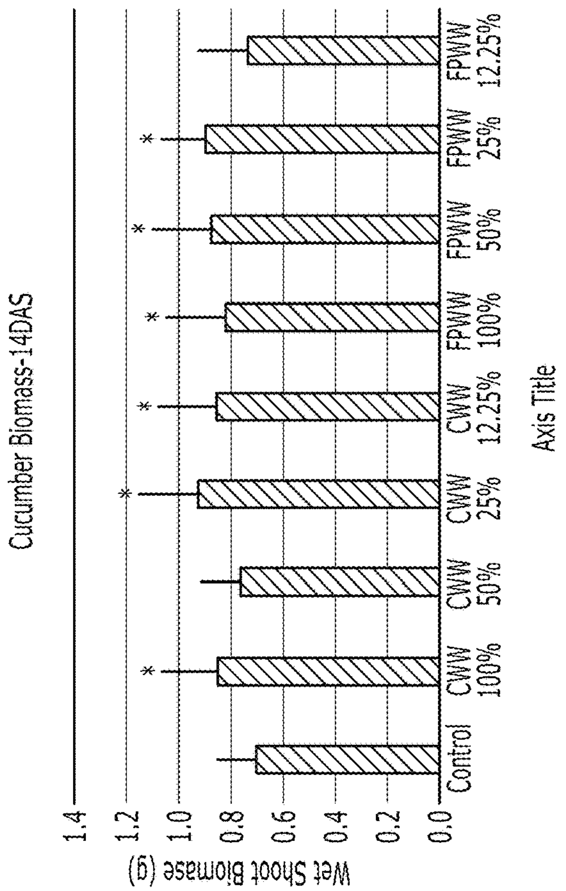
FIGS. 86*a-g*, show results from biochar extracts used in germination and growth tests with cucumbers, tall fescue, and corn seeds.
Figure 86A:
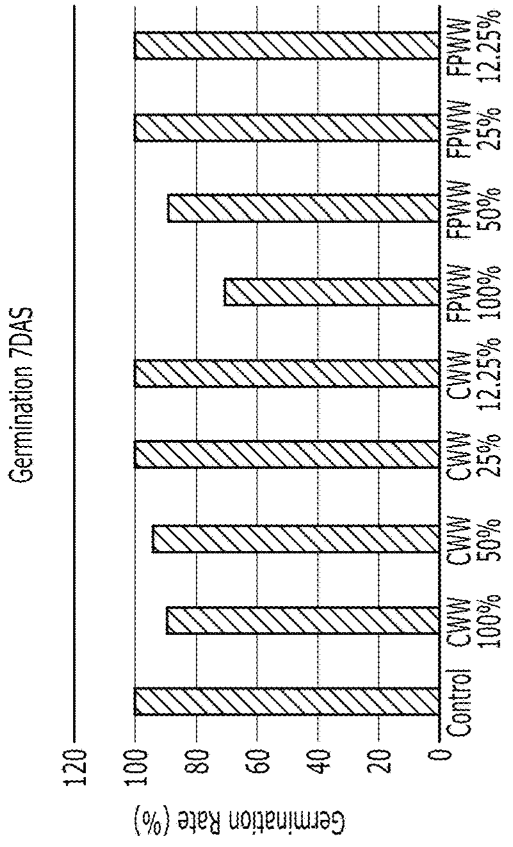
Figure 86C:
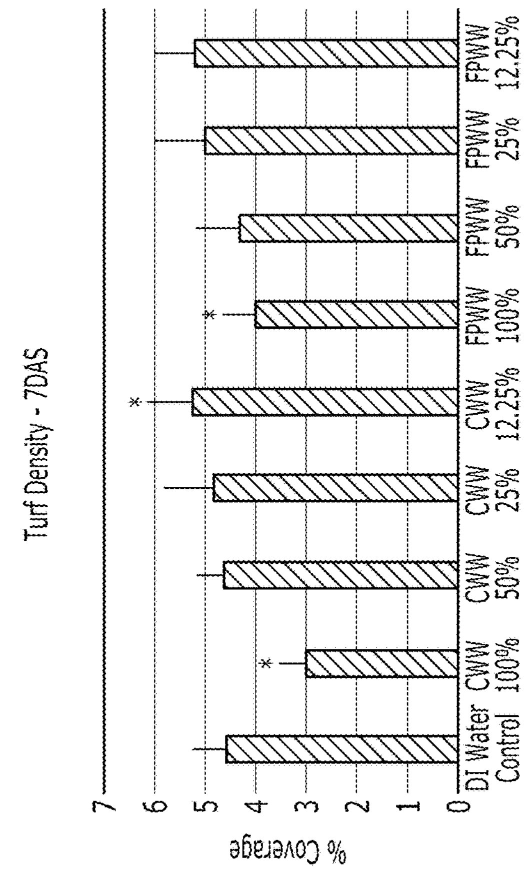
Figure 86D:
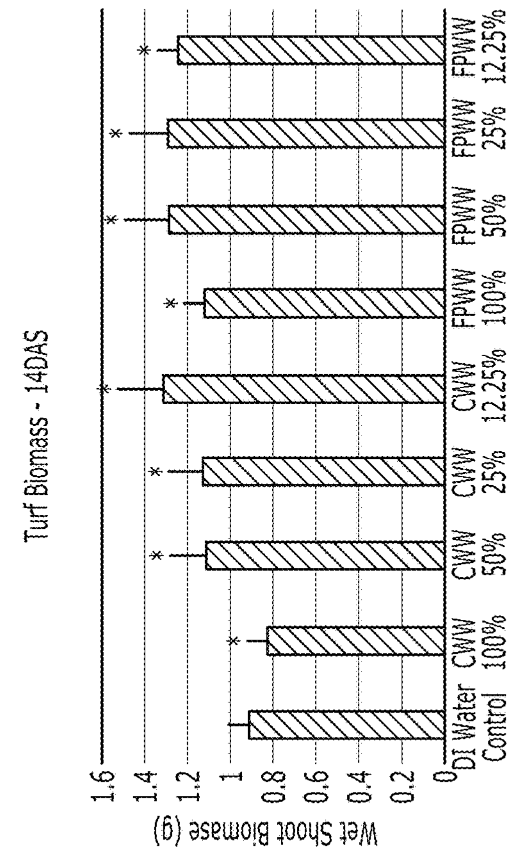
Figure 86E:
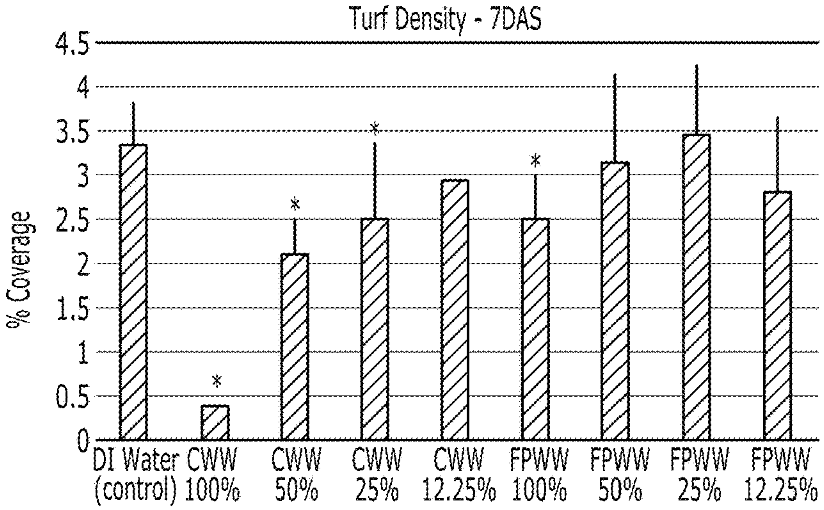
Figure 86F:
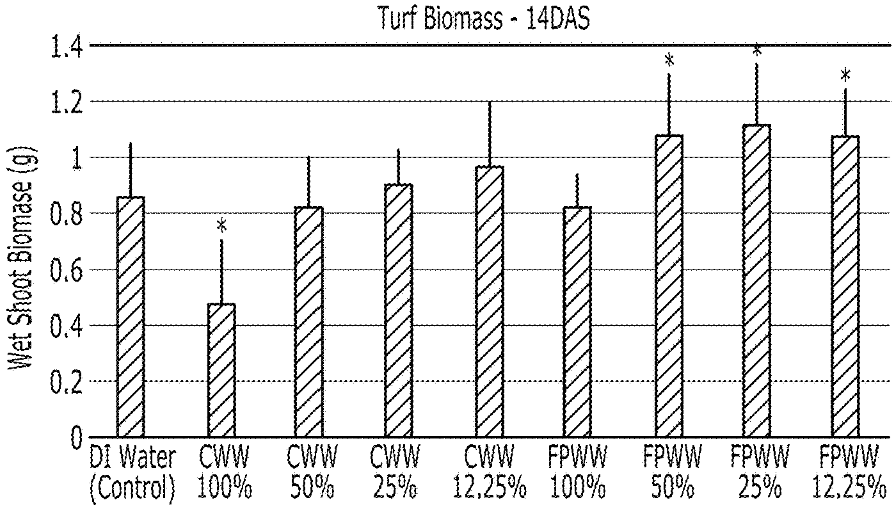
Figure 86G:
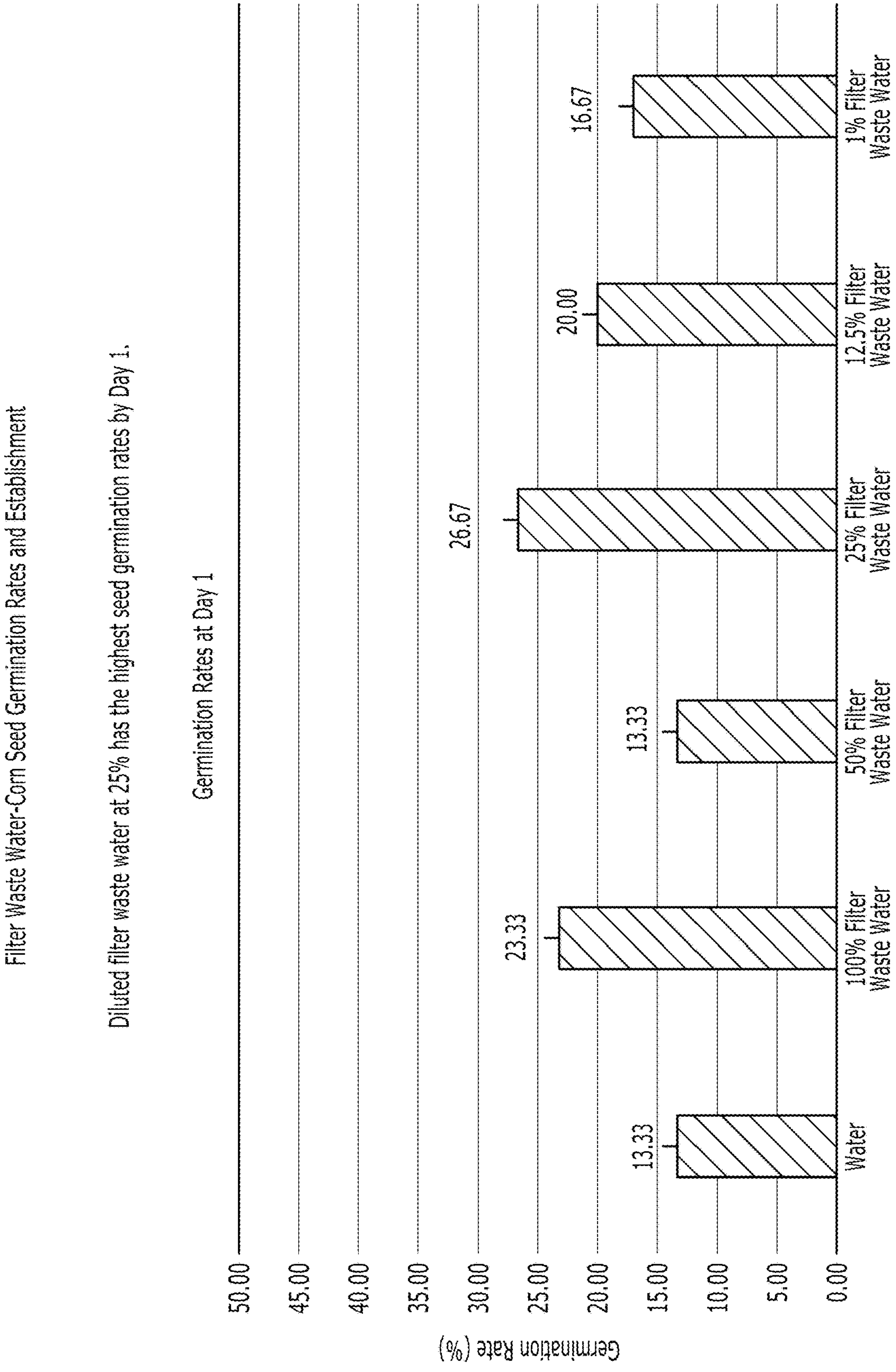

Next, the Soxhlet ethanol extract of Biochar 1 was separated into fractions of compounds using an HPLC. Extracts were evaporated and resuspended in 50% Acetonitrile and water at ~15× concentration. 100 μL of this solution was injected into the C18 reverse phase column (250 mm, 4.6 mm ID with 5 μm diameter packing). Eluant was flowed at 0.8 mL/min with the composition increasing from 10% ACN in water to 50% over 30 minutes. Between 30 and 31 minutes the concentration of ACN was increased to 100%. Between 31 and 40 minutes pure ACN was used to flush the remaining compounds from the column. Fractions were created by collecting retentates for every 4 minutes between 0 and 40 minutes. These fractioned extracts were then diluted sufficiently to match isolated chemical concentration equivalent to a 100× dilution of the original extract and used in a corn germination test. Images were taken on day four and analyzed for extent of early development based on pixel counts of germinated seeds, as depicted in FIG. 82. Many of the fractionations were neutral or slightly negative. The biggest impacts were for the retentate of the HPLC from 28-32-minute retention time, which was a negative impact, and from 32-36-minute retention time which was a positive impact on the corn seed early development. Looking at a standard reference $KAR_1$ on the HPLC analysis at 325 nm, shown in FIG. 83, $KAR_1$ should be in the 12-16 retentate, but unexpectedly a slightly negative impact was seen. Looking at the HPLC analysis at 325 nm for the extract, shown in FIG. 84, there does appear to be a peak for $KAR_1$ with other small peaks in the retentate. However, if instead the HPLC analysis for the extract is looked at a 210 signal, as shown in FIG. 85, significantly more compound peaks are visible in that same retentate time period of 12-16, which likely indicates that there are both signaling compounds and inhibiting compounds impacting the corn germination results in this specific fraction.

Overall these tests show that biochars and their extracts can contain a complex mix of compounds, containing both growth-promoting compounds and growth-inhibiting compounds. Butenolides, and specifically karrikins, while important germination promotors, are not the only important organic compound that can be found in a biochar or its extract. Other potential biologically important compounds that have been identified in some biochars and their extracts include but are not limited to other butenolides, anyhdrosugars, carboxylic acids, fatty acids, alkanes, ketones, aldehydes, aromatics and phenolics. Even more specifically, methylparaben, vanillin, furfural, and levoglucosan have been consistently identified in extracts. It should be remembered that the concentration or amount of these compounds in an extract and the application rate can impact the resulting biological effect. Thus, concentration level changes in an extract or application rate of an extract with a specific compound concentration may switch a compound between the categories of growth-promoting compound, growth-inhibiting compound, and neutral compound.

4. Production of $KAR_1$

Tests have also shown that it is possible to alter the amount of $KAR_1$ production via pyrolysis by varying feedstock, temperature and hold time at the higher heating rate. To demonstrate this, batch pyrolysis was performed on 2 gallons of material using a tube furnace reactor with a nitrogen sweep gas set to ensure a maximum gas residence time of <5 seconds within the heated region of the reactor. Oils were condensed using a helical coil condenser set to 10° C. Char was cooled in a water jacketed tube under nitrogen to avoid oxidation of surface compounds or modification by quench. Collected oils were mixed with methanol at a 50/50 volume ratio and stored at 4° C. until analysis to minimize reaction.

Soluble compounds are then separated from the resulting char using a Soxhlet apparatus with acetone. Acetone was refluxed a minimum of 5 times over 2 hours to ensure near complete removal of soluble compounds. The refluxed acetone, containing the char extracts, is then concentrated by rotary evaporation to enhance detection of extracted compounds.

Figure 91:
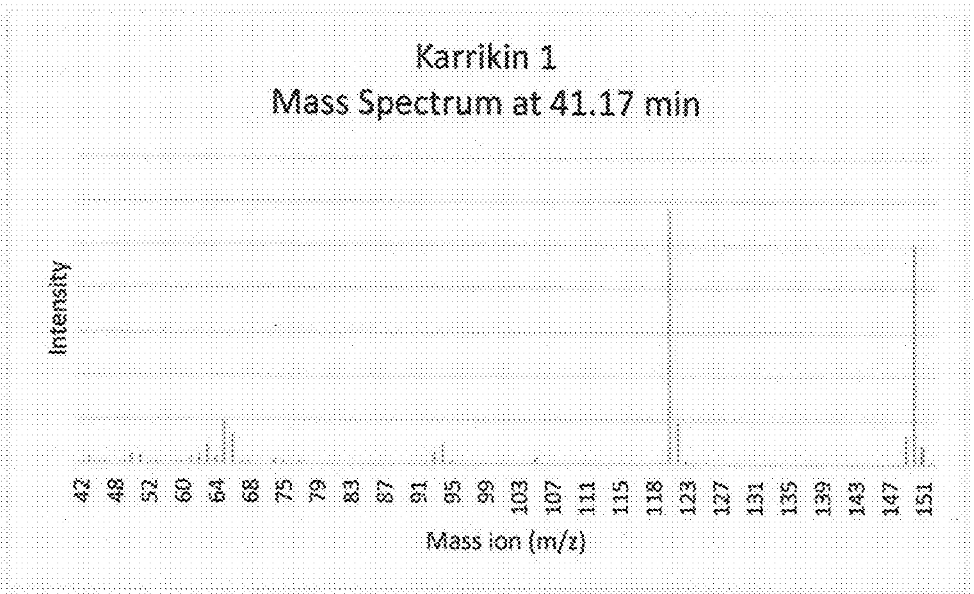
FIG. 91 is a mass spectrum reading of a $KAR_1$ reference material tested to confirm retention time.
Figure 92:
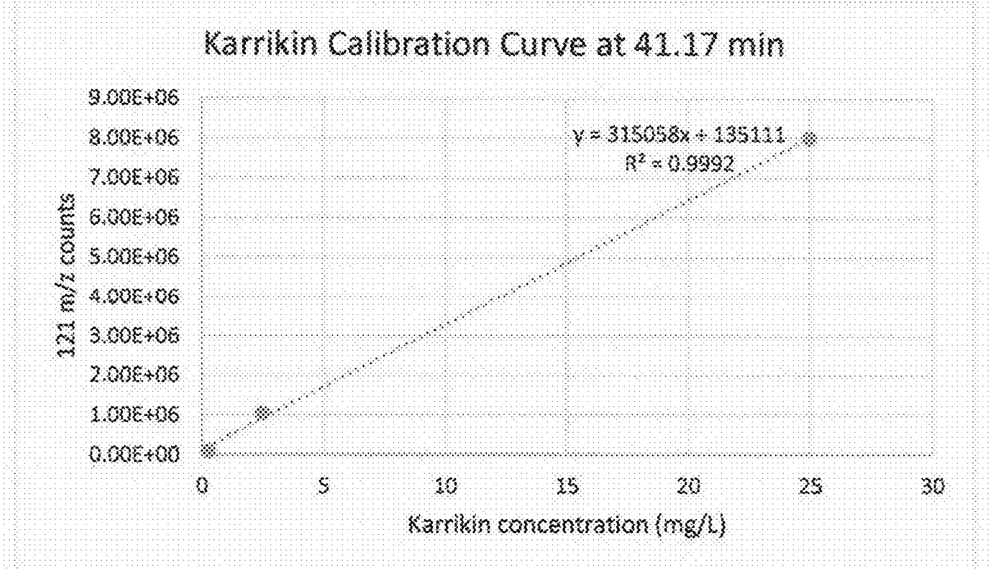
FIG. 92 is a karrikin calibration curve.

To determine the amount of karrikin in the extracted compounds, analysis by gas chromatography mass spectroscopy was performed on both a $KAR_1$ reference material and the concentrated extracts. FIG. 91 is a mass spectrum reading of a $KAR_1$ reference material tested to confirm retention time and signal. In particular, as seen in FIG. 91, $KAR_1$ reference material was tested using GC-MS, which confirmed a retention time of 41.17 minutes and mass ions (m/z: % of maximum ion. 121: 100%, 150: 86%, 65: 17%, 94: 8% using an in-house method. Using this data, a karrikin calibration curve was constructed from 0.25-25 ppm using m/121 peak intensity at 41.17 min., which karrikin calibration curve is illustrated in FIG. 92.

To show variations in the production of $KAR_1$ through varying feedstock, temperature, and hold time at the higher heating rate, multiple tests were performed using the same analytical method as above but at various conditions.

Figure 93:
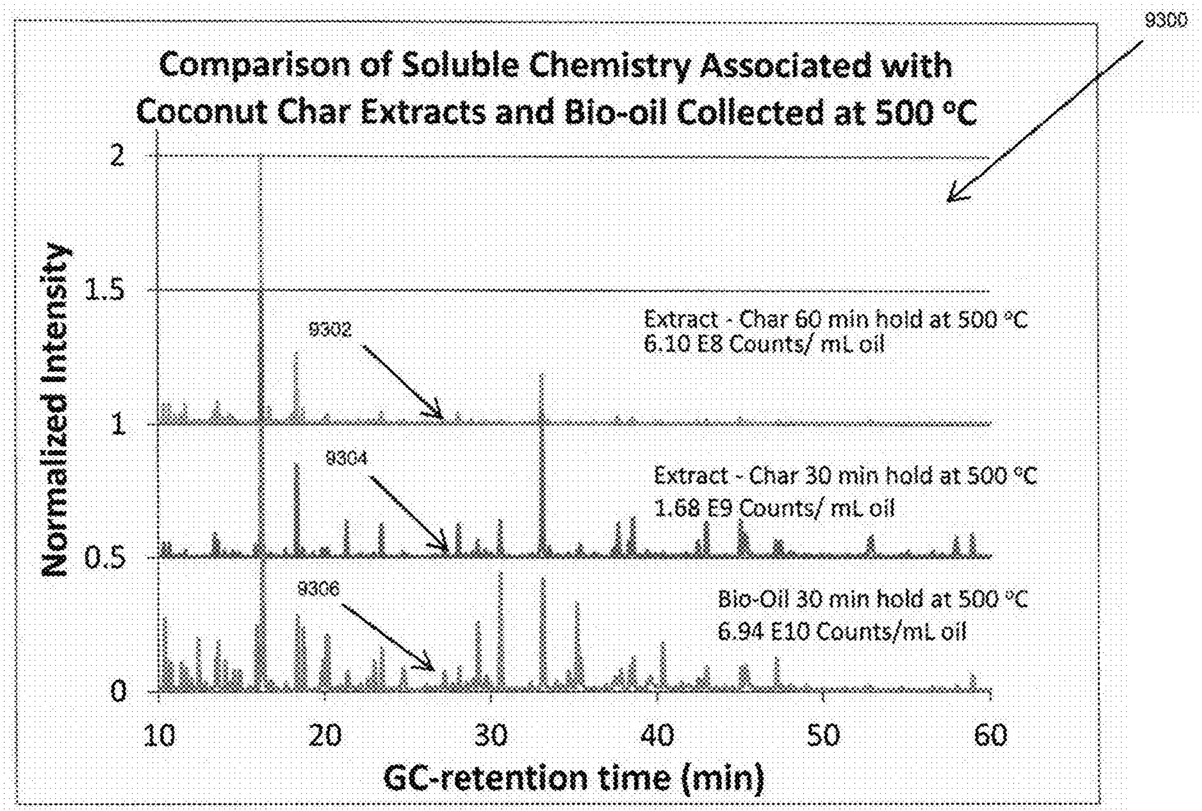
FIG. 93 is a chart showing the variation in chemistry between bio-oil and residual extractive chemistry on char.

FIG. 93 depicts chart 9300 which shows the variation in chemistry between the bio-oil and residual extractive chemistry on char for runs conducted using coconut feedstock pyrolyzed at 500° C. The chart compares normalized peak intensity against GC-retention time (min). Reading 9302 is a GC-MS signal for char extract where the coconut shells were pyrolyzed at 500° C. for an hour hold time. Reading 9304 is a GC-MS signal for char extract where the coconut shells were pyrolyzed at 500° C. for a 30 minute hold time. Reading 9306 is a GC-MS signal for bio-oil where the coconut shells were pyrolyzed at 500° C. for a 30 minute hold time.

From this comparison, it can be seen that both the residual soluble chemistry associated with the biochar and the bio-oil represent rich sources of diverse organic compounds. The residuals on the biochar however, show reduced diversity after a 30 minute hold time at 500° C. compared to the bio-oil collected from the same run. Hold times of one hour, further reduced the diversity and concentration of soluble compounds on the char compared to the char collected after a 30 minute time frame. The variances observed here support that adjusting the time and temperature of pyrolysis will affect both the quantity and chemistry of biochar extracts. While much of the chemistry associated with the biochar extract was also found in the bio-oil, the bio-oil presents a substantially more complex matrix, requiring additional effort to refine.

Figure 94:
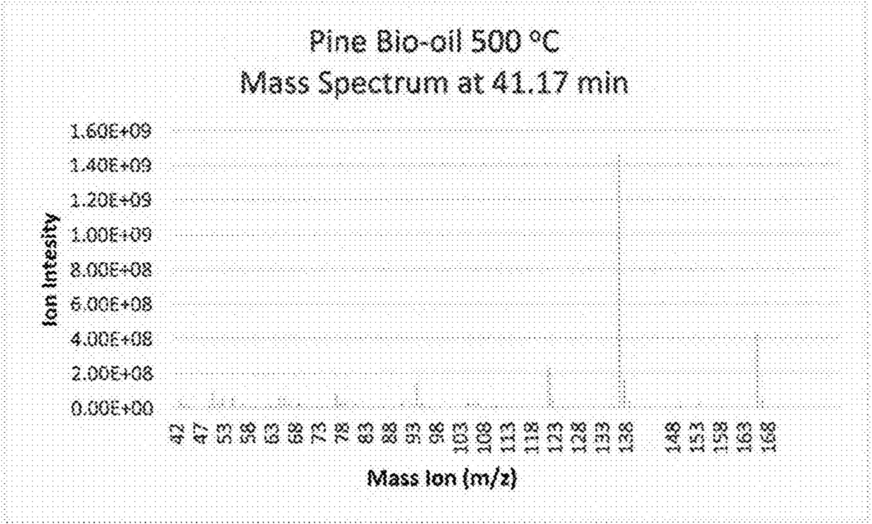
FIG. 94 is a mass spectrum reading of pine based bio-oil.

As demonstrated above, and in connection with FIG. 93, $KAR_1$ was identified in bio-oil produced from the pyrolysis of coconut shells. In contrast, when the same pyrolysis and extraction methods set forth above were performed on pine, substantive Karrikin signals were not clearly detected in pine samples pyrolyzed in the same reactor at the same conditions. FIG. 94 is a mass spectrum reading of pine based bio-oil produced at 500° C. with a 30 minute hold time. The mass spectrum shows the signal obtained at 41.17 minutes, previously identified as the retention time of $KAR_1$. For the pine bio-oil sample the only compound clearly identified was 2-methoxy-4-propylphenol.

Figure 95:
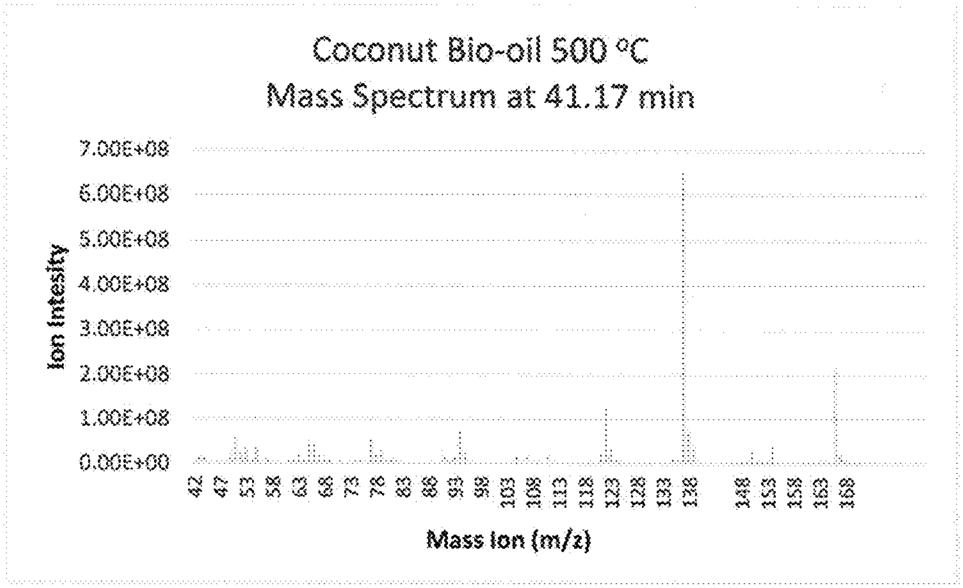
FIG. 95 is a mass spectrum reading of coconut based bio-oil.

Similarly, FIG. 95 is a mass spectrum reading of coconut based bio-oil produced at 500° C. at a hold time of 30 minutes. The signal at 41.17 minutes is suspected to be composed primarily of 2-methoxy-4-propylphenol and 4-hydroxy-3methoxy benzyl. However neither compound suitably explains the residual intensity at 121 m/z and 150 m/z not accounted for by other compounds.

Figure 96:
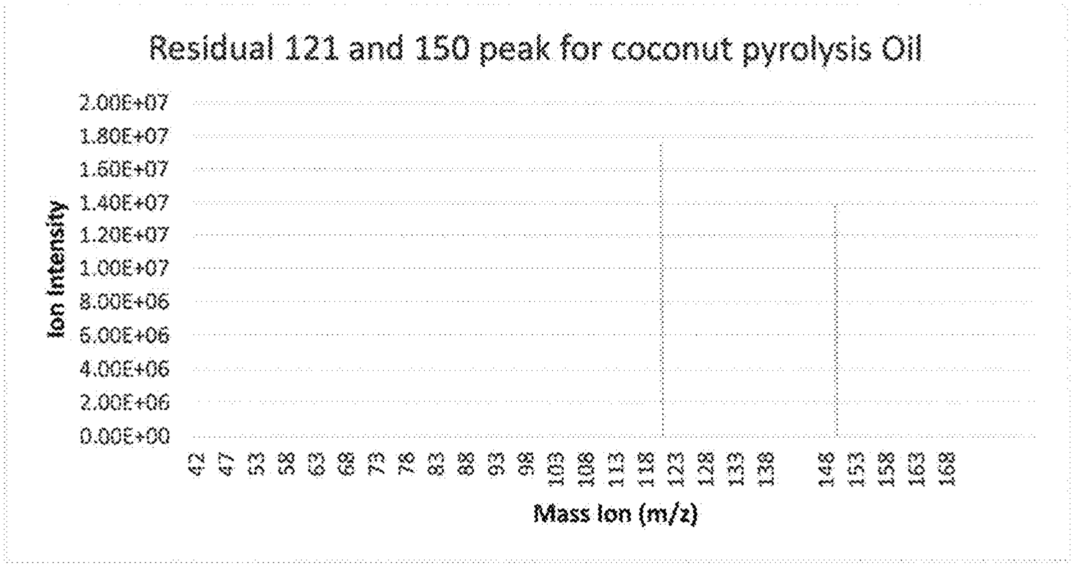
FIG. 96 is a chart showing the residual peaks for coconut pyrolysis oil.

To account for these compounds, interference from 4 hydroxy-3methoxy benzyl alcohol was removed by normalization of the m/z 154 ion and phenol 2 methoxy-4-propylphenol by normalization and removal of the 137 mass ion, allowing the residual mass 121 and 150 ions to be determined. These mass ions, while the strongest signals for $KAR_1$, are only very minor components of the signal for the other suspect compounds. FIG. 96 is a chart showing the residual 121 and 150 peaks for coconut pyrolysis oil of analyzed in FIG. 95. Other mass ions have been masked to highlight the effect on ions 121 and 150. The residual mass 121/150 ratio was 1.27 while for a reference Karrikin 1 standard the ratio was 1.16. These values are in good agreement and are consistent with the identification of karrikin one at 41.17 minutes using the peak intensity observed at m/z=121. Thus, this reading strongly implies the presence of $KAR_1$ in bio-oil produced from the pyrolysis of coconut shells.

Figure 97:
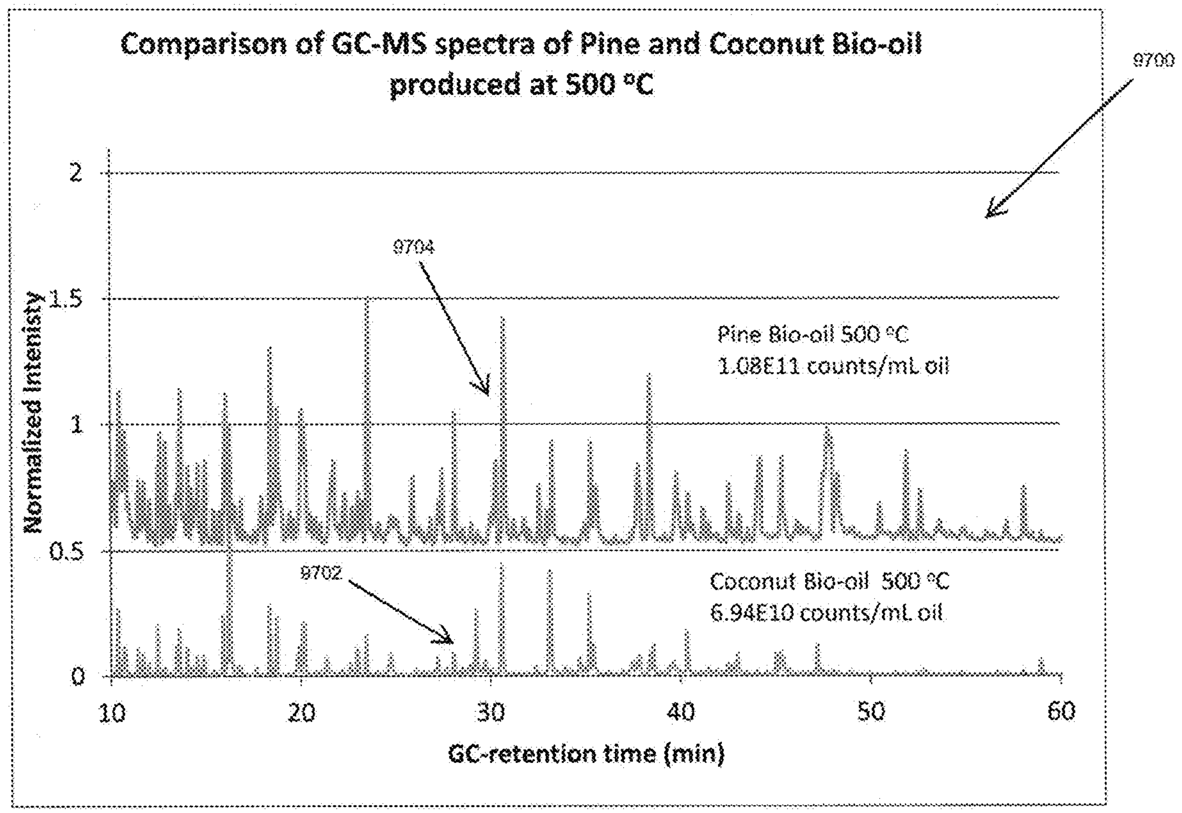
FIG. 97 is a chart showing the comparative chemistry of pine and coconut bio-oil.

Further comparison testing was performed using pine and coconut as the biomass feedstock. Chart 9700 in FIG. 97 shows the comparative chemistry of pine and coconut bio-oil. The chart compares measured normalized intensity over GC-retention time (min) of bio-oils produced using pine and coconut shells at 500° C. for a hold time of 30 minutes. Reading 9702 is a GC-MS signal for bio-oil produced from coconut shells. Reading 9704 is a GC-MS signal for bio-oil produced from pine. Bio-oil collected from pine shows more complex spectra than the bio-oil obtained from coconut shells. Many of the primary peaks appear to originate with the cellulose fraction of the char and include increased production of compounds such as levoglucosan.

Figure 98:
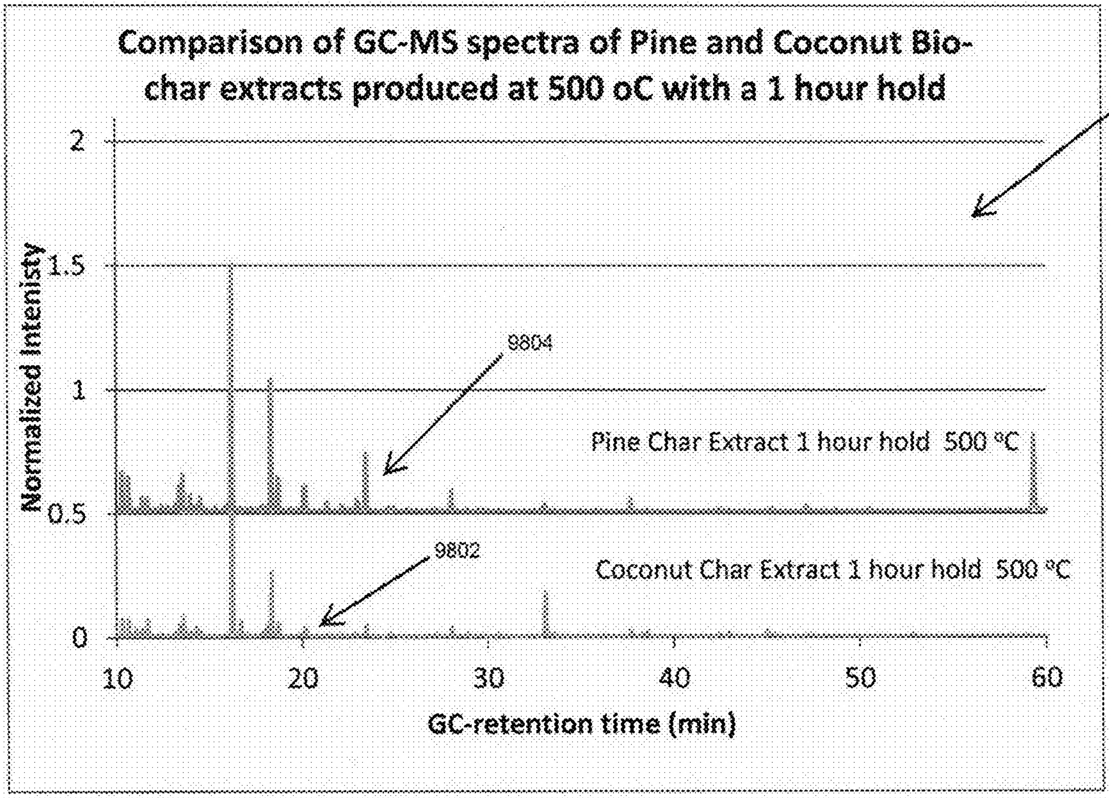
FIG. 98 is another a chart showing the comparative chemistry of pine and coconut bio-oil.

FIG. 98 is another a chart 9800 showing the comparative chemistry of pine and coconut bio-oil. Chart 9800 compares measured normalized intensity over GC-retention time (min) of bio-oils produced using pine and coconut shells at 500° C. for a hold time of one hour. Reading 9802 is a GC-MS signal for bio-oil produced from coconut shells. Reading 9804 is a GC-MS signal for bio-oil produced from pine. Variance between the char extracts obtained from material produced at 500° C. with a 1 hour hold time show substantially lower variability than observed for the bio-oil. Most peaks are observed in both samples, however distribution of compounds does vary.

Figure 99:
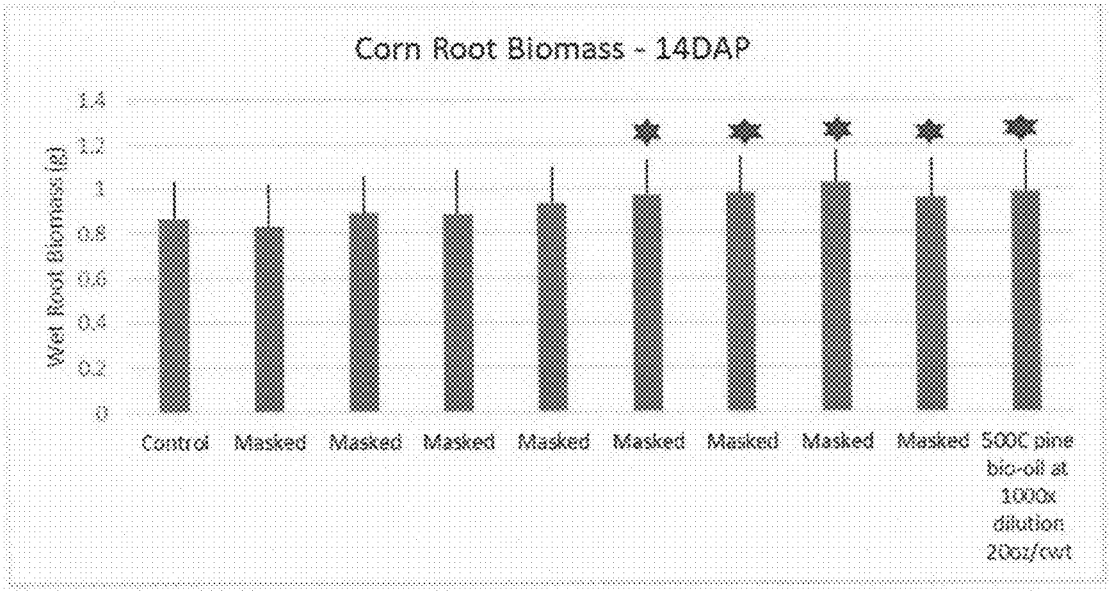
FIG. 99 is a growth chart for corn root biomass.

In the substantial chemistry observed within both bio-oils, and extracts to a lesser extent, potential exists for multiple additional beneficial or detrimental compounds. While Karrikin was not clearly observed in the pine bio-oil, germination and early growth results obtained for a diluted pine bio-oil show statistically significant increases in root biomass 14 days after planting. FIG. 99 is a growth chart for corn root biomass illustrating such statistically significant increases in root biomass 14 days after planting.

Further tests were performed using the pyrolysis and extract methods first set forth above using coconut shell as feedstock and a 30-minute hold time at peak pyrolysis temperature, but each test was at various max temperatures.

Table 1 below shows the resulting calculated karrikin concentration on the coconut chars produced at the varying pyrolysis temperatures (all 30 minute hold time at the specified temperature except where noted).

TABLE 1

| Pyrolysis temp C. | Char yield | Weight in (g) | Solvent (mL) | 121 signal at 41.17 min | concentration (mg/L) | concentration on char (mg/kg) |
|---|---|---|---|---|---|---|
| 450 | 80% | 36.76 | 4.45 | 6.56E+06 | 20.4 | 2.47 |
| 500 | 59% | 45 | 7.29 | 3.31E+06 | 10.1 | 1.63 |
| 550 | 51% | 44.47 | 6.62 | 1.64E+06 | 4.8 | 0.71 |
| 600 | 32% | 45.42 | 6.52 | 1.73E+05 | 0.1 | 0.02 |
| 500 1 hr | 35% | 45 | 6.43 | 2.12E+05 | 0.2 | 0.03 |

Table 2 below shows the resulting calculated karrikin concentration in the coconut pyrolysis oils produced at varying pyrolysis temperatures (all 30 minutes hold time at the specified temperature except where noted)

TABLE 2

| Pyrolysis temp C. | Oil Yield | Dilution factor | 121 signal at 41.17 min | Estimated concentration (mg/L) in oil | Estimated yield from biomass (mg/kg) |
|---|---|---|---|---|---|
| 450 | 12% | 2 | 9.81E+06 | 31 | 7 |
| 500 | 29% | 2 | 2.72E+07 | 86 | 49 |
| 550 | 33% | 2 | 3.09E+07 | 98 | 65 |
| 600 | 45% | 2 | 2.42E+07 | 76 | 69 |
| 500 1 hr | 45% | 2 | 2.26E+07 | 71 | 64 |

From the above pyrolysis tests and analysis, it is demonstrated that $KAR_1$ production can be varied via pyrolysis conditions, dependent on pyrolysis feedstock, temperature and hold time at the higher heating rate. Further, $KAR_1$ was identified in the pyrolysis oils produced from coconut shell, and was identified as a residual organic in biochars produced from coconut shells. $KAR_1$ 1 signals were detected in both the bio-oil and residual solids of coconut that was minimally processed (<400° C. for 30 minutes) or torrified. However, $KAR_1$ was lost on coconut chars that were held at pyrolysis temperature for an extended period of time-indicating reaction or volatilization from the surface. Thus, $KAR_1$ signals decreased in biochar extracts as pyrolysis temperature increased. Lastly, $KAR_1$ signals, as a function of initial biomass, were not strongly impacted by pyrolysis temperature above 500° C. This in combination with the detection of potential $KAR_1$ signals in material processed at 450° C., indicates that formation at relatively low temperatures is the primary route.

In summary, as demonstrated above, $KAR_1$ can be produced through the pyrolysis of biomass at varying temperatures and hold times, by collecting the resulting bio-oil and biochar extracts, using the methods first described above. Further, as demonstrated above, testing shows that the amount of $KAR_1$ or signal solubilizing compounds produced can be anticipated and controlled to produce a desired result, by varying temperature and hold times of the biomass. Certain biomass will produce distinct distributions of soluble signaling compounds, such as $KAR_1$, and for each biomass, the production of these compounds, such as $KAR_1$, will further vary when pyrolysis is performed at different temperatures, at varying hold times.

While the above method illustrates how $KAR_1$ can be produced through the pyrolysis of biomass at varying temperatures and hold times, in this same manner, other inorganic compounds, organic compounds, or soluble signaling compounds, including but not limited to, butenolides, anyhdrosugars, carboxylic acids, fatty acids, alkanes, ketones, aldehydes, aromatics, phenolics and complex macromolecular organics similar to humic and fulvic acids can also be produced. Even more specifically, methylparaben, vanillin, furfural, and levoglucosan have been consistently identified in extracts from all sources. Biomass can be selected from sources other than pine and coconut to yield varying results. Biomass selection may include but is not be limited to softwoods, hardwoods, straw, corn stover, bagasse, and nut shells. Temperatures can vary for each biomass and desired product of soluble signaling compounds from any temperature ranging from 400 to 600° C., with solid hold times ranging at any particular temperature for any time between 1 minute and 24 hours. Reactions may be carried out with or without a sweep gas and/or vacuum to modify the vapor residence time. Sweep gas may include inert gases such as $CO_2$ and $N_2$ and may or may not include recycle of the gases from the pyrolysis system itself. Although these tests have been focused on desirable compounds in relationship to seed germination and early plant growth, the same methods for selecting feedstock and pyrolysis conditions to create specific inorganic or organic compounds can be used for desired compounds for other applications including but not limited to animal feed, pharmaceutical, or chemical feedstocks for other commercial goods. The beneficial compound could improve seed germination, increase plant growth, improve crop yield, promote microbial communities, improve animal health, or act as an active ingredient in pharmaceuticals. In addition, some desirable compounds could actually lead to harm for plants, microbes, or animals, but be desirable in the fact that they could be used as insecticides, herbicides, anti-microbials, or anti-fungals. In addition although the focus of this invention has been to collect the compounds through the biochar extraction method, the invention also covers collection of desirable compounds through resulting bio-oils or off-gas from the pyrolysis.

5. Use and Application of Extract

As set forth above, a key application of extracts is to promote plant growth. FIGS. 86*a*, 86*b*, 86*c*, 86*d*, 86*e*, 86*f*, and 86*g*, show results from biochar extracts used in germination and growth tests with cucumbers, tall fescue, and corn seeds. The extract was shown to statistically improve cucumber biomass growth 14 days after seeding and turf biomass growth 14 days after seeding when flood irrigated or top down irrigated. The extract also showed improved corn seed germination rates.

As shown above, different biomass sources and different post-treatment process may be more effective than others for use on different cultivars and varieties of plants as well as at what stage of development for the plant, such as at seed germination, early plant development, at transplant, at propagation through cuttings, or in conjunction with certain microbials. The biomass, the biochar extract source and the post-treatment processes, including extraction and purification steps, may also be varied to achieve different results depending upon the purpose for which the biochar or extract is being used which may include improvement of germination, early plant development and growth, or enhanced plant-microbial interactions.

When improved germination and early plant growth are desired, a liquid biochar extract could be applied directly to seeds as a seed treatment, either in an upstream, commercial setting or downstream by a seed conditioner or retail applicator. It could also be applied directly to soil, either broadcast or in-furrow, at the time of planting. These applications could be stand alone or could be applied in combination with fertilizers, fungicides, insecticides, plant growth regulators, biostimulants, biologicals, or biorationals.

Figure 87:
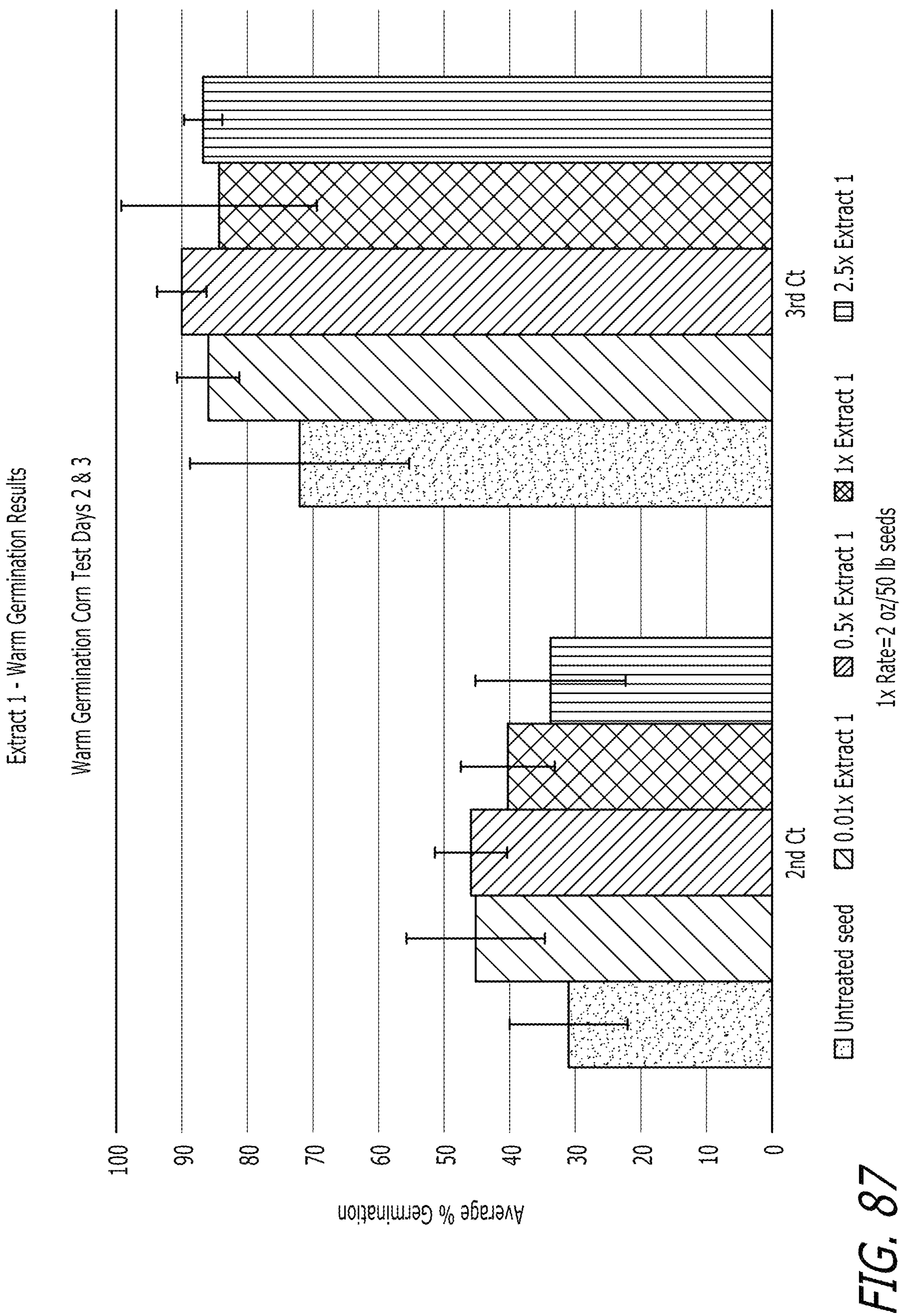
FIG. 87 is a chart showing warm germination results on days 2 and 3 with extract 1 treated seeds.
Figure 88:
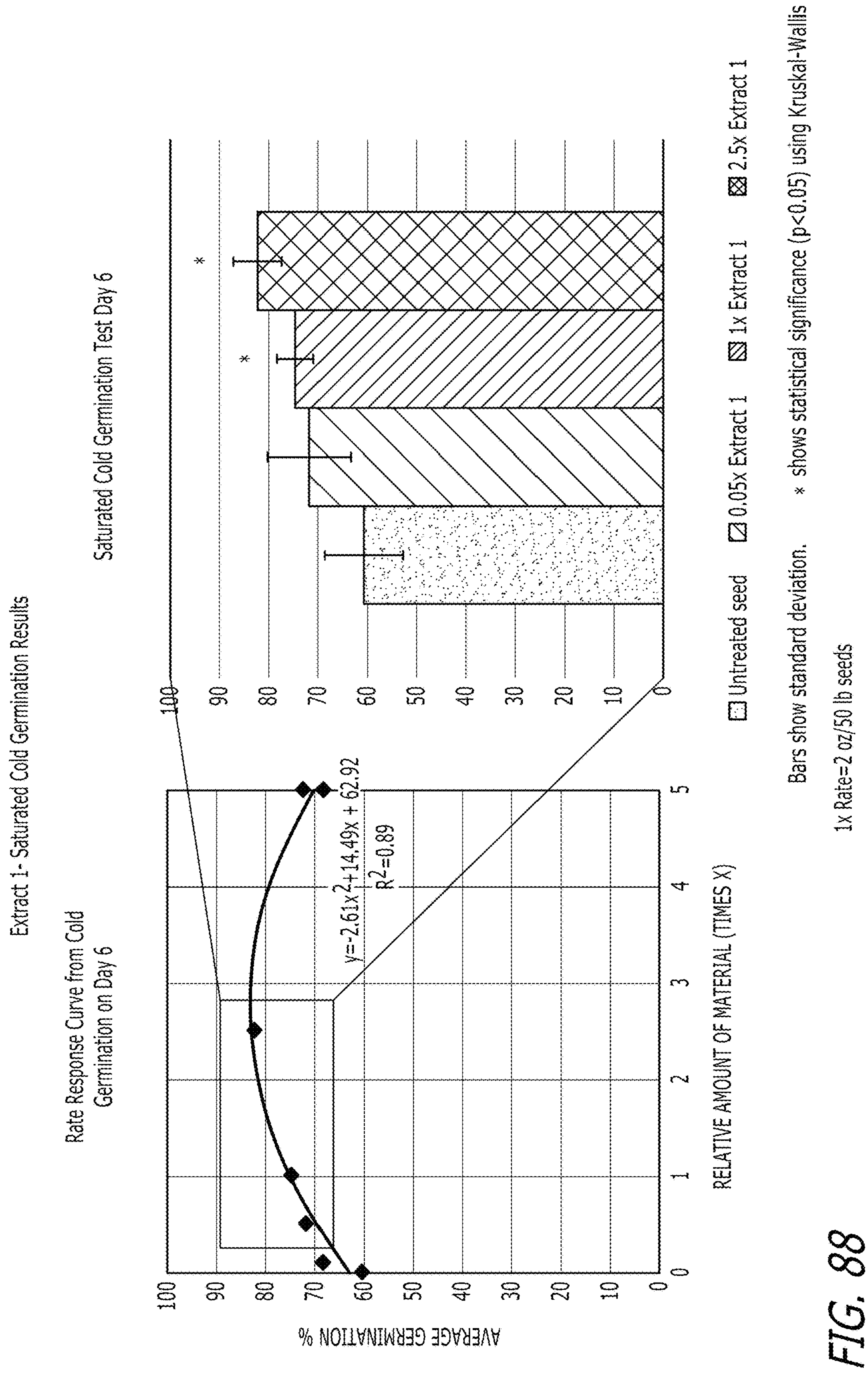
FIG. 88 is a chart showing cold germination results on day 6 with extract 1 treated seeds.

To test seed treatment application, corn seeds were treated (coated) with various biochar extracts and then put into standard replicated warm and saturated cold germination tests, where daily counts and evaluations were made through first 6 days of germination. Quicker germination was seen with Extract 1 treated seeds at various application rates versus the untreated seeds, particularly when comparing average percent of germinated seeds on days 2 & 3 as depicted in FIG. 87. The best performing rate in this test for this extract, which was not concentrated or diluted after extraction, was 2 oz of extract per 50 lbs of corn seed, but there was not a strong rate response seen. However, as seen in FIG. 88, the same extract in the saturated cold germination test showed a strong rate response on day 6 and the most improved germination was seen with the 5 oz/50 lbs of corn seed. Germination improvement on day 6 for both the 5 oz/50 lbs and the 2 oz/50 lbs of Extract 1 were statistically significant.

Figure 89:
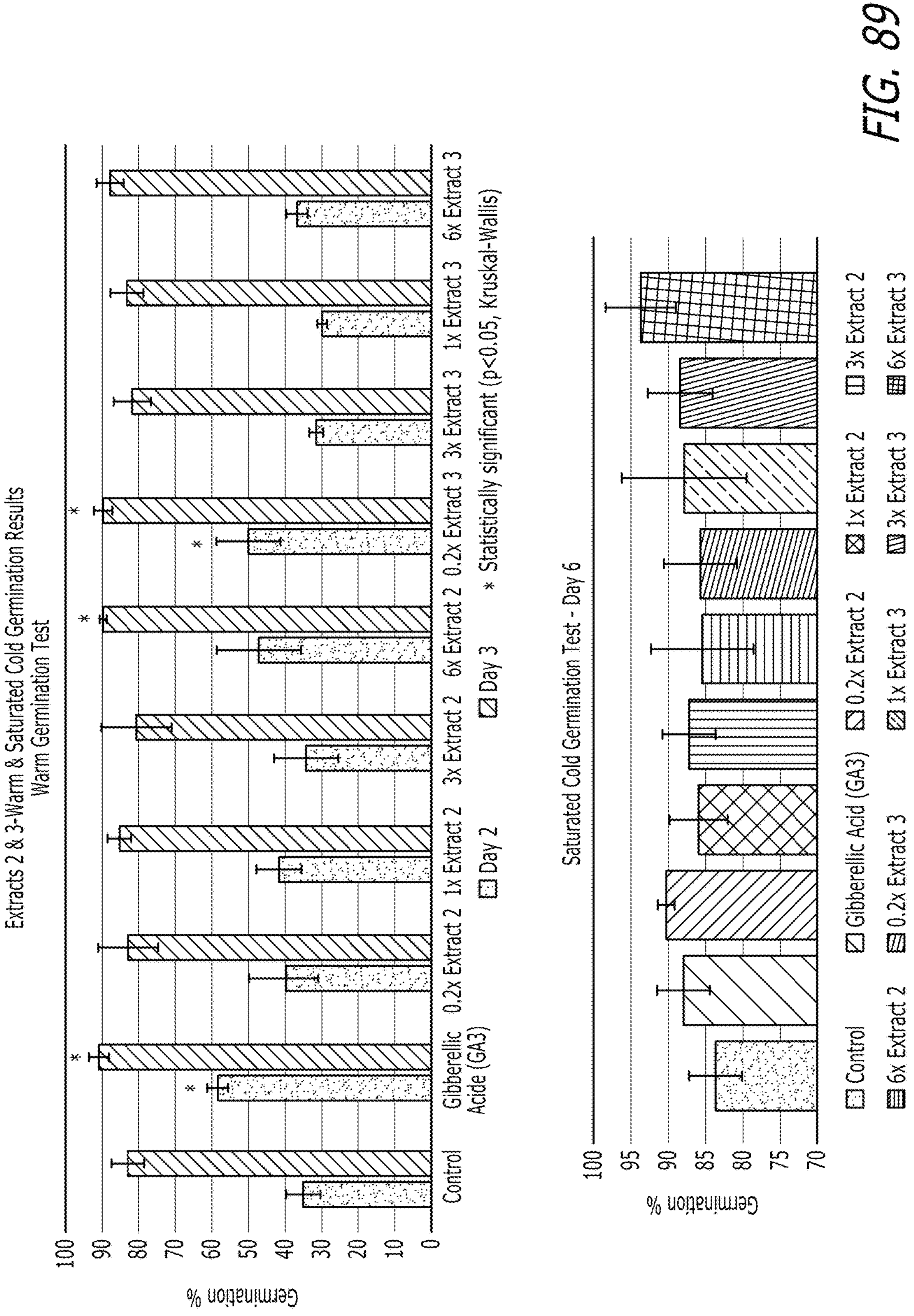
FIG. 89 is a chart showing warm germination testing and saturated cold germination testing on extracts 2 and 3 on days 2, 3 and 6.

An additional test was done to compare two biochar extracts made from two different biochars (different biomass feedstocks and different pyrolysis methods) and two different extraction methods. The chosen extraction method was specifically developed for each biochar to find the best germination-promoting extract for that specific biochar without additional purification for corn seeds. In addition, the biochar extract treated seeds were compared to both untreated seeds and a commercially available gibberellic acid (GA3), a plant hormone that regulates growth and currently used to improve germination. Results from warm germination testing and saturated cold germination testing are depicted in FIG. 89. As can be seen in the results, Extract 2 and Extract 3 were able to outperform the untreated seed control at different application rates. A 1$x$ rate here is equivalent to 1 oz of extract/50 lb seeds. Even though the two extracts had different compounds, different starting biochars, and different extraction methods, a customized extraction process could be made to get improved results in the warm and saturated cold germination tests over the control, that were similar to GA3.

These tests show that commercially viable extracts can be made for seed treatment application at application rates that are commonly used by seed companies. An individual signaling compound's or combined signaling compounds' concentrations in a biochar extract can be as low as 1 ppt, 1 ppb, or 0.01 ppm and can be as high as 10 ppm, 100 ppm, or 1000 ppm. In addition, a biochar extract application rate for seed treatment could be as high as 10 oz/100 lb seeds, 5 oz/100 lb seeds, 2 oz/100 lb seeds and as low as 0.01 oz/100 lb seeds, 0.1 oz/100 lb seeds, or 0.5 oz/100 lb seeds.

For in-furrow application to soil and seeds at planting, similar concentrations for individual or combined signaling compounds in a biochar extract can be used: as low as 1 ppt, 1 ppb, or 0.01 ppm and can be as high as 10 ppm, 100 ppm, or 1000 ppm. In-furrow application rates can be as low as 0.1 oz/acre, 0.5 oz/acre, or 1 oz/acre and as high as 25 oz/acre, 10 oz/acre, or 5 oz/acre.

Besides applying biochar extracts directly to seeds or soil, by itself, they could also be applied in combination with other agricultural products, such as fertilizers, fungicides, insecticides, plant growth regulators, biostimulants, biologicals, or biorationals. Another option would be to apply a biochar extract to another agricultural product after production or include it into the production of the other agricultural product, prior to application of the agricultural product. These agricultural products could include but are not limited to granular fertilizers, compost, biochar, or inert carriers (e.g. clay, cellulose, peat). Again the extract could be combined with other agricultural products, such as microbial inoculants, insecticides, fungicides, fertilizers, plant growth regulators, biostimulants, biologicals, or biorationals.

Biochar extracts could also be applied to plant roots prior to transplant or broadcast as a foliar spray alone or in combination with other agricultural products as described above.

Figure 90:
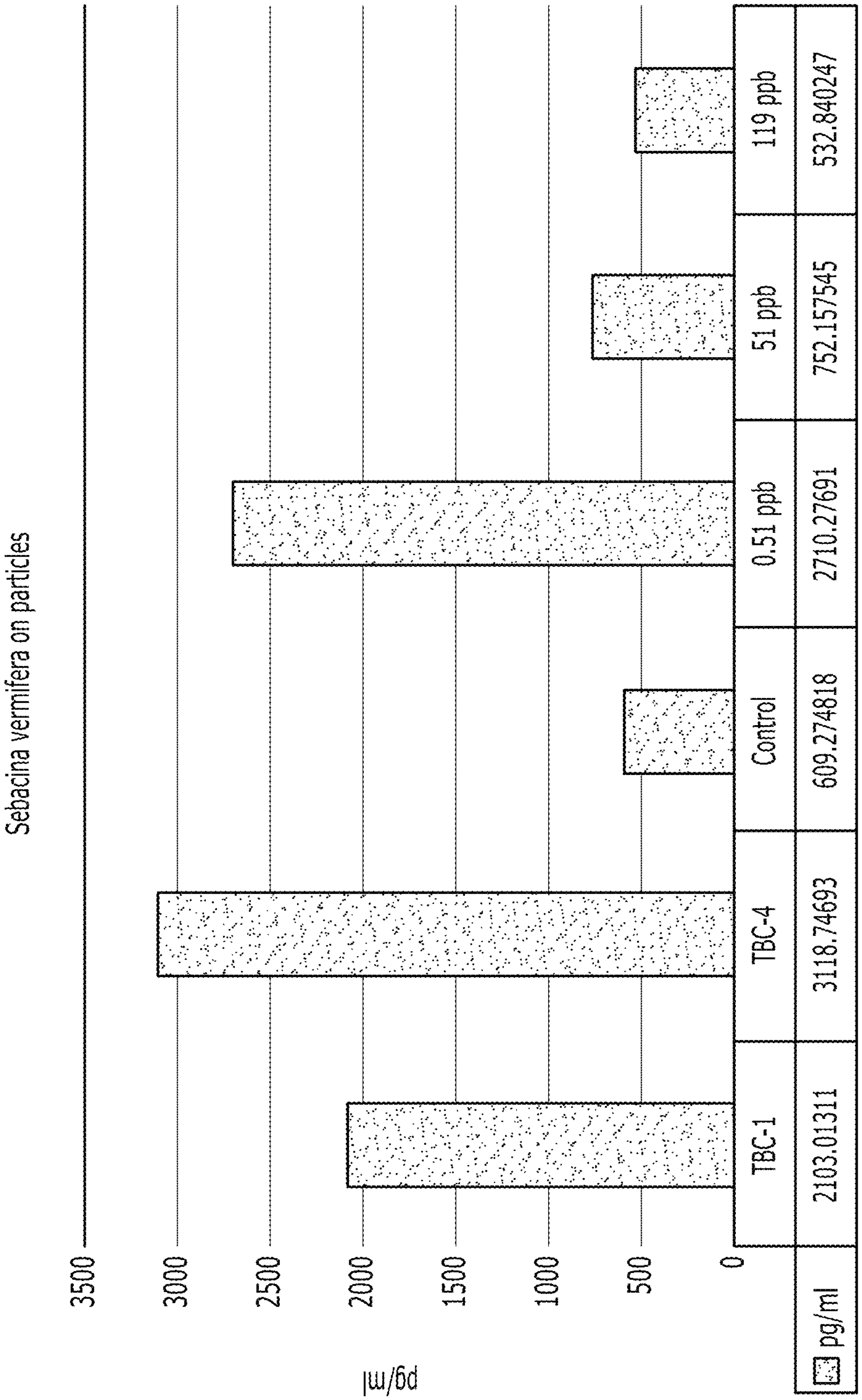
FIG. 90 is a chart showing the impact on sebacina growth over the glass bead control using vacuum treated biochars from different biomass feedstocks and various levels of karrikin.

Biochar extracts with signaling compounds could be designed for specific plants or crops, including but not limited to row crops like corn, cotton, soybeans, wheat, rice and other cereal crops as well as vegetable crops, like tomatoes, bell peppers, carrots, broccoli, and lettuce, to nursery and ornamental plants, and to turf and forage grasses Signaling compounds may have other applications other than promoting plant growth directly. Previous research has shown that signaling compounds, such as karrikins, may also modulate plant-microbial interactions, such as with arbuscular mycorrhizal fungi or bacteria. See Gutjahr C, et al., *Rice perception of symbiotic arbuscular mycorrhizal fungi requires the karrikin receptor complex*, Dec. 18, 2015, Science and Mandabi A., et al, *Karrikins from plant smoke modulate bacterial quorum sensing*, May 25, 2014, Chem Commun (Camb). FIG. 90 shows results of an experiment growing a mycorrhizal fungus, *Sebacina vermifera*, which is known for its plant growth promoting abilities. Treated Biochar 1 (TBC-1) and Treated Biochar 4 (TBC-4) were compared to glass bead controls and glass beads loaded with a reference karrikin ($KAR_1$) at various concentrations (0.51 ppb, 51 ppb, and 119 ppb). A plug of *Sebacina vermifera* was placed in the middle of each material (biochar or glass beads) and incubated for three weeks. Following incubation, RNA was extracted from the material and analyzed through qPCR to determine the amount of *Sebacina vermifera* in pg/ml on each material. As seen in FIG. 80, both vacuum treated biochars, from different biomass feedstocks, and the reference karrikin at 0.5 showed an order of magnitude improvement in sebacina growth over the glass bead control, whereas the references with higher levels of karrikin showed similar levels of growth to the control. In addition, TBC-4 showed almost 50% more growth than TBC-1 and slightly more growth than the 0.51 ppb $KAR_1$ reference. Recalling FIG. 70, TBC-1 had 47 ppb $KAR_1$ and Biochar 4, prior to treatment, had approximately 0.49 ppb. These results again likely point to karrikin availability in the biochars, inhibitor compound interactions, or being a factor as TBC-1 significantly outperformed the 51-ppb reference despite having similar amounts of $KAR_1$. These results highlight the potential for soluble signaling molecules to impact microbial growth, but they may need to be available at lower levels for impact.

In summary, as shown above, biochar and biochar extracts can be produced with higher levels of karrikins than previously found to exist by selecting the biomass and controlling the pyrolysis parameters and processes. By controlling the biomass from which the biochar is created and by establishing predetermined, pyrolysis processes and parameters proved to yield the highest soluble signaling compounds bound to the biochar, biochar with soluble signaling compounds may be achieved. For example, as illustrated above, it is possible to create biochars with concentrations of more than 10 ng/g, more than 20 ng/g, more than 40 ng/g, or more than 100 ng/g of $KAR_1$. These soluble signaling compounds in the biochars or in extracts from the biochars can be used to enhance seed germination and early plant development or microbial growth. Further, post-treatment processing of biochar can be used to adjust the levels of these signaling compounds, such as karrikins, and increase their availability in order to make the resulting biochars more effective. Such post-treatment process may include all the various treatments described above, which may include, but are not limited to, vacuum treatment, surfactant treatment, solvent extraction, placing the biochar in suspension or in a slurry, introducing further additives and/or adding of the extracts back with, on, or into the biochars. The biochar or extracts from the biochar can also be used in creating products in a granular, slurry, or liquid form that can be used in various applications including but not limited to soil treatments, plant treatments, or seed treatments.

Both signaling compounds and other residual biochar compounds may lend themselves to other applications. One example is creating a biochar extract to add to an inert microbial carrier, such as biochar, peat, clay, cellulose, or another material, prior to or in conjunction with inoculation to improve microbial loading or reduce the decay curve, thus improving shelf-life of the microbial product. Another example is to create a biochar extract that is designed as an anti-microbial or anti-fungal additive. Another example is to be able to create a biochar extract that is a natural or organic insecticide, fungicide, or herbicide. Other uses may come in incorporating into animal feed or into composting process, to get similar results seen from adding biochar itself.

As set forth above, the treated biochar, or the extracts outlined herein, of the present invention may be used in various agriculture activities, as well as other activities and in other fields. Additionally, the treated biochar or extracts may be used, for example, with: farming systems and technologies, operations or activities that may be developed in the future; and with such existing systems, operations or activities which may be modified, in part, based on the teachings of this specification. Further, the various treated biochar, extracts, and treatment processes set forth in this specification may be used with each other in different and various combinations. Thus, for example, the processes and resulting biochar compositions provided in the various examples provided in this specification may be used with each other; and the scope of protection afforded the present inventions should not be limited to any particular example, process, configuration, application or arrangement that is set forth in a particular example or figure.

Although this specification focuses on applications related to the production and optimization of biochar extracts, it should be understood that the materials, compositions, structures, apparatus, methods, and systems, taught and disclosed herein, may have applications and uses for many other activities in addition to agriculture for example, as filters, additives, and in remediation activities, among other things.

It is understood that one or more of these may be preferred for one application, and another of these may be preferred for a different application. Thus, these are only a general list of preferred features and are not required, necessary and may not be preferred in all applications and uses.

It is noted that there is no requirement to provide or address the theory underlying the novel and groundbreaking functionality, performance or other beneficial features and properties that are the subject of, or associated with, implementations of the present inventions. Nevertheless, to the extent that various theories are provided in this specification it is done to further advance the art in this important area. These theories put forth in this specification, unless expressly stated otherwise, in no way limit, restrict or narrow the scope of protection to be afforded the claimed inventions. These theories many not be required or practiced to utilize the present inventions. It is further understood that the present inventions may lead to new, and heretofore unknown theories to explain the functionality, performance or other beneficial features and properties that are the subject of, or associated with, embodiments of the methods, articles, materials, and devices of the present inventions; and such later developed theories shall not limit the scope of protection afforded the present inventions.

Those skilled in the art will recognize that there are other methods that may be used to treat biochar in a manner that forces the infusion of liquids into the pores of the biochar without departing from the scope of the invention. The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

We claim:

1. A method for producing a highest concentration of a desired compound from the pyrolysis of biomass, the method comprising steps of:

obtaining a biomass source;

pyrolyzing the biomass source at least two different temperatures between 400-600° C. and, at each of the at least two different temperatures, retaining the biomass while pyrolyzing the biomass source at the at least two different temperatures for a period of not longer than one day and not less than 1 minute whereby the pyrolysis of the biomass at the at least two different temperatures for the period produces at least two different biochars;

creating extracts from each of the at least two different biochars by contacting the at least two different biochars with a first solution containing at least one solvent selected from the group consisting of acetone, acetonitrile, dichloromethane, ethanol, ethyl acetate, and hydrochloric acid, where the extracts comprise the first solution and the desired compound;

determining which of the extracts from each of the at least two different biochars produces a highest concentration of the desired compound; and collecting biochar extract from the at least two different biochars that produced the extract containing the highest concentration of the desired compound, where the collected biochar extract continues to comprise the first solution and the desired compound;

further processing the collected biochar extract by removing biochar particles from the collected biochar extract or distilling, refining or concentrating the collected biochar extract, where the further processed collected biochar extract comprises a second solution that comprise at least the first solution and the desired compound for purposes; and applying the second solution to seeds, soil, or plants.

2. The method of claim 1 where the biomass source is coconut shells.

3. The method of claim 1 where the biomass source is wood.

4. The method of claim 1 where one of the at least two different temperatures is 450° C.

5. The method of claim 1 where pyrolyzing the biomass source at the least two different temperatures further includes pyrolyzing the biomass source at the at least two different temperatures each for different time periods, where at least one of the different time periods is one half hour.

6. The method of claim 1 where prior to applying the second solution to seeds, soil, or plants the second solution is reincorporated into a biochar product and the biochar product with reincorporated second solution is applied to seeds, soil or plants.

7. The method of claim 1 where the desired compound is a cyanohydrin.

8. The method of claim 1 where the desired compound is a butenolide.

9. The method of claim 1 where the desired compound is a karrikin.

10. The method of claim 1 where the desired compound is a macromolecule with a molecular weight in excess of 1 kilodalton (kD).

11. A method for producing a desired compound, the method comprising steps of:

selecting a biomass source;

pyrolyzing the biomass source at a predetermined temperature for a predetermined hold time, where the pyrolysis produces bio-oil and biochar;

creating extracts from the bio-oil or biochar by contacting the bio-oil or biochar with a first solution containing at least one solvent selected from the group consisting of acetone, acetonitrile, dichloromethane, ethanol, ethyl acetate, and hydrochloric acid; and collecting the extracts from the bio-oil or biochar to recover the desired compound, where the collected extract continues to comprise the first solution and the desired compound; and applying the collected extract to seeds, soil, or plants.

12. The method of claim 11 where the biomass source is coconut shells.

13. The method of claim 11 where the biomass source is wood.

14. The method of claim 11 where the predetermined temperature is 450° C.

15. The method of claim 11 where the predetermined hold time is one half hour.

16. The method of claim 11 where the desired compound is a cyanohydrin.

17. The method of claim 11 where the desired compound is a butanolide or karrikin.

18. The method of claim 11 further includes the step of further processing the collected extracts separate from, or prior to, disposal, by removing biochar particles from the collected extract or distilling, refining or concentrating the collected extract, where the further processed collected extract comprises a second solution that continues to comprise at least the first solution and the desired compound, and the second solution is the collected extract applied to seeds, soil, or plants.

19. A method for producing KAR1, the method comprising steps of:

selecting a biomass for pyrolysis, where the biomass is coconut shells;

pyrolyzing the biomass at temperatures at 600° C. or less;

holding a pyrolysis temperature at 600° C. or less for a period of at least 1 minute but less than 24 hours, where the pyrolysis produces bio-oil and biochar; and creating an extract of the KAR1 from either the bio-oil or the biochar, where the created extract comprises at least a washing or cleaning solution and the KARL;

further processing the created extract by removing biochar particles from the created extract or distilling, refining or concentrating the created extract, where the further processed created extract comprises a solution of at least the washing or cleaning solution and the $KAR_1$;

reincorporating the created extract into a biochar product; and applying the biochar product with reincorporated created extract to seeds, soil, or plants.

* * * * *